US011827639B2

(12) United States Patent
Pei et al.

(10) Patent No.: US 11,827,639 B2
(45) Date of Patent: Nov. 28, 2023

(54) TDO2 AND IDO1 INHIBITORS

(71) Applicants: Genentech, Inc., South San Francisco, CA (US); NewLink Genetics Corporation, Ames, IA (US)

(72) Inventors: Zhonghua Pei, South San Francisco, CA (US); Brendan Parr, South San Francisco, CA (US); Wendy Liu, South San Francisco, CA (US); Richard Pastor, South San Francisco, CA (US); Lewis Gazzard, South San Francisco, CA (US); Firoz Jaipuri, Ames, IA (US); Sanjeev Kumar, Ames, IA (US); Hima Potturi, Ames, IA (US); Guoshen Wu, Beijing (CN); Xingyu Lin, Beijing (CN); Yanyan Chu, Beijing (CN); Powai Yuen, Beijing (CN)

(73) Assignees: GENENTECH, INC., San Francisco, CA (US); NEWLINK GENETICS CORPORATION, Ames, IA (US)

( * ) Notice: Subject to any disclaimer, the term of this patent is extended or adjusted under 35 U.S.C. 154(b) by 0 days.

(21) Appl. No.: 16/626,191

(22) PCT Filed: Jun. 28, 2018

(86) PCT No.: PCT/US2018/039880
§ 371 (c)(1),
(2) Date: Dec. 23, 2019

(87) PCT Pub. No.: WO2019/006047
PCT Pub. Date: Jan. 3, 2019

(65) Prior Publication Data
US 2020/0216456 A1    Jul. 9, 2020

(30) Foreign Application Priority Data

Jun. 28, 2017  (WO) ................ PCT/CN2017/090526

(51) Int. Cl.
| C07D 487/04 | (2006.01) |
| A61K 31/4188 | (2006.01) |
| A61K 31/438 | (2006.01) |
| A61K 31/439 | (2006.01) |
| A61K 31/4439 | (2006.01) |
| A61K 31/454 | (2006.01) |
| A61K 31/437 | (2006.01) |
| A61K 31/4725 | (2006.01) |
| A61K 31/5377 | (2006.01) |
| A61K 45/06 | (2006.01) |

(52) U.S. Cl.
CPC ................... *C07D 487/04* (2013.01)

(58) Field of Classification Search
CPC .............. A61K 31/4725; A61K 31/439; A61K 31/454; A61K 31/4439; A61K 31/437; A61K 31/4188; A61K 31/438; A61K 31/5377; A61K 45/06; A61K 2300/00; C07D 487/04
See application file for complete search history.

(56) References Cited

U.S. PATENT DOCUMENTS 9,260,434 B2 *   2/2016   Mautino ................. A61P 43/00
10,899,764 B2 *   1/2021   Tu ........................... A61P 35/02

FOREIGN PATENT DOCUMENTS

| WO | WO2012/142237 | 10/2012 |
| WO | WO2016/059412 | 4/2016 |
| WO | WO2016/165613 | 10/2016 |

OTHER PUBLICATIONS

Mautino et al., 2012, caplus an 2012:1519166.*
Tu et al., 2016, caplus an 2016:1734501.*
RN1884560-84-2, 2016, registry database compound.*
International Search Report dated Sep. 26, 2018 for International Application No. PCT/US2018/039880, 3 pages.

* cited by examiner

*Primary Examiner* — Sun Jae Yoo
(74) *Attorney, Agent, or Firm* — McDonnell Boehnen Hulbert & Berghoff LLP

(57) ABSTRACT

Presently provided are inhibitors of TDO2 and IDO1 and pharmaceutical compositions thereof, useful for modulating an activity of tryptophan 2,3 dioxygenase and indoleamine 2,3-dioxygenase 1; treating immunosuppression; treating a medical conditions that benefit from the inhibition of tryptophan degradation; enhancing the effectiveness of an anti-cancer treatment comprising administering an anti-cancer agent; and treating tumor-specific immunosuppression associated with cancer.

14 Claims, No Drawings

TDO2 AND IDO1 INHIBITORS

CROSS-REFERENCES TO RELATED APPLICATIONS

This application is a U.S. national phase application of International Patent Application no. PCT/US2018/039880, filed Jun. 28, 2018, which claims the benefit of priority of International Patent Application no. PCT/CN2017/090526, filed Jun. 28, 2017, the disclosures of each of which is hereby incorporated herein by reference in its entirety.

BACKGROUND OF THE INVENTION

Field of the Invention

The present disclosure relates to compounds and methods for inhibition of tryptophan 2,3-dioxygenase (TDO2) and indoleamine 2,3-dioxygenase 1 (IDO1); further the disclosure relates to method of treatment of diseases and disorders mediated by tryptophan deficiency.

Summary of the Related Art

Tryptophan (Trp) is an essential amino acid required for the biosynthesis of proteins, niacin and the neurotransmitter 5-hydroxytryptamine (serotonin). The enzymes indoleamine 2,3-dioxygenase 1 (also known as INDO1 or IDO1), indoleamine-2,3-dioxygenase 2 (INDOL1 or IDO2) and tryptophan-2,3-dioxygenase (TDO2) catalyze the first and rate limiting step in the degradation of L-tryptophan to N-formyl-kynurenine. Although these enzymes catalyze the same reaction, differential expression and compartamentalization of IDO1 and TDO2 in different tissues is thought to mediate their different biological roles. IDO1 is normally expressed in cells of the gastrointestinal and pulmonary epithelia, epididymus, placenta, pDCs in draining lymph nodes and tumor cells. IDO2 is expressed mainly in brain and placenta, but certain splice variants are also detected in liver, small intestine, spleen, placenta, thymus lung, brain, kidney and colon. TDO2 is expressed mainly in liver, and controls the flux of dietary Trp to the serotonin and kynurenine pathways, and is also expressed in tumors and tumor cell lines.

Several lines of evidence suggest that IDO1 and TDO2 are involved in induction of immune tolerance. Studies of mammalian pregnancy, tumor resistance, chronic infections and autoimmune diseases have shown that cells expressing IDO1 can suppress T-cell responses and promote tolerance. Accelerated Trp catabolism has been observed in diseases and disorders associated with cellular immune activation, such as infection, malignancy, autoimmune diseases and AIDS, as well as during pregnancy. It was proposed that IDO1 is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol., 294: 425-35). To this end, it has recently been shown that IDO1 inhibition can enhance the levels of virus-specific T cells and, concomitantly, reduce the number of virally infected macrophages in a mouse model of HIV (Portula et al., 2005, Blood, 106:2382-90).

IDO1 is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO1 is expressed by human syncytiotrophoblast cells and systemic tryptophan concentration falls during normal pregnancy, it was hypothesized that IDO1 expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Munn, et al., 1998, Science 281: 1191-3).

Further evidence for a tumoral immune resistance mechanism based on tryptophan degradation by IDO1 comes from the observation that most human tumors constitutively express IDO, and that expression of IDO1 by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO1 inhibitor (Uyttenhove et al., 2003, Nature Med., 9: 1269-74). It has also been shown that the IDO1 inhibitor, 1-MT, can synergize with chemotherapeutic agents to reduce tumor growth in mice, suggesting that IDO1 inhibition may also enhance the anti-tumor activity of conventional cytotoxic therapies (Muller et al., 2005, Nature Med., 11:312-9).

A similar situation has been observed with TDO2. It has been shown that a significant proportion of primary human tumors express elevated levels of TDO2 or TDO2 plus IDO1 (Pilotte et al. 2012, P.N.A.S). Moreover, pharmacological inhibition of TDO2 activity with TDO2 inhibitors, leads to immune-mediated rejection of tumors overexpressing TDO2, which means that TDO2, just as seen in IDO1, can mediate tumor-promoting immunosuppressive effects.

Small molecule inhibitors of IDO1 are being developed to treat or prevent IDO1-related diseases such as those described above. For example, PCT Publication WO 99/29310 reports methods for altering T cell-mediated immunity comprising altering local extracellular concentrations of tryptophan and tryptophan metabolites, using an inhibitor of IDO1 such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; WO 2009/073620; WO 2009/132238; WO 2011/056652 and WO 2012/142237. In particular, the compounds of WO 2012/142237 encompass a series of tricyclic imidazoisoindoles with potent IDO1 inhibitory activity.

SUMMARY OF THE INVENTION

We recognized that in light of the experimental data indicating a role for IDO1 and/or TDO2 in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO1 and/or TDO2 activity are desirable. Specific or dual inhibitors of IDO1 and TDO2 can be used to activate T cells and therefore enhance T cell activation when the T cells are suppressed by pregnancy, malignancy or a virus such as HIV. Inhibition of IDO1 and/or TDO2 may also be an important treatment strategy for patients with neurological or neuropsychiatric diseases or disorders such as depression. The compounds, compositions and methods herein help meet the current need for IDO1 and TDO2 modulators.

In this disclosure, we describe novel structures related to imidazoisoindoles that can exert combined inhibition of tryptophan degradation mediated by both IDO1 and TDO2 enzymes.

In one aspect, the invention comprises compounds according to the formula (I),

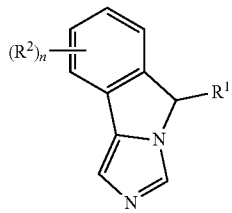
(I)

or a stereoisomer thereof, or a pharmaceutically acceptable salt thereof, wherein $R^1$ is $C_{1-6}$alkyl, aryl, heteroaryl, $C_{1-3}$alkyl-heteroaryl, $C_{3-7}$cycloalkyl, $C_{1-3}$alkyl-$C_{3-7}$cycloalkyl, 3-7 membered heterocyclyl or $C_1$alkyl-3-7 membered heterocyclyl,
  wherein the $C_{3-7}$cycloalkyl, aryl, heteroaryl, or 3-7 membered heterocyclyl is optionally fused to aryl, heteroaryl, $C_{3-7}$cycloalkyl or 3-7 membered heterocyclyl; or
  wherein the $C_{3-7}$cycloalkyl or 3-7 membered heterocyclyl is optionally substituted by =(spiro-$C_{3-7}$cycloalkyl) or =(spiro-(3-7 membered heterocyclyl));
  wherein $R^1$ is substituted by one, two, three, or four $R^a$ groups, wherein each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, $C_{3-7}$cycloalkyl, 3-7 membered heterocyclyl, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —$NR_2$ or —SR; and each R is hydrogen, $C_{1-6}$alkyl, $C_{1-6}$haloalkyl, aryl substituted with cyano, 3-7 membered heterocyclyl or $C_{3-6}$cycloalkyl;

provided that
  (a) $R^1$ is not substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl; and
  (b) when $R^1$ is cyclohexyl, piperidinyl or pyrrolidinyl, n is 0.

In an embodiment, the invention provides compounds of formula (I), provided that when $R^1$ is $C_{3-7}$cycloalkyl or 3-7 membered heterocyclyl, n is 0.

In an embodiment, the invention provides compounds of formula (I), wherein $R^1$ is substituted by one, two, three, or four $R^a$ groups, wherein each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

In an embodiment, the invention provides compounds of formula (I), wherein $R^1$ is substituted by one, two or three $R^a$ groups, wherein each $R^a$ is independently oxo, halogen, cyano, $C_{1-6}$alkyl, —$C_{1-6}$alkyl-OR, —$C_{1-6}$haloalkyl, —OR, —C(O)OR, —C(O)N(R)$_2$, —C(O)R, —C(O)-aryl, —S(O)$_2$R, —N(R)S(O)$_2$R or —S(O)$_2$N(R)$_2$;
wherein the aryl or heteroaryl is optionally substituted with —$NR_2$ or cyano;
n is 0 or 1;
each $R^2$ is halogen; and
each R is hydrogen, $C_{1-6}$alkyl, 3-7 membered heterocyclyl or $C_{3-6}$cycloalkyl.

In an embodiment, the invention provides compounds of formula (I), wherein $R^1$ is substituted by one, two or three $R^a$ groups, wherein each $R^a$ is independently oxo, halogen, cyano, $C_{1-6}$alkyl, —$C_{1-6}$alkyl-OR, —$C_{1-6}$haloalkyl, —C(O)OR, —C(O)N(R)$_2$, —C(O)R, —C(O)-aryl, —S(O)$_2$R, —N(R)S(O)$_2$R or —S(O)$_2$N(R)$_2$;
wherein the aryl or heteroaryl is optionally substituted with —$NR_2$ or cyano;
n is 0 or 1;
each $R^2$ is halogen; and
each R is hydrogen, $C_{1-6}$alkyl, 3-7 membered heterocyclyl or $C_{3-6}$cycloalkyl.

In an embodiment, the invention comprises compounds of Formula (II),

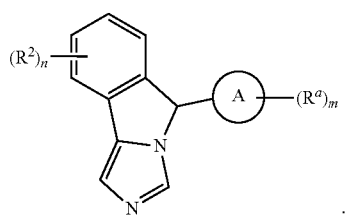
(II)

which are compounds of Formula (I) wherein
$R^1$ is

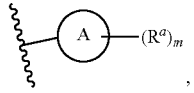
, ring A is aryl, heteroaryl, $C_{3-7}$cycloalkyl, $C_{1-3}$alkyl-$C_{3-7}$cycloalkyl, 3-7 membered heterocyclyl or $C_1$alkyl-3-7 membered heterocyclyl;

m is 0, 1, 2, 3 or 4; and each $R^a$ is independently oxo, halogen, cyano, nitro, $C_{1-6}$-alkyl, —$C_{1-6}$alkyl-OR, —$C_{1-6}$haloalkyl, $C_{1-6}$alkyl-cyano, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$, wherein each R is hydrogen, $C_{1-6}$alkyl, $C_{1-6}$haloalkyl, aryl substituted with cyano, 3-7 membered heterocyclyl or $C_{3-6}$cycloalkyl.

In one embodiment, the invention comprises compounds of Formula (II) wherein n is 0. In other embodiments, n is 1.

In another embodiment, the invention comprises compounds of Formula (III),

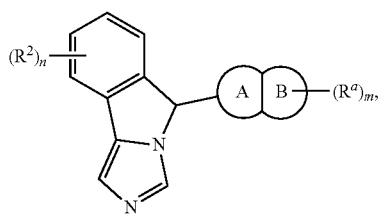

(III)

which are compounds of Formula (I) wherein
$R^1$ is

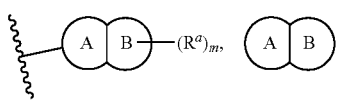

is a fused bicyclic ring system consisting of a ring A and a ring B;

ring A is $C_{3-7}$cycloalkyl, aryl, heteroaryl or 3-7 membered heterocyclyl;

ring B is aryl, heteroaryl, $C_{3-7}$cycloalkyl or 3-7 membered heterocyclyl;

m is 0, 1, 2, 3 or 4; and each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, 3-7 membered heterocyclyl, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

In one embodiment, the invention comprises compounds of Formula (III) wherein n is 0. In other embodiments, n is 1.

In another embodiment, the invention comprises compounds of Formula (IV),

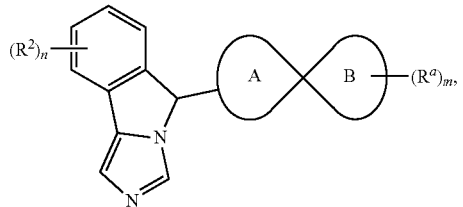

(IV)

which are compounds of Formula (I) wherein
$R^1$ is

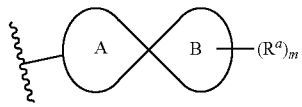

ring A is $C_{3-7}$cycloalkyl or 3-7 membered heterocyclyl;
ring B is $C_{3-7}$cycloalkyl or 3-7 membered heterocyclyl;
m is 0, 1, 2, 3 or 4; and each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

In one embodiment, the invention comprises compounds of Formula (IV) wherein n is 0. In other embodiments, n is 1.

In another aspect, pharmaceutical compositions are provided comprising a pharmaceutically acceptable excipient, diluent, or carrier, and a compound according to formula (I), (II), (III) or (IV).

In another aspect, pharmaceutical compositions are provided comprising a pharmaceutically acceptable excipient, diluent, or carrier, a compound according to formula (I), (II), (III) or (IV), and a second therapeutic agent.

In another aspect, a kit is provided comprising a pharmaceutically acceptable excipient, diluent, or carrier, a compound according to formula (I), (II), (III) or (IV), and a second therapeutic agent.

In another aspect methods are provided for
a) modulating an activity of IDO1 or TDO2 in a cell-free system or in a cell (ex vivo or in vivo) comprising contacting an IDO1 or TDO2 with a modulation effective amount of a compound according to formula (I), or a pharmaceutical composition comprising a compound according to formula (I);
b) treating IDO1 or TDO2 mediated immunosuppression in a subject in need thereof, comprising administering an effective inhibiting amount of a compound according to formula (I), or a pharmaceutical composition comprising a compound according to formula (I);
c) treating a medical condition that benefits from the inhibition of tryptophan degradation mediated by IDO1 and/or TDO2 comprising administering an effective amount of a compound of formula (I), or a pharmaceutical composition comprising a compound according to formula (I);
d) enhancing the effectiveness of an anti-cancer treatment comprising administering an anti-cancer agent and a compound according to formula (I), or a pharmaceutical composition comprising a compound according to formula (I); and e) treating immunosuppression associated with cancer comprising administering an effective amount of a compound according to formula (I), or a pharmaceutical composition comprising a compound according to formula (I).

In another aspect, the invention comprises use of any genus of compounds or species defined herein for the manufacture of a medicament for the treatment of medical conditions that benefit from the inhibition of enzymatic activity of IDO1 or TDO2.

In another aspect, the invention comprises any genus of compounds or species defined herein for use in the inhibition of enzymatic activity of IDO1 or TDO2 and the treatment of medical conditions that benefit from the inhibition of enzymatic activity of IDO1 or TDO2.

In another aspect, the invention comprises use of any genus of compounds or species defined herein for the treatment of immunosuppression associated with cancer, infectious diseases, or viral infections.

DETAILED DESCRIPTION OF THE INVENTION

The purpose of the present invention to develop small molecules that inhibit the enzymatic activity of TDO2. Alignment between IDO1 and IDO2 amino acid sequences reveals highly conserved features that mediate heme and substrate binding. Even though the amino acid sequence identity between IDO1 and IDO2 or IDO1 and TDO2 are not particularly high, significant residues determined to be important for catalytic activity by IDO1 and TDO2 mutagenesis and by crystallographic analysis are highly conserved between IDO1, IDO2 and TDO2, suggesting a structural and functional analogy in the mechanism of tryophan dioxygenation. Despite these structural similarities at the active site, IDO1 and TDO2 have different substrate specificity with TDO2 being almost exclusively specific for L-Trp and L-Trp derivatives substituted at the 5- and 6-positions of the indole group, while IDO1 can accept and oxygenate a wider variety of substrates such as D-Trp, tryptamine, serotonin and 1-methyl-L-Trp. These minor structural differences in the active site of IDO1 and TDO2 determine that these two proteins show differential response to the same enzymatic inhibitor molecules, with some inhibitors showing TDO2-specific response, others showing IDO1-specific response and some showing dual IDO1 and TDO2 inhibition. Moreover, the specificity of IDO1 and TDO2 inhibition by a particular class of small molecule inhibitors depends on whether IDO1 and TDO2 activity is measured using bioassays that employ recombinant purified IDO1 or TDO2 protein, or IDO1 or TDO2 protein expressed within a cell. For example, compounds described in patent applications WO2012142237 and WO2014159248 show potent IDO1 inhibition when tested against the purified recombinant protein and against cellularly expressed IDO1, or against recombinant purified TDO2 protein. However, compounds of that class show a remarkable 10-100 fold decreased potency when tested against TDO2 expressed within a cell. Therefore, those compounds are not likely to contribute to significant inhibition of TDO2 in vivo. For this reason, the present invention describes a novel class of molecules that show potent TDO2 inhibition in cellular bioassays and in vivo.

In one aspect, the invention provides compounds of formula (I),

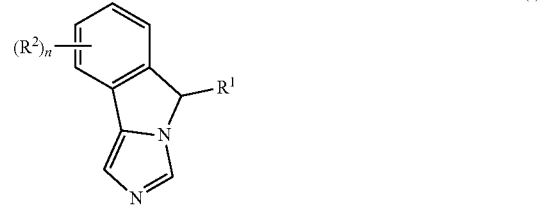

or a stereoisomer thereof, or a pharmaceutically acceptable salt thereof, wherein $R^1$ is $C_{1-6}$alkyl, aryl, heteroaryl, $C_{1-3}$alkyl-heteroaryl, $C_{3-7}$cycloalkyl, $C_{1-3}$alkyl-$C_{3-7}$cycloalkyl, 3-7 membered heterocyclyl or $C_1$alkyl-3-7 membered heterocyclyl, wherein the $C_{3-7}$cycloalkyl, aryl, heteroaryl, or 3-7 membered heterocyclyl is optionally fused to aryl, heteroaryl, $C_{3-7}$cycloalkyl or 3-7 membered heterocyclyl; or wherein the $C_{3-7}$cycloalkyl or 3-7 membered heterocyclyl is optionally substituted by =(spiro-$C_{3-7}$cycloalkyl) or =(spiro-(3-7 membered heterocyclyl));

wherein $R^1$ is substituted by one, two, three, or four $R^a$ groups, wherein each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, $C_{3-7}$cycloalkyl, 3-7 membered heterocyclyl, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —$NR_2$ or —SR; and each R is hydrogen, $C_{1-6}$alkyl, $C_{1-6}$haloalkyl, aryl substituted with cyano, 3-7 membered heterocyclyl or $C_{3-6}$cycloalkyl;

provided that (a) $R^1$ is not substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl; and (b) when $R^1$ is $C_{3-7}$cycloalkyl or 3-7 membered heterocyclyl, n is 0.

In an embodiment, the invention provides compounds of formula (I), provided that when $R^1$ is cyclohexyl, piperidinyl or pyrrolidinyl, n is 0.

In an embodiment, the invention provides compounds of formula (I), wherein $R^1$ is substituted by one, two, three, or four $R^a$ groups, wherein each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

In an embodiment, the invention provides compounds of formula (I), wherein

R[1] is substituted by one, two or three R[a] groups, wherein each R[a] is independently oxo, halogen, cyano, $C_{1-6}$alkyl, —$C_{1-6}$alkyl-OR, —$C_{1-6}$haloalkyl, —OR, —C(O)OR, —C(O)N(R)$_2$, —C(O)R, —C(O)-aryl, —S(O)$_2$R, —N(R)S(O)$_2$R or —S(O)$_2$N(R)$_2$;

wherein the aryl or heteroaryl is optionally substituted with —NR$_2$ or cyano;

n is 0 or 1;

each $R^2$ is halogen; and each R is hydrogen, $C_{1-6}$alkyl, 3-7 membered heterocyclyl or $C_{3-6}$cycloalkyl.

In an embodiment, the invention provides compounds of formula (I), wherein

R[1] is substituted by one, two or three R[a] groups, wherein each R[a] is independently oxo, halogen, cyano, $C_{1-6}$alkyl, —$C_{1-6}$alkyl-OR, —$C_{1-6}$haloalkyl, —C(O)OR, —C(O)N(R)$_2$, —C(O)R, —C(O)-aryl, —S(O)$_2$R, —N(R)S(O)$_2$R or —S(O)$_2$N(R)$_2$;

wherein the aryl or heteroaryl is optionally substituted with —NR$_2$ or cyano;

n is 0 or 1;

each $R^2$ is halogen; and each R is hydrogen, $C_{1-6}$alkyl, 3-7 membered heterocyclyl or $C_{3-6}$cycloalkyl.

In another embodiment, the invention provides compounds of formula (I),

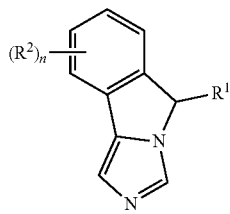

(I)

or a stereoisomer thereof, or a pharmaceutically acceptable salt thereof, wherein $R^1$ is $C_{1-6}$alkyl, aryl, heteroaryl, $C_{1-3}$alkyl-$C_{3-7}$cycloalkyl or $C_1$alkyl-3-7 membered heterocyclyl, or $R^1$ is

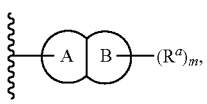

wherein ring A is $C_{3-7}$cycloalkyl, aryl, heteroaryl or 3-7 membered heterocyclyl, ring B is aryl, heteroaryl, $C_{3-7}$cycloalkyl or 3-7 membered heterocyclyl, or $R^1$ is

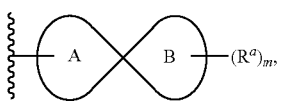

wherein ring A is $C_{3-7}$cycloalkyl or 3-7 membered heterocyclyl;

ring B is $C_{3-7}$cycloalkyl or 3-7 membered heterocyclyl;

m is 0, 1, 2, 3 or 4;

each R[a] is independently oxo, halogen, cyano, nitro, $C_{1-6}$alkyl, —$C_{1-6}$alkyl-OR, —$C_{1-6}$haloalkyl, $C_{1-6}$alkyl-cyano, —OR, —NR$_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$;

n is 0, 1, 2, 3 or 4;

each $R^2$ is independently halogen, cyano, $C_{1-6}$alkyl, $C_3$cycloalkyl, —$C_{1-6}$haloalkyl, —OR, —NR$_2$ or —SR; and each R is hydrogen, $C_{1-6}$alkyl, $C_{1-6}$haloalkyl, aryl substituted with cyano, 3-7 membered heterocyclyl or $C_{3-6}$cycloalkyl;

provided that (a) $R^1$ is not substituted with —NR$_2$ or —OH on the carbon atom bonded to the 5H-imidazo[5,1-a]isoindolyl, or on a carbon atom adjacent to the carbon atom bonded to the 5H-imidazo[5,1-a]isoindolyl.

In another embodiment, the invention provides compounds of formula (I),

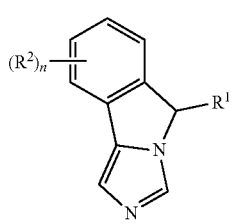

(I)

or a stereoisomer thereof, or a pharmaceutically acceptable salt thereof, wherein $R^1$ is $C_{1-6}$alkyl, aryl, heteroaryl, $C_{1-3}$alkyl-$C_{3-7}$cycloalkyl or $C_1$alkyl-3-7 membered heterocyclyl, or $R^1$ is

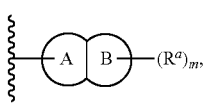

wherein ring A is $C_{3-7}$cycloalkyl, aryl, heteroaryl or 3-7 membered heterocyclyl, ring B is aryl, heteroaryl, $C_{3-7}$cycloalkyl or 3-7 membered heterocyclyl, or $R^1$ is

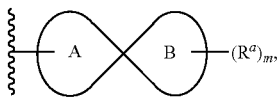

wherein ring A is $C_{3-7}$cycloalkyl or 3-7 membered heterocyclyl;

ring B is $C_{3-7}$cycloalkyl or 3-7 membered heterocyclyl;

m is 0, 1, 2, 3 or 4;

each R[a] is independently oxo, halogen, cyano, nitro, $C_{1-6}$alkyl, —$C_{1-6}$alkyl-OR, —$C_{1-6}$haloalkyl, $C_{1-6}$alkyl-cyano, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$ N(R)$_2$, —OC(O)R, —OC(O)OR, —OC(O)N(R)$_2$, —N(R)C(O)R, —N(R)C(O)OR or —N(R)C(O)N(R)$_2$;

n is 0, 1, 2, 3 or 4;

each R$^2$ is independently halogen, cyano, C$_{1-6}$alkyl, C$_3$cycloalkyl, —C$_{1-6}$haloalkyl, —OR, —NR$_2$ or —SR; and each R is hydrogen, C$_{1-6}$alkyl, C$_{1-6}$haloalkyl, aryl substituted with cyano, 3-7 membered heterocyclyl or C$_{3-6}$cycloalkyl.

The invention further comprises subgenera and species of formula (I) that are any combination of species and genera of structural formula (I), n, R$^1$, and R$^2$, as defined herein below. So, for example, the invention also comprises the subgenus of compounds of structural formula (I) where n is defined as in (1c) below, R$^2$ is defined in (2 h) below, and R$^3$ is defined in (3k) below.

n is selected from one of the following groups (1a)-(1k):
(1a) n is 1, 2, 3, or 4.
(1b) n is 0, 1, 2, or 3.
(1c) n is 0, 1, or 2.
(1d) n is 0 or 1.
(1e) n is 1 or 2.
(1f) n is 2 or 3.
(1g) n is 1.
(1h) n is 2.
(1i) n is 3.
(1j) n is 4.
(1k) n is 0.

R$^2$ is selected from one of the following groups (2a)-(2t):
(2a) R$^2$ is independently halogen, cyano, C$_{1-6}$alkyl, C$_3$cycloalkyl, —C$_{1-6}$haloalkyl, —OR, or —NR$_2$.
(2b) R$^2$ is independently halogen, cyano, C$_{1-6}$alkyl, C$_3$cycloalkyl, —OR, or —NR$_2$.
(2c) R$^2$ is independently halogen, cyano, C$_{1-6}$alkyl, C$_3$cycloalkyl, or —OR.
(2d) R$^2$ is independently halogen, C$_{1-6}$alkyl, C$_3$cycloalkyl, or —OR.
(2e) R$^2$ is independently halogen, cyano, C$_{1-6}$alkyl, or —OR.
(2f) R$^2$ is independently halogen, C$_{1-6}$alkyl or —OR.
(2g) R$^2$ is independently halogen or —OR.
(2h) R$^2$ is independently C$_{1-6}$alkyl or —OR.
(2i) R$^2$ is independently —OR.
(2j) R$^2$ is independently halogen, methyl or —OR.
(2k) R$^2$ is independently halogen, methyl, —OH or —OMe.
(2l) R$^2$ is independently chloro, fluoro, methyl or —OR.
(2m) R$^2$ is independently chloro, fluoro, methyl, —OH or —OMe.
(2n) R$^2$ is independently chloro, fluoro, methyl or —OH.
(2o) R$^2$ is independently fluoro, methyl or —OH.
(2p) R$^2$ is independently fluoro or —OH.
(2q) R$^2$ is independently fluoro or methyl.
(2r) R$^2$ is fluoro.
(2s) R$^2$ is methyl.
(2t) R$^2$ is —OH.

R$^1$ is selected from one of the following groups (3a)-(3cccc):
(3a) R$^1$ is C$_{1-6}$alkyl, aryl, heteroaryl, C$_{1-3}$alkyl-heteroaryl, C$_{3-7}$cycloalkyl, C$_{1-3}$alkyl-C$_{3-7}$cycloalkyl, 3-7 membered heterocyclyl or C$_1$alkyl-3-7 membered heterocyclyl,
wherein the C$_{3-7}$cycloalkyl, aryl, heteroaryl, or 3-7 membered heterocyclyl is optionally fused to aryl, heteroaryl, C$_{3-7}$cycloalkyl or 3-7 membered heterocyclyl; or
wherein the C$_{3-7}$cycloalkyl or 3-7 membered heterocyclyl is optionally substituted by =(spiro-C$_{3-7}$cycloalkyl) or =(spiro-(3-7 membered heterocyclyl));
wherein R$^1$ is substituted by one, two, three, or four R$^a$ groups, wherein each R$^a$ is independently oxo, halogen, cyano, nitro, C$_{1-6}$alkyl, —C$_{1-6}$alkyl-OR, —C$_{1-6}$haloalkyl, C$_{1-6}$alkyl-cyano, C$_{3-7}$cycloalkyl, 3-7 membered heterocyclyl, —OR, —NR$_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$.

(3b) Group (3a), wherein R$^1$ is C$_{4-6}$cycloalkyl or 5-6 membered heterocyclyl,
wherein the C$_{4-6}$cycloalkyl or 5-6-membered heterocyclyl is optionally fused to aryl or heteroaryl; or
wherein the C$_{4-6}$cycloalkyl is optionally substituted by =(spiro-C$_4$cycloalkyl) or =(spiro-(4-membered heterocyclyl)).

(3c) Group (3a), wherein R$^1$ is C$_{4-6}$cycloalkyl or 5-6 membered heterocyclyl,
wherein the C$_{4-6}$cycloalkyl or 5-6 membered heterocyclyl is optionally fused to aryl or heteroaryl; or
wherein the C$_{4-6}$cycloalkyl or 5-6 membered heterocyclyl is optionally substituted by =(spiro-C$_4$cycloalkyl) or =(spiro-(4-membered heterocyclyl)).

(3d) Group (3a), wherein R$^1$ is cyclobutyl, cyclopentyl, cyclohexyl, pyrrolidinyl or piperidinyl,
wherein the cyclopentyl is optionally fused to phenyl, the cyclohexyl is optionally fused to pyridinyl or phenyl, and the piperidinyl is optionally fused to pyrrolidinyl or phenyl; or
wherein the cyclobutyl is optionally substituted by =(spiro-cyclobutyl) or =(spiro-azetidinyl).

(3e) Group (3a), wherein R$^1$ is C$_{3-7}$cycloalkyl or 3-7 membered heterocyclyl.
(3f) Group (3a), wherein R$^1$ is C$_{3-7}$cycloalkyl.
(3g) Group (3a), wherein R$^1$ is C$_{5-8}$bridged bicyclic.
(3h) Group (3a), wherein R$^1$ is cyclobutyl or cyclopentyl.
(3i) Group (3a), wherein R$^1$ is cyclobutyl.
(3j) Group (3a), wherein R$^1$ is cyclopentyl.
(3k) Group (3a), wherein R$^1$ is 3-7 membered heterocyclyl.
(3l) Group (3a), wherein R$^1$ is pyrrolidinyl or piperdinyl.
(3m) Group (3a), wherein R$^1$ is pyrrolidinyl.
(3n) Group (3a), wherein R$^1$ is piperdinyl.
(3o) Group (3a), wherein R$^1$ is C$_{3-7}$cycloalkyl or 3-7 membered heterocyclyl (e.g., a 4-6 membered heterocyclyl or a 5-6 membered heterocyclyl), wherein the C$_{3-7}$cycloalkyl or 3-7 membered heterocyclyl is fused to aryl, heteroaryl, C$_{3-7}$ cycloalkyl or 3-7 membered heterocyclyl.
(3p) Group (3a), wherein R$^1$ is C$_{3-7}$cycloalkyl,
wherein the C$_{3-7}$cycloalkyl is fused to aryl, heteroaryl, C$_{3-7}$cycloalkyl or 3-7 membered heterocyclyl.
(3q) Group (3a), wherein R$^1$ is C$_{3-7}$cycloalkyl,
wherein the C$_{3-7}$cycloalkyl is fused to heteroaryl, C$_{3-7}$cycloalkyl or 3-7 membered heterocyclyl.
(3r) Group (3a), wherein R$^1$ is C$_{3-7}$cycloalkyl,
wherein the C$_{3-7}$cycloalkyl is fused to aryl, C$_{3-7}$cycloalkyl or 3-7 membered heterocyclyl.
(3s) Group (3a), wherein R$^1$ is C$_{3-7}$cycloalkyl,
wherein the C$_{3-7}$cycloalkyl is fused to aryl, heteroaryl, or 3-7 membered heterocyclyl.

(3t) Group (3a), wherein $R^1$ is $C_{3-7}$cycloalkyl,
wherein the $C_{3-7}$cycloalkyl is fused to aryl, heteroaryl or $C_{3-7}$cycloalkyl.
(3u) Group (3a), wherein $R^1$ is $C_{3-7}$cycloalkyl,
wherein the $C_{3-7}$cycloalkyl is fused to aryl.
(3v) Group (3a), wherein $R^1$ is $C_{3-7}$cycloalkyl,
wherein the $C_{3-7}$cycloalkyl is fused to heteroaryl.
(3w) Group (3a), wherein $R^1$ is $C_{3-7}$cycloalkyl,
wherein the $C_{3-7}$cycloalkyl is fused to $C_{3-7}$cycloalkyl.
(3x) Group (3a), wherein $R^1$ is $C_{3-7}$cycloalkyl,
wherein the $C_{3-7}$cycloalkyl is fused to 3-7 membered heterocyclyl.
(3y) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to aryl, heteroaryl, $C_{3-7}$cycloalkyl or 3-7 membered heterocyclyl.
(3z) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to heteroaryl, $C_{3-7}$cycloalkyl or 3-7 membered heterocyclyl.
(3aa) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to aryl, $C_{3-7}$cycloalkyl or 3-7 membered heterocyclyl.
(3bb) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to aryl, heteroaryl, or 3-7 membered heterocyclyl.
(3cc) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to aryl, heteroaryl or $C_{3-7}$cycloalkyl.
(3dd) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to aryl.
(3ee) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to heteroaryl.
(3ff) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to $C_{3-7}$cycloalkyl.
(3gg) Group (3a), wherein $R^1$ is 3-7 membered heterocyclyl (e.g., a 4-6 membered heterocyclyl or a 5-6 membered heterocyclyl),
wherein the 3-7 membered heterocyclyl is fused to 3-7 membered heterocyclyl.
(3hh) Group (3a), wherein $R^1$ is $C_{3-7}$cycloalkyl or 3-7 membered heterocyclyl (e.g., a 4-6 membered heterocyclyl or a 5-6 membered heterocyclyl),
wherein the $C_{3-7}$cycloalkyl or 3-7 membered heterocyclyl is substituted by =(spiro-$C_{3-7}$cycloalkyl) or =(spiro-(3-7 membered heterocyclyl)).
(3ii) Group (3a), wherein $R^1$ is $C_{3-7}$cycloalkyl,
wherein the $C_{3-7}$cycloalkyl is substituted by =(spiro-$C_{3-7}$cycloalkyl).
(3jj) Group (3a), wherein $R^1$ is $C_{3-7}$cycloalkyl,
wherein the $C_{3-7}$cycloalkyl is substituted by =(spiro-(3-7 membered heterocyclyl)).
(3kk) Group (3a), wherein $R^1$ is 3-7 membered heterocyclyl (e.g., a 4-6 membered heterocyclyl or a 5-6 membered heterocyclyl),
wherein the 3-7 membered heterocyclyl is substituted by =(spiro-$C_{3-7}$cycloalkyl).
(3ll) Group (3a), wherein $R^1$ is aryl, heteroaryl, $C_{3-7}$cycloalkyl, $C_{1-3}$alkyl-$C_{3-7}$cycloalkyl, 3-7 membered heterocyclyl or $C_1$alkyl-3-7 membered heterocyclyl,
wherein the $C_{3-7}$cycloalkyl, aryl, heteroaryl, or 3-7 membered heterocyclyl is optionally fused to aryl, heteroaryl, $C_{3-7}$cycloalkyl or 3-7 membered heterocyclyl; or
wherein the $C_{3-7}$cycloalkyl or 3-7 membered heterocyclyl is optionally substituted by =(spiro-$C_{3-7}$cycloalkyl) or =(spiro-(3-7 membered heterocyclyl)).
(3mm) Any of groups (3b)-(3ll), wherein $R^1$ is substituted by at least one $R^a$ group selected from halogen and $C_{1-6}$alkyl.
(3nn) Any of groups (3b)-(3ll), wherein $R^1$ is substituted by at least one $R^a$ group selected from halogen.
(3oo) Any of groups (3b)-(3ll), wherein $R^1$ is substituted by at least one $R^a$ group selected from $C_{1-6}$alkyl.
(3pp) Any of groups (3b)-(3ll), wherein $R^1$ is substituted by one, two or three $R^a$ groups independently selected from oxo, halogen, cyano, nitro, $C_{1-6}$alkyl, —$C_{1-6}$alkyl-OR, —$C_{1-6}$haloalkyl, $C_{1-6}$alkyl-cyano, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.
(3qq) Any of groups (3b)-(3ll), wherein $R^1$ is substituted by one, two or three $R^a$ groups independently selected from oxo, halogen, cyano, $C_{1-6}$alkyl, —$C_{1-6}$alkyl-OR, —$C_{1-6}$haloalkyl, —OR, —C(O)OR, —C(O)N(R)$_2$, —C(O)R, —C(O)-aryl, —S(O)$_2$R, —N(R)S(O)$_2$R or —S(O)$_2$N(R)$_2$.
(3rr) Any of groups (3b)-(3ll), wherein $R^1$ is substituted by one, two or three $R^a$ groups independently selected from oxo, halogen, cyano, $C_{1-6}$alkyl, —$C_{1-6}$alkyl-OR, —$C_{1-6}$haloalkyl, —C(O)OR, —C(O)N(R)$_2$, —C(O)R, —C(O)-aryl, —S(O)$_2$R, —N(R)S(O)$_2$R or —S(O)$_2$N(R)$_2$.
(3ss) Any of groups (3b)-(3ll), wherein $R^1$ is substituted by one, two or three $R^a$ groups independently selected from oxo, halogen, $C_{1-6}$alkyl, —$C_{1-6}$haloalkyl, $C_{1-6}$alkyl-cyano, —S(O)R, —S(O)OR, —S(O)N(R)$_2$, —S(O)$_2$R, —S(O)$_2$OR, —S(O)$_2$N(R)$_2$, —N(R)C(O)R, —N(R)C(O)OR, and —N(R)C(O)N(R)$_2$.
(3tt) Any of groups (3b)-(3ll), wherein $R^1$ is substituted by one, two or three $R^a$ groups independently selected from oxo, halogen, $C_{1-6}$alkyl, —$C_{1-6}$haloalkyl, $C_{1-6}$alkyl-cyano, —S(O)$_2$R, —S(O)$_2$OR and —S(O)$_2$N(R)$_2$.
(3uu) Any of groups (3b)-(3ll), wherein $R^1$ is substituted by one, two or three $R^a$ groups independently selected from oxo, halogen, $C_{1-6}$alkyl, —$C_{1-6}$haloalkyl, $C_{1-6}$alkyl-cyano, —S(O)$_2$R, —S(O)$_2$OR and —S(O)$_2$N(R)$_2$.
(3vv) Any of groups (3b)-(3ll), wherein $R^1$ is substituted by one, two or three $R^a$ groups independently selected from $C_{1-6}$alkyl, —S(O)$_2$R, —S(O)$_2$OR and —S(O)$_2$N(R)$_2$.

(3ww) Any of groups (3b)-(3ll), wherein $R^1$ is substituted by one, two or three $R^a$ groups independently selected from oxo, halogen, $C_{1-6}$alkyl, —$S(O)_2R$, —$S(O)_2OR$ and —$S(O)_2N(R)_2$.

(3xx) Any of groups (3b)-(3ll), wherein $R^1$ is substituted by one, two or three $R^a$ groups independently selected from oxo, halogen, $C_{1-6}$alkyl, —$S(O)_2R$ and —$S(O)_2N(R)_2$.

(3yy) Any of groups (3b)-(3ll), wherein $R^1$ is substituted by one, two or three $R^a$ groups independently selected from $C_{1-6}$alkyl, —$S(O)_2R$ and —$S(O)_2N(R)_2$.

(3zz) Any of groups (3b)-(3ll), wherein $R^1$ is substituted by one or two $R^a$ groups independently selected from $C_{1-6}$alkyl, —OR, —$S(O)_2R$ and —$S(O)_2N(R)_2$.

(3aaa) Any of groups (3b)-(3ll), wherein $R^1$ is substituted by one or two $R^a$ groups independently selected from $C_{1-6}$alkyl and —$S(O)_2N(R)_2$.

(3bbb) Any of groups (3b)-(3ll), wherein $R^1$ is substituted by one or two $R^a$ groups independently selected from $C_{1-6}$alkyl and —$S(O)_2R$.

(3ccc) Any of groups (3b)-(3ll), wherein $R^1$ is substituted by one or two $R^a$ groups independently selected from $C_{1-6}$alkyl.

(3ddd) Any of groups (3b)-(3ll), wherein $R^1$ is substituted by one or two $R^a$ groups independently selected from methyl, ethyl, propyl and iso-propyl.

(3eee) Any of groups (3b)-(3ll), wherein $R^1$ is substituted by one or two $R^a$ groups independently selected from methyl and ethyl.

(3fff) Any of groups (3b)-(3ll), wherein $R^1$ is substituted by one $R^a$ group independently selected from $C_{1-6}$alkyl, —$S(O)_2R$ and —$S(O)_2N(R)_2$.

(3ggg) Any of groups (3b)-(3ll), wherein $R^1$ is substituted by one $R^a$ group independently selected from $C_{1-6}$alkyl and —$S(O)_2N(R)_2$.

(3hhh) Any of groups (3b)-(3ll), wherein $R^1$ is substituted by one $R^a$ group independently selected from $C_{1-6}$alkyl and —$S(O)_2R$.

(3iii) Any of groups (3b)-(3ll), wherein $R^1$ is substituted by one $R^a$ group independently selected from $C_{1-6}$alkyl and halogen.

(3jjj) Any of groups (3b)-(3ll), wherein $R^1$ is substituted by one $R^a$ group independently selected from methyl, ethyl, propyl, -iso-propyl, chloro and fluoro.

(3kkk) Any of groups (3b)-(3ll), wherein $R^1$ is substituted by one $R^a$ group independently selected from methyl, chloro and fluoro.

(3lll) Any of groups (3b)-(3ll), wherein $R^1$ is substituted by one methyl group.

(3mmm) Any of groups (3b)-(3ll), wherein $R^1$ is substituted by one fluoro group.

(3nnn) $R^1$ is $C_{1-6}$alkyl, $C_{3-7}$cycloalkyl, 3-7 membered heterocyclyl (e.g., a 4-6 membered heterocyclyl or a 5-6 membered heterocyclyl), —$C_1$alkyl-$C_{3-7}$cycloalkyl, —$C_1$alkyl-3-7 membered heterocyclyl (e.g., a —$C_1$alkyl-4-6 membered heterocyclyl or a —$C_1$alkyl-5-6 membered heterocyclyl) or —$C_1$alkyl-heteroaryl
wherein the $C_{3-7}$cycloalkyl or 3-7 membered heterocyclyl is optionally fused to aryl, heteroaryl, $C_{3-7}$cycloalkyl or 3-7 membered heterocyclyl; or
wherein the $C_{3-7}$cycloalkyl or 3-7 membered heterocyclyl is optionally substituted by =(spiro-$C_{3-7}$cycloalkyl) or =(spiro-(3-7 membered heterocyclyl));
wherein $R^1$ is optionally substituted by one, two, three, or four $R^a$ groups independently selected from oxo, halogen, cyano, nitro, $C_{1-6}$alkyl, —$C_{1-6}$haloalkyl, $C_{1-6}$alkyl-cyano, —OR, —$NR_2$, —SR, —$C(O)OR$, —$C(O)N(R)_2$, —$C(O)R$, —$S(O)R$, —$S(O)OR$, —$S(O)N(R)_2$, —$S(O)_2R$, —$S(O)_2OR$, —$S(O)_2N(R)_2$, —$OC(O)R$, —$OC(O)OR$, —$OC(O)N(R)_2$, —$N(R)C(O)R$, —$N(R)C(O)OR$, and —$N(R)C(O)N(R)_2$.

(3ooo) Group (3nnn), wherein $R^1$ is $C_{1-6}$alkyl, $C_{4-6}$cycloalkyl or 5-6 membered heterocyclyl,
wherein the $C_{4-6}$cycloalkyl or 5-6-membered heterocyclyl is optionally fused to aryl or heteroaryl; or
wherein the $C_4$cycloalkyl is optionally substituted by =(spiro-$C_4$cycloalkyl) or =(spiro-(4-membered heterocyclyl)).

(3ppp) Group (3nnn), wherein $R^1$ is $C_{1-6}$alkyl, $C_{4-6}$cycloalkyl or 5-6 membered heterocyclyl,
wherein the $C_{4-6}$cycloalkyl or 5-6 membered heterocyclyl is optionally fused to aryl or heteroaryl; or
wherein the $C_{4-6}$cycloalkyl or 5-6 membered heterocyclyl is optionally substituted by =(spiro-$C_4$cycloalkyl) or =(spiro-(4-membered heterocyclyl)).

(3qqq) Group (3nnn), wherein $R^1$ is $C_{1-6}$alkyl.

(3rrr) Group (3nnn), wherein $R^1$ is methyl, ethyl, propyl, butyl, pentyl or hexyl.

(3sss) Group (3nnn), wherein $R^1$ is methyl, ethyl, propyl or butyl.

(3ttt) Group (3nnn), wherein $R^1$ is methyl, ethyl or butyl.

(3uuu) Group (3nnn), wherein $R^1$ is methyl or ethyl.

(3vvv) Group (3nnn), wherein $R^1$ is methyl.

(3www) Group (3nnn), wherein $R^1$ is ethyl.

(3xxx) Group (3nnn), wherein $R^1$ is butyl.

(3yyy) Any of groups (3nnn)-(3xxx), wherein $R^1$ is substituted by one or two $R^a$ groups independently selected from halogen, $C_{1-6}$alkyl, —$C_{1-6}$haloalkyl, $C_3$cycloalkyl or —OR.

(3zzz) Any of groups (3nnn)-(3xxx), wherein $R^1$ is substituted by $C_3$cycloalkyl and —OH.

(3aaaa) Any of groups (3nnn)-(3xxx), wherein $R^1$ is substituted by one or two —OH.

(3bbbb) Any of groups (3nnn)-(3xxx), wherein $R^1$ is substituted by one —OH.

(3cccc) Any of groups (3nnn)-(3xxx), wherein $R^1$ is substituted by two —OH.

The invention further comprises subgenera and species of formula (I) that are any combination of species and genera of structural formula (I) can be any of formula (Ia)-(Ii) wherein n, $R^2$ and $R^1$ are defined above. So, for example, the invention also comprises the subgenus of compounds of structural formula (Ie) where n is defined as in (1g) above, and $R^2$ is defined in (2r) above.

Structural Formula I is One of Formulae (Ia)-(Ii):

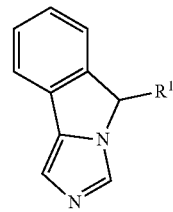

(Ia)

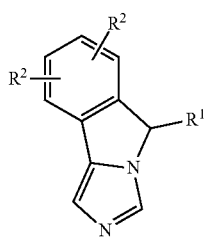 (Ib)

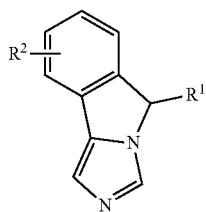 (Ic)

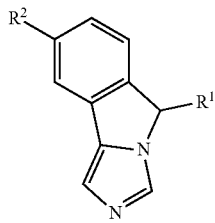 (Id)

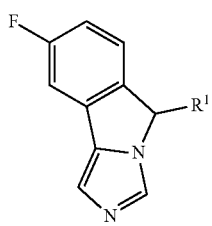 (Ie)

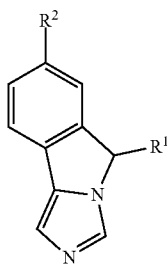 (If)

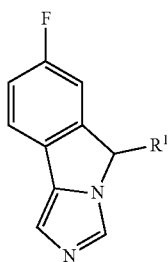 (Ig)

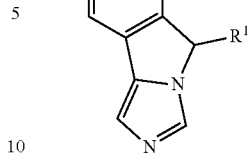 (Ih)

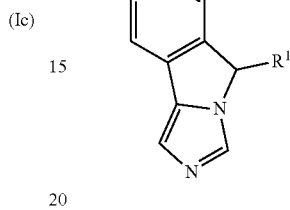 (Ii)

Particular embodiments of this aspect of the invention include compounds of any one of the formulae (I) and (Ia)-(Ii), each as defined in each of the following rows, wherein each entry is a group number as defined above (e.g., (2r) refers to $R^2$ is fluoro), an "X" indicates that the variable is defined by another group in the embodiment (e.g., in embodiment (1)-32 below, n is defined in Formula (Ia)) and a dash "-" indicates that the variable is as defined for Formula (I) or (Ia)-(Ii) or defined according to any one of the applicable variable definitions (1a)-(3cccc) [e.g., when the entry for $R^2$ is a dash, it can be either as defined for Formula (I)-(IVi) or any one of definitions (2a)-(2t)]:

|  | (I) | n | $R^2$ | $R^1$ |
| --- | --- | --- | --- | --- |
| (1)-1 | (I) | (1a) | (2a) | (3e) |
| (1)-2 | (I) | (1a) | (2b) | (3f) |
| (1)-3 | (I) | (1a) | (2f) | (3k) |
| (1)-4 | (I) | (1a) | (2h) | (3u) |
| (1)-5 | (I) | (1a) | (2k) | (3v) |
| (1)-6 | (I) | (1a) | (2n) | (3e) |
| (1)-7 | (I) | (1b) | (2a) | (3ee) |
| (1)-8 | (I) | (1b) | (2b) | (3ii) |
| (1)-9 | (I) | (1b) | (2f) | (3jj) |
| (1)-10 | (I) | (1b) | (2h) | (3kk) |
| (1)-11 | (I) | (1b) | (2k) | (3ll) |
| (1)-12 | (I) | (1b) | (2n) | (3mm) |
| (1)-13 | (I) | (1c) | — | (3nn) |
| (1)-14 | (I) | (1c) | (2b) | (3oo) |
| (1)-15 | (I) | — | (2f) | (3e) |
| (1)-16 | (I) | (1c) | (2h) | (3f) |
| (1)-17 | (I) | (1c) | (2k) | (3k) |
| (1)-18 | (I) | (1c) | (2n) | (3u) |
| (1)-19 | (I) | (1e) | (2a) | (3mm) |
| (1)-20 | (I) | (1e) | — | (3nn) |
| (1)-21 | (I) | (1e) | (2f) | (3oo) |
| (1)-22 | (I) | (1e) | (2h) | (3kk) |
| (1)-23 | (I) | (1e) | (2k) | (3e) |
| (1)-24 | (I) | (1e) | (2n) | (3f) |
| (1)-25 | (I) | (1f) | (2a) | (3k) |
| (1)-26 | (I) | (1f) | (2b) | (3u) |
| (1)-27 | (I) | (1f) | (2f) | (3nn) |
| (1)-28 | (I) | — | (2h) | (3oo) |
| (1)-29 | (I) | (1f) | (2k) | (3v) |
| (1)-30 | (I) | (1f) | — | (3e) |
| (1)-31 | (Ia) | X | X | (3ee) |
| (1)-32 | (Ia) | X | X | (3ii) |
| (1)-33 | (Ia) | X | X | (3jj) |
| (1)-34 | (Ia) | X | X | (3kk) |
| (1)-35 | (Ia) | X | X | (3mm) |
| (1)-36 | (Ia) | X | X | (3nn) |
| (1)-37 | (Ia) | X | X | (3f) |

| | (I) | n | R² | R¹ |
|---|---|---|---|---|
| (1)-38 | (Ia) | X | X | (3k) |
| (1)-39 | (Ia) | X | X | (3u) |
| (1)-40 | (Ia) | X | X | (3k) |
| (1)-41 | (Ia) | X | X | (3u) |
| (1)-42 | (Ia) | X | X | (3v) |
| (1)-43 | (Ia) | X | X | (3e) |
| (1)-44 | (Ia) | X | X | (3ee) |
| (1)-45 | (Ia) | X | X | (3e) |
| (1)-46 | (Ia) | X | X | (3f) |
| (1)-47 | (Ia) | X | X | — |
| (1)-48 | (Ia) | X | X | (3u) |
| (1)-49 | (Ia) | X | X | (3mm) |
| (1)-50 | (Ia) | X | X | (3nn) |
| (1)-51 | (Ia) | X | X | (3oo) |
| (1)-52 | (Ia) | X | X | (3mm) |
| (1)-53 | (Ia) | X | X | (3nn) |
| (1)-54 | (Ia) | X | X | (3u) |
| (1)-55 | (Ia) | X | X | (3v) |
| (1)-56 | (Ia) | X | X | (3e) |
| (1)-57 | (Ia) | X | X | (3ee) |
| (1)-58 | (Ia) | X | X | — |
| (1)-59 | (Ia) | X | X | (3f) |
| (1)-60 | (Ib) | X | (2a) | (3k) |
| (1)-61 | (Ib) | X | (2b) | (3u) |
| (1)-62 | (Ib) | X | (2f) | (3kk) |
| (1)-63 | (Ib) | X | (2h) | (3mm) |
| (1)-64 | (Ib) | X | (2k) | (3nn) |
| (1)-65 | (Ib) | X | (2n) | (3u) |
| (1)-66 | (Ib) | X | (2a) | (3v) |
| (1)-67 | (Ib) | X | (2b) | (3e) |
| (1)-68 | (Ib) | X | — | (3ee) |
| (1)-69 | (Ib) | X | (2h) | (3mm) |
| (1)-70 | (Ib) | X | (2k) | (3nn) |
| (1)-71 | (Ib) | X | (2n) | (3f) |
| (1)-72 | (Ib) | X | (2b) | — |
| (1)-73 | (Ib) | X | (2f) | (3u) |
| (1)-74 | (Ib) | X | (2h) | (3jj) |
| (1)-75 | (Ib) | X | (2b) | (3kk) |
| (1)-76 | (Ib) | X | (2f) | (3u) |
| (1)-77 | (Ib) | X | (2h) | — |
| (1)-78 | (Ib) | X | (2b) | (3e) |
| (1)-79 | (Ib) | X | (2f) | (3ee) |
| (1)-80 | (Ib) | X | (2h) | (3e) |
| (1)-81 | (Ib) | X | (2a) | (3f) |
| (1)-82 | (Ib) | X | (2b) | (3k) |
| (1)-83 | (Ib) | X | (2f) | (3u) |
| (1)-84 | (Ib) | X | (2h) | (3ll) |
| (1)-85 | (Ib) | X | (2k) | (3mm) |
| (1)-86 | (Ib) | X | — | (3nn) |
| (1)-87 | (Ib) | X | (2b) | (3oo) |
| (1)-88 | (Ib) | X | (2f) | (3u) |
| (1)-89 | (Ib) | X | (2h) | (3v) |
| (1)-90 | (Ib) | X | (2b) | (3e) |
| (1)-91 | (Ic) | X | (2f) | (3ee) |
| (1)-92 | (Ic) | X | (2h) | — |
| (1)-93 | (Ic) | X | (2k) | (3nn) |
| (1)-94 | (Ic) | X | (2n) | (3kk) |
| (1)-95 | (Ic) | X | (2b) | (3ll) |
| (1)-96 | (Ic) | X | (2f) | (3mm) |
| (1)-97 | (Ic) | X | (2h) | (3nn) |
| (1)-98 | (Ic) | X | (2b) | (3oo) |
| (1)-99 | (Ic) | X | — | (3kk) |
| (1)-100 | (Ic) | X | (2f) | (3mm) |
| (1)-101 | (Ic) | X | (2h) | (3nn) |
| (1)-102 | (Ic) | X | (2a) | (3f) |
| (1)-103 | (Ic) | X | (2b) | (3k) |
| (1)-104 | (Ic) | X | (2f) | — |
| (1)-105 | (Ic) | X | (2h) | (3k) |
| (1)-106 | (Ic) | X | (2k) | (3u) |
| (1)-107 | (Ic) | X | (2n) | (3v) |
| (1)-108 | (Ic) | X | (2b) | (3e) |
| (1)-109 | (Ic) | X | (2h) | (3ee) |
| (1)-110 | (Ic) | X | (2h) | (3mm) |
| (1)-111 | (Ic) | X | (2b) | (3nn) |
| (1)-112 | (Ic) | X | (2f) | (3ll) |
| (1)-113 | (Ic) | X | (2h) | (3mm) |
| (1)-114 | (Ic) | X | (2k) | (3nn) |
| (1)-115 | (Ic) | X | (2n) | (3oo) |
| (1)-116 | (Ic) | X | (2a) | (3ii) |
| (1)-117 | (Ic) | X | (2b) | (3jj) |
| (1)-118 | (Ic) | X | (2f) | (3kk) |
| (1)-119 | (Ic) | X | (2h) | (3e) |
| (1)-120 | (Ic) | X | — | (3f) |
| (1)-121 | (Id) | X | (2n) | (3k) |
| (1)-122 | (Id) | X | (2f) | (3u) |
| (1)-123 | (Id) | X | (2h) | (3k) |
| (1)-124 | (Id) | X | (2k) | (3u) |
| (1)-125 | (Id) | X | (2n) | (3v) |
| (1)-126 | (Id) | X | (2k) | (3e) |
| (1)-127 | (Id) | X | (2n) | — |
| (1)-128 | (Id) | X | (2f) | (3e) |
| (1)-129 | (Id) | X | (2h) | (3f) |
| (1)-130 | (Id) | X | — | (3k) |
| (1)-131 | (Id) | X | (2n) | (3u) |
| (1)-132 | (Id) | X | (2a) | (3jj) |
| (1)-133 | (Id) | X | — | (3kk) |
| (1)-134 | (Id) | X | (2f) | — |
| (1)-135 | (Id) | X | (2h) | (3nn) |
| (1)-136 | (Id) | X | (2k) | (3jj) |
| (1)-137 | (Id) | X | (2n) | (3kk) |
| (1)-138 | (Id) | X | (2a) | (3k) |
| (1)-139 | (Id) | X | (2b) | (3u) |
| (1)-140 | (Id) | X | (2f) | (3v) |
| (1)-141 | (Id) | X | — | (3e) |
| (1)-142 | (Id) | X | (2k) | (3ee) |
| (1)-143 | (Id) | X | (2n) | (3mm) |
| (1)-144 | (Id) | X | (2a) | (3nn) |
| (1)-145 | (Id) | X | (2b) | (3e) |
| (1)-146 | (Id) | X | — | (3kk) |
| (1)-147 | (Id) | X | (2h) | (3ll) |
| (1)-148 | (Id) | X | (2k) | (3mm) |
| (1)-149 | (Id) | X | (2n) | (3nn) |
| (1)-150 | (Id) | X | (2n) | — |
| (1)-151 | (Ie) | X | X | (3v) |
| (1)-152 | (Ie) | X | X | (3e) |
| (1)-153 | (Ie) | X | X | (3ee) |
| (1)-154 | (Ie) | X | X | (3e) |
| (1)-155 | (Ie) | X | X | (3f) |
| (1)-156 | (Ie) | X | X | (3k) |
| (1)-157 | (Ie) | X | X | (3u) |
| (1)-158 | (Ie) | X | X | (3kk) |
| (1)-159 | (Ie) | X | X | (3ll) |
| (1)-160 | (Ie) | X | X | (3mm) |
| (1)-161 | (Ie) | X | X | (3nn) |
| (1)-162 | (Ie) | X | X | — |
| (1)-163 | (Ie) | X | X | (3ii) |
| (1)-164 | (Ie) | X | X | (3jj) |
| (1)-165 | (Ie) | X | X | (3kk) |
| (1)-166 | (Ie) | X | X | (3mm) |
| (1)-167 | (Ie) | X | X | (3nn) |
| (1)-168 | (Ie) | X | X | (3ii) |
| (1)-169 | (Ie) | X | X | (3jj) |
| (1)-170 | (Ie) | X | X | (3kk) |
| (1)-171 | (Ie) | X | X | (3mm) |
| (1)-172 | (Ie) | X | X | (3nn) |
| (1)-173 | (Ie) | X | X | (3ll) |
| (1)-174 | (Ie) | X | X | — |
| (1)-175 | (Ie) | X | X | (3nn) |
| (1)-176 | (Ie) | X | X | (3oo) |
| (1)-177 | (Ie) | X | X | (3e) |
| (1)-178 | (Ie) | X | X | (3ee) |
| (1)-179 | (Ie) | X | X | (3mm) |
| (1)-180 | (Ie) | X | X | — |
| (1)-181 | (If) | X | (2a) | (3f) |
| (1)-182 | (If) | X | (2b) | (3k) |
| (1)-183 | (If) | X | — | (3u) |
| (1)-184 | (If) | X | (2h) | (3ll) |
| (1)-185 | (If) | X | (2k) | (3mm) |
| (1)-186 | (If) | X | (2n) | — |
| (1)-187 | (If) | X | (2f) | (3oo) |
| (1)-188 | (If) | X | — | (3kk) |
| (1)-189 | (If) | X | (2k) | (3e) |
| (1)-190 | (If) | X | (2n) | (3e) |
| (1)-191 | (If) | X | (2a) | (3f) |

-continued

| (I) | n | R² | R¹ |
|---|---|---|---|
| (1)-192 | (If) | X | (2b) | (3k) |
| (1)-193 | (If) | X | (2f) | (3u) |
| (1)-194 | (If) | X | (2h) | (3v) |
| (1)-195 | (If) | X | (2k) | (3e) |
| (1)-196 | (If) | X | (2n) | (3ee) |
| (1)-197 | (If) | X | (2f) | (3kk) |
| (1)-198 | (If) | X | (2h) | (3ll) |
| (1)-199 | (If) | X | (2k) | (3mm) |
| (1)-200 | (If) | X | (2n) | (3nn) |
| (1)-201 | (If) | X | (2f) | (3oo) |
| (1)-202 | (If) | X | (2h) | (3mm) |
| (1)-203 | (If) | X | (2k) | (3nn) |
| (1)-204 | (If) | X | (2n) | (3ii) |
| (1)-205 | (If) | X | (2a) | (3jj) |
| (1)-206 | (If) | X | (2b) | (3kk) |
| (1)-207 | (If) | X | (2f) | — |
| (1)-208 | (If) | X | (2h) | (3nn) |
| (1)-209 | (If) | X | (2k) | (3e) |
| (1)-210 | (If) | X | — | (3kk) |
| (1)-211 | (Ig) | X | X | (3ll) |
| (1)-212 | (Ig) | X | X | (3mm) |
| (1)-213 | (Ig) | X | X | (3nn) |
| (1)-214 | (Ig) | X | X | (3oo) |
| (1)-215 | (Ig) | X | X | (3mm) |
| (1)-216 | (Ig) | X | X | (3nn) |
| (1)-217 | (Ig) | X | X | (3k) |
| (1)-218 | (Ig) | X | X | — |
| (1)-219 | (Ig) | X | X | (3v) |
| (1)-220 | (Ig) | X | X | (3e) |
| (1)-221 | (Ig) | X | X | (3ee) |
| (1)-222 | (Ig) | X | X | (3kk) |
| (1)-223 | (Ig) | X | X | (3ll) |
| (1)-224 | (Ig) | X | X | (3mm) |
| (1)-225 | (Ig) | X | X | (3nn) |
| (1)-226 | (Ig) | X | X | (3oo) |
| (1)-227 | (Ig) | X | X | (3jj) |
| (1)-228 | (Ig) | X | X | — |
| (1)-229 | (Ig) | X | X | (3e) |
| (1)-230 | (Ig) | X | X | (3e) |
| (1)-231 | (Ig) | X | X | (3kk) |
| (1)-232 | (Ig) | X | X | (3ll) |
| (1)-233 | (Ig) | X | X | (3mm) |
| (1)-234 | (Ig) | X | X | (3nn) |
| (1)-235 | (Ig) | X | X | (3oo) |
| (1)-236 | (Ig) | X | X | (3kk) |
| (1)-237 | (Ig) | X | X | (3e) |
| (1)-238 | (Ig) | X | X | (3f) |
| (1)-239 | (Ig) | X | X | (3k) |
| (1)-240 | (Ig) | X | X | (3u) |
| (1)-241 | (Ih) | X | (2b) | (3u) |
| (1)-242 | (Ih) | X | — | (3v) |
| (1)-243 | (Ih) | X | (2h) | — |
| (1)-244 | (Ih) | X | (2k) | (3ee) |
| (1)-245 | (Ih) | X | (2n) | (3ii) |
| (1)-246 | (Ih) | X | (2f) | (3jj) |
| (1)-247 | (Ih) | X | (2h) | (3kk) |
| (1)-248 | (Ih) | X | (2k) | (3e) |
| (1)-249 | (Ih) | X | — | (3f) |
| (1)-250 | (Ih) | X | (2a) | (3k) |
| (1)-251 | (Ih) | X | (2b) | (3mm) |
| (1)-252 | (Ih) | X | (2f) | (3nn) |
| (1)-253 | (Ih) | X | (2h) | (3oo) |
| (1)-254 | (Ih) | X | (2k) | (3e) |
| (1)-255 | (Ih) | X | (2n) | (3k) |
| (1)-256 | (Ih) | X | (2f) | (3u) |
| (1)-257 | (Ih) | X | (2h) | (3v) |
| (1)-258 | (Ih) | X | (2k) | (3e) |
| (1)-259 | (Ih) | X | (2n) | (3ee) |
| (1)-260 | (Ih) | X | (2f) | (3ii) |
| (1)-261 | (Ih) | X | (2h) | — |
| (1)-262 | (Ih) | X | (2k) | (3kk) |
| (1)-263 | (Ih) | X | (2n) | (3e) |
| (1)-264 | (Ih) | X | — | (3f) |
| (1)-265 | (Ih) | X | (2b) | (3k) |
| (1)-266 | (Ih) | X | (2f) | (3kk) |
| (1)-267 | (Ih) | X | (2h) | (3e) |
| (1)-268 | (Ih) | X | (2k) | (3f) |
| (1)-269 | (Ih) | X | (2n) | (3k) |
| (1)-270 | (Ih) | X | — | (3u) |
| (1)-271 | (Ii) | X | X | (3ll) |
| (1)-272 | (Ii) | X | X | (3mm) |
| (1)-273 | (Ii) | X | X | (3nn) |
| (1)-274 | (Ii) | X | X | (3oo) |
| (1)-275 | (Ii) | X | X | (3v) |
| (1)-276 | (Ii) | X | X | (3e) |
| (1)-277 | (Ii) | X | X | (3ee) |
| (1)-278 | (Ii) | X | X | (3e) |
| (1)-279 | (Ii) | X | X | (3f) |
| (1)-280 | (Ii) | X | X | (3k) |
| (1)-281 | (Ii) | X | X | (3u) |
| (1)-282 | (Ii) | X | X | (3mm) |
| (1)-283 | (Ii) | X | X | (3nn) |
| (1)-284 | (Ii) | X | X | (3k) |
| (1)-285 | (Ii) | X | X | (3u) |
| (1)-286 | (Ii) | X | X | (3v) |
| (1)-287 | (Ii) | X | X | (3e) |
| (1)-288 | (Ii) | X | X | (3ee) |
| (1)-289 | (Ii) | X | X | (3ii) |
| (1)-290 | (Ii) | X | X | (3jj) |
| (1)-291 | (Ii) | X | X | (3kk) |
| (1)-292 | (Ii) | X | X | (3e) |
| (1)-293 | (Ii) | X | X | — |
| (1)-294 | (Ii) | X | X | (3k) |
| (1)-295 | (Ii) | X | X | (3ll) |
| (1)-296 | (Ii) | X | X | (3mm) |
| (1)-297 | (Ii) | X | X | (3nn) |
| (1)-298 | (Ii) | X | X | (3oo) |
| (1)-299 | (Ii) | X | X | (3mm) |
| (1)-300 | (Ii) | X | X | (3nn) |
| (1)-301 | (Ia) | X | X | (3nnn) |
| (1)-302 | (Ia) | X | X | (3ooo) |
| (1)-303 | (Ia) | X | X | (3ppp) |
| (1)-304 | (Ia) | X | X | (3qqq) |
| (1)-305 | (Ia) | X | X | (3rrr) |
| (1)-306 | (Ia) | X | X | (3sss) |
| (1)-307 | (Ia) | X | X | (3ttt) |
| (1)-308 | (Ia) | X | X | (3uuu) |
| (1)-309 | (Ia) | X | X | (3vvv) |
| (1)-310 | (Ia) | X | X | (3www) |
| (1)-311 | (Ia) | X | X | (3xxx) |
| (1)-312 | (Ia) | X | X | (3yyy) |
| (1)-313 | (Ia) | X | X | (3zzz) |
| (1)-314 | (Ia) | X | X | (3aaaa) |
| (1)-315 | (Ia) | X | X | (3bbbb) |
| (1)-316 | (Ia) | X | X | (3cccc) |

In an embodiment, the invention comprises compounds of Formula (II),

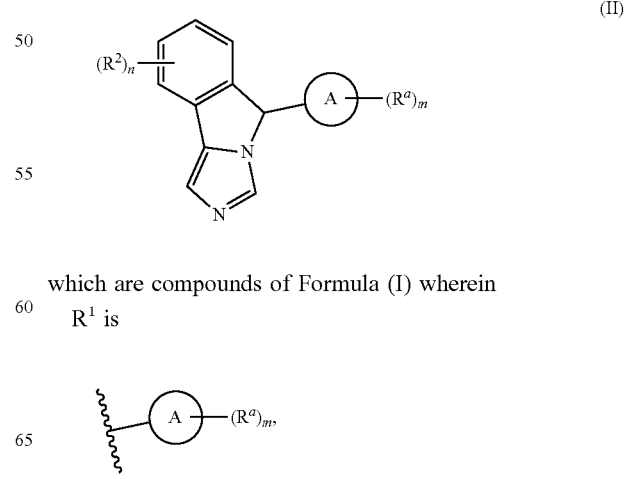

which are compounds of Formula (I) wherein

R¹ is ring A is aryl, heteroaryl, $C_{3-7}$cycloalkyl, $C_{1-3}$alkyl-$C_{3-7}$cycloalkyl, 3-7 membered heterocyclyl or $C_1$alkyl-3-7 membered heterocyclyl; and m is 0, 1, 2, 3 or 4; and each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

In one embodiment, the invention comprises compounds of Formula (II) wherein n is 0. In other embodiments, n is 1.

The invention further comprises subgenera of formula (II) in which the substituents are selected as any and all combinations of one or more of structural formula (II), $R^2$, $R^a$, m and ring A, as defined herein, including without limitation, the following:

Structural Formula I is One of Formulae (IIa)-(IIi):

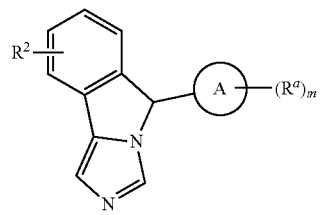
(IIa)

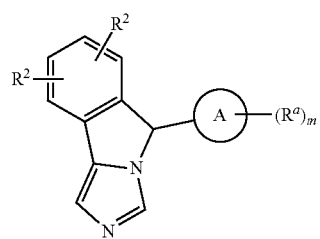
(IIb)

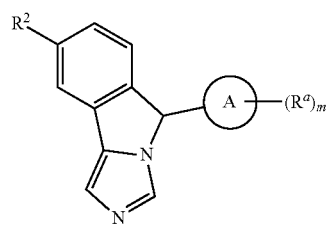
(IIc)

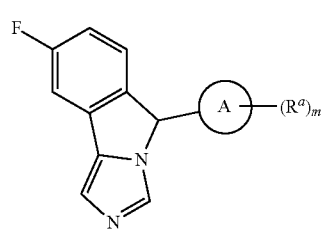
(IId)

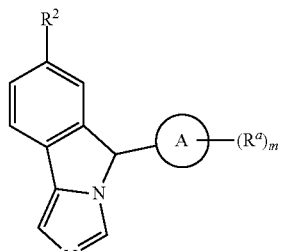
(IIe)

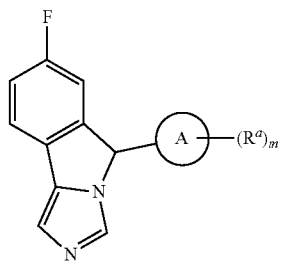
(IIf)

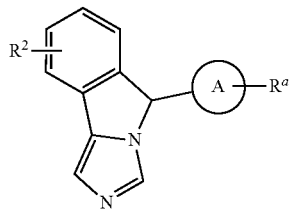
(IIg)

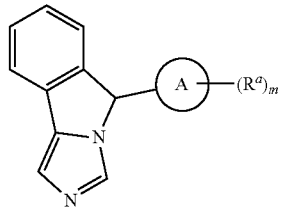
(IIh)

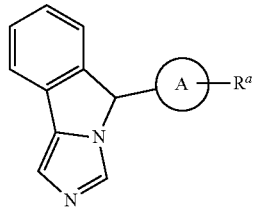
(IIi)

Ring a is Selected from One of the Following Groups (4a)-(4ccc):

(4a) Ring A is aryl, heteroaryl, $C_{3-7}$cycloalkyl, $C_{1-3}$alkyl-$C_{3-7}$cycloalkyl, 3-7 membered heterocyclyl or $C_1$alkyl-3-7 membered heterocyclyl;

m is 0, 1, 2, 3 or 4; and each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$, wherein each R is hydrogen, $C_{1-6}$alkyl, $C_{1-6}$haloalkyl, aryl substituted with cyano, 3-7 membered heterocyclyl or $C_{3-6}$cycloalkyl.

(4b) Group (4a), wherein ring A is aryl, heteroaryl, $C_{3-7}$cycloalkyl or 3-7 membered heterocyclyl.
(4c) Group (4a), wherein ring A is $C_{1-3}$alkyl-$C_{3-7}$cycloalkyl, 3-7 membered heterocyclyl or $C_1$alkyl-3-7 membered heterocyclyl.
(4d) Group (4a), wherein ring A is aryl, heteroaryl or $C_{3-7}$cycloalkyl.
(4e) Group (4a), wherein ring A is aryl or heteroaryl.
(4f) Group (4a), wherein ring A is aryl or $C_{3-7}$cycloalkyl.
(4g) Group (4a), wherein ring A is heteroaryl or $C_{3-7}$cycloalkyl.
(4h) Group (4a), wherein ring A is aryl.
(4i) Group (4a), wherein ring A is heteroaryl.
(4j) Group (4a), wherein ring A is $C_{3-7}$cycloalkyl.
(4k) Group (4a), wherein ring A is $C_{1-3}$alkyl-$C_{3-7}$cycloalkyl or $C_1$alkyl-3-7 membered heterocyclyl.
(4l) Group (4a), wherein ring A is $C_{1-3}$alkyl-$C_{3-7}$cycloalkyl.
(4m) Group (4a), wherein ring A is $C_1$alkyl-3-7 membered heterocyclyl.
(4n) Group (4a), wherein ring A is phenyl, pyrazolyl, pyridinyl, pyrrolidinyl, piperidinyl, tetrahydropyranyl, cyclobutyl, cyclopentyl, cyclohexyl, azetidinyl, tetrahydro-2H-thiopyran 1,1-dioxidyl, 3-azabicyclo[3.1.1]heptan-6-yl or 3-azabicyclo[3.1.0]hexan-6-yl.
(4o) Group (4a), wherein ring A is phenyl, pyrazolyl, pyridinyl, pyrrolidinyl, piperidinyl, tetrahydropyranyl, cyclobutyl, cyclopentyl, cyclohexyl, azetidinyl or tetrahydro-2H-thiopyran 1,1-dioxidyl.
(4p) Group (4a), wherein ring A is phenyl, pyrazolyl, pyridinyl, pyrrolidinyl, piperidinyl, tetrahydropyranyl, cyclobutyl, cyclopentyl, cyclohexyl or azetidinyl.
(4q) Group (4a), wherein ring A is phenyl, pyrazolyl, pyridinyl, pyrrolidinyl, piperidinyl, cyclobutyl, cyclopentyl, cyclohexyl or azetidinyl.
(4r) Group (4a), wherein ring A is pyrazolyl, pyridinyl, pyrrolidinyl, piperidinyl, tetrahydropyranyl, cyclobutyl, cyclopentyl, cyclohexyl or azetidinyl.
(4s) Group (4a), wherein ring A is phenyl, tetrahydropyranyl, cyclobutyl, cyclopentyl or cyclohexyl.
(4t) Group (4a), wherein ring A is phenyl, cyclobutyl, cyclopentyl or cyclohexyl.
(4u) Group (4a), wherein ring A is phenyl.
(4v) Group (4a), wherein ring A is cyclobutyl, cyclopentyl or cyclohexyl.
(4w) Group (4a), wherein ring A is cyclobutyl.
(4x) Group (4a), wherein ring A is cyclobutyl or cyclohexyl.
(4y) Group (4a), wherein ring A is cyclopentyl or cyclohexyl.
(4z) Group (4a), wherein ring A is cyclohexyl.
(4aa) Group (4a), wherein ring A is phenyl, pyrazolyl, pyridinyl, pyrrolidinyl, piperidinyl, tetrahydropyranyl, azetidinyl, tetrahydro-2H-thiopyran 1,1-dioxidyl, 3-azabicyclo[3.1.1]heptan-6-yl or 3-azabicyclo[3.1.0]hexan-6-yl.
(4bb) Group (4a), wherein ring A is pyrazolyl, pyridinyl, pyrrolidinyl, piperidinyl, tetrahydropyranyl, azetidinyl, tetrahydro-2H-thiopyran 1,1-dioxidyl, 3-azabicyclo[3.1.1]heptan-6-yl or 3-azabicyclo[3.1.0]hexan-6-yl.
(4cc) Group (4a), wherein ring A is pyrrolidinyl, piperidinyl, tetrahydropyranyl, azetidinyl, tetrahydro-2H-thiopyran 1,1-dioxidyl, 3-azabicyclo[3.1.1]heptan-6-yl or 3-azabicyclo[3.1.0]hexan-6-yl.
(4dd) Group (4a), wherein ring A is pyrrolidinyl, piperidinyl, tetrahydropyranyl, tetrahydro-2H-thiopyran 1,1-dioxidyl, 3-azabicyclo[3.1.1]heptan-6-yl or 3-azabicyclo[3.1.0]hexan-6-yl.
(4ee) Group (4a), wherein ring A is pyrrolidinyl, piperidinyl, 3-azabicyclo[3.1.1]heptan-6-yl or 3-azabicyclo[3.1.0]hexan-6-yl.
(4ff) Group (4a), wherein ring A is 3-azabicyclo[3.1.1]heptan-6-yl or 3-azabicyclo[3.1.0]hexan-6-yl.
(4gg) Group (4a), wherein ring A is pyrrolidinyl or piperidinyl.
(4hh) Group (4a), wherein ring A is pyrrolidinyl.
(4ii) Group (4a), wherein ring A is piperidinyl.
(4jj) Group (4a), wherein ring A is phenyl, pyrazolyl, pyridinyl, tetrahydropyranyl, azetidinyl, tetrahydro-2H-thiopyran 1,1-dioxidyl, 3-azabicyclo[3.1.1]heptan-6-yl or 3-azabicyclo[3.1.0]hexan-6-yl.
(4kk) Group (4a), wherein ring A is phenyl, pyrazolyl, pyridinyl, 3-azabicyclo[3.1.1]heptan-6-yl or 3-azabicyclo[3.1.0]hexan-6-yl.
(4ll) Group (4a), wherein ring A is phenyl, pyrazolyl or pyridinyl.
(4mm) Group (4a), wherein ring A is pyrazolyl or pyridinyl.
(4nn) Group (4a), wherein ring A is pyridinyl.
(4oo) Group (4a), wherein ring A is pyrazolyl.
(4pp) $R^1$ is

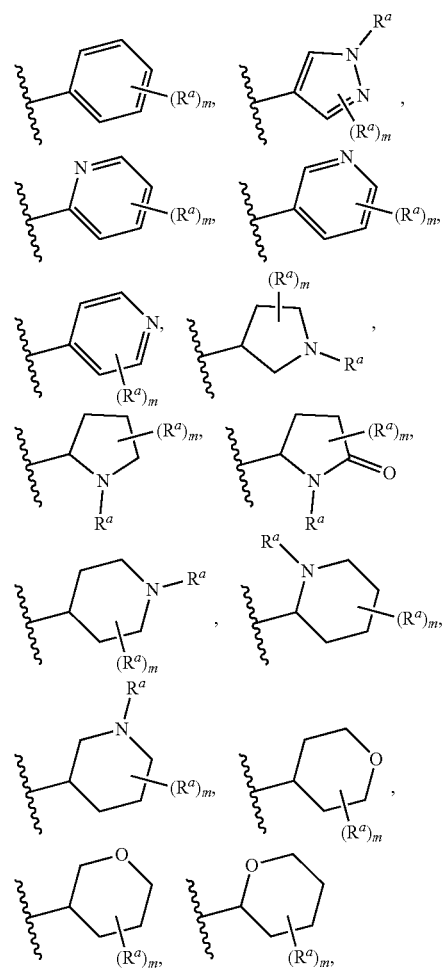

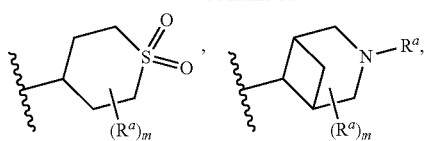
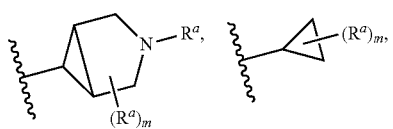
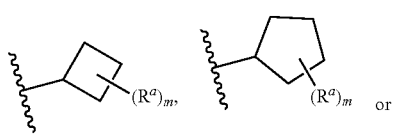
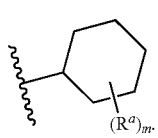
(4qq) R¹ is
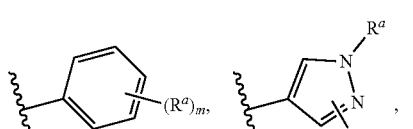
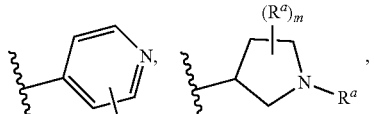
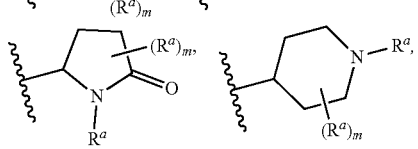
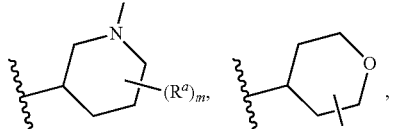
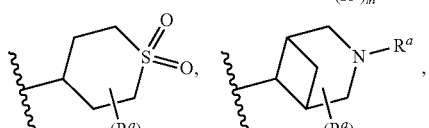
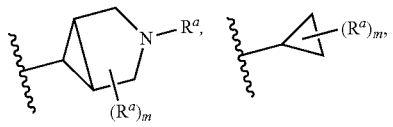
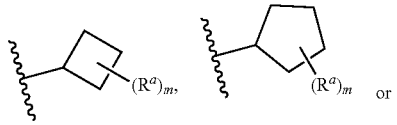
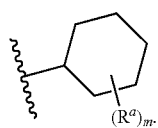
(4rr) R¹ is
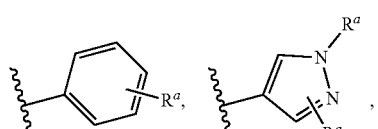
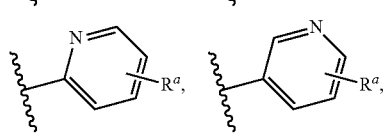
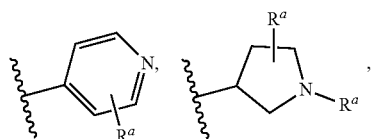
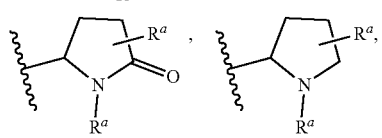
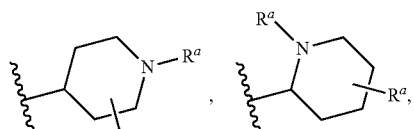
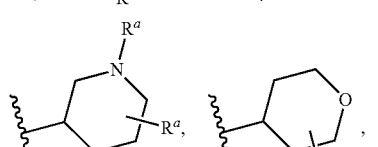
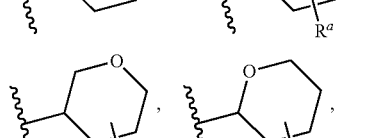
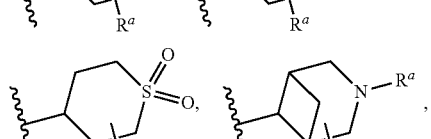
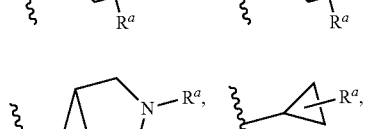
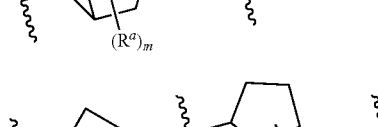
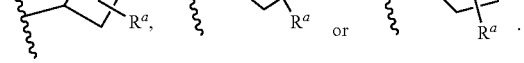

(4ss) R[1] is
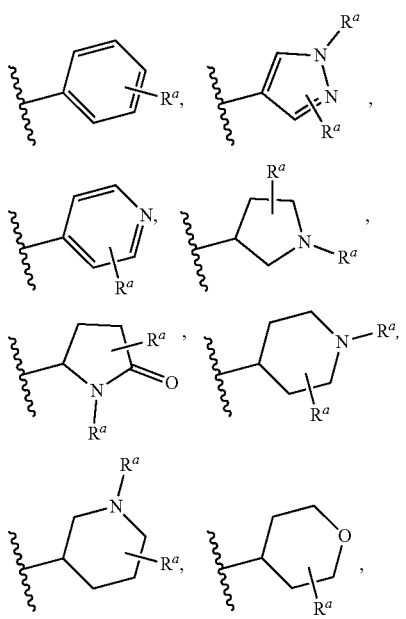
(4tt) R[1] is
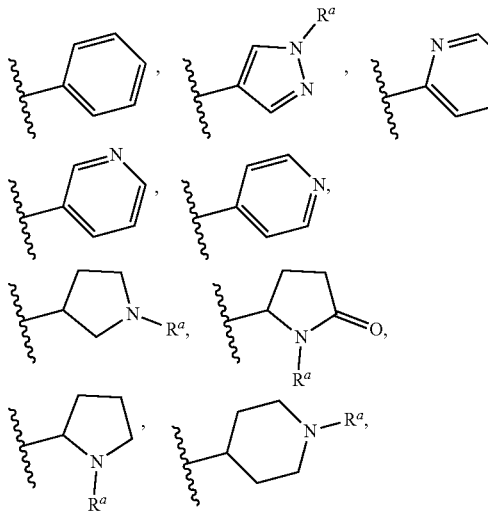
-continued
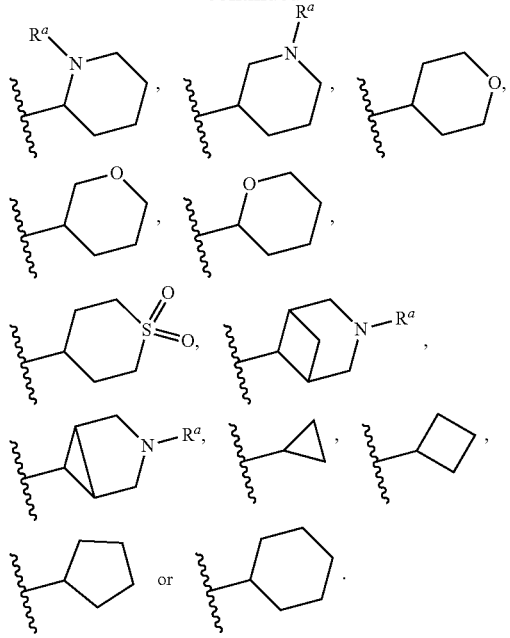
(4uu) R[1] is
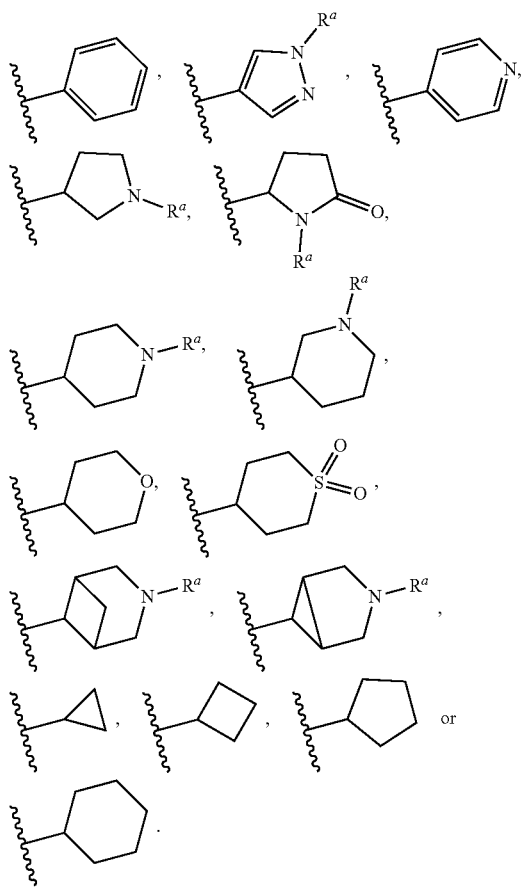
(4vv) Any of groups (4b)-(4uu) wherein each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, —SR, —C(O)OR, —C(O)N(R)$_2$, —C(O)R, —C(O)- aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$, wherein each R is hydrogen, C$_{1-6}$alkyl, C$_{1-6}$haloalkyl, aryl substituted with cyano, 3-7 membered heterocyclyl or C$_{3-6}$cycloalkyl.

(4ww) Any of groups (4b)-(4uu) wherein each R$^a$ is independently oxo, halogen, cyano, C$_{1-6}$alkyl, —C$_{1-6}$alkyl-OR, —C$_{1-6}$haloalkyl, C$_{1-6}$alkyl-cyano, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$, wherein each R is hydrogen, C$_{1-6}$alkyl, C$_{1-6}$haloalkyl, aryl substituted with cyano, 3-7 membered heterocyclyl or C$_{3-6}$cycloalkyl.

(4xx) Any of groups (4b)-(4uu) wherein each R$^a$ is independently oxo, halogen, cyano, C$_1$-6alkyl, —C$_{1-6}$alkyl-OR, —C$_{1-6}$haloalkyl, C$_{1-6}$alkyl-cyano, —C(O)N(R)$_2$, —C(O)R, —S(O)$_2$R, or —S(O)$_2$N(R)$_2$, wherein each R is hydrogen, C$_{1-6}$alkyl, C$_{1-6}$haloalkyl, aryl substituted with cyano, 3-7 membered heterocyclyl or C$_{3-6}$cycloalkyl.

(4yy) Any of groups (4b)-(4uu) wherein each R$^a$ is independently oxo, halogen, cyano, C$_{1-6}$alkyl, —C$_{1-6}$alkyl-OR, —C$_{1-6}$haloalkyl, C$_{1-6}$alkyl-cyano, —C(O)N(R)$_2$, —C(O)R, —S(O)$_2$R, or —S(O)$_2$N(R)$_2$, wherein each R is hydrogen, C$_{1-6}$alkyl, C$_{1-6}$haloalkyl, aryl substituted with cyano, oxetanyl, azetidinyl or cyclopropyl.

(4zz) Any of groups (4b)-(4), wherein m is 1, 2 or 3.
(4aaa) Any of groups (4b)-(4), wherein m is 1 or 2.
(4bbb) Any of groups (4b)-(4), wherein m is 1.
(4ccc) Any of groups (4b)-(4), wherein m is 0.

In another embodiment, the invention comprises compounds of Formula (IIa),

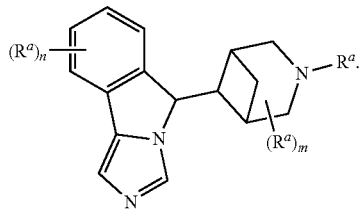

(IIa)

In another embodiment, the invention comprises compounds of Formula (III),

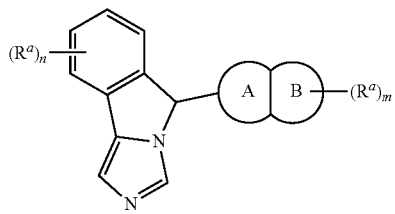

(III)

which are compounds of Formula (I) wherein R$^1$ is

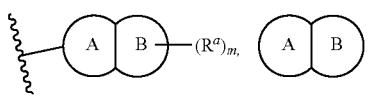

is a fused bicyclic ring system consisting of a ring A and a ring B;

ring A is C$_{3-7}$cycloalkyl, aryl, heteroaryl or 3-7 membered heterocyclyl;

ring B is aryl, heteroaryl, C$_{3-7}$cycloalkyl or 3-7 membered heterocyclyl;

m is 0, 1, 2, 3 or 4; and each R$^a$ is independently oxo, halogen, cyano, nitro, C$_{1-6}$alkyl, —C$_{1-6}$alkyl-OR, —C$_{1-6}$haloalkyl, C$_{1-6}$alkyl-cyano, —OR, —NR$_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

In one embodiment, the invention comprises compounds of Formula (III) wherein n is 0. In other embodiments, n is 1.

The invention further comprises subgenera of formula (III) in which the substituents are selected as any and all combinations of one or more of structural formula (III), R$^2$, R$^a$, m, ring A and ring B, as defined herein, including without limitation, the following:

Structural Formula I is One of Formulae (IIIa)-(IIIi):

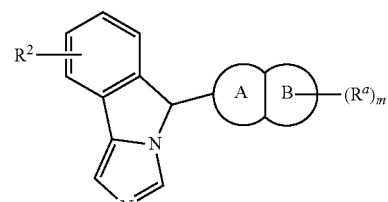

(IIIa)

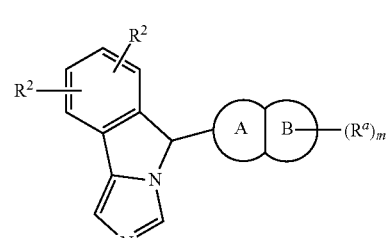

(IIIb)

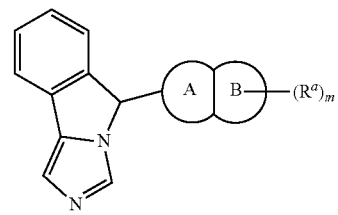

(IIIc)

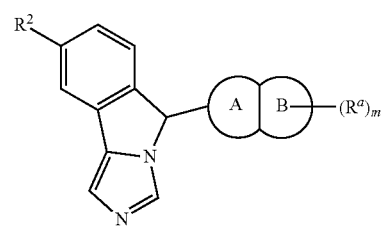

(IIId)

-continued

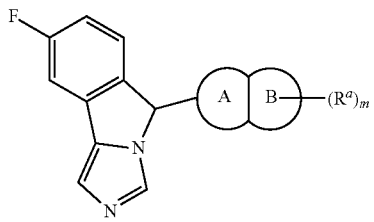
(IIIe)

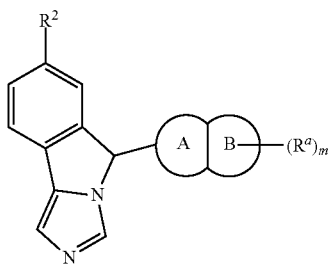
(IIIf)

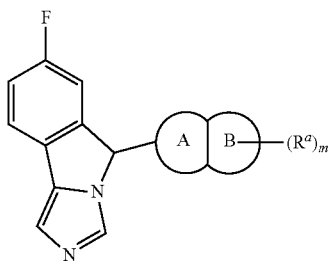
(IIIg)

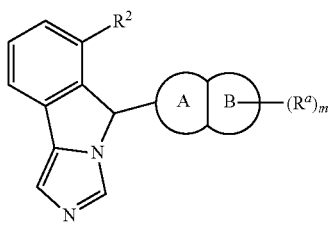
(IIIh)

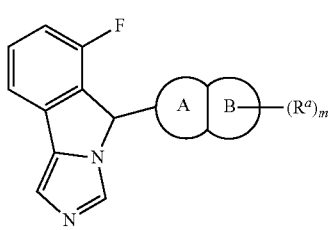
(IIIi)

Ring A/B is Selected from One of the Following Groups (5a)-(5yy):

(5a) Ring A is $C_{3-7}$cycloalkyl, aryl, heteroaryl or 3-7 membered heterocyclyl (e.g., a 4-6 membered heterocyclyl or a 5-6 membered heterocyclyl), and ring B is aryl, heteroaryl, $C_{3-7}$cycloalkyl or 3-7 membered heterocyclyl (e.g., a 4-6 membered heterocyclyl or a 5-6 membered heterocyclyl), wherein m is 0, 1, 2, 3 or 4; and each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, 3-7 membered heterocyclyl, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$, wherein each R is hydrogen, $C_{1-6}$alkyl, $C_{1-6}$haloalkyl, aryl substituted with cyano, 3-7 membered heterocyclyl or $C_{3-6}$cycloalkyl.

(5b) Group (5a), wherein ring A is $C_{3-7}$cycloalkyl, heteroaryl or 3-7 membered heterocyclyl, and ring B is aryl, heteroaryl, $C_{3-7}$cycloalkyl or 3-7 membered heterocyclyl.

(5c) Group (5a), wherein ring A is $C_{3-7}$cycloalkyl or 3-7 membered heterocyclyl, and ring B is aryl, heteroaryl, $C_{3-7}$cycloalkyl or 3-7 membered heterocyclyl.

(5d) Group (5a), wherein ring A is $C_{3-7}$cycloalkyl, and ring B is aryl, heteroaryl, $C_3$-7cycloalkyl or 3-7 membered heterocyclyl.

(5e) Group (5a), wherein ring A is $C_{3-7}$cycloalkyl, and ring B is aryl, heteroaryl, $C_3$-7cycloalkyl or 3-7 membered heterocyclyl.

(5f) Group (5a), wherein ring A is $C_{3-7}$cycloalkyl, and ring B is 3-7 membered heterocyclyl.

(5g) Group (5a), wherein ring A is heteroaryl or 3-7 membered heterocyclyl, and ring B is aryl, heteroaryl, $C_{3-7}$cycloalkyl or 3-7 membered heterocyclyl.

(5h) Group (5a), wherein ring A is heteroaryl, and ring B is aryl, heteroaryl, $C_{3-7}$cycloalkyl or 3-7 membered heterocyclyl.

(5i) Group (5a), wherein ring A is heteroaryl, and ring B is heteroaryl or 3-7 membered heterocyclyl.

(5j) Group (5a), wherein ring A is heteroaryl, and ring B is heteroaryl.

(5k) Group (5a), wherein ring A is aryl, and ring B is heteroaryl.

(5l) Group (5a), wherein ring A is 3-7 membered heterocyclyl, and ring B is heteroaryl or 3-7 membered heterocyclyl.

(5m) Group (5a), wherein ring A is 3-7 membered heterocyclyl, and ring B is heteroaryl.

(5n) Group (5a), wherein ring A is 3-7 membered heterocyclyl, and ring B is 3-7 membered heterocyclyl.

(5o) Group (5a), wherein ring A is $C_{3-7}$cycloalkyl, aryl, heteroaryl or 3-7 membered heterocyclyl, and ring B is pyridinyl, pyrazinyl, pyrimidinyl, pyridazinyl, pyrazolyl, imidazolyl, thiazolyl, triazolyl, oxazolyl, oxadiazolyl, pyrrolidinyl or piperidinyl.

(5p) Group (5a), wherein ring A is $C_{3-7}$cycloalkyl, aryl, heteroaryl or 3-7 membered heterocyclyl, and ring B is pyridinyl, pyrazinyl, pyrimidinyl, pyridazinyl, pyrazolyl, imidazolyl, thiazolyl, triazolyl, oxazolyl, oxadiazolyl, pyrrolidinyl or piperidinyl.

(5q) Group (5a), wherein ring A is $C_{3-7}$cycloalkyl, aryl or 3-7 membered heterocyclyl, and ring B is pyridinyl, pyrazinyl, pyrimidinyl, pyridazinyl, pyrazolyl, imidazolyl, thiazolyl, triazolyl, oxazolyl, oxadiazolyl, pyrrolidinyl or piperidinyl.

(5r) Group (5a), wherein ring A is $C_{3-7}$cycloalkyl or 3-7 membered heterocyclyl, and ring B is pyridinyl, pyrazinyl, pyrimidinyl, pyridazinyl, pyrazolyl, imidazolyl, thiazolyl, triazolyl, oxazolyl, oxadiazolyl, pyrrolidinyl or piperidinyl.

(5s) Group (5a), wherein ring A is cyclopentyl, cyclohexyl, phenyl, piperidinyl, pyrazolyl, 1,2,3,6-tetrahydropyridinyl, imidazolyl or pyridinyl, and ring B is cyclopentadienyl, pyridinyl, pyrazinyl, pyrimidinyl, pyridazinyl, pyrazolyl, imidazolyl, thiazolyl, triazolyl, oxazolyl, oxadiazolyl, pyrrolidinyl or piperidinyl.

(5t) Group (5a), wherein ring A is cyclopentyl, cyclohexyl, phenyl, piperidinyl, pyrazolyl, 1,2,3,6-tetrahydropyridinyl, imidazolyl or pyridinyl, and ring B is cyclopentadienyl, pyridinyl, pyrazolyl, imidazolyl, pyrrolidinyl or piperidinyl.

(5u) Group (5a), wherein ring A is cyclopentyl, cyclohexyl, phenyl, piperidinyl, pyrazolyl, 1,2,3,6-tetrahydropyridinyl, imidazolyl or pyridinyl, and ring B is cyclopentadienyl, pyridinyl, pyrazolyl, imidazolyl, pyrrolidinyl or piperidinyl.

(5v) Group (5a), wherein ring A is phenyl, piperidinyl, pyrazolyl, 1,2,3,6-tetrahydropyridinyl, imidazolyl or pyridinyl, and ring B is cyclopentadienyl, pyridinyl, pyrazolyl or imidazolyl.

(5w) Group (5a), wherein ring A is cyclopentyl, and ring B is pyrrolidinyl.

(5x) Any of groups (5b)-(5w), wherein each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, 3-7 membered heterocyclyl, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$, wherein each R is hydrogen, $C_{1-6}$alkyl, $C_{1-6}$haloalkyl, aryl substituted with cyano, 3-7 membered heterocyclyl or $C_{3-6}$cycloalkyl.

(5y) Group (5x), wherein each $R^a$ is independently oxo, halogen, cyano, $C_{1-6}$alkyl, —$C_{1-6}$alkyl-OR, —$C_{1-6}$haloalkyl, $C_{1-6}$alkyl-cyano, oxetanyl, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

(5z) Group (5x), wherein each $R^a$ is independently halogen, cyano, $C_{1-6}$alkyl, —$C_{1-6}$alkyl-OR, —$C_{1-6}$haloalkyl, $C_{1-6}$alkyl-cyano, oxetanyl, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

(5aa) Group (5x), wherein each $R^a$ is independently $C_{1-6}$alkyl, —$C_{1-6}$alkyl-OR, —$C_{1-6}$haloalkyl, oxetanyl, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

(5bb) Group (5x), wherein each $R^a$ is independently $C_{1-6}$alkyl, oxetanyl, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

(5cc) Group (5x), wherein each $R^a$ is independently $C_{1-6}$alkyl, oxetanyl, —C(O)OR, —C(O)N(R)$_2$, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

(5dd) Group (5x), wherein each $R^a$ is independently $C_{1-6}$alkyl, oxetanyl, —C(O)OR, —C(O)N(R)$_2$, —S(O)OR, —S(O)N(R)$_2$, —S(O)$_2$R, —N(R)S(O)$_2$R, —S(O)$_2$OR or —S(O)$_2$N(R)$_2$.

(5ee) Group (5x), wherein each $R^a$ is independently $C_{1-6}$alkyl, oxetanyl, —C(O)OR, —S(O)$_2$R, —N(R)S(O)$_2$R, —S(O)$_2$OR or —S(O)$_2$N(R)$_2$.

(5ff) Group (5x), wherein each $R^a$ is independently $C_{1-6}$alkyl, oxetanyl, —C(O)OR, —S(O)$_2$R, —N(R)S(O)$_2$R or —S(O)$_2$N(R)$_2$.

(5gg) Group (5x), wherein each $R^a$ is independently $C_{1-6}$alkyl, oxetanyl, —C(O)OR, —S(O)$_2$R, —N(R)S(O)$_2$R or —S(O)$_2$N(R)$_2$.

(5hh) Group (5x), wherein each $R^a$ is independently methyl, oxetanyl, —C(O)OC$_{1-6}$alkyl, —S(O)$_2$C$_{1-6}$alkyl, —NHS(O)$_2$C$_{1-6}$alkyl or —S(O)$_2$NH$_2$.

(5ii) Group (5x), wherein each $R^a$ is independently —S(O)$_2$C$_{1-6}$alkyl, —NHS(O)$_2$C$_{1-6}$alkyl or —S(O)$_2$NH$_2$.

(5jj) Group (5x), wherein each $R^a$ is independently methyl, oxetanyl or —C(O)OC$_{1-6}$alkyl.

(5kk) Group (5x), wherein each $R^a$ is independently methyl, oxetanyl, —C(O)O-tert-butyl, —S(O)$_2$CH$_3$, —NHS(O)$_2$ethyl or —S(O)$_2$NH$_2$.

(5ll) Any of groups (5a)-(5kk), wherein m is 1, 2 or 3.
(5mm) Any of groups (5a)-(5kk), wherein m is 1 or 2.
(5nn) Any of groups (5a)-(5kk), wherein m is 1.
(5oo) Any of groups (5a)-(5w), wherein m is 0.
(5pp) $R^1$ is

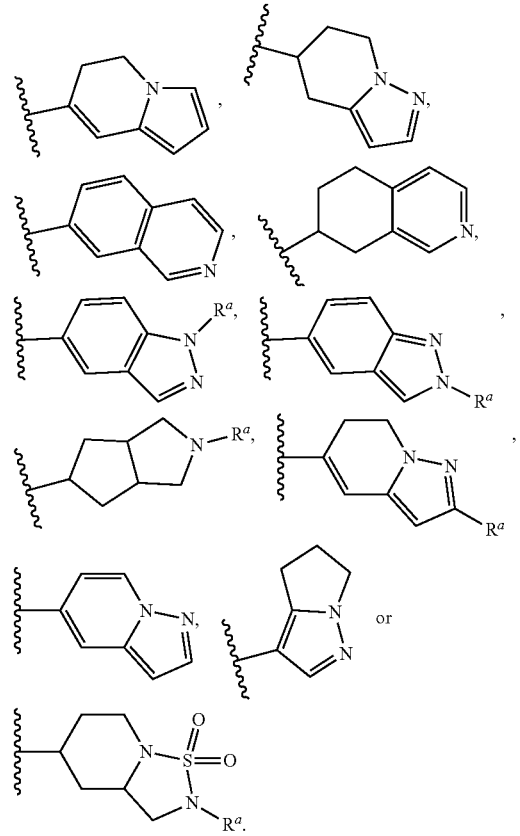

(5qq) $R^1$ is

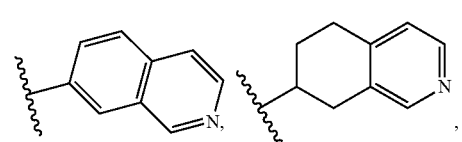

-continued
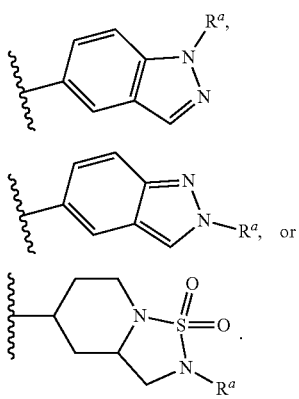
(5rr) Any of groups (5pp)-(5qq), wherein each $R^a$ is independently $C_{1-6}$alkyl, oxetanyl, —C(O)OR, —S(O)$_2$R, —N(R)S(O)$_2$R, —S(O)$_2$N(R)$_2$ or —OC(O)R.
(5ss) $R^1$ is
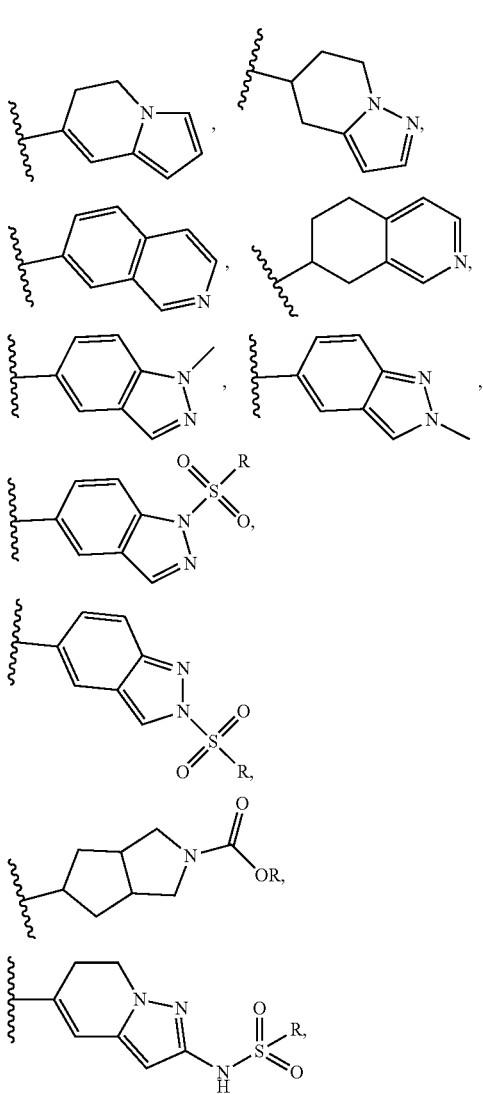
-continued
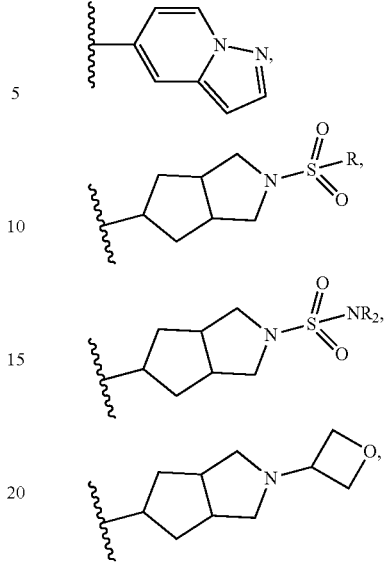
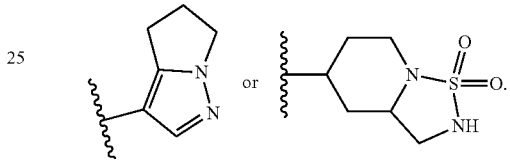
(5tt) $R^1$ is
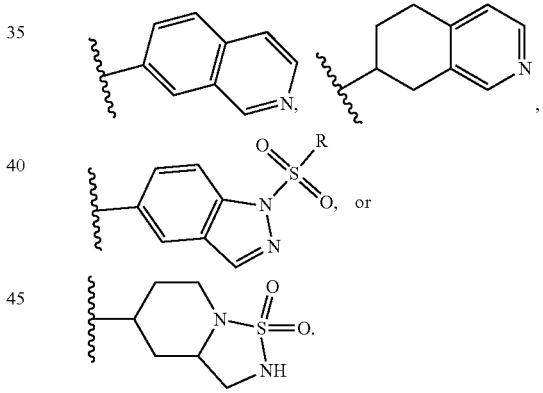
(5uu) Any of groups (5pp)-(5tt), wherein each R is hydrogen, $C_{1-6}$alkyl or 3-7 membered heterocyclyl.
(5vv) $R^1$ is
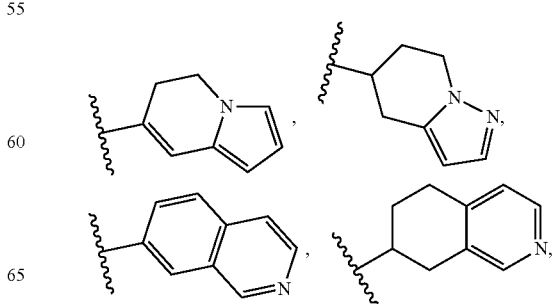

-continued
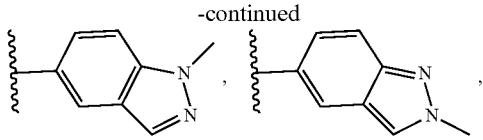
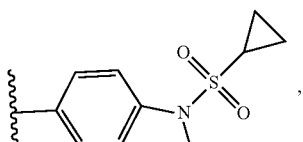
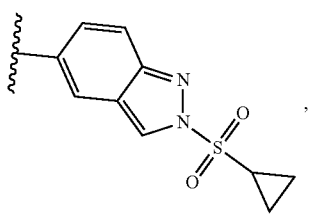
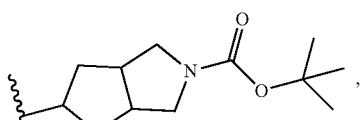
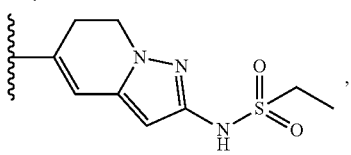
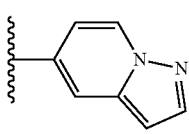
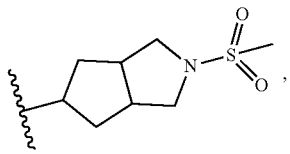
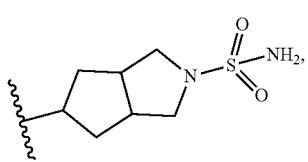
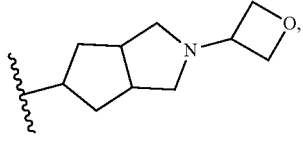
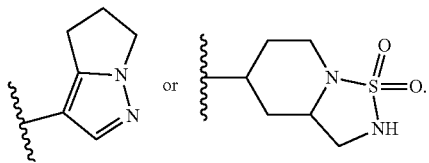
(5ww) $R^1$ is
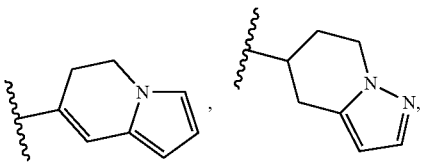
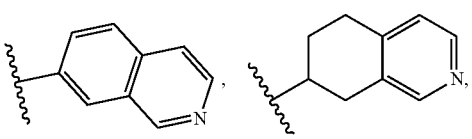
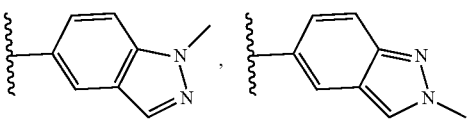
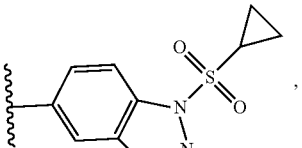
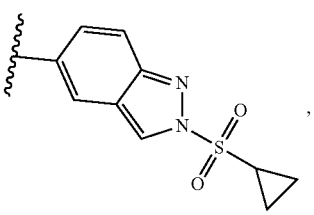
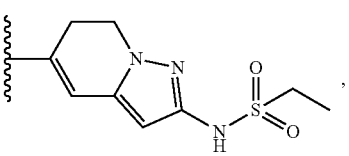
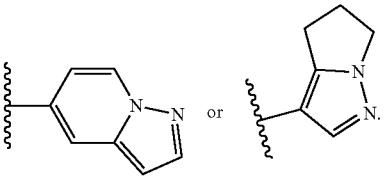
(5xx) $R^1$ is
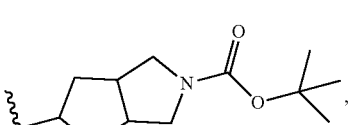
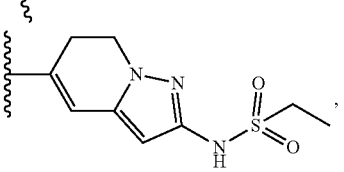

-continued

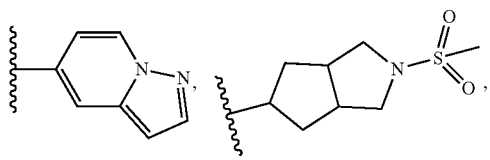

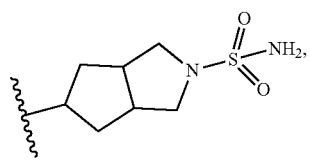

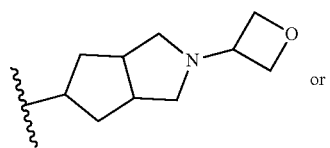

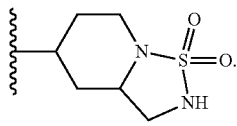

(5yy) R¹ is

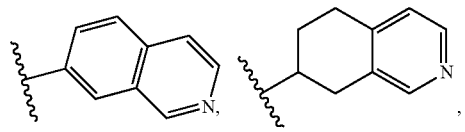

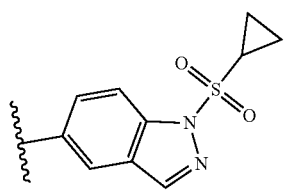

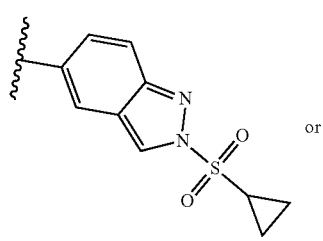

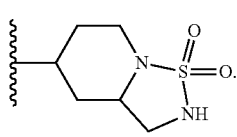

In another embodiment, the invention comprises compounds of Formula (IV),

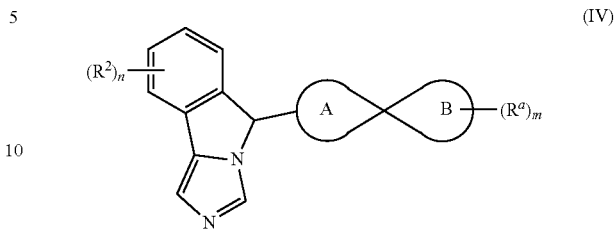

(IV)

which are compounds of Formula (I) wherein R¹ is

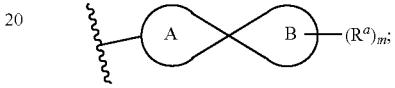

ring A is $C_{3-7}$cycloalkyl or 3-7 membered heterocyclyl;
ring B is $C_{3-7}$cycloalkyl or 3-7 membered heterocyclyl;
m is 0, 1, 2, 3 or 4; and
each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

In one embodiment, the invention comprises compounds of Formula (IV) wherein n is 0. In other embodiments, n is 1.

The invention further comprises subgenera of formula (IV) in which the substituents are selected as any and all combinations of one or more of structural formula (IV), $R^2$, $R^a$, m, ring A and ring B, as defined herein, including without limitation, the following:

Structural Formula I is One of Formulae (IVa)-(IVi):

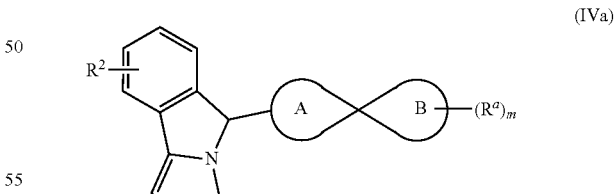

(IVa)

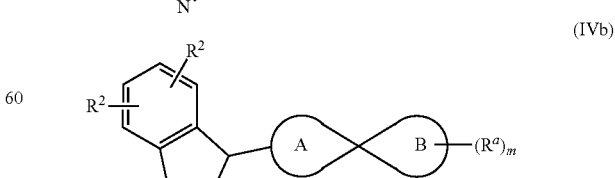

(IVb)

-continued (IVc)
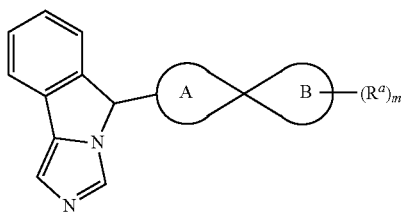

(IVd)
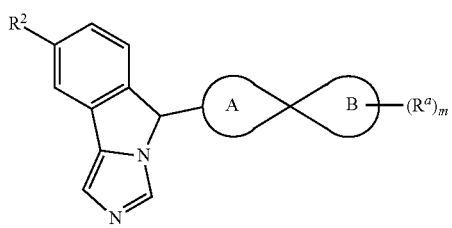

(IVe)
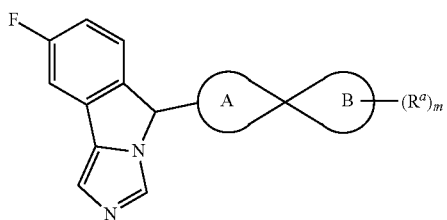

(IVf)
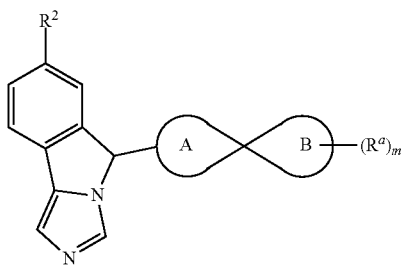

(IVg)
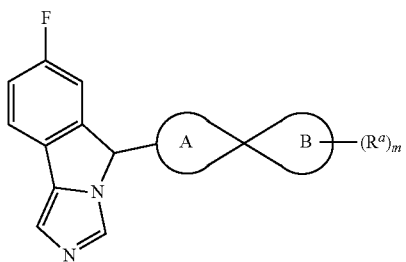

(IVh)
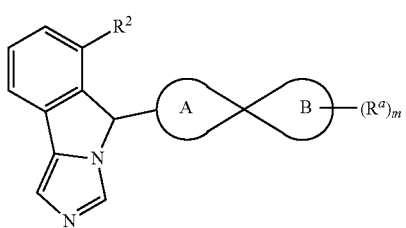

-continued (IVi)
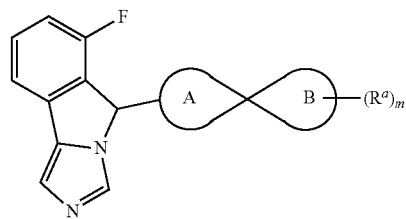

Ring A/B is Selected from One of the Following Groups (6a)-(6zz):

(6a) Ring A is $C_{3-7}$cycloalkyl or 3-7 membered heterocyclyl (e.g., a 4-6 membered heterocyclyl or a 5-6 membered heterocyclyl), and ring B is $C_{3-7}$cycloalkyl or 3-7 membered heterocyclyl (e.g., a 4-6 membered heterocyclyl or a 5-6 membered heterocyclyl), wherein m is 0, 1, 2, 3 or 4; and
each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, 3-7 membered heterocyclyl, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$, wherein each R is hydrogen, $C_{1-6}$alkyl, $C_{1-6}$haloalkyl, aryl substituted with cyano, 3-7 membered heterocyclyl or $C_{3-6}$cycloalkyl.

(6b) Group (6a), wherein ring A is $C_{4-5}$cycloalkyl or 4-6 membered heterocyclyl, and ring B is $C_{4-6}$cycloalkyl or 4-6 membered heterocyclyl.

(6c) Group (6a), wherein ring A is $C_{3-7}$cycloalkyl, and ring B is $C_{3-7}$cycloalkyl or 3-7 membered heterocyclyl.

(6d) Group (6a), wherein ring A is 3-7 membered heterocyclyl (e.g., a 4-6 membered heterocyclyl or a 5-6 membered heterocyclyl), and ring B is $C_{3-7}$cycloalkyl.

(6e) Group (6a), wherein ring A is $C_{3-7}$cycloalkyl or 3-7 membered heterocyclyl (e.g., a 4-6 membered heterocyclyl or a 5-6 membered heterocyclyl), and ring B is $C_{3-7}$cycloalkyl.

(6f) Group (6a), wherein ring A is $C_{3-7}$cycloalkyl or 3-7 membered heterocyclyl (e.g., a 4-6 membered heterocyclyl or a 5-6 membered heterocyclyl), and ring B is 3-7 membered heterocyclyl.

(6g) Group (6a), wherein ring A is $C_{3-7}$cycloalkyl, and ring B is azetidinyl, oxatanyl, piperidinyl, thietane 1,1-dioxidyl, 1,3-dioxolanyl or tetrahydropyranyl.

(6h) Group (6a), wherein ring A is $C_{3-7}$cycloalkyl, and ring B is azetidinyl, oxatanyl, piperidinyl, thietane 1,1-dioxidyl or 1,3-dioxolanyl.

(6i) Group (6a), wherein ring A is $C_{3-7}$cycloalkyl, and ring B is azetidinyl, oxatanyl or piperidinyl.

(6j) Group (6a), wherein ring A is $C_{3-7}$cycloalkyl, and ring B is azetidinyl or piperidinyl.

(6k) Group (6a), wherein ring A is cyclobutyl, and ring B is azetidinyl, oxatanyl, piperidinyl, thietane 1,1-dioxidyl or 1,3-dioxolanyl.

(6l) Group (6a), wherein ring A is cyclobutyl, and ring B is $C_{3-7}$cycloalkyl.

(6m) Group (6a), wherein ring A is cyclobutyl, and ring B is cyclobutyl.

(6n) Group (6a), wherein ring A is cyclobutyl, and ring B is 3-7 membered heterocyclyl.

(6o) Group (6a), wherein ring A is cyclobutyl, and ring B is 4-6 membered heterocyclyl.
(6p) Group (6a), wherein ring A is cyclobutyl, and ring B is 4-membered heterocyclyl.
(6q) Group (6a), wherein ring A is cyclobutyl, and ring B is 5-membered heterocyclyl.
(6r) Group (6a), wherein ring A is cyclobutyl, and ring B is 6-membered heterocyclyl.
(6s) Group (6a), wherein ring A is cyclobutyl, and ring B is azetidinyl, oxatanyl, piperidinyl, thietane 1,1-dioxidyl, 1,3-dioxolanyl or tetrahydropyranyl.
(6t) Group (6a), wherein ring A is cyclobutyl, and ring B is azetidinyl, oxatanyl, piperidinyl, thietane 1,1-dioxidyl, 1,3-dioxolanyl or tetrahydropyranyl.
(6u) Group (6a), wherein ring A is cyclobutyl, and ring B is azetidinyl or oxatanyl.
(6v) Group (6a), wherein ring A is cyclobutyl, and ring B is piperidinyl, thietane 1,1-dioxidyl or 1,3-dioxolanyl.
(6w) Group (6a), wherein ring A is cyclobutyl, and ring B is azetidinyl or piperidinyl.
(6x) Group (6a), wherein ring A is cyclobutyl, and ring B is oxatanyl, thietane 1,1-dioxidyl or 1,3-dioxolanyl.
(6y) Any of groups (6b)-(6x), wherein each $R^a$ is independently oxo, halogen, cyano, nitro, $C_{1-6}$alkyl, —$C_{1-6}$alkyl-OR, —$C_{1-6}$haloalkyl, $C_{1-6}$alkyl-cyano, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$, wherein each R is hydrogen, $C_{1-6}$alkyl, $C_{1-6}$haloalkyl, aryl substituted with cyano, 3-7 membered heterocyclyl or $C_{3-6}$cycloalkyl.
(6z) Group (6y), wherein each $R^a$ is independently oxo, halogen, cyano, $C_{1-6}$alkyl, —$C_{1-6}$alkyl-OR, —$C_{1-6}$haloalkyl, $C_{1-6}$alkyl-cyano, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.
(6aa) Group (6y), wherein each $R^a$ is independently halogen, cyano, $C_{1-6}$alkyl, —$C_{1-6}$alkyl-OR, —$C_{1-6}$haloalkyl, $C_{1-6}$alkyl-cyano, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.
(6bb) Group (6y), wherein each $R^a$ is independently $C_{1-6}$alkyl, —$C_{1-6}$alkyl-OR, —$C_{1-6}$haloalkyl, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.
(6cc) Group (6y), wherein each $R^a$ is independently $C_{1-6}$alkyl, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.
(6dd) Group (6y), wherein each $R^a$ is independently $C_{1-6}$alkyl, —C(O)OR, —C(O)N(R)$_2$, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.
(6ee) Group (6y), wherein each $R^a$ is independently $C_{1-6}$alkyl, —C(O)OR, —C(O)N(R)$_2$, —S(O)OR, —S(O)N(R)$_2$, —S(O)$_2$R, —N(R)S(O)$_2$R, —S(O)$_2$OR or —S(O)$_2$N(R)$_2$.
(6ff) Group (6y), wherein each $R^a$ is independently $C_{1-6}$alkyl, —C(O)OR, —S(O)$_2$R, —N(R)S(O)$_2$R, —S(O)$_2$OR or —S(O)$_2$N(R)$_2$.
(6gg) Group (6y), wherein each $R^a$ is independently $C_{1-6}$alkyl, —C(O)OR, —S(O)$_2$R, —N(R)S(O)$_2$R or —S(O)$_2$N(R)$_2$.
(6hh) Group (6y), wherein each $R^a$ is independently $C_{1-6}$alkyl, —C(O)OR, —S(O)$_2$R, —N(R)S(O)$_2$R or —S(O)$_2$N(R)$_2$.
(6ii) Group (6y), wherein each $R^a$ is independently methyl, —C(O)O$C_{1-6}$alkyl, —S(O)$_2$$C_{1-6}$alkyl, —NHS(O)$_2$$C_{1-6}$alkyl or —S(O)$_2$NH$_2$.
(6jj) Group (6y), wherein each $R^a$ is independently —S(O)$_2$$C_{1-6}$alkyl, —NHS(O)$_2$$C_{1-6}$alkyl or —S(O)$_2$NH$_2$.
(6kk) Group (6y), wherein each $R^a$ is independently methyl or —C(O)O$C_{1-6}$alkyl.
(6ll) Group (6y), wherein each $R^a$ is independently methyl, —C(O)O-tert-butyl, —S(O)$_2$CH$_3$, —NHS(O)$_2$ethyl or —S(O)$_2$NH$_2$.
(6mm) Any of groups (6a)-(6ll), wherein m is 1, 2 or 3.
(6nn) Any of groups (6a)-(6ll), wherein m is 1 or 2.
(6oo) Any of groups (6a)-(6ll), wherein m is 1.
(6pp) Any of groups (6a)-(6x), wherein m is 0.
(6qq) $R^1$ is (6rr) R¹ is
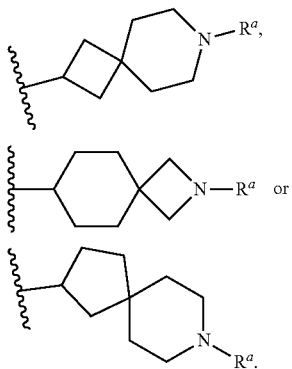
(6ss) Any of groups (6qq)-(6rr), wherein each R^a is independently C_{1-6}alkyl, —C(O)OR, —S(O)_2R, —N(R)S(O)_2R, —S(O)_2N(R)_2 or —OC(O)R.
(6tt) R¹ is
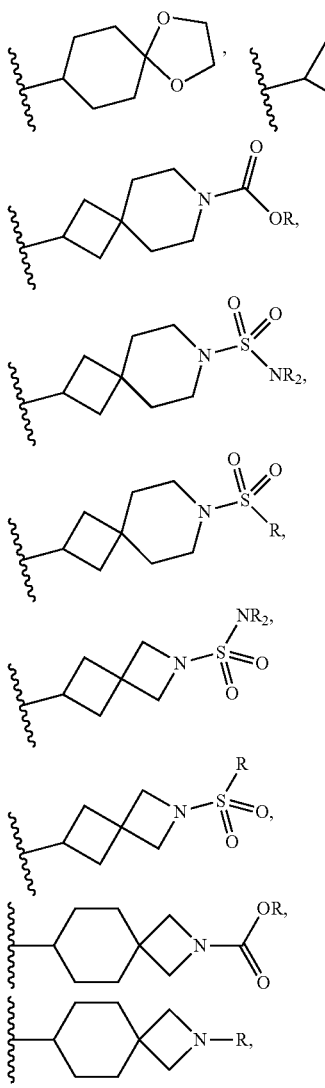
-continued
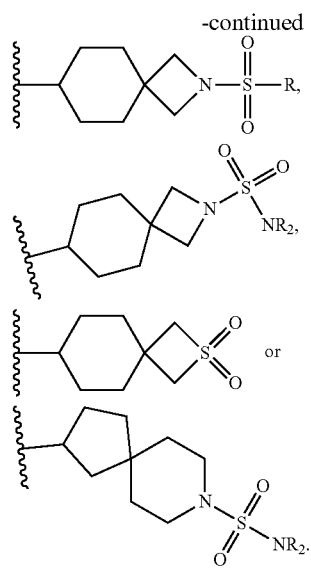
(6uu) R¹ is
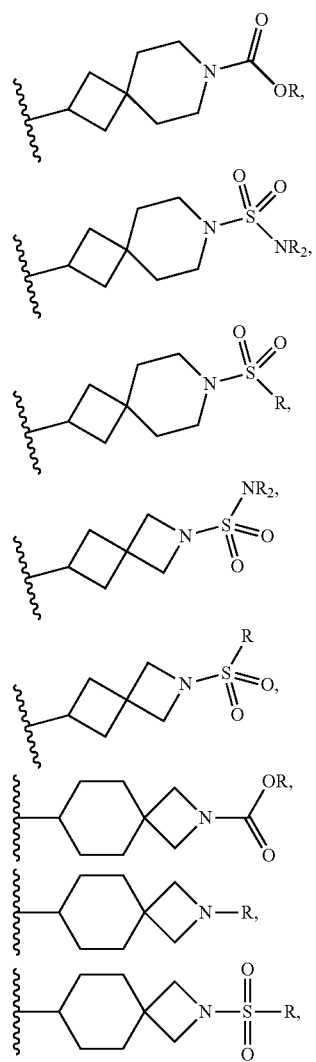

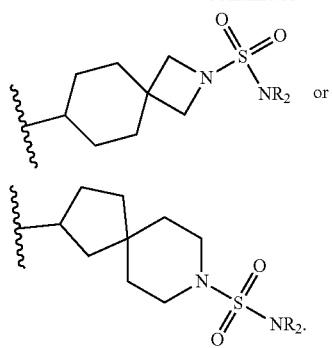
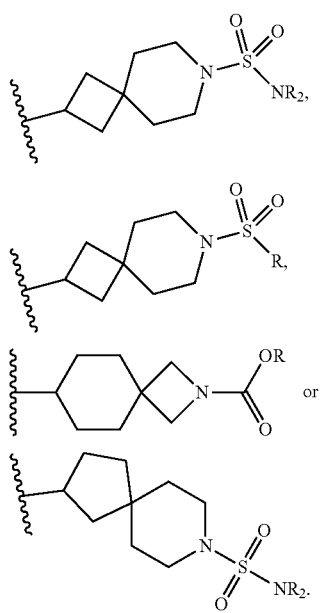
(6vv) R¹ is
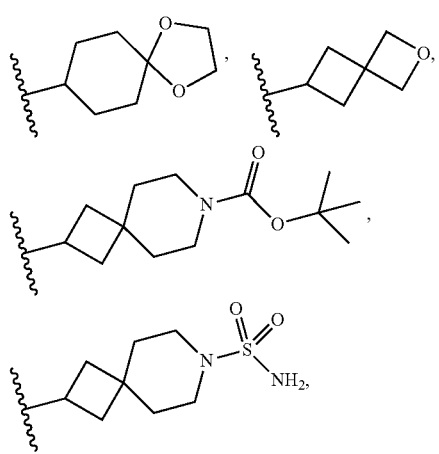
(6ww) Any of groups (6tt)-(6uu), wherein each R is hydrogen or $C_{1-6}$alkyl.
(6xx) R¹ is
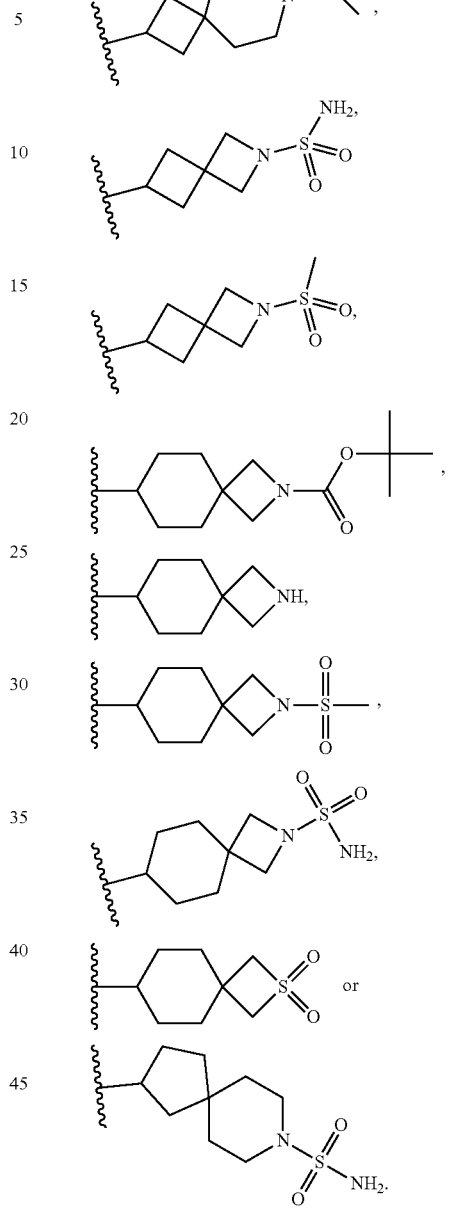
(6yy) R¹ is
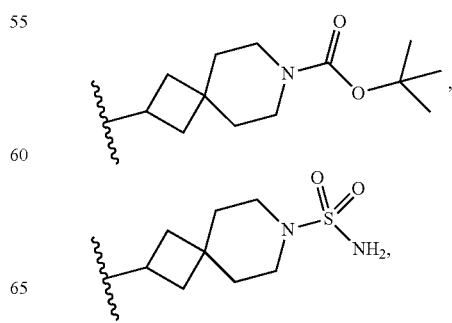

-continued

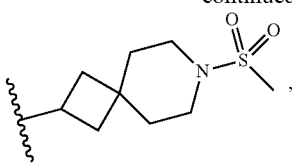

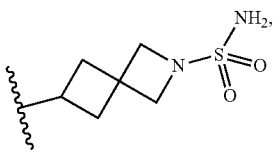

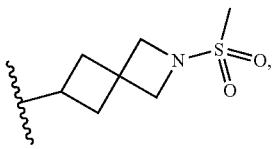

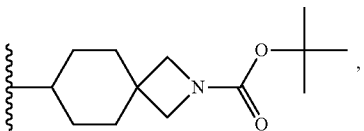

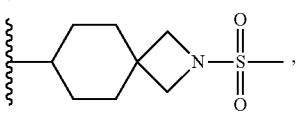

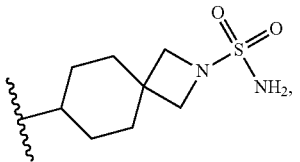

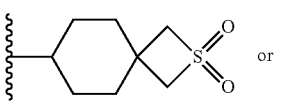

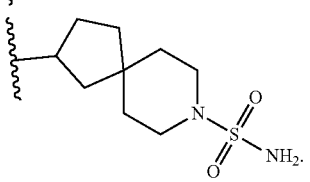

(6zz) R$^1$ is

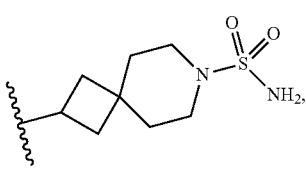

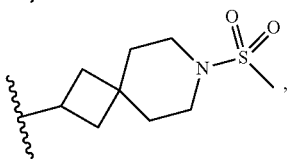

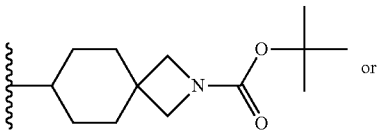

-continued

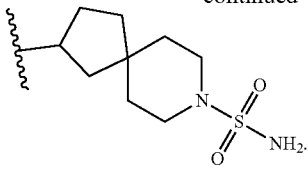

Particular embodiments of this aspect of the invention include compounds of any one of the formulae (II), (IIa)-(IIi), (III), (IIIa)-(IIIi), (IV) and (IVa)-(IVi), each as defined in each of the following rows, wherein each entry is a group number as defined above (e.g., (2r) refers to R$^2$ is fluoro), an "X" indicates that the variable is defined by another group in the embodiment (2)-X below (e.g., in embodiment (2)-X below, ring A is defined in Formula (X)) and a dash "-" indicates that the variable is as defined for Formula (I)-(IVf) or defined according to any one of the applicable variable definitions (1a)-(7xx) [e.g., when the entry for R$^2$ is a dash, it can be either as defined for Formula (II)-(IVf) or any one of definitions (2a)-(2t)]:

|  | (I) | R$^2$ | A or A/B |
|---|---|---|---|
| (2)-1 | (IIa) | (2a) | (4a) |
| (2)-2 | (IIa) | (2b) | (4b) |
| (2)-3 | (IIa) | (2f) | (4c) |
| (2)-4 | (IIa) | (2h) | (4d) |
| (2)-5 | (IIa) | (2k) | (4n) |
| (2)-6 | (IIa) | (2n) | (4r) |
| (2)-7 | (IIa) | (2s) | (4z) |
| (2)-8 | (IIa) | (2t) | (4dd) |
| (2)-9 | (IIa) | (2a) | (4ff) |
| (2)-10 | (IIa) | (2b) | (4kk) |
| (2)-11 | (IIa) | (2f) | (4b) |
| (2)-12 | (IIa) | (2h) | (4c) |
| (2)-13 | (IIa) | (2k) | (4d) |
| (2)-14 | (IIa) | (2n) | (4n) |
| (2)-15 | (IIa) | (2s) | (4r) |
| (2)-16 | (IIa) | (2a) | (4a) |
| (2)-17 | (IIa) | (2b) | (4b) |
| (2)-18 | (IIa) | (2b) | (4c) |
| (2)-19 | (IIa) | (2f) | (4d) |
| (2)-20 | (IIa) | (2h) | (4n) |
| (2)-21 | (IIb) | (2k) | (4r) |
| (2)-22 | (IIb) | (2s) | (4z) |
| (2)-23 | (IIb) | (2t) | (4dd) |
| (2)-24 | (IIb) | (2a) | (4ff) |
| (2)-25 | (IIb) | (2a) | (4kk) |
| (2)-26 | (IIb) | (2b) | (4n) |
| (2)-27 | (IIb) | (2f) | (4r) |
| (2)-28 | (IIb) | (2h) | (4n) |
| (2)-29 | (IIb) | (2k) | (4r) |
| (2)-30 | (IIb) | (2a) | (4a) |
| (2)-31 | (IIb) | (2b) | (4b) |
| (2)-32 | (IIb) | (2t) | (4c) |
| (2)-33 | (IIb) | (2a) | (4d) |
| (2)-34 | (IIb) | (2s) | (4n) |
| (2)-35 | (IIb) | (2t) | (4r) |
| (2)-36 | (IIb) | (2a) | (4z) |
| (2)-37 | (IIb) | (2b) | (4dd) |
| (2)-38 | (IIb) | (2f) | (4ff) |
| (2)-39 | (IIb) | (2s) | (4kk) |
| (2)-40 | (IIb) | (2t) | (4c) |
| (2)-41 | (IIc) | X | (4d) |
| (2)-42 | (IIc) | X | (4n) |
| (2)-43 | (IIc) | X | (4r) |
| (2)-44 | (IIc) | X | (4z) |
| (2)-45 | (IIc) | X | (4dd) |
| (2)-46 | (IIc) | X | (4ff) |
| (2)-47 | (IIc) | X | (4kk) |
| (2)-48 | (IIc) | X | (4b) |
| (2)-49 | (IIc) | X | (4c) |
| (2)-50 | (IIc) | X | (4d) |
| (2)-51 | (IIc) | X | (4r) |

-continued

| | (I) | R² | A or A/B |
|---|---|---|---|
| (2)-52 | (IIc) | X | (4b) |
| (2)-53 | (IIc) | X | (4c) |
| (2)-54 | (IIc) | X | (4d) |
| (2)-55 | (IIc) | X | (4c) |
| (2)-56 | (IIc) | X | (4d) |
| (2)-57 | (IIc) | X | (4n) |
| (2)-58 | (IIc) | X | (4r) |
| (2)-59 | (IIc) | X | (4z) |
| (2)-60 | (IIc) | X | (4dd) |
| (2)-61 | (IId) | (2a) | (4ff) |
| (2)-62 | (IId) | (2b) | (4kk) |
| (2)-63 | (IId) | (2f) | (4n) |
| (2)-64 | (IId) | (2h) | (4r) |
| (2)-65 | (IId) | (2k) | (4b) |
| (2)-66 | (IId) | (2n) | (4c) |
| (2)-67 | (IId) | (2s) | (4d) |
| (2)-68 | (IId) | (2t) | (4n) |
| (2)-69 | (IId) | (2a) | (4r) |
| (2)-70 | (IId) | (2b) | (4b) |
| (2)-71 | (IId) | (2f) | (4c) |
| (2)-72 | (IId) | (2h) | (4d) |
| (2)-73 | (IId) | (2k) | (4c) |
| (2)-74 | (IId) | (2n) | (4d) |
| (2)-75 | (IId) | (2s) | (4n) |
| (2)-76 | (IId) | (2a) | (4r) |
| (2)-77 | (IId) | (2b) | (4z) |
| (2)-78 | (IId) | (2b) | (4dd) |
| (2)-79 | (IId) | (2f) | (4ff) |
| (2)-80 | (IId) | (2h) | (4b) |
| (2)-81 | (IIe) | X | (4c) |
| (2)-82 | (IIe) | X | (4d) |
| (2)-83 | (IIe) | X | (4n) |
| (2)-84 | (IIe) | X | (4r) |
| (2)-85 | (IIe) | X | (4b) |
| (2)-86 | (IIe) | X | (4c) |
| (2)-87 | (IIe) | X | (4d) |
| (2)-88 | (IIe) | X | (4n) |
| (2)-89 | (IIe) | X | (4r) |
| (2)-90 | (IIe) | X | (4z) |
| (2)-91 | (IIe) | X | (4a) |
| (2)-92 | (IIe) | X | (4b) |
| (2)-93 | (IIe) | X | (4c) |
| (2)-94 | (IIe) | X | (4d) |
| (2)-95 | (IIe) | X | (4n) |
| (2)-96 | (IIe) | X | (4r) |
| (2)-97 | (IIe) | X | (4z) |
| (2)-98 | (IIe) | X | (4dd) |
| (2)-99 | (IIe) | X | (4ff) |
| (2)-100 | (IIe) | X | (4kk) |
| (2)-101 | (IIIa) | (2a) | (5a) |
| (2)-102 | (IIIa) | (2b) | (5b) |
| (2)-103 | (IIIa) | (2f) | (5c) |
| (2)-104 | (IIIa) | (2h) | (5i) |
| (2)-105 | (IIIa) | (2k) | (5r) |
| (2)-106 | (IIIa) | (2n) | (5p) |
| (2)-107 | (IIIa) | (2s) | (5x) |
| (2)-108 | (IIIa) | (2t) | (5gg) |
| (2)-109 | (IIIa) | (2a) | (5oo) |
| (2)-110 | (IIIa) | (2b) | (5b) |
| (2)-111 | (IIIa) | (2f) | (5c) |
| (2)-112 | (IIIa) | (2h) | (5i) |
| (2)-113 | (IIIa) | (2k) | (5r) |
| (2)-114 | (IIIa) | (2n) | (5x) |
| (2)-115 | (IIIa) | (2s) | (5gg) |
| (2)-116 | (IIIa) | (2a) | (5oo) |
| (2)-117 | (IIIa) | (2b) | (5c) |
| (2)-118 | (IIIa) | (2b) | (5i) |
| (2)-119 | (IIIa) | (2f) | (5r) |
| (2)-120 | (IIIa) | (2h) | (5gg) |
| (2)-121 | (IIIb) | (2k) | (5oo) |
| (2)-122 | (IIIb) | (2s) | (5b) |
| (2)-123 | (IIIb) | (2t) | (5c) |
| (2)-124 | (IIIb) | (2a) | (5i) |
| (2)-125 | (IIIb) | (2a) | (5r) |
| (2)-126 | (IIIb) | (2b) | (5p) |
| (2)-127 | (IIIb) | (2f) | (5x) |
| (2)-128 | (IIIb) | (2h) | (5gg) |
| (2)-129 | (IIIb) | (2k) | (5oo) |
| (2)-130 | (IIIb) | (2a) | (5x) |
| (2)-131 | (IIIb) | (2b) | (5gg) |
| (2)-132 | (IIIb) | (2t) | (5oo) |
| (2)-133 | (IIIb) | (2a) | (5vv) |
| (2)-134 | (IIIb) | (2s) | (5x) |
| (2)-135 | (IIIb) | (2t) | (5a) |
| (2)-136 | (IIIb) | (2a) | (5b) |
| (2)-137 | (IIIb) | (2b) | (5c) |
| (2)-138 | (IIIb) | (2f) | (5i) |
| (2)-139 | (IIIb) | (2s) | (5r) |
| (2)-140 | (IIIb) | (2t) | (5ww) |
| (2)-141 | (IIIc) | X | (5x) |
| (2)-142 | (IIIc) | X | (5gg) |
| (2)-143 | (IIIc) | X | (5oo) |
| (2)-144 | (IIIc) | X | (5c) |
| (2)-145 | (IIIc) | X | (5i) |
| (2)-146 | (IIIc) | X | (5r) |
| (2)-147 | (IIIc) | X | (5oo) |
| (2)-148 | (IIIc) | X | (5c) |
| (2)-149 | (IIIc) | X | (5i) |
| (2)-150 | (IIIc) | X | (5r) |
| (2)-151 | (IIIc) | X | (5p) |
| (2)-152 | (IIIc) | X | (5x) |
| (2)-153 | (IIIc) | X | (5gg) |
| (2)-154 | (IIIc) | X | (5oo) |
| (2)-155 | (IIIc) | X | (5b) |
| (2)-156 | (IIIc) | X | (5c) |
| (2)-157 | (IIIc) | X | (5i) |
| (2)-158 | (IIIc) | X | (5r) |
| (2)-159 | (IIIc) | X | (5vv) |
| (2)-160 | (IIIc) | X | (5ww) |
| (2)-161 | (IIId) | (2a) | (5gg) |
| (2)-162 | (IIId) | (2b) | (5oo) |
| (2)-163 | (IIId) | (2f) | (5c) |
| (2)-164 | (IIId) | (2h) | (5i) |
| (2)-165 | (IIId) | (2k) | (5r) |
| (2)-166 | (IIId) | (2n) | (5gg) |
| (2)-167 | (IIId) | (2s) | (5oo) |
| (2)-168 | (IIId) | (2t) | (5c) |
| (2)-169 | (IIId) | (2a) | (5i) |
| (2)-170 | (IIId) | (2b) | (5r) |
| (2)-171 | (IIId) | (2f) | (5p) |
| (2)-172 | (IIId) | (2h) | (5x) |
| (2)-173 | (IIId) | (2k) | (5gg) |
| (2)-174 | (IIId) | (2n) | (5oo) |
| (2)-175 | (IIId) | (2s) | (5c) |
| (2)-176 | (IIId) | (2a) | (5i) |
| (2)-177 | (IIId) | (2b) | (5r) |
| (2)-178 | (IIId) | (2b) | (5a) |
| (2)-179 | (IIId) | (2f) | (5b) |
| (2)-180 | (IIId) | (2h) | (5c) |
| (2)-181 | (IIIe) | X | (5i) |
| (2)-182 | (IIIe) | X | (5r) |
| (2)-183 | (IIIe) | X | (5p) |
| (2)-184 | (IIIe) | X | (5x) |
| (2)-185 | (IIIe) | X | (5gg) |
| (2)-186 | (IIIe) | X | (5oo) |
| (2)-187 | (IIIe) | X | (5c) |
| (2)-188 | (IIIe) | X | (5i) |
| (2)-189 | (IIIe) | X | (5r) |
| (2)-190 | (IIIe) | X | (5c) |
| (2)-191 | (IIIe) | X | (5i) |
| (2)-192 | (IIIe) | X | (5r) |
| (2)-193 | (IIIe) | X | (5b) |
| (2)-194 | (IIIe) | X | (5c) |
| (2)-195 | (IIIe) | X | (5i) |
| (2)-196 | (IIIe) | X | (5r) |
| (2)-197 | (IIIe) | X | (5vv) |
| (2)-198 | (IIIe) | X | (5ww) |
| (2)-199 | (IIIe) | X | (5gg) |
| (2)-200 | (IIIe) | X | (5oo) |
| (2)-201 | (IVa) | (2a) | (6a) |
| (2)-202 | (IVa) | (2b) | (6b) |
| (2)-203 | (IVa) | (2f) | (6c) |
| (2)-204 | (IVa) | (2h) | (6g) |
| (2)-205 | (IVa) | (2k) | (6k) |

-continued

| | (I) | R² | A or A/B |
|---|---|---|---|
| (2)-206 | (IVa) | (2n) | (6m) |
| (2)-207 | (IVa) | (2s) | (6u) |
| (2)-208 | (IVa) | (2t) | (6ss) |
| (2)-209 | (IVa) | (2a) | (6tt) |
| (2)-210 | (IVa) | (2b) | (6b) |
| (2)-211 | (IVa) | (2f) | (6c) |
| (2)-212 | (IVa) | (2h) | (6g) |
| (2)-213 | (IVa) | (2k) | (6c) |
| (2)-214 | (IVa) | (2n) | (6g) |
| (2)-215 | (IVa) | (2s) | (6ss) |
| (2)-216 | (IVa) | (2a) | (6tt) |
| (2)-217 | (IVa) | (2b) | (6b) |
| (2)-218 | (IVa) | (2b) | (6m) |
| (2)-219 | (IVa) | (2f) | (6u) |
| (2)-220 | (IVa) | (2h) | (6ss) |
| (2)-221 | (IVb) | (2k) | (6tt) |
| (2)-222 | (IVb) | (2s) | (6b) |
| (2)-223 | (IVb) | (2t) | (6g) |
| (2)-224 | (IVb) | (2a) | (6a) |
| (2)-225 | (IVb) | (2a) | (6b) |
| (2)-226 | (IVb) | (2b) | (6c) |
| (2)-227 | (IVb) | (2f) | (6g) |
| (2)-228 | (IVb) | (2h) | (6k) |
| (2)-229 | (IVb) | (2k) | (6m) |
| (2)-230 | (IVb) | (2a) | (6u) |
| (2)-231 | (IVb) | (2b) | (6ss) |
| (2)-232 | (IVb) | (2t) | (6tt) |
| (2)-233 | (IVb) | (2a) | (6b) |
| (2)-234 | (IVb) | (2s) | (6c) |
| (2)-235 | (IVb) | (2t) | (6g) |
| (2)-236 | (IVb) | (2a) | (6k) |
| (2)-237 | (IVb) | (2b) | (6m) |
| (2)-238 | (IVb) | (2f) | (6u) |
| (2)-239 | (IVb) | (2s) | (6ss) |
| (2)-240 | (IVb) | (2t) | (6tt) |
| (2)-241 | (IVc) | X | (6b) |
| (2)-242 | (IVc) | X | (6c) |
| (2)-243 | (IVc) | X | (6g) |
| (2)-244 | (IVc) | X | (6ss) |
| (2)-245 | (IVc) | X | (6tt) |
| (2)-246 | (IVc) | X | (6b) |
| (2)-247 | (IVc) | X | (6m) |
| (2)-248 | (IVc) | X | (6u) |
| (2)-249 | (IVc) | X | (6a) |
| (2)-250 | (IVc) | X | (6b) |
| (2)-251 | (IVc) | X | (6c) |
| (2)-252 | (IVc) | X | (6g) |
| (2)-253 | (IVc) | X | (6k) |
| (2)-254 | (IVc) | X | (6m) |
| (2)-255 | (IVc) | X | (6u) |
| (2)-256 | (IVc) | X | (6ss) |
| (2)-257 | (IVc) | X | (6tt) |
| (2)-258 | (IVc) | X | (6ss) |
| (2)-259 | (IVc) | X | (6tt) |
| (2)-260 | (IVc) | X | (6b) |
| (2)-261 | (IVd) | (2a) | (6u) |
| (2)-262 | (IVd) | (2b) | (6a) |
| (2)-263 | (IVd) | (2f) | (6b) |
| (2)-264 | (IVd) | (2h) | (6c) |
| (2)-265 | (IVd) | (2k) | (6g) |
| (2)-266 | (IVd) | (2n) | (6k) |
| (2)-267 | (IVd) | (2s) | (6m) |
| (2)-268 | (IVd) | (2t) | (6u) |
| (2)-269 | (IVd) | (2a) | (6ss) |
| (2)-270 | (IVd) | (2b) | (6tt) |
| (2)-271 | (IVd) | (2f) | (6ss) |
| (2)-272 | (IVd) | (2h) | (6tt) |
| (2)-273 | (IVd) | (2k) | (6b) |
| (2)-274 | (IVd) | (2n) | (6k) |
| (2)-275 | (IVd) | (2s) | (6m) |
| (2)-276 | (IVd) | (2a) | (6u) |
| (2)-277 | (IVd) | (2b) | (6ss) |
| (2)-278 | (IVd) | (2b) | (6tt) |
| (2)-279 | (IVd) | (2f) | (6b) |
| (2)-280 | (IVd) | (2h) | (6g) |
| (2)-281 | (IVe) | X | (6ss) |
| (2)-282 | (IVe) | X | (6tt) |
| (2)-283 | (IVe) | X | (6b) |
| (2)-284 | (IVe) | X | (6c) |
| (2)-285 | (IVe) | X | (6g) |
| (2)-286 | (IVe) | X | (6k) |
| (2)-287 | (IVe) | X | (6m) |
| (2)-288 | (IVe) | X | (6u) |
| (2)-289 | (IVe) | X | (6ss) |
| (2)-290 | (IVe) | X | (6tt) |
| (2)-291 | (IVe) | X | (6k) |
| (2)-292 | (IVe) | X | (6m) |
| (2)-293 | (IVe) | X | (6u) |
| (2)-294 | (IVe) | X | (6b) |
| (2)-295 | (IVe) | X | (6c) |
| (2)-296 | (IVe) | X | (6g) |
| (2)-297 | (IVe) | X | (6k) |
| (2)-298 | (IVe) | X | (6m) |
| (2)-299 | (IVe) | X | (6u) |
| (2)-300 | (IVe) | X | (6ss) |
| (2)-301 | (IIf) | X | (4a) |
| (2)-302 | (IIf) | X | (4b) |
| (2)-303 | (IIf) | X | (4c) |
| (2)-304 | (IIf) | X | (4d) |
| (2)-305 | (IIf) | X | (4n) |
| (2)-306 | (IIf) | X | (4r) |
| (2)-307 | (IIf) | X | (4z) |
| (2)-308 | (IIf) | X | (4dd) |
| (2)-309 | (IIf) | X | (4ff) |
| (2)-310 | (IIf) | X | (4kk) |
| (2)-311 | (IIf) | X | (4b) |
| (2)-312 | (IIf) | X | (4c) |
| (2)-313 | (IIf) | X | (4d) |
| (2)-314 | (IIf) | X | (4n) |
| (2)-315 | (IIf) | X | (4r) |
| (2)-316 | (IIg) | (2a) | (4a) |
| (2)-317 | (IIg) | (2b) | (4b) |
| (2)-318 | (IIg) | (2b) | (4c) |
| (2)-319 | (IIg) | (2f) | (4d) |
| (2)-320 | (IIg) | (2h) | (4n) |
| (2)-321 | (IIh) | X | (4f) |
| (2)-322 | (IIh) | X | (4g) |
| (2)-323 | (IIh) | X | (4k) |
| (2)-324 | (IIh) | X | (4l) |
| (2)-325 | (IIh) | X | (4m) |
| (2)-326 | (IIh) | X | (4bbb) |
| (2)-327 | (IIh) | X | (4ccc) |
| (2)-328 | (IIh) | X | (4a) |
| (2)-329 | (IIh) | X | (4c) |
| (2)-330 | (IIh) | X | (4f) |
| (2)-331 | (IIh) | X | (4g) |
| (2)-332 | (IIh) | X | (4k) |
| (2)-333 | (IIh) | X | (4l) |
| (2)-334 | (IIh) | X | (4m) |
| (2)-335 | (IIh) | X | (4bbb) |
| (2)-336 | (IIh) | X | (4ccc) |
| (2)-337 | (IIh) | X | (4a) |
| (2)-338 | (IIh) | X | (4c) |
| (2)-339 | (IIh) | X | (4f) |
| (2)-340 | (IIh) | X | (4g) |
| (2)-341 | (IIi) | X | (4k) |
| (2)-342 | (IIi) | X | (4l) |
| (2)-343 | (IIi) | X | (4m) |
| (2)-344 | (IIi) | X | (4bbb) |
| (2)-345 | (IIi) | X | (4ccc) |
| (2)-346 | (IIi) | X | (4a) |
| (2)-347 | (IIi) | X | (4c) |
| (2)-348 | (IIi) | X | (4f) |
| (2)-349 | (IIi) | X | (4g) |
| (2)-350 | (IIi) | X | (4k) |
| (2)-351 | (IIi) | X | (4l) |
| (2)-352 | (IIi) | X | (4m) |
| (2)-353 | (IIi) | X | (4bbb) |
| (2)-354 | (IIi) | X | (4ccc) |
| (2)-355 | (IIi) | X | (5ww) |
| (2)-356 | (IIi) | X | (5xx) |
| (2)-357 | (IIi) | X | (5yy) |
| (2)-358 | (Vb) | X | (7b) |
| (2)-359 | (Vb) | X | (7c) |

-continued

|  | (I) | R² | A or A/B |
|---|---|---|---|
| (2)-360 | (Vb) | X | (7x) |
| (2)-361 | (Vb) | X | (7bb) |
| (2)-362 | (Vb) | X | (7f) |
| (2)-363 | (Vc) | X | (7aa) |
| (2)-364 | (Vc) | X | (7b) |
| (2)-365 | (Vc) | X | (7c) |
| (2)-366 | (Vc) | X | (7x) |
| (2)-367 | (Vc) | X | (7bb) |
| (2)-368 | (Vd) | X | (7f) |
| (2)-369 | (Vd) | X | (7aa) |
| (2)-370 | (Vd) | X | (7b) |
| (2)-371 | (Vd) | X | (7c) |
| (2)-372 | (Vd) | X | (7x) |
| (2)-373 | (Ve) | X | (7b) |
| (2)-374 | (Ve) | X | (7c) |
| (2)-375 | (Ve) | X | (7e) |

-continued

|  | (I) | R² | A or A/B |
|---|---|---|---|
| (2)-376 | (Ve) | X | (7i) |
| (2)-377 | (Ve) | X | (7l) |
| (2)-378 | (Vf) | X | (7b) |
| (2)-379 | (Vf) | X | (7c) |
| (2)-380 | (Vf) | X | (7e) |
| (2)-381 | (Vf) | X | (7i) |
| (2)-382 | (Vf) | X | (7l) |
| (2)-383 | (Vf) | X | (7f) |

In another embodiment, each R is independently hydrogen or $C_{1-6}$alkyl. In other embodiments, R is independently hydrogen, methyl, ethyl or trifluoromethyl.

In another aspect, the present disclosure provides compounds that are:

| No. | Structure | Name |
|---|---|---|
| 1 | 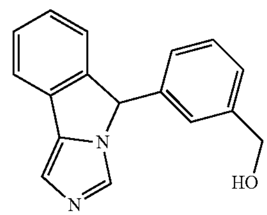 [SMILES: OCc1cccc(C2c3ccccc3-c3cncn32)c1] | (3-(5H-imidazo[5,1-a]isoindol-5-yl)phenyl)methanol |
| 2 | 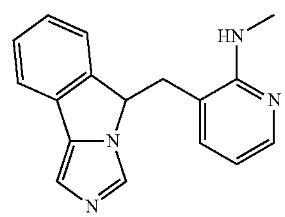 [SMILES: CNc1ncccc1CC1c2ccccc2-c2cncn21] | 3-((5H-imidazo[5,1-a]isoindol-5-yl)methyl)-N-methylpyridin-2-amine |
| 3 | 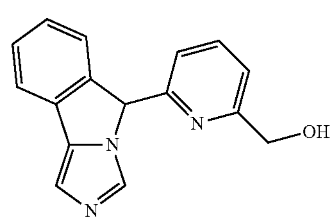 [SMILES: OCc1cccc(C2c3ccccc3-c3cncn32)n1] | (6-(5H-imidazo[5,1-a]isoindol-5-yl)pyridin-2-yl)methanol |
| 4 | 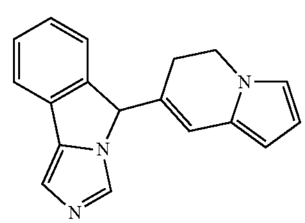 [SMILES: C1=C(C2c3ccccc3-c3cncn32)CCn2cccc21] | 5-(5,6-dihydroindolizin-7-yl)-5H-imidazo[5,1-a]isoindole |
| 5 | 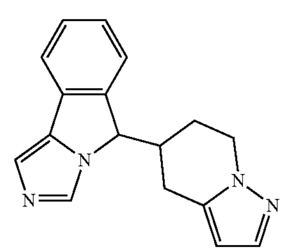 [SMILES: c1ccc2c(c1)-c1cncn1C2C1CCn2nccc2C1] | 5-(4,5,6,7-tetrahydropyrazolo[1,5-a]pyridin-5-yl)-5H-imidazo[5,1-a]isoindole |

-continued

| No. | Structure | Name |
|---|---|---|
| 6 | 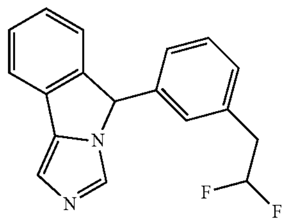 [SMILES: FC(F)Cc1cccc(C2c3ccccc3-c3cncn32)c1] | 5-(3-(2,2-difluoroethyl)phenyl)-5H-imidazo[5,1-a]isoindole |
| 7 | 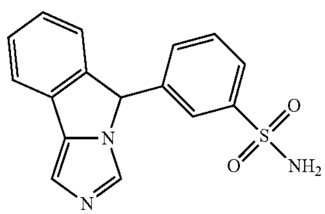 [SMILES: NS(=O)(=O)c1cccc(C2c3ccccc3-c3cncn32)c1] | 3-(5H-imidazo[5,1-a]isoindol-5-yl)benzenesulfonamide |
| 8 | 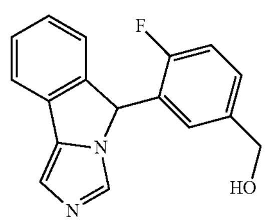 [SMILES: OCc1ccc(F)c(C2c3ccccc3-c3cncn32)c1] | (4-fluoro-3-(5H-imidazo[5,1-a]isoindol-5-yl)phenyl)methanol |
| 9 | 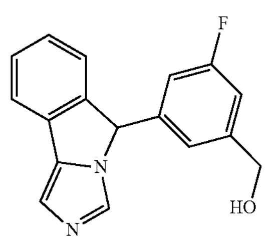 [SMILES: OCc1cc(F)cc(C2c3ccccc3-c3cncn32)c1] | (3-fluoro-5-(5H-imidazo[5,1-a]isoindol-5-yl)phenyl)methanol |
| 10 | 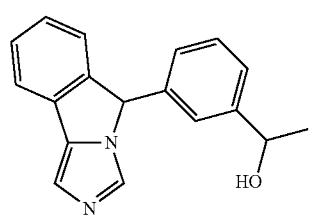 [SMILES: CC(O)c1cccc(C2c3ccccc3-c3cncn32)c1] | 1-(3-(5H-imidazo[5,1-a]isoindol-5-yl)phenyl)ethan-1-ol |
| 11 | 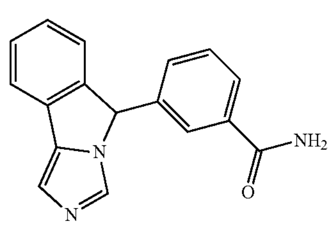 [SMILES: NC(=O)c1cccc(C2c3ccccc3-c3cncn32)c1] | 3-(5H-imidazo[5,1-a]isoindol-5-yl)benzamide |
| 12 | 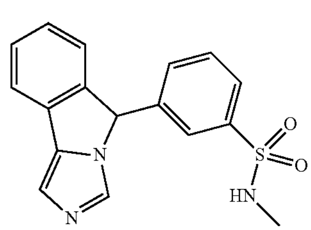 [SMILES: CNS(=O)(=O)c1cccc(C2c3ccccc3-c3cncn32)c1] | 3-(5H-imidazo[5,1-a]isoindol-5-yl)-N-methylbenzenesulfonamide |

-continued

| No. | Structure | Name |
|---|---|---|
| 13 | 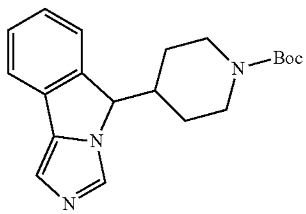 [SMILES: CC(C)(C)OC(=O)N1CCC(C2c3ccccc3-c3cncn32)CC1] | tert-butyl 4-(5H-imidazo[5,1-a]isoindol-5-yl)piperidine-1-carboxylate |
| 14 | 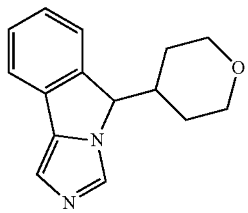 [SMILES: c1ccc2c(c1)-c1cncn1C2C1CCOCC1] | 5-(tetrahydro-2H-pyran-4-yl)-5H-imidazo[5,1-a]isoindole |
| 15 | 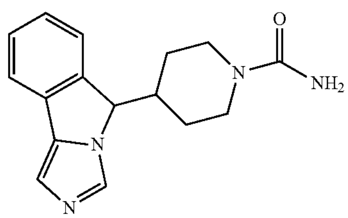 [SMILES: NC(=O)N1CCC(C2c3ccccc3-c3cncn32)CC1] | 4-(5H-imidazo[5,1-a]isoindol-5-yl)piperidine-1-carboxamide |
| 16 | 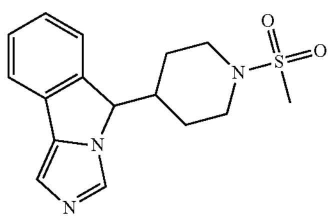 [SMILES: CS(=O)(=O)N1CCC(C2c3ccccc3-c3cncn32)CC1] | 5-(1-(methylsulfonyl)piperidin-4-yl)-5H-imidazo[5,1-a]isoindole |
| 17 | 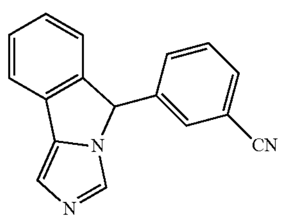 [SMILES: N#Cc1cccc(C2c3ccccc3-c3cncn32)c1] | 3-(5H-imidazo[5,1-a]isoindol-5-yl)benzonitrile |
| 18 | 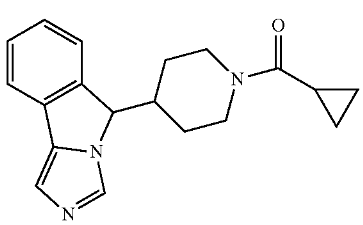 [SMILES: O=C(C1CC1)N1CCC(C2c3ccccc3-c3cncn32)CC1] | (4-(5H-imidazo[5,1-a]isoindol-5-yl)piperidin-1-yl)(cyclopropyl)methanone |
| 19 | 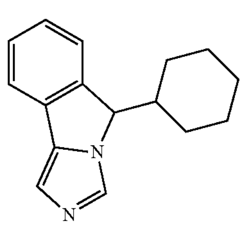 [SMILES: c1ccc2c(c1)-c1cncn1C2C1CCCCC1] | 5-cyclohexyl-5H-imidazo[5,1-a]isoindole |

| No. | Structure | Name |
|---|---|---|
| 20 | 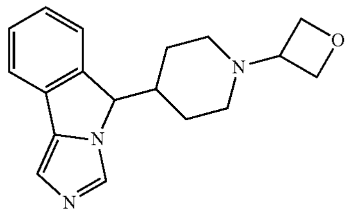 [SMILES: c1ccc2c(c1)-c1cncn1C2C1CCN(C2COC2)CC1] | 5-(1-(oxetan-3-yl)piperidin-4-yl)-5H-imidazo[5,1-a]isoindole |
| 21 | 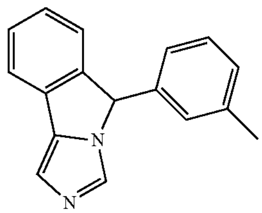 [SMILES: Cc1cccc(C2c3ccccc3-c3cncn32)c1] | 5-(m-tolyl)-5H-imidazo[5,1-a]isoindole |
| 22 | 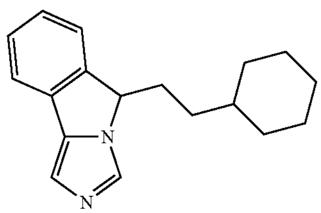 [SMILES: c1ccc2c(c1)-c1cncn1C2CCC1CCCCC1] | 5-(2-cyclohexylethyl)-5H-imidazo[5,1-a]isoindole |
| 23 | 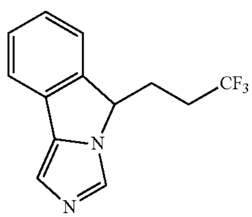 [SMILES: FC(F)(F)CCC1c2ccccc2-c2cncn21] | 5-(3,3,3-trifluoropropyl)-5H-imidazo[5,1-a]isoindole |
| 24 | 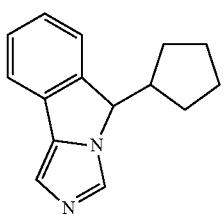 [SMILES: c1ccc2c(c1)-c1cncn1C2C1CCCC1] | 5-cyclopentyl-5H-imidazo[5,1-a]isoindole |
| 25 | 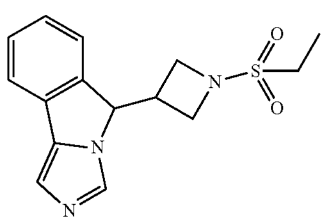 [SMILES: CCS(=O)(=O)N1CC(C2c3ccccc3-c3cncn32)C1] | 5-(1-(ethylsulfonyl)azetidin-3-yl)-5H-imidazo[5,1-a]isoindole |
| 26 | 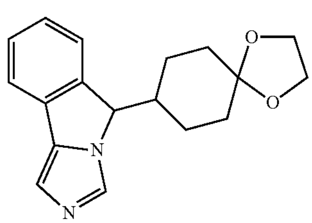 [SMILES: c1ccc2c(c1)-c1cncn1C2C1CCC2(CC1)OCCO2] | 5-(1,4-dioxaspiro[4.5]decan-8-yl)-5H-imidazo[5,1-a]isoindole |

-continued

| No. | Structure | Name |
|---|---|---|
| 27 | 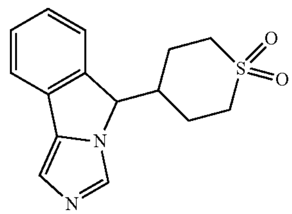 [SMILES: O=S1(=O)CCC(C2c3ccccc3-c3cncn32)CC1] | 4-(5H-imidazo[5,1-a]isoindol-5-yl)tetrahydro-2H-thiopyran 1,1-dioxide |
| 28 | 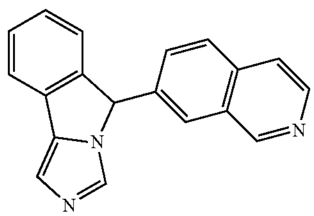 [SMILES: c1ccc2c(c1)-c1cncn1C2c1ccc2ccncc2c1] | 5-(isoquinolin-7-yl)-5H-imidazo[5,1-a]isoindole |
| 29 | 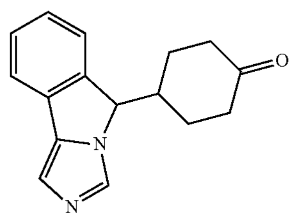 [SMILES: O=C1CCC(C2c3ccccc3-c3cncn32)CC1] | 4-(5H-imidazo[5,1-a]isoindol-5-yl)cyclohexan-1-one |
| 30 | 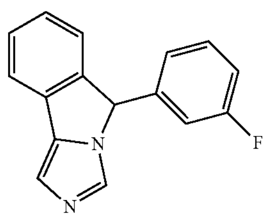 [SMILES: Fc1cccc(C2c3ccccc3-c3cncn32)c1] | 5-(3-fluorophenyl)-5H-imidazo[5,1-a]isoindole |
| 31 | 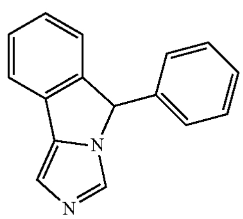 | 5-phenyl-5H-imidazo[5,1-a]isoindole |
| 32 | 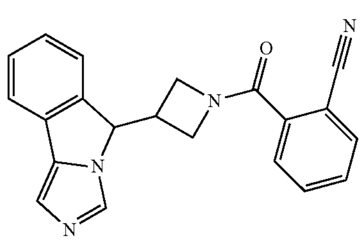 [SMILES: N#Cc1ccccc1C(=O)N1CC(C2c3ccccc3-c3cncn32)C1] | 2-(3-(5H-imidazo[5,1-a]isoindol-5-yl)azetidine-1-carbonyl)benzonitrile |
| 33 | 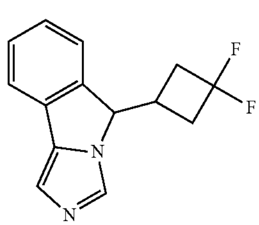 [SMILES: FC1(F)CC(C2c3ccccc3-c3cncn32)C1] | 5-(3,3-difluorocyclobutyl)-5H-imidazo[5,1-a]isoindole |

-continued

| No. | Structure | Name |
| --- | --- | --- |
| 34 | 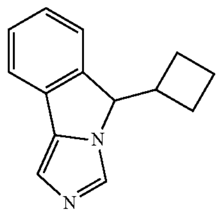 [SMILES: c1ccc2c(c1)-c1cncn1C2C1CCC1] | 5-cyclobutyl-5H-imidazo[5,1-a]isoindole |
| 35 | 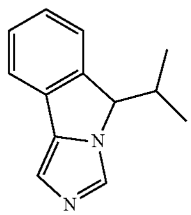 | 5-isopropyl-5H-imidazo[5,1-a]isoindole |
| 36 | 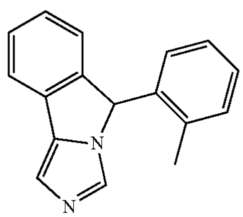 [SMILES: Cc1ccccc1C1c2ccccc2-c2cncn21] | 5-(o-tolyl)-5H-imidazo[5,1-a]isoindole |
| 37 | 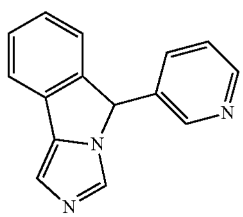 [SMILES: c1cncc(C2c3ccccc3-c3cncn32)c1] | 5-(pyridin-3-yl)-5H-imidazo[5,1-a]isoindole |
| 38 | 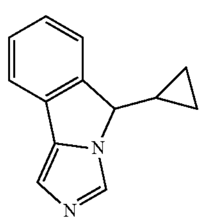 [SMILES: c1ccc2c(c1)-c1cncn1C2C1CC1] | 5-cyclopropyl-5H-imidazo[5,1-a]isoindole |
| 39 | 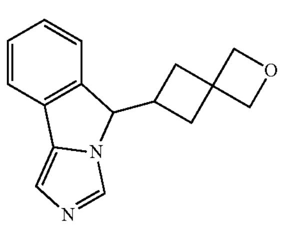 [SMILES: c1ccc2c(c1)-c1cncn1C2C1CC2(COC2)C1] | 5-(2-oxaspiro[3.3]heptan-6-yl)-5H-imidazo[5,1-a]isoindole |
| 40 | 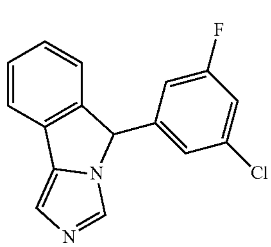 [SMILES: Fc1cc(Cl)cc(C2c3ccccc3-c3cncn32)c1] | 5-(3-chloro-5-fluorophenyl)-5H-imidazo[5,1-a]isoindole |

-continued

| No. | Structure | Name |
|---|---|---|
| 41 | 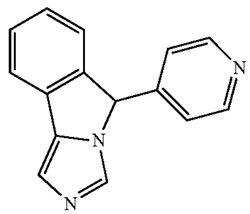 [SMILES: c1ccc2c(c1)-c1cncn1C2c1ccncc1] | 5-(pyridin-4-yl)-5H-imidazo[5,1-a]isoindole |
| 42 | 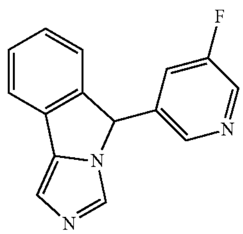 [SMILES: Fc1cncc(C2c3ccccc3-c3cncn32)c1] | 5-(5-fluoropyridin-3-yl)-5H-imidazo[5,1-a]isoindole |
| 43 | 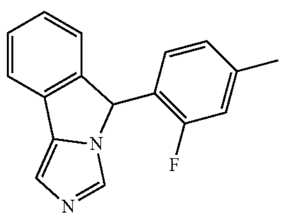 [SMILES: Cc1ccc(C2c3ccccc3-c3cncn32)c(F)c1] | 5-(2-fluoro-4-methylphenyl)-5H-imidazo[5,1-a]isoindole |
| 44 | 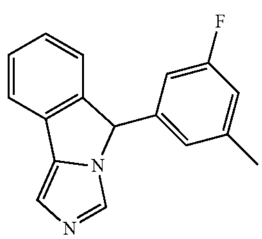 [SMILES: Cc1cc(F)cc(C2c3ccccc3-c3cncn32)c1] | 5-(3-fluoro-5-methylphenyl)-5H-imidazo[5,1-a]isoindole |
| 45 | 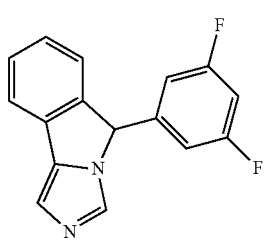 [SMILES: Fc1cc(F)cc(C2c3ccccc3-c3cncn32)c1] | 5-(3,5-difluorophenyl)-5H-imidazo[5,1-a]isoindole |
| 46 | 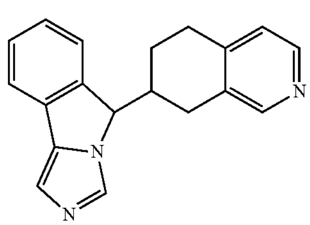 [SMILES: c1ccc2c(c1)-c1cncn1C2C1CCc2ccncc2C1] | 5-(5,6,7,8-tetrahydroisoquinolin-7-yl)-5H-imidazo[5,1-a]isoindole |
| 47 | 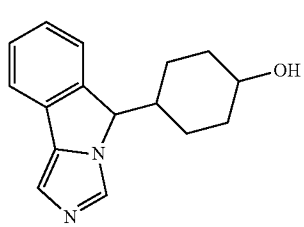 [SMILES: OC1CCC(C2c3ccccc3-c3cncn32)CC1] | 4-(5H-imidazo[5,1-a]isoindol-5-yl)cyclohexan-1-ol |

-continued

| No. | Structure | Name |
|---|---|---|
| 48 | 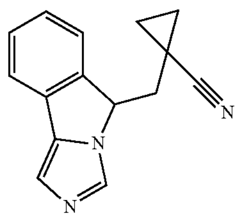 [SMILES: N#CC1(CC2c3ccccc3-c3cncn32)CC1] | 1-((5H-imidazo[5,1-a]isoindol-5-yl)methyl)cyclopropane-1-carbonitrile |
| 49 | 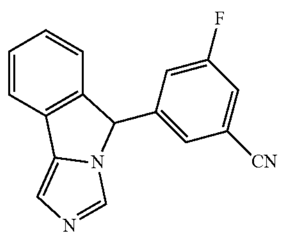 [SMILES: N#Cc1cc(F)cc(C2c3ccccc3-c3cncn32)c1] | 3-fluoro-5-(5H-imidazo[5,1-a]isoindol-5-yl)benzonitrile |
| 50 | 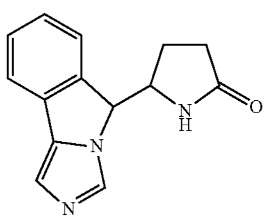 [SMILES: O=C1CCC(C2c3ccccc3-c3cncn32)N1] | 5-(5H-imidazo[5,1-a]isoindol-5-yl)pyrrolidin-2-one |
| 51 | 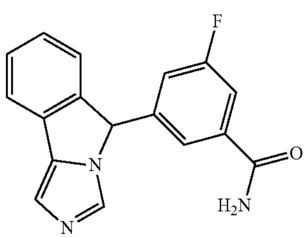 [SMILES: NC(=O)c1cc(F)cc(C2c3ccccc3-c3cncn32)c1] | 3-fluoro-5-(5H-imidazo[5,1-a]isoindol-5-yl)benzamide |
| 52 | 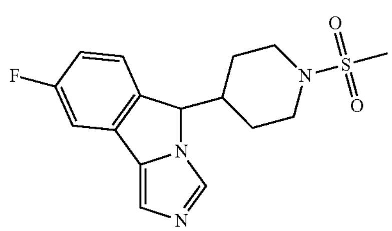 [SMILES: CS(=O)(=O)N1CCC(C2c3ccc(F)cc3-c3cncn32)CC1] | 8-fluoro-5-(1-(methylsulfonyl)piperidin-4-yl)-5H-imidazo[5,1-a]isoindole |
| 53 | 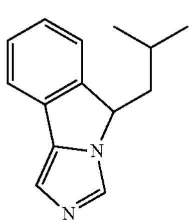 [SMILES: CC(C)CC1c2ccccc2-c2cncn21] | 5-isobutyl-5H-imidazo[5,1-a]isoindole |

-continued

| No. | Structure | Name |
|---|---|---|
| 54 | 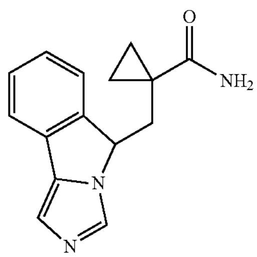 [SMILES: NC(=O)C1(CC2c3ccccc3-c3cncn32)CC1] | 1-((5H-imidazo[5,1-a]isoindol-5-yl)methyl)cyclopropane-1-carboxamide |
| 55 | 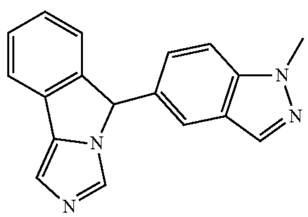 [SMILES: Cn1ncc2cc(C3c4ccccc4-c4cncn43)ccc21] | 5-(1-methyl-1H-indazol-5-yl)-5H-imidazo[5,1-a]isoindole |
| 56 | 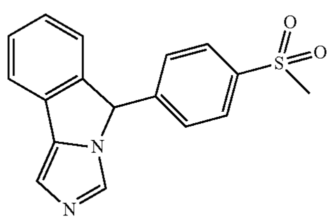 [SMILES: CS(=O)(=O)c1ccc(C2c3ccccc3-c3cncn32)cc1] | 5-(4-(methylsulfonyl)phenyl)-5H-imidazo[5,1-a]isoindole |
| 57 | 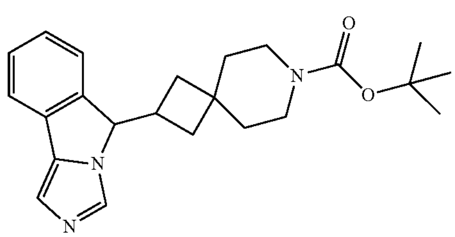 [SMILES: CC(C)(C)OC(=O)N1CCC2(CC1)CC(C1c3ccccc3-c3cncn31)C2] | tert-butyl 2-(5H-imidazo[5,1-a]isoindol-5-yl)-7-azaspiro[3.5]nonane-7-carboxylate |
| 58 | 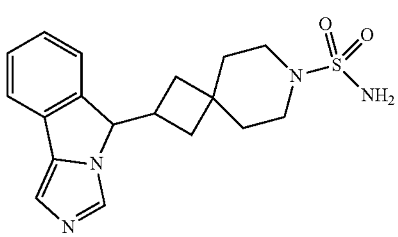 [SMILES: NS(=O)(=O)N1CCC2(CC1)CC(C1c3ccccc3-c3cncn31)C2] | 2-(5H-imidazo[5,1-a]isoindol-5-yl)-7-azaspiro[3.5]nonane-7-sulfonamide |
| 59 | 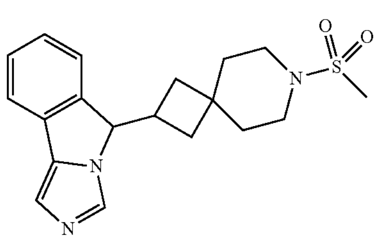 [SMILES: CS(=O)(=O)N1CCC2(CC1)CC(C1c3ccccc3-c3cncn31)C2] | 5-(7-(methylsulfonyl)-7-azaspiro[3.5]nonan-2-yl)-5H-imidazo[5,1-a]isoindole |

-continued

| No. | Structure | Name |
|---|---|---|
| 60 | 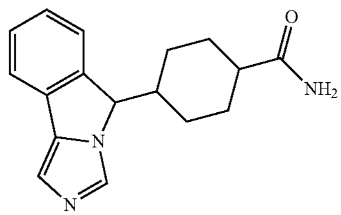 [SMILES: NC(=O)C1CCC(C2c3ccccc3-c3cncn32)CC1] | 4-(5H-imidazo[5,1-a]isoindol-5-yl)cyclohexane-1-carboxamide |
| 61 | 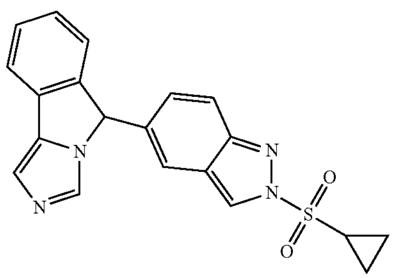 [SMILES: O=S(=O)(C1CC1)n1cc2cc(C3c4ccccc4-c4cncn43)ccc2n1] | 5-(2-(cyclopropylsulfonyl)-2H-indazol-5-yl)-5H-imidazo[5,1-a]isoindole |
| 62 | 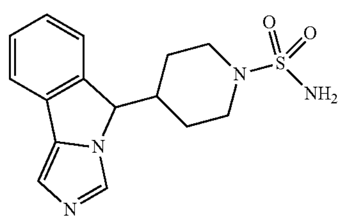 [SMILES: NS(=O)(=O)N1CCC(C2c3ccccc3-c3cncn32)CC1] | 4-(5H-imidazo[5,1-a]isoindol-5-yl)piperidine-1-sulfonamide |
| 63 | 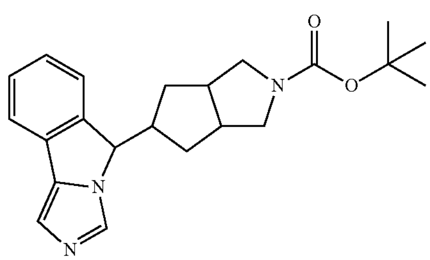 [SMILES: CC(C)(C)OC(=O)N1CC2CC(C3c4ccccc4-c4cncn43)CC2C1] | tert-butyl 5-(5H-imidazo[5,1-a]isoindol-5-yl)hexahydrocyclopenta[c]pyrrole-2(1H)-carboxylate |
| 64 | 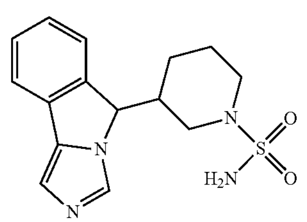 [SMILES: NS(=O)(=O)N1CCCC(C2c3ccccc3-c3cncn32)C1] | 3-(5H-imidazo[5,1-a]isoindol-5-yl)piperidine-1-sulfonamide |
| 65 | 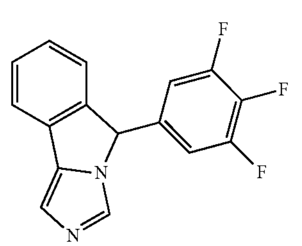 [SMILES: Fc1cc(C2c3ccccc3-c3cncn32)cc(F)c1F] | 5-(3,4,5-trifluorophenyl)-5H-imidazo[5,1-a]isoindole |

-continued

| No. | Structure | Name |
|---|---|---|
| 66 | 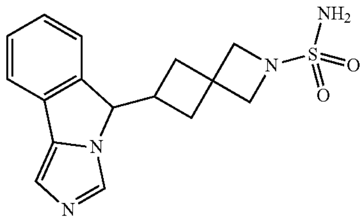 [SMILES: NS(=O)(=O)N1CC2(CC(C3c4ccccc4-c4cncn43)C2)C1] | 6-(5H-imidazo[5,1-a]isoindol-5-yl)-2-azaspiro[3.3]heptane-2-sulfonamide |
| 67 | 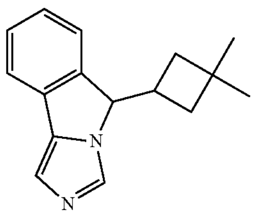 [SMILES: CC1(C)CC(C2c3ccccc3-c3cncn32)C1] | 5-(3,3-dimethylcyclobutyl)-5H-imidazo[5,1-a]isoindole |
| 68 | 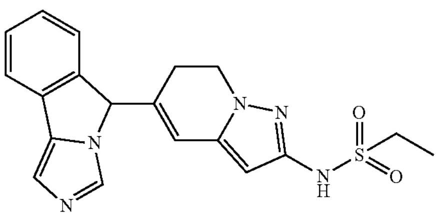 [SMILES: CCS(=O)(=O)Nc1cc2n(n1)CCC(C1c3ccccc3-c3cncn31)=C2] | N-(5-(5H-imidazo[5,1-a]isoindol-5-yl)-6,7-dihydropyrazolo[1,5-a]pyridin-2-yl)ethanesulfonamide |
| 69 | 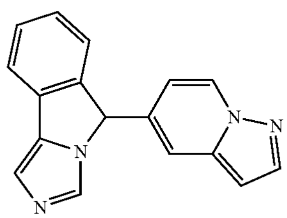 [SMILES: c1ccc2c(c1)-c1cncn1C2c1ccn2nccc2c1] | 5-(pyrazolo[1,5-a]pyridin-5-yl)-5H-imidazo[5,1-a]isoindole |
| 70 | 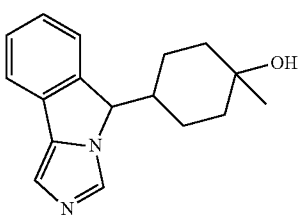 [SMILES: CC1(O)CCC(C2c3ccccc3-c3cncn32)CC1] | 4-(5H-imidazo[5,1-a]isoindol-5-yl)-1-methylcyclohexan-1-ol |
| 71 | 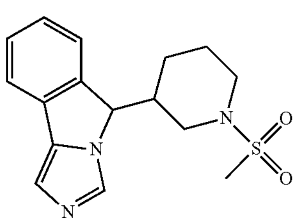 [SMILES: CS(=O)(=O)N1CCCC(C2c3ccccc3-c3cncn32)C1] | 5-(1-(methylsulfonyl)piperidin-3-yl)-5H-imidazo[5,1-a]isoindole |
| 72 | 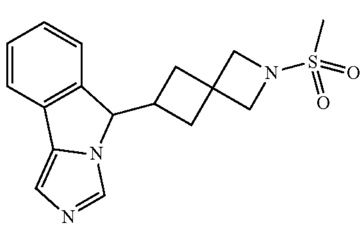 [SMILES: CS(=O)(=O)N1CC2(CC(C3c4ccccc4-c4cncn43)C2)C1] | 5-(2-(methylsulfonyl)-2-azaspiro[3.3]heptan-6-yl)-5H-imidazo[5,1-a]isoindole |

| No. | Structure | Name |
|---|---|---|
| 73 | 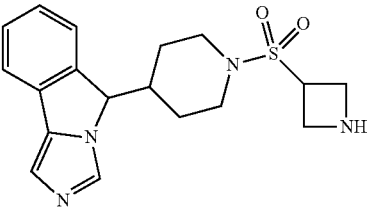 [SMILES: O=S(=O)(C1CNC1)N1CCC(C2c3ccccc3-c3cncn32)CC1] | 5-(1-(azetidin-3-ylsulfonyl)piperidin-4-yl)-5H-imidazo[5,1-a]isoindole |
| 74 | 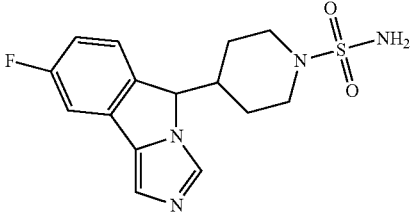 [SMILES: NS(=O)(=O)N1CCC(C2c3ccc(F)cc3-c3cncn32)CC1] | 4-(8-fluoro-5H-imidazo[5,1-a]isoindol-5-yl)piperidine-1-sulfonamide |
| 75a | 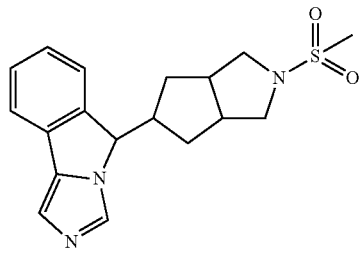 [SMILES: CS(=O)(=O)N1CC2CC(C3c4ccccc4-c4cncn43)CC2C1] | 5-(2-(methylsulfonyl)octahydrocyclopenta[c]pyrrol-5-yl)-5H-imidazo[5,1-a]isoindole |
| 75b | 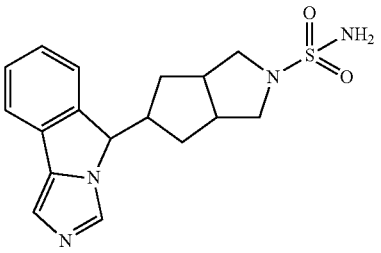 [SMILES: NS(=O)(=O)N1CC2CC(C3c4ccccc4-c4cncn43)CC2C1] | 5-(5H-imidazo[5,1-a]isoindol-5-yl)hexahydrocyclopenta[c]pyrrole-2(1H)-sulfonamide |
| 76 | 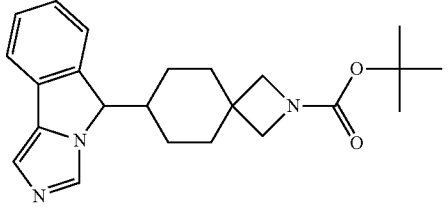 [SMILES: CC(C)(C)OC(=O)N1CC2(CCC(C3c4ccccc4-c4cncn43)CC2)C1] | tert-butyl 7-(5H-imidazo[5,1-a]isoindol-5-yl)-2-azaspiro[3.5]nonane-2-carboxylate |
| 77 | 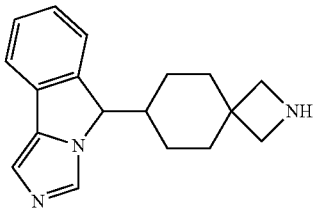 [SMILES: c1ccc2c(c1)-c1cncn1C2C1CCC2(CC1)CNC2] | 5-(2-azaspiro[3.5]nonan-7-yl)-5H-imidazo[5,1-a]isoindole |

-continued

| No. | Structure | Name |
|---|---|---|
| 78 | 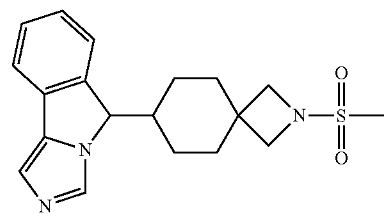 [SMILES: CS(=O)(=O)N1CC2(CCC(C3c4ccccc4-c4cncn43)CC2)C1] | 5-(2-(methylsulfonyl)-2-azaspiro[3.5]nonan-7-yl)-5H-imidazo[5,1-a]isoindole |
| 79 | 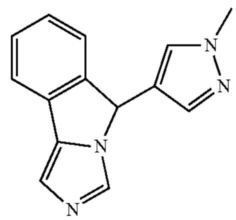 [SMILES: Cn1cc(C2c3ccccc3-c3cncn32)cn1] | 5-(1-methyl-1H-pyrazol-4-yl)-5H-imidazo[5,1-a]isoindole |
| 80 | 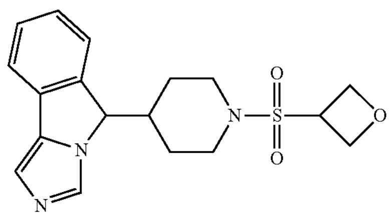 [SMILES: O=S(=O)(C1COC1)N1CCC(C2c3ccccc3-c3cncn32)CC1] | 5-(1-(oxetan-3-ylsulfonyl)piperidin-4-yl)-5H-imidazo[5,1-a]isoindole |
| 81 | 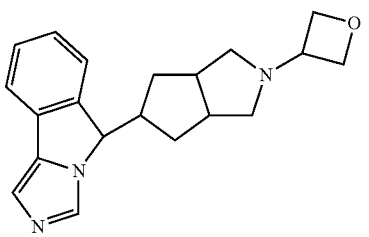 [SMILES: c1ccc2c(c1)-c1cncn1C2C1CC2CN(C3COC3)CC2C1] | 5-(2-(oxetan-3-yl)octahydrocyclopenta[c]pyrrol-5-yl)-5H-imidazo[5,1-a]isoindole |
| 82 | 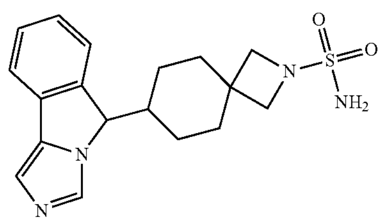 [SMILES: NS(=O)(=O)N1CC2(CCC(C3c4ccccc4-c4cncn43)CC2)C1] | 7-(5H-imidazo[5,1-a]isoindol-5-yl)-2-azaspiro[3.5]nonane-2-sulfonamide |
| 83 | 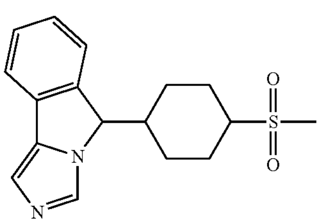 [SMILES: CS(=O)(=O)C1CCC(C2c3ccccc3-c3cncn32)CC1] | 5-(4-(methylsulfonyl)cyclohexyl)-5H-imidazo[5,1-a]isoindole |
| 84 | 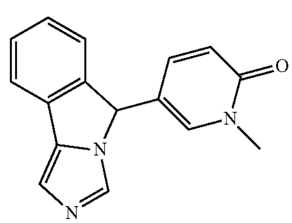 [SMILES: Cn1cc(C2c3ccccc3-c3cncn32)ccc1=O] | 5-(5H-imidazo[5,1-a]isoindol-5-yl)-1-methylpyridin-2(1H)-one |

| No. | Structure | Name |
| --- | --- | --- |
| 85 | 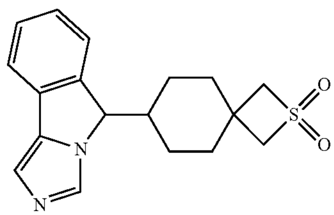 [SMILES: O=S1(=O)CC2(CCC(C3c4ccccc4-c4cncn43)CC2)C1] | 7-(5H-imidazo[5,1-a]isoindol-5-yl)-2-thiaspiro[3.5]nonane 2,2-dioxide |
| 86 | 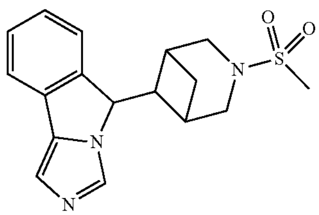 [SMILES: CS(=O)(=O)N1CC2CC(C1)C2C1c2ccccc2-c2cncn21] | 5-(3-(methylsulfonyl)-3-azabicyclo[3.1.1]heptan-6-yl)-5H-imidazo[5,1-a]isoindole |
| 87 | 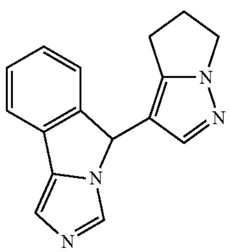 [SMILES: c1ccc2c(c1)-c1cncn1C2c1cnn2c1CCC2] | 5-(5,6-dihydro-4H-pyrrolo[1,2-b]pyrazol-3-yl)-5H-imidazo[5,1-a]isoindole |
| 88 | 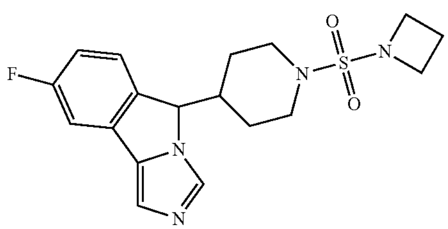 [SMILES: O=S(=O)(N1CCC1)N1CCC(C2c3ccc(F)cc3-c3cncn32)CC1] | 5-(1-(azetidin-1-ylsulfonyl)piperidin-4-yl)-8-fluoro-5H-imidazo[5,1-a]isoindole |
| 89 | 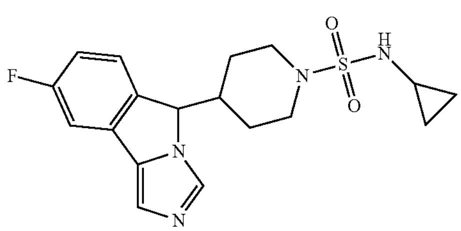 [SMILES: O=S(=O)(NC1CC1)N1CCC(C2c3ccc(F)cc3-c3cncn32)CC1] | N-cyclopropyl-4-(8-fluoro-5H-imidazo[5,1-a]isoindol-5-yl)piperidine-1-sulfonamide |
| 90 | 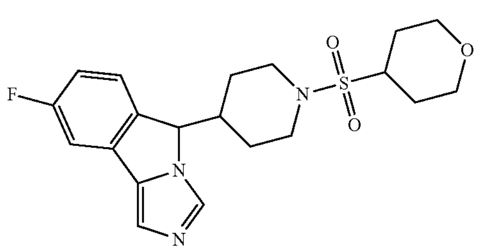 [SMILES: O=S(=O)(C1CCOCC1)N1CCC(C2c3ccc(F)cc3-c3cncn32)CC1] | 4-((4-(8-fluoro-5H-imidazo[5,1-a]isoindol-5-yl)piperidin-1-yl)sulfonyl)morpholine |

| No. | Structure | Name |
|---|---|---|
| 91 | 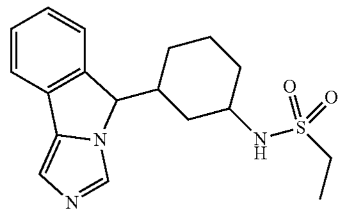 [SMILES: CCS(=O)(=O)NC1CCCC(C2c3ccccc3-c3cncn32)C1] | N-(3-(5H-imidazo[5,1-a]isoindol-5-yl)cyclohexyl)ethanesulfonamide |
| 92 | 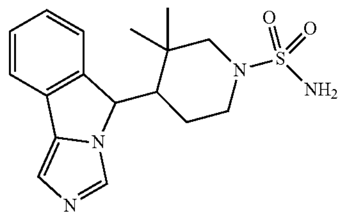 [SMILES: CC1(C)CN(S(N)(=O)=O)CCC1C1c2ccccc2-c2cncn21] | 4-(5H-imidazo[5,1-a]isoindol-5-yl)-3,3-dimethylpiperidine-1-sulfonamide |
| 93 | 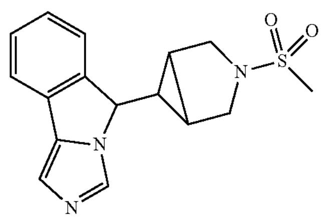 [SMILES: CS(=O)(=O)N1CC2C(C1)C2C1c2ccccc2-c2cncn21] | 5-(3-(methylsulfonyl)-3-azabicyclo[3.1.0]hexan-6-yl)-5H-imidazo[5,1-a]isoindole |
| 94 | 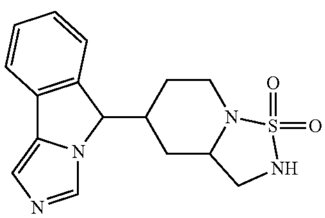 [SMILES: O=S1(=O)NCC2CC(C3c4ccccc4-c4cncn43)CCN21] | 5-(5H-imidazo[5,1-a]isoindol-5-yl)hexahydro-2H-[1,2,5]thiadiazolo[2,3-a]pyridine 1,1-dioxide |
| 95 | 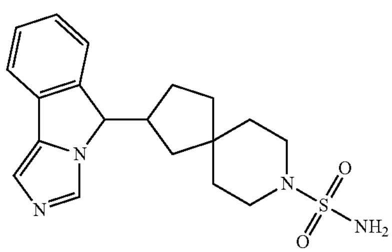 [SMILES: NS(=O)(=O)N1CCC2(CCC(C3c4ccccc4-c4cncn43)C2)CC1] | 2-(5H-imidazo[5,1-a]isoindol-5-yl)-8-azaspiro[4.5]decane-8-sulfonamide |
| 96 | | 6-(5H-imidazo[5,1-a]isoindol-5-yl)-3-azabicyclo[3.1.0]hexane-3-sulfonamide | or a pharmaceutically acceptable salt thereof, or an enantiomer or diastereoisomer thereof, or a racemic mixture thereof.

In one embodiment, the compounds of the invention are (3-(5H-imidazo[5,1-a]isoindol-5-yl)phenyl)methanol
5-(3-(2,2-difluoroethyl)phenyl)-5H-imidazo[5,1-a]isoindole
3-(5H-imidazo[5,1-a]isoindol-5-yl)benzenesulfonamide
(3-fluoro-5-(5H-imidazo[5,1-a]isoindol-5-yl)phenyl)methanol
1-(3-(5H-imidazo[5,1-a]isoindol-5-yl)phenyl)ethan-1-ol
3-(5H-imidazo[5,1-a]isoindol-5-yl)benzamide
5-(tetrahydro-2H-pyran-4-yl)-5H-imidazo[5,1-a]isoindole
5-(1-(methylsulfonyl)piperidin-4-yl)-5H-imidazo[5,1-a]isoindole
5-cyclohexyl-5H-imidazo[5,1-a]isoindole 5-(m-tolyl)-5H-imidazo[5,1-a]isoindole
5-(3,3,3-trifluoropropyl)-5H-imidazo[5,1-a]isoindole
5-cyclopentyl-5H-imidazo[5,1-a]isoindole
4-(5H-imidazo[5,1-a]isoindol-5-yl)tetrahydro-2H-thiopyran 1,1-dioxide
5-(isoquinolin-7-yl)-5H-imidazo[5,1-a]isoindole
4-(5H-imidazo[5,1-a]isoindol-5-yl)cyclohexan-1-one
5-(3-fluorophenyl)-5H-imidazo[5,1-a]isoindole
5-phenyl-5H-imidazo[5,1-a]isoindole
5-(3,3-difluorocyclobutyl)-5H-imidazo[5,1-a]isoindole
5-cyclobutyl-5H-imidazo[5,1-a]isoindole
5-(2-oxaspiro[3.3]heptan-6-yl)-5H-imidazo[5,1-a]isoindole
5-(3-chloro-5-fluorophenyl)-5H-imidazo[5,1-a]isoindole
5-(2-fluoro-4-methylphenyl)-5H-imidazo[5,1-a]isoindole
5-(3-fluoro-5-methylphenyl)-5H-imidazo[5,1-a]isoindole
5-(3,5-difluorophenyl)-5H-imidazo[5,1-a]isoindole
5-(5,6,7,8-tetrahydroisoquinolin-7-yl)-5H-imidazo[5,1-a]isoindole
4-(5H-imidazo[5,1-a]isoindol-5-yl)cyclohexan-1-ol
3-fluoro-5-(5H-imidazo[5,1-a]isoindol-5-yl)benzonitrile
5-(5H-imidazo[5,1-a]isoindol-5-yl)pyrrolidin-2-one
3-fluoro-5-(5H-imidazo[5,1-a]isoindol-5-yl)benzamide
8-fluoro-5-(1-(methylsulfonyl)piperidin-4-yl)-5H-imidazo[5,1-a]isoindole
5-isobutyl-5H-imidazo[5,1-a]isoindole
5-(1-methyl-1H-indazol-5-yl)-5H-imidazo[5,1-a]isoindole
5-(4-(methylsulfonyl)phenyl)-5H-imidazo[5,1-a]isoindole
tert-butyl 2-(5H-imidazo[5,1-a]isoindol-5-yl)-7-azaspiro[3.5]nonane-7-carboxylate
2-(5H-imidazo[5,1-a]isoindol-5-yl)-7-azaspiro[3.5]nonane-7-sulfonamide
5-(7-(methylsulfonyl)-7-azaspiro[3.5]nonan-2-yl)-5H-imidazo[5,1-a]isoindole
4-(5H-imidazo[5,1-a]isoindol-5-yl)cyclohexane-1-carboxamide
5-(2-(cyclopropylsulfonyl)-2H-indazol-5-yl)-5H-imidazo[5,1-a]isoindole
4-(5H-imidazo[5,1-a]isoindol-5-yl)piperidine-1-sulfonamide
3-(5H-imidazo[5,1-a]isoindol-5-yl)piperidine-1-sulfonamide
5-(3,4,5-trifluorophenyl)-5H-imidazo[5,1-a]isoindole
5-(3,3-dimethylcyclobutyl)-5H-imidazo[5,1-a]isoindole
4-(5H-imidazo[5,1-a]isoindol-5-yl)-1-methylcyclohexan-1-ol
5-(1-(methylsulfonyl)piperidin-3-yl)-5H-imidazo[5,1-a]isoindole
5-(2-(methylsulfonyl)-2-azaspiro[3.3]heptan-6-yl)-5H-imidazo[5,1-a]isoindole
5-(1-(azetidin-3-ylsulfonyl)piperidin-4-yl)-5H-imidazo[5,1-a]isoindole
4-(8-fluoro-5H-imidazo[5,1-a]isoindol-5-yl)piperidine-1-sulfonamide
tert-butyl 7-(5H-imidazo[5,1-a]isoindol-5-yl)-2-azaspiro[3.5]nonane-2-carboxylate
5-(1-methyl-1H-pyrazol-4-yl)-5H-imidazo[5,1-a]isoindole
5-(1-(oxetan-3-ylsulfonyl)piperidin-4-yl)-5H-imidazo[5,1-a]isoindole
5-(4-(methylsulfonyl)cyclohexyl)-5H-imidazo[5,1-a]isoindole
5-(5H-imidazo[5,1-a]isoindol-5-yl)-1-methylpyridin-2(1H)-one
5-(3-(methylsulfonyl)-3-azabicyclo[3.1.1]heptan-6-yl)-5H-imidazo[5,1-a]isoindole
5-(1-(azetidin-1-ylsulfonyl)piperidin-4-yl)-8-fluoro-5H-imidazo[5,1-a]isoindole
N-cyclopropyl-4-(8-fluoro-5H-imidazo[5,1-a]isoindol-5-yl)piperidine-1-sulfonamide
4-((4-(8-fluoro-5H-imidazo[5,1-a]isoindol-5-yl)piperidin-1-yl)sulfonyl)morpholine
N-(3-(5H-imidazo[5,1-a]isoindol-5-yl)cyclohexyl)ethanesulfonamide
4-(5H-imidazo[5,1-a]isoindol-5-yl)-3,3-dimethylpiperidine-1-sulfonamide
5-(3-(methylsulfonyl)-3-azabicyclo[3.1.0]hexan-6-yl)-5H-imidazo[5,1-a]isoindole
5-(5H-imidazo[5,1-a]isoindol-5-yl)hexahydro-2H-[1,2,5]thiadiazolo[2,3-a]pyridine 1,1-dioxide
2-(5H-imidazo[5,1-a]isoindol-5-yl)-8-azaspiro[4.5]decane-8-sulfonamide
6-(5H-imidazo[5,1-a]isoindol-5-yl)-3-azabicyclo[3.1.0]hexane-3-sulfonamide or a pharmaceutically acceptable salt thereof, or an enantiomer or diastereoisomer thereof, or a racemic mixture thereof.

In another embodiment, the compounds of the invention are (3-(5H-imidazo[5,1-a]isoindol-5-yl)phenyl)methanol
(3-fluoro-5-(5H-imidazo[5,1-a]isoindol-5-yl)phenyl)methanol
1-(3-(5H-imidazo[5,1-a]isoindol-5-yl)phenyl)ethan-1-ol
5-(1-(methylsulfonyl)piperidin-4-yl)-5H-imidazo[5,1-a]isoindole
5-cyclohexyl-5H-imidazo[5,1-a]isoindole
5-(m-tolyl)-5H-imidazo[5,1-a]isoindole
5-cyclopentyl-5H-imidazo[5,1-a]isoindole
4-(5H-imidazo[5,1-a]isoindol-5-yl)tetrahydro-2H-thiopyran 1,1-dioxide
5-(isoquinolin-7-yl)-5H-imidazo[5,1-a]isoindole
5-(3-fluorophenyl)-5H-imidazo[5,1-a]isoindole
5-phenyl-5H-imidazo[5,1-a]isoindole
5-(3-chloro-5-fluorophenyl)-5H-imidazo[5,1-a]isoindole
5-(2-fluoro-4-methylphenyl)-5H-imidazo[5,1-a]isoindole
5-(3-fluoro-5-methylphenyl)-5H-imidazo[5,1-a]isoindole
5-(3,5-difluorophenyl)-5H-imidazo[5,1-a]isoindole
5-(5,6,7,8-tetrahydroisoquinolin-7-yl)-5H-imidazo[5,1-a]isoindole
4-(5H-imidazo[5,1-a]isoindol-5-yl)cyclohexan-1-ol
5-(5H-imidazo[5,1-a]isoindol-5-yl)pyrrolidin-2-one
3-fluoro-5-(5H-imidazo[5,1-a]isoindol-5-yl)benzamide
8-fluoro-5-(1-(methylsulfonyl)piperidin-4-yl)-5H-imidazo[5,1-a]isoindole
2-(5H-imidazo[5,1-a]isoindol-5-yl)-7-azaspiro[3.5]nonane-7-sulfonamide
5-(7-(methylsulfonyl)-7-azaspiro[3.5]nonan-2-yl)-5H-imidazo[5,1-a]isoindole
4-(5H-imidazo[5,1-a]isoindol-5-yl)cyclohexane-1-carboxamide
5-(2-(cyclopropylsulfonyl)-2H-indazol-5-yl)-5H-imidazo[5,1-a]isoindole
4-(5H-imidazo[5,1-a]isoindol-5-yl)piperidine-1-sulfonamide
3-(5H-imidazo[5,1-a]isoindol-5-yl)piperidine-1-sulfonamide
5-(3,4,5-trifluorophenyl)-5H-imidazo[5,1-a]isoindole
5-(3,3-dimethylcyclobutyl)-5H-imidazo[5,1-a]isoindole
4-(5H-imidazo[5,1-a]isoindol-5-yl)-1-methylcyclohexan-1-ol
4-(8-fluoro-5H-imidazo[5,1-a]isoindol-5-yl)piperidine-1-sulfonamide
tert-butyl 7-(5H-imidazo[5,1-a]isoindol-5-yl)-2-azaspiro[3.5]nonane-2-carboxylate 5-(1-(oxetan-3-ylsulfonyl)piperidin-4-yl)-5H-imidazo[5,1-a]isoindole
5-(4-(methylsulfonyl)cyclohexyl)-5H-imidazo[5,1-a]isoindole
5-(5H-imidazo[5,1-a]isoindol-5-yl)-1-methylpyridin-2(1H)-one
5-(3-(methylsulfonyl)-3-azabicyclo[3.1.1]heptan-6-yl)-5H-imidazo[5,1-a]isoindole
5-(1-(azetidin-1-ylsulfonyl)piperidin-4-yl)-8-fluoro-5H-imidazo[5,1-a]isoindole
N-cyclopropyl-4-(8-fluoro-5H-imidazo[5,1-a]isoindol-5-yl)piperidine-1-sulfonamide
4-((4-(8-fluoro-5H-imidazo[5,1-a]isoindol-5-yl)piperidin-1-yl)sulfonyl)morpholine
N-(3-(5H-imidazo[5,1-a]isoindol-5-yl)cyclohexyl)ethanesulfonamide
4-(5H-imidazo[5,1-a]isoindol-5-yl)-3,3-dimethylpiperidine-1-sulfonamide
5-(5H-imidazo[5,1-a]isoindol-5-yl)hexahydro-2H-[1,2,5]thiadiazolo[2,3-a]pyridine 1,1-dioxide
2-(5H-imidazo[5,1-a]isoindol-5-yl)-8-azaspiro[4.5]decane-8-sulfonamide
6-(5H-imidazo[5,1-a]isoindol-5-yl)-3-azabicyclo[3.1.0]hexane-3-sulfonamide
or a pharmaceutically acceptable salt thereof, or an enantiomer or diastereoisomer thereof, or a racemic mixture thereof.

In another embodiment, the compounds of the invention are
(3-(5H-imidazo[5,1-a]isoindol-5-yl)phenyl)methanol
(3-fluoro-5-(5H-imidazo[5,1-a]isoindol-5-yl)phenyl)methanol
5-cyclohexyl-5H-imidazo[5,1-a]isoindole
5-(3-fluoro-5-methylphenyl)-5H-imidazo[5,1-a]isoindole
4-(5H-imidazo[5,1-a]isoindol-5-yl)cyclohexan-1-ol
4-(5H-imidazo[5,1-a]isoindol-5-yl)piperidine-1-sulfonamide
4-(8-fluoro-5H-imidazo[5,1-a]isoindol-5-yl)piperidine-1-sulfonamide
5-(1-(oxetan-3-ylsulfonyl)piperidin-4-yl)-5H-imidazo[5,1-a]isoindole
2-(5H-imidazo[5,1-a]isoindol-5-yl)-8-azaspiro[4.5]decane-8-sulfonamide
or a pharmaceutically acceptable salt thereof, or an enantiomer or diastereoisomer thereof, or a racemic mixture thereof.

The invention further comprises subgenera of formula (I), in which the structure of any of formulae (I), (Ia)-(Ii), (II), (IIa)-(IIi), (III), (IIIa)-(IIIi), (IV) or (IVa)-(IVi) has the stereoisomeric configuration of any of configurations 1 or 2:

Structural Formula I is One of Stereoisomeric Configurations (1)-(2):

| Configuration Number | Configuration Structure |
|---|---|
| 1 | 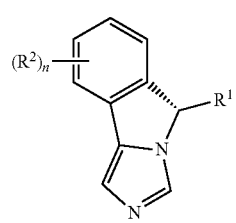 |
| 2 | (second structure) |

In one embodiment, the compounds of the disclosure have a stereoconfiguration of configuration 1.

In another embodiment, the compounds of the disclosure are in the stereoconfiguration of configuration 2.

In another aspect, the present disclosure provides each of compounds 1-96 in each of stereoisomeric configurations 1 or 2. For example:

| No. | Con. |
|---|---|
| 1 | 1 |
| 1 | 2 |
| 2 | 1 |
| 2 | 2 |
| 3 | 1 |
| 3 | 2 |
| 4 | 1 |
| 4 | 2 |
| 5 | 1 |
| 5 | 2 |
| 6 | 1 |
| 6 | 2 |
| 7 | 1 |
| 7 | 2 |
| 8 | 1 |
| 8 | 2 |
| 9 | 1 |
| 9 | 2 |
| 10 | 1 |
| 10 | 2 |
| 11 | 1 |
| 11 | 2 |
| 12 | 1 |
| 12 | 2 |
| 13 | 1 |
| 13 | 2 |
| 14 | 1 |
| 14 | 2 |
| 15 | 1 |
| 15 | 2 |
| 16 | 1 |
| 16 | 2 |
| 17 | 1 |
| 17 | 2 |
| 18 | 1 |
| 18 | 2 |
| 19 | 1 |
| 19 | 2 |
| 20 | 1 |
| 20 | 2 |
| 21 | 1 |
| 21 | 2 |
| 22 | 1 |
| 22 | 2 |
| 23 | 1 |
| 23 | 2 |
| 24 | 1 |
| 24 | 2 |
| 25 | 1 |
| 25 | 2 |
| 26 | 1 |

| No. | Con. |
|---|---|
| 26 | 2 |
| 27 | 1 |
| 27 | 2 |
| 28 | 1 |
| 28 | 2 |
| 29 | 1 |
| 29 | 2 |
| 30 | 1 |
| 30 | 2 |
| 31 | 1 |
| 31 | 2 |
| 32 | 1 |
| 32 | 2 |
| 33 | 1 |
| 33 | 2 |
| 34 | 1 |
| 34 | 2 |
| 35 | 1 |
| 35 | 2 |
| 36 | 1 |
| 36 | 2 |
| 37 | 1 |
| 37 | 2 |
| 38 | 1 |
| 38 | 2 |
| 39 | 1 |
| 39 | 2 |
| 40 | 1 |
| 40 | 2 |
| 41 | 1 |
| 41 | 2 |
| 42 | 1 |
| 42 | 2 |
| 43 | 1 |
| 43 | 2 |
| 44 | 1 |
| 44 | 2 |
| 45 | 1 |
| 45 | 2 |
| 46 | 1 |
| 46 | 2 |
| 47 | 1 |
| 47 | 2 |
| 48 | 1 |
| 48 | 2 |
| 49 | 1 |
| 49 | 2 |
| 50 | 1 |
| 50 | 2 |
| 51 | 1 |
| 51 | 2 |
| 52 | 1 |
| 52 | 2 |
| 53 | 1 |
| 53 | 2 |
| 54 | 1 |
| 54 | 2 |
| 55 | 1 |
| 55 | 2 |
| 56 | 1 |
| 56 | 2 |
| 57 | 1 |
| 57 | 2 |
| 58 | 1 |
| 58 | 2 |
| 59 | 1 |
| 59 | 2 |
| 60 | 1 |
| 60 | 2 |
| 61 | 1 |
| 61 | 2 |
| 62 | 1 |
| 62 | 2 |
| 63 | 1 |
| 63 | 2 |
| 64 | 1 |
| 64 | 2 |
| 65 | 1 |
| 65 | 2 |
| 66 | 1 |
| 66 | 2 |
| 67 | 1 |
| 67 | 2 |
| 68 | 1 |
| 68 | 2 |
| 69 | 1 |
| 69 | 2 |
| 70 | 1 |
| 70 | 2 |
| 71 | 1 |
| 71 | 2 |
| 72 | 1 |
| 72 | 2 |
| 73 | 1 |
| 73 | 2 |
| 74 | 1 |
| 74 | 2 |
| 75a | 1 |
| 75a | 2 |
| 75b | 1 |
| 75b | 2 |
| 77 | 1 |
| 77 | 2 |
| 78 | 1 |
| 78 | 2 |
| 79 | 1 |
| 79 | 2 |
| 80 | 1 |
| 80 | 2 |
| 81 | 1 |
| 81 | 2 |
| 82 | 1 |
| 82 | 2 |
| 83 | 1 |
| 83 | 2 |
| 84 | 1 |
| 84 | 2 |
| 85 | 1 |
| 85 | 2 |
| 86 | 1 |
| 86 | 2 |
| 87 | 1 |
| 87 | 2 |
| 88 | 1 |
| 88 | 2 |
| 89 | 1 |
| 89 | 2 |
| 90 | 1 |
| 90 | 2 |
| 91 | 1 |
| 91 | 2 |
| 92 | 1 |
| 92 | 2 |
| 93 | 1 |
| 93 | 2 |
| 94 | 1 |
| 94 | 2 |
| 95 | 1 |
| 95 | 2 |
| 96 | 1 |
| 96 | 2 |

In another aspect, the present disclosure provides a compound according to any one of the preceding aspects includes one or more stable isotopes. The stable isotope may replace any atom, for example, hydrogen, and may include any stable isotope, for example, deuterium.

In another aspect, the present disclosure provides compounds and pharmaceutical compositions comprising the compounds according to any one of the preceding aspects of the invention or any embodiment thereof, together with a pharmaceutically acceptable excipient, diluent, or carrier.

In another aspect, the invention provides methods for treating tryptophan 2,3-dioxygenase (TDO2) mediated immunosuppression in a subject in need thereof, comprising administering an effective tryptophan 2,3-dioxygenase inhibiting amount of a compound or a pharmaceutical composition according to any of the preceding aspects of the invention or any embodiment thereof.

In one embodiment, the immunosuppression is associated with cancer.

In an embodiment, the immunosuppression is tumor-specific immunosuppression associated with cancer.

In another embodiment, the immunosuppression is associated with a cancer, wherein the cancer is colon, pancreas, breast, prostate, lung, brain, ovary, cervix, testes, renal, head, or neck cancer, or lymphoma, leukemia, or melanoma.

In another aspect, the invention provides the use of compounds described by any one of the preceding aspects (and any embodiment thereof), as defined above, for the preparation of a medicament for the treatment of medical conditions that benefit from the inhibition of enzymatic activity of IDO1 or TDO2. Medical conditions contemplated in this aspect include all the conditions described herein.

In another aspect, the invention provides a use of compounds described by any one of the preceding aspects (and any embodiment thereof), as defined above, for the preparation of a medicament to stimulate T cell proliferation or to reverse an immunologic state of anergy or immunosuppression.

In another aspect, the invention provides the use of compounds described by any one of the preceding aspects (and any embodiment thereof), as defined above, for the preparation of a medicament for the treatment of immunosuppression associated with cancer or viral infections.

In one embodiment, the invention provides the use of compounds described in to any one of the preceding aspects (and any embodiment thereof), as defined above, for the preparation of a medicament for the treatment of tumor-specific immunosuppression associated with cancer. Preferably, the cancer is cancer of the colon, pancreas, breast, prostate, lung, brain, ovary, cervix, testes, renal, or head and neck, lymphoma, leukemia, melanoma, and the like.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl, arylalkyl-, and -alkylaryl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3 (4H)-on-5-yl, 2H-benzo[b][1,4]oxazin3 (4H)-on-6-yl, 2H-benzo[b][1,4]oxazin3 (4H)-on-7-yl, 2H-benzo[b][1,4]oxazin3 (4H)-on-8-yl, benzo[d]oxazin-2 (3H)-on-5-yl, benzo[d]oxazin-2 (3H)-on-6-yl, benzo[d]oxazin-2 (3H)-on-7-yl, benzo[d]oxazin-2 (3H)-on-8-yl, quinazolin-4 (3H)-on-5-yl, quinazolin-4 (3H)-on-6-yl, quinazolin-4 (3H)-on-7-yl, quinazolin-4 (3H)-on-8-yl, quinoxalin-2 (1H)-on-5-yl, quinoxalin-2 (1H)-on-6-yl, quinoxalin-2 (1H)-on-7-yl, quinoxalin-2 (1H)-on-8-yl, benzo[d]thiazol-2 (3H)-on-4-yl, benzo[d]thiazol-2 (3H)-on-5-yl, benzo[d]thiazol-2 (3H)-on-6-yl, and, benzo[d]thiazol-2 (3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl," "-alkylaryl," and "arylalkyl-" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 10 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, 3 or 4). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane and adamantane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 10 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —$(CH_2)_w$—, where w is 1, 2, 3 or 4). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4 (5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkyl-heteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. Bicyclic heterocycles that are fused through a heteroatom can be categorized according to the ring A/B convention of the present disclosure as if the heteroatom was in either of ring A or ring B. For example, 6,7,8,9-tetrahydro-4H-quinolizin-4-on-yl:

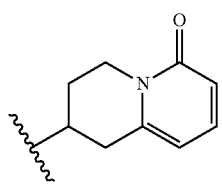 [SMILES: *C1CCn2c(cccc2=O)C1]

can be categorized as a ring A=C$_6$cycloalkyl and ring B=6-membered heterocyclyl substituted with an oxo group, or A=6-membered heterocyclyl and ring B=C$_6$cycloalkenyl substituted with an oxo group. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy" as used herein, means an —OH group.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "spiro" as used herein refers to a cyclic moiety formed by the substituted atom and two available substitutable positions on that same atom. For example, moiety such as

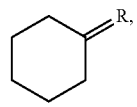

where R is a spiro-cycloalkyl=group includes compounds such as

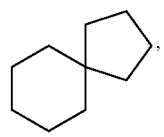

where the spiro-cyclopentyl group is the R group attached to the parent cyclohexyl ring by two single bonds. Similarly, where R is a spiro-heterocyclyl group, such compounds include

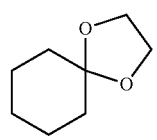

where the spiro-1,3-dioxolanyl ring is the R group attached to the parent cyclohexyl ring by two single bonds.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the TDO2 enzyme with a compound includes the administration of a compound described herein to an individual or patient, such as a human, having TDO2, as well as, for example, introducing a compound into a sample containing a cellular or purified preparation containing the TDO2 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for
 (1) preventing the disease; for example, preventing a disease, condition or disorder in an individual who may be predisposed to the disease, condition or disorder but does not yet experience or display the pathology or symptomatology of the disease;
 (2) inhibiting the disease; for example, inhibiting a disease, condition or disorder in an individual who is experiencing or displaying the pathology or symptomatology of the disease, condition or disorder; or
 (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., TDO2 modulation or tryptophan degradation inhibition).

Manifestation of amelioration of a disease condition with underlying TDO2-mediated immunosuppression may require the concomitant or sequential administration of additional therapeutic agents, such as antineoplastic agents in the case of cancer, or antiretroviral agents in the case of viral diseases. For example, administration of TDO2 inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Methods of Use

The compounds and pharmaceutical compositions described herein can modulate activity of the enzyme tryptophan 2,3-dioxygenase (TDO2). The term "modulate" is meant to refer to an ability to decrease activity of an enzyme or receptor. Accordingly, compounds described herein can be used in methods of modulating TDO2 by contacting the enzyme with any one or more of the compounds or compositions described herein. In some embodiments, the compounds described herein can act as inhibitors of TDO2. In further embodiments, the compounds described herein can be used to modulate activity of TDO2 in cell or in an individual in need of modulation of the enzyme by administering a modulating (e.g., inhibiting) amount of a compound described herein.

Further provided are methods of inhibiting the degradation of tryptophan and preventing the production of N-formylkynurenine in a system containing cells expressing TDO2 such as a tissue, living organism, or cell culture. In some embodiments methods of altering (e.g., increasing) extracellular tryptophan levels in a mammal comprise administering an effective amount of a compound or pharmaceutical composition provided herein. Methods of measuring tryptophan levels and tryptophan degradation are routine in the art.

Further provided are methods of inhibiting immunosuppression such as TDO2-mediated immunosuppression in a patient by administering to the patient an effective amount of a compound or composition recited herein. TDO2-mediated immunosuppression has been associated with, for example, cancers, tumor growth, metastasis, infectious diseases (e.g., viral infection), viral replication, etc.

Further provided are methods for treating tumor-specific immunosuppression associated with cancer in a patient by administering to the patient an effective amount of a compound or composition recited herein. Example tumor-specific immunosuppression associated with cancers treatable by the methods herein include immunosuppression associated with cancer of the colon, pancreas, breast, prostate, lung, brain, ovary, cervix, testes, renal, head and neck, lymphoma, leukemia, melanoma, and the like.

For example, a patient undergoing or having completed a course of chemotherapy and/or radiation therapy for the treatment of a disease state, such as a cancer, can benefit from administering to the patient a therapeutically effective amount of a compound or composition recited herein for inhibiting immunosuppression resulting from the disease state and/or treatment thereof.

Further provided are methods of treating diseases associated with activity or expression, including abnormal activity and/or overexpression, of TDO2 in an individual (e.g., patient) by administering to the individual in need of such treatment a therapeutically effective amount or dose of a compound described herein or a pharmaceutical composition thereof. Example diseases can include any disease, disorder or condition that is directly or indirectly linked to expression or activity of the TDO2 enzyme, such as over expression or abnormal activity. An TDO2-associated disease can also include any disease, disorder or condition that can be prevented, ameliorated, or cured by modulating enzyme activity.

Examples of TDO2-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.

Combination Therapy

One or more additional pharmaceutical agents for treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or indoleamine 2,3-dioxygenase (IDO) inhibitors can be used in combination with the compounds and pharmaceutical compositions described herein for treatment of TDO2-associated diseases, disorders or conditions (as noted above) or for enhancing the effectiveness of the treatment of a disease state or condition, such as cancer. The agents can be combined with the present compounds in a single dosage form, or the agents can be administered simultaneously or sequentially as separate dosage forms.

Therapeutic agents that constitute the standard of care for a particular cancer type or infectious disease are expected to benefit when combined with TDO2 inhibitors of the present invention. For example, for the case of tumors, is it preferable that the tumor is sensitive to the cytotoxic effects of the chemotherapeutic agent in order to stimulate the release of antigens that will eventually mediate an immune response that will be enhanced by addition of TDO2 inhibitors to the combination treatment. A person of skill in the art will know how to select such chemotherapeutic agent based on the clinical characteristics and known sensitivity of each tumor to different antineoplastic agents.

Suitable antiviral agents contemplated for use in combination with the compounds described herein can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), docetaxel, mithramycin, deoxyco-formycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, or antibodies to cytokines (IL-10, TGF-β, etc.).

Other anti-cancer agents also include those that block immune cell migration such as antagonists to chemokine receptors, including CCR2, CCR4 and CCR6.

Other anti-cancer agents also include those that augment the immune system such adoptive T cell transfer.

Anti-cancer vaccines include dendritic cells, synthetic peptides, DNA vaccines and recombinant viruses.

The compounds of the present application can also be used in combination therapy with therapeutic treatments suppressing or inhibiting biologic pathways modulated by PD-1 (programmed cell death protein 1) or its ligand PD-L1. Such therapeutic treatments include those that suppress or inhibit the expression of PD-1 or PD-L1 as well as those that suppress or inhibit the activity of the PD-1 or PD-L1 proteins themselves. Examples of anti-PD-1 compounds include, for example, pembrolizumab, nivolumab, pidilizumab, and BMS 936559. Examples of anti-PD-L1 include, for example, atezolizumab and avelumab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of TDO2 according to one or more of the assays described herein.

Kits

Also included are pharmaceutical kits useful, for example, in the treatment or prevention of TDO2-associated diseases or disorders, obesity, diabetes and other diseases referred to herein which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of TDO2 according to one or more of the assays described herein.

EXAMPLES

All reagents and solvents were purchased from commercial sources. All commercial reagents and solvents were used as received without further purification. The reactions were monitored using analytical thin layer chromatography (TLC) with 0.25 mm EM Science silica gel plates (60F-254). The developed TLC plates were visualized by short wave UV light (254 nm) or immersion in potassium permanganate solution followed by heating on a hot plate. Flash chromatography was performed with Selecto Scientific silica gel, 32-63 µm particle sizes. All reactions were performed in flame or oven-dried glassware under a nitrogen atmosphere. All reactions were stirred magnetically at ambient temperature unless otherwise indicated. $^1$H NMR spectra were obtained with a Bruker DRX400, Varian VXR400 or VXR300. $^1$H NMR spectra were reported in parts per million (δ) relative to TMS (0.0), DMSO-d6 (2.50) or CD$_3$OD (4.80) as an internal reference. All $^1$H NMR spectra were taken in CDCl3 unless otherwise indicated. The phosphonates were prepared according to the literature procedure: (U.S. Pat. No. 5,807,892 A1, 1998; Patent: US2012/033245; Patent: US2008/306084 A1, 2008). 1-(azidomethyl)-2,4-dimethoxybenzene was synthesized according to ChemMedChem, 2011, vol. 6, #5, 840-847.

TABLE 1

| Example # | Structure | $^1$H NMR | MS (M + H)$^+$ |
|---|---|---|---|
| 1a | 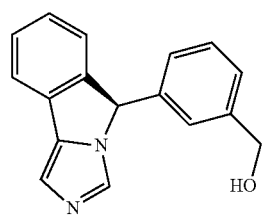 [SMILES: OCc1cccc([C@@H]2c3ccccc3-c3cncn32)c1] | $^1$H NMR (300 MHz, CD$_3$OD) δ 7.71 (d, J = 7.5 Hz, 2H), 7.51-7.35 (m, 3H), 7.35-7.24 (m, 3H), 7.24-7.10 (m, 2H), 6.39 (s, 1H), 4.59 (s, 2H). | 263.2 |

TABLE 1-continued
| Example # | Structure | ¹H NMR | MS (M + H)⁺ |
|---|---|---|---|
| 1b | 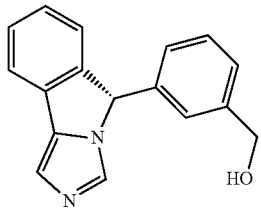 [SMILES: OCc1cccc([C@H]2c3ccccc3-c3cncn32)c1] | The same as 01a. | 263.2 |
| 2a | 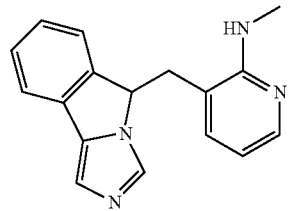 | ¹H NMR (300 MHz, CDCl₃) δ 8.24 (dd, J = 5.1, 1.8 Hz, 1H), 8.00 (s, 1H), 7.62 (d, J = 7.6 Hz, 1H), 7.44 (dd, J = 8.1, 7.0 Hz, 1H), 7.33-7.23 (m, 2H), 7.23-7.10 (m, 2H), 6.64 (dd, J = 7.2, 5.1 Hz, 1H), 5.62 (t, J = 7.3 Hz, 1H), 5.00 (s, 1H), 3.24-3.04 (m, 5H). | 277.2 |
| 2b | 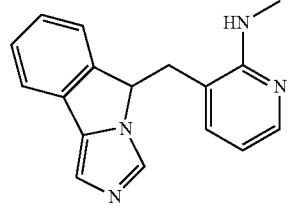 [SMILES: CNc1ncccc1CC1c2ccccc2-c2cncn21] | The same as 02a. | 277.2 |
| 03 | 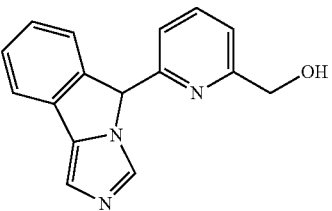 [SMILES: OCc1cccc(C2c3ccccc3-c3cncn32)n1] | ¹H NMR (Chloroform-d, 400 MHz): δ (ppm) 8.09 (s, 1H), 7.66 (dt, J = 7.9, 3.8 Hz, 2H), 7.46 (t, J = 7.0 Hz, 2H), 7.39-7.24 (m, 2H), 6.83 (d, J = 8.0 Hz, 1H), 6.45 (s, 1H), 4.85 (s, 2H). | 264.1 |
| 04 | 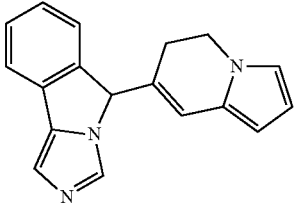 [SMILES: C1=C(C2c3ccccc3-c3cncn32)CCn2cccc21] | | 274 |
| 05a | 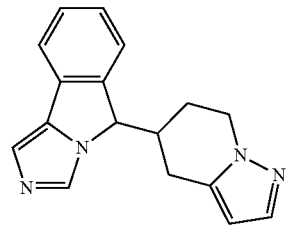 | | 277 |

TABLE 1-continued

| Example # | Structure | ¹H NMR | MS (M + H)⁺ |
|---|---|---|---|
| 05b | 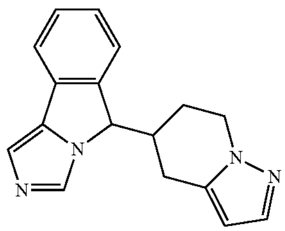 [SMILES: c1ccc2c(c1)-c1cncn1C2C1CCn2nccc2C1] | | 277 |
| 05c | 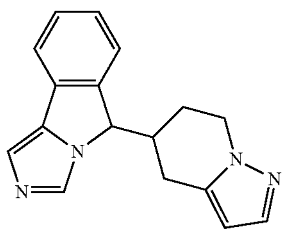 [SMILES: c1ccc2c(c1)-c1cncn1C2C1CCn2nccc2C1] | | 277 |
| 06 | 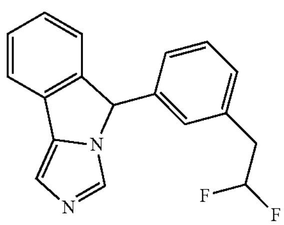 [SMILES: FC(F)Cc1cccc(C2c3ccccc3-c3cncn32)c1] | | 297 |
| 07a | 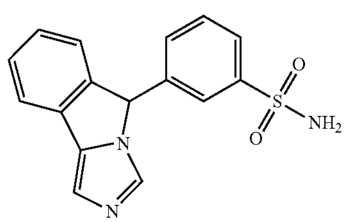 [SMILES: NS(=O)(=O)c1cccc(C2c3ccccc3-c3cncn32)c1] | 7.93-7.89 (m, 1H), 7.85 (m, 1H), 7.57 (d, J = 7.7 Hz, 1H), 7.47 (s, 1H), 7.45 (t, J = 7.8 Hz, 1H), 7.39 (t, J = 6.9 Hz, 1H), 7.27-7.10 (m, 4H), 6.15 (s, 1H). | 312.2 |
| 07b | 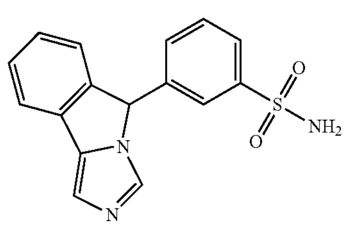 [SMILES: NS(=O)(=O)c1cccc(C2c3ccccc3-c3cncn32)c1] | Same as 06a | 312.2 |
| 08 | 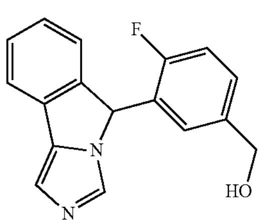 [SMILES: OCc1ccc(F)c(C2c3ccccc3-c3cncn32)c1] | | 281 |

TABLE 1-continued

| Example # | Structure | ¹H NMR | MS (M + H)⁺ |
|---|---|---|---|
| 09a | 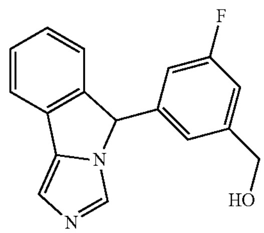 [SMILES: OCc1cc(F)cc(C2c3ccccc3-c3cncn32)c1] | 1H NMR (400 MHz, DMSO-d6) δ 7.79 (t, J = 0.7 Hz, 1H), 7.69 (dt, J = 7.6, 0.9 Hz, 1H), 7.40 (tdd, J = 7.7, 1.3, 0.6 Hz, 1H), 7.31-7.21 (m, 4H), 7.11 (ddt, J = 9.7, 2.6, 1.1 Hz, 1H), 6.99 (dt, J = 9.5, 2.0 Hz, 1H), 6.85 (td, J = 1.5, 0.7 Hz, 1H), 6.51 (s, 1H), 5.35 (t, J = 5.7 Hz, 1H), 4.46 (s, 2H). | 281.3 |
| 09b | 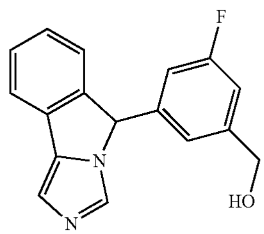 [SMILES: OCc1cc(F)cc(C2c3ccccc3-c3cncn32)c1] | Same as 10a | 281.3 |
| 10a | 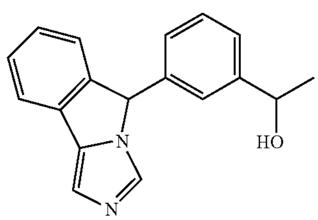 [SMILES: CC(O)c1cccc(C2c3ccccc3-c3cncn32)c1] | ¹H NMR (400 MHz, DMSO-d₆) δ 7.73 (s, 1H), 7.67 (d, J = 7.6 Hz, 1H), 7.43-7.36 (m, 1H), 7.35-7.27 (m, 2H), 7.26-7.20 (m, 3H), 7.17 (s, 1H), 6.99 (dt, J = 6.9, 1.9 Hz, 1H), 6.47 (s, 1H), 5.15 (d, J = 4.2 Hz, 1H), 4.68 (qd, J = 6.5, 4.2 Hz, 1H), 1.28 (d, J = 6.4 Hz, 3H). | 277.2 |
| 10b | 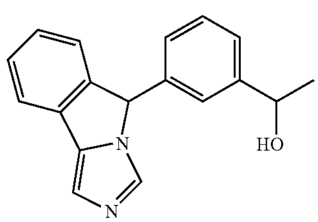 [SMILES: CC(O)c1cccc(C2c3ccccc3-c3cncn32)c1] | ¹H NMR (400 MHz, DMSO-d₆) δ 7.73 (s, 1H), 7.67 (dd, J = 7.6, 1.0 Hz, 1H), 7.43-7.36 (m, 1H), 7.35-7.28 (m, 2H), 7.23 (dt, J = 3.9, 1.0 Hz, 3H), 7.17 (d, J = 2.0 Hz, 1H), 6.98 (dt, J = 6.5, 2.2 Hz, 1H), 6.47 (s, 1H), 5.17 (d, J = 4.2 Hz, 1H), 4.68 (qd, J = 6.4, 4.1 Hz, 1H), 1.28 (d, J = 6.4 Hz, 3H). | 277.2 |
| 10c | 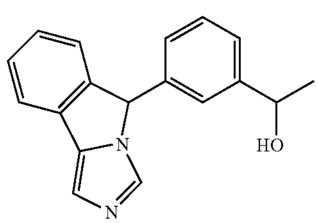 [SMILES: CC(O)c1cccc(C2c3ccccc3-c3cncn32)c1] | Same as 10b | 277.2 |
| 10d | 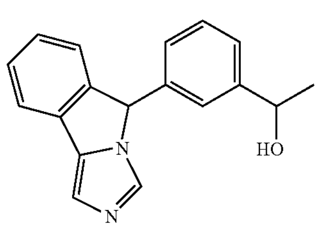 [SMILES: CC(O)c1cccc(C2c3ccccc3-c3cncn32)c1] | Same as 10c | 277.2 |

TABLE 1-continued
| Example # | Structure | ¹H NMR | MS (M + H)⁺ |
|---|---|---|---|
| 11 | 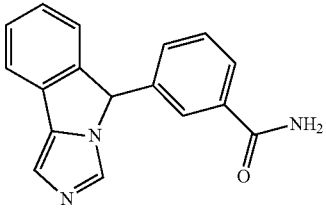 [SMILES: NC(=O)c1cccc(C2c3ccccc3-c3cncn32)c1] | 1H NMR (400 MHz, DMSO-d6) δ 8.06 (s, 1H), 7.85 (ddd, J = 7.8, 1.8, 1.1 Hz, 1H), 7.78 (t, J = 0.7 Hz, 1H), 7.72-7.67 (m, 2H), 7.50-7.43 (m, 2H), 7.40 (dddd, J = 7.5, 6.8, 1.7, 0.6 Hz, 1H), 7.32-7.19 (m, 5H), 6.54 (s, 1H). | 276.3 |
| 12 | 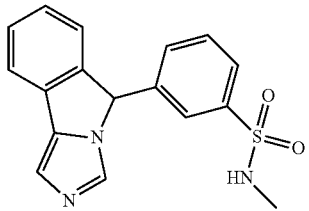 [SMILES: CNS(=O)(=O)c1cccc(C2c3ccccc3-c3cncn32)c1] | (400 MHz, DMSO-d₆) δ 7.82 (s, 1H), 7.75 (dt, J = 7.8, 1.5 Hz, 1H), 7.70 (d, J = 7.7 Hz, 1H), 7.64 (t, J = 7.8 Hz, 1H), 7.57 (t, J = 1.7 Hz, 1H), 7.52 (q, J = 4.6 Hz, 1H), 7.47-7.39 (m, 2H), 7.29-7.21 (m, 3H), 6.65 (s, 1H), 2.38 (d, J = 5.0 Hz, 3H). | 326.2 |
| 13 | 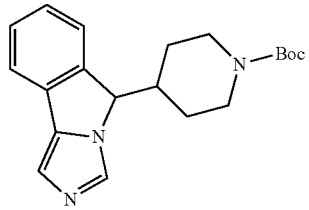 [SMILES: CC(C)(C)OC(=O)N1CCC(C2c3ccccc3-c3cncn32)CC1] | | 340 |
| 14 | 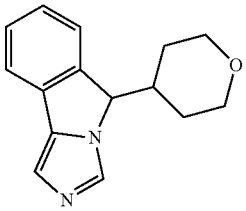 [SMILES: c1ccc2c(c1)-c1cncn1C2C1CCOCC1] | | 241 |
| 15 | 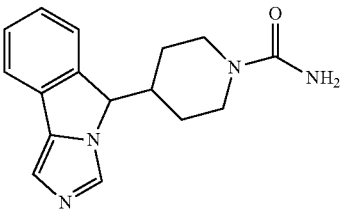 [SMILES: NC(=O)N1CCC(C2c3ccccc3-c3cncn32)CC1] | | 283 |
| 16 | 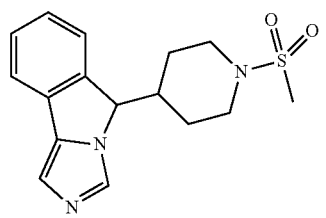 [SMILES: CS(=O)(=O)N1CCC(C2c3ccccc3-c3cncn32)CC1] | | 318 |

TABLE 1-continued
| Example # | Structure | ¹H NMR | MS (M + H)⁺ |
|---|---|---|---|
| 17 | 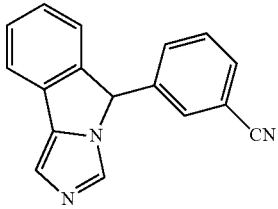 [SMILES: N#Cc1cccc(C2c3ccccc3-c3cncn32)c1] | | 258 |
| 18 | 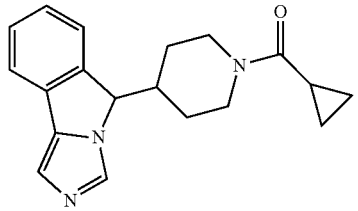 [SMILES: O=C(C1CC1)N1CCC(C2c3ccccc3-c3cncn32)CC1] | | 308 |
| 19a | 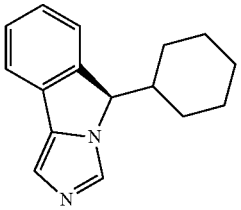 [SMILES: c1ccc2c(c1)-c1cncn1[C@@H]2C1CCCCC1] | | 239 |
| 19b | 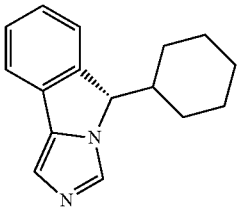 [SMILES: c1ccc2c(c1)-c1cncn1[C@H]2C1CCCCC1] | | 239 |
| 20 | 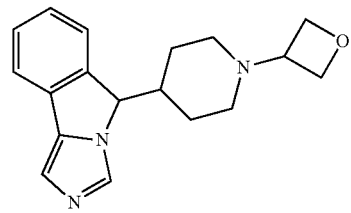 [SMILES: c1ccc2c(c1)-c1cncn1C2C1CCN(C2COC2)CC1] | | 296 |
| 21 | 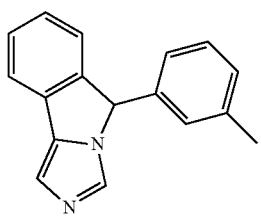 [SMILES: Cc1cccc(C2c3ccccc3-c3cncn32)c1] | | 247 |

TABLE 1-continued

| Example # | Structure | ¹H NMR | MS (M + H)⁺ |
|---|---|---|---|
| 22 | 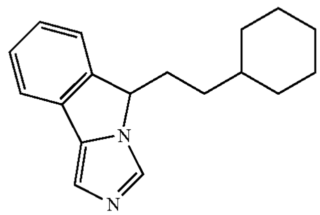 [SMILES: c1ccc2c(c1)-c1cncn1C2CCC1CCCCC1] | ¹H NMR (Chloroform-d, 400 MHz): δ (ppm) 7.58 (s, 1H), 7.39 (d, J = 7.5 Hz, 1H), 7.25-7.18 (m, 2H), 7.15-7.09 (m, 1H), 7.08 (s, 1H), 4.98 (t, J = 5.7 Hz, 1H), 2.09-1.95 (m, 1H), 1.80 (ddt, J = 11.3, 8.9, 6.2 Hz, 1H), 1.63-1.46 (m, 5H), 1.16-0.92 (m, 6H), 0.81-0.65 (m, 2H). | 267.2 |
| 23 | 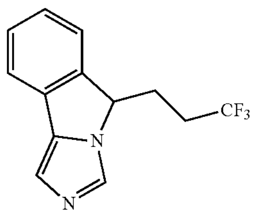 [SMILES: FC(F)(F)CCC1c2ccccc2-c2cncn21] | 1H NMR (400 MHz, Chloroform-d) δ 7.86 (s, 1H), 7.59 (dt, J = 7.6, 1.0 Hz, 1H), 7.43 (tdd, J = 7.6, 1.3, 0.6 Hz, 1H), 7.40-7.36 (m, 1H), 7.34 (dd, J = 7.4, 1.1 Hz, 1H), 5.40 (t, J = 4.8 Hz, 1H), 2.56-2.44 (m, 1H), 2.41-2.29 (m, 1H), 1.76 (dddd, J = 21.2, 10.5, 6.3, 4.7 Hz, 2H). | 253.1 |
| 24a | 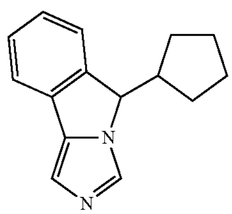 [SMILES: c1ccc2c(c1)-c1cncn1C2C1CCCC1] | | 225 |
| 24b | 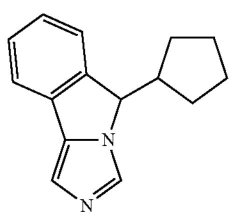 [SMILES: c1ccc2c(c1)-c1cncn1C2C1CCCC1] | | 225 |
| 25 | 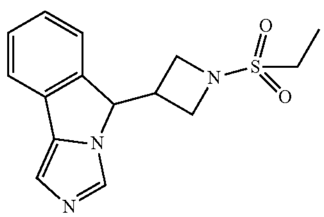 [SMILES: CCS(=O)(=O)N1CC(C2c3ccccc3-c3cncn32)C1] | | 304 |
| 26 | 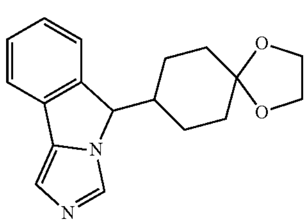 [SMILES: c1ccc2c(c1)-c1cncn1C2C1CCC2(CC1)OCCO2] | | 297 |

TABLE 1-continued

| Example # | Structure | ¹H NMR | MS (M + H)⁺ |
|---|---|---|---|
| 27 | 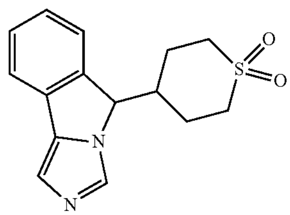 [SMILES: O=S1(=O)CCC(C2c3ccccc3-c3cncn32)CC1] | | 289 |
| 28 | 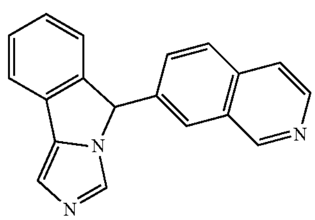 [SMILES: c1ccc2c(c1)-c1cncn1C2c1ccc2ccncc2c1] | | 284 |
| 29 | 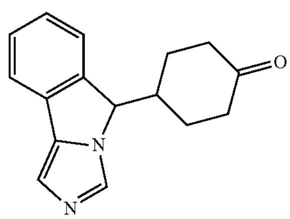 [SMILES: O=C1CCC(C2c3ccccc3-c3cncn32)CC1] | | 253 |
| 30 | 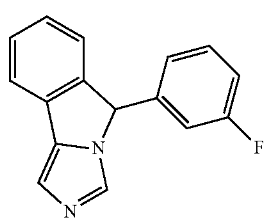 [SMILES: Fc1cccc(C2c3ccccc3-c3cncn32)c1] | | 251 |
| 31a | 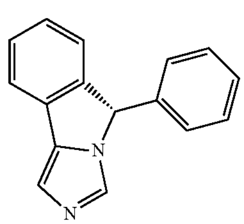 [SMILES: c1ccc([C@H]2c3ccccc3-c3cncn32)cc1] | | 233 |
| 31b | 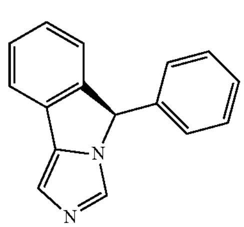 [SMILES: c1ccc([C@@H]2c3ccccc3-c3cncn32)cc1] | | 233 |

TABLE 1-continued

| Example # | Structure | ¹H NMR | MS (M + H)⁺ |
|---|---|---|---|
| 32 | 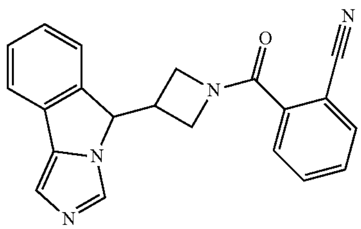 [SMILES: N#Cc1ccccc1C(=O)N1CC(C2c3ccccc3-c3cncn32)C1] | | 341 |
| 33 | 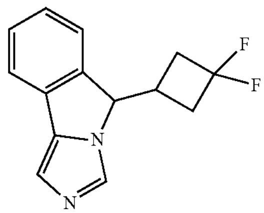 [SMILES: FC1(F)CC(C2c3ccccc3-c3cncn32)C1] | | 247 |
| 34 | 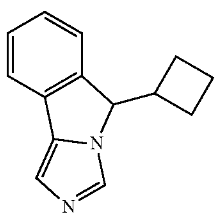 [SMILES: c1ccc2c(c1)-c1cncn1C2C1CCC1] | | 211 |
| 35 | 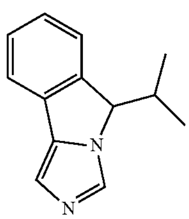 | | 199 |
| 36 | 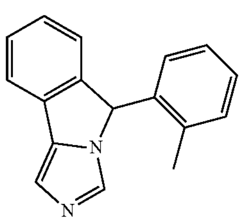 [SMILES: Cc1ccccc1C1c2ccccc2-c2cncn21] | | 247 |
| 37 | 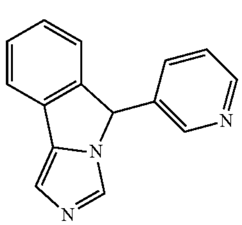 [SMILES: c1cncc(C2c3ccccc3-c3cncn32)c1] | | 234 |

TABLE 1-continued
| Example # | Structure | ¹H NMR | MS (M + H)⁺ |
|---|---|---|---|
| 38 | 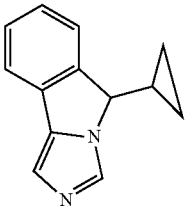 [SMILES: c1ccc2c(c1)-c1cncn1C2C1CC1] | | 197 |
| 39 | 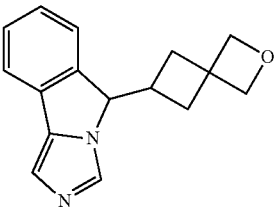 [SMILES: c1ccc2c(c1)-c1cncn1C2C1CC2(COC2)C1] | | 253 |
| 40 | 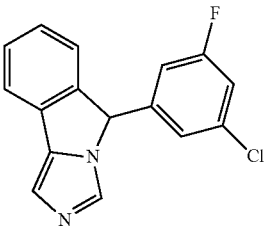 [SMILES: Fc1cc(Cl)cc(C2c3ccccc3-c3cncn32)c1] | | 285/287 |
| 41 | 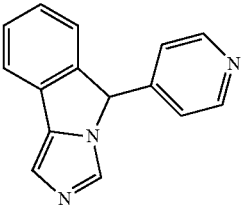 [SMILES: c1ccc2c(c1)-c1cncn1C2c1ccncc1] | | 234 |
| 42 | 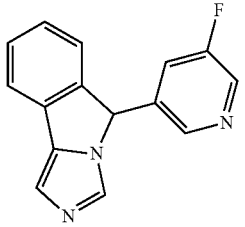 [SMILES: Fc1cncc(C2c3ccccc3-c3cncn32)c1] | | 252 |
| 43a | 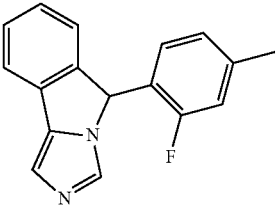 [SMILES: Cc1ccc(C2c3ccccc3-c3cncn32)c(F)c1] | ¹H NMR (300 MHz, CDCl₃) δ 7.77-7.65 (m, 2H), 7.52-7.37 (m, 1H), 7.36-7.20 (m, 3H), 7.09 (dd, J = 11.6, 1.4 Hz, 1H), 6.98 (d, J = 7.8 Hz, 1H), 6.77 (t, J = 7.8 Hz, 1H), 6.62 (s, 1H), 2.37 (s, 3H). | 265.2 |

TABLE 1-continued

| Example # | Structure | ¹H NMR | MS (M + H)⁺ |
|---|---|---|---|
| 43b | 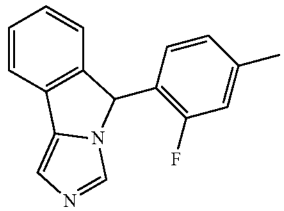 [SMILES: Cc1ccc(C2c3ccccc3-c3cncn32)c(F)c1] | The same as 43a. | 265.2 |
| 44a | 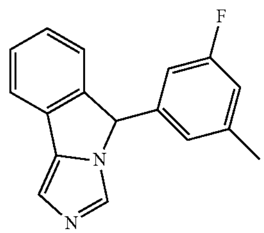 [SMILES: Cc1cc(F)cc(C2c3ccccc3-c3cncn32)c1] | ¹H NMR (300 MHz, CDCl₃) δ 7.77-7.66 (m, 2H), 7.46-7.42 (m, 1H), 7.34-7.23 (m, 3H), 6.95 (d, J = 9.6 Hz, 1H), 6.83 (s, 1H), 6.70 (d, J = 9.6 Hz, 1H), 6.34 (s, 1H), 2.33 (d, J = 0.9 Hz, 3H). | 265.2 |
| 44b | 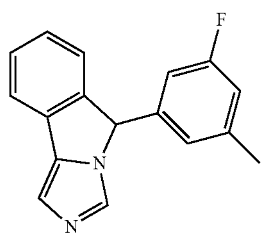 [SMILES: Cc1cc(F)cc(C2c3ccccc3-c3cncn32)c1] | The same as 44a. | 265.2 |
| 45 | 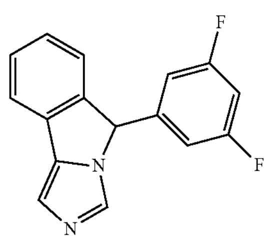 [SMILES: Fc1cc(F)cc(C2c3ccccc3-c3cncn32)c1] | | 269 |
| 46 | 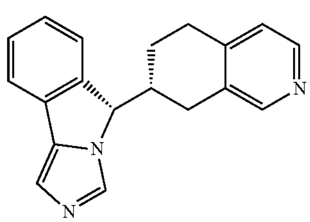 [SMILES: c1ccc2c(c1)-c1cncn1[C@H]2[C@@H]1CCc2ccncc2C1] | | 288 |
| 47a | 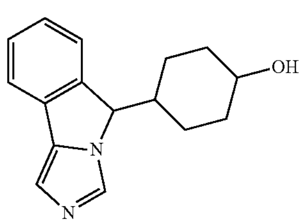 [SMILES: OC1CCC(C2c3ccccc3-c3cncn32)CC1] | | 255 |

TABLE 1-continued

| Example # | Structure | ¹H NMR | MS (M + H)⁺ |
|---|---|---|---|
| 47b | 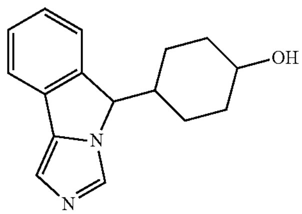 [SMILES: OC1CCC(C2c3ccccc3-c3cncn32)CC1] | | 255 |
| 47c | 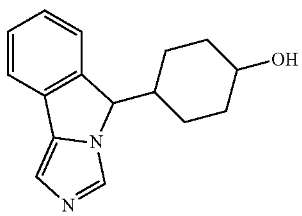 [SMILES: OC1CCC(C2c3ccccc3-c3cncn32)CC1] | | 255 |
| 47d | 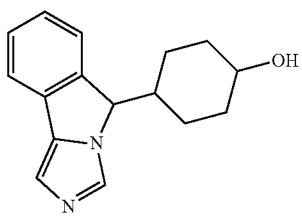 [SMILES: OC1CCC(C2c3ccccc3-c3cncn32)CC1] | | 255 |
| 48 | 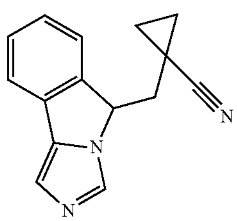 [SMILES: N#CC1(CC2c3ccccc3-c3cncn32)CC1] | ¹H NMR (400 MHz, DMSO-d₆) δ 7.98 (s, 1H), 7.64-7.58 (m, 2H), 7.43-7.38 (m, 1H), 7.29 (td, J = 7.6, 1.1 Hz, 1H), 7.15 (s, 1H), 5.58-5.44 (m, 1H), 2.48-2.43 (m, 1H), 2.12 (dd, J = 14.9, 7.0 Hz, 1H), 1.26-1.12 (m, 2H), 0.88-0.81 (m, 2H). | 236.2 |
| 49 | 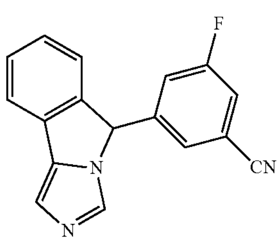 [SMILES: N#Cc1cc(F)cc(C2c3ccccc3-c3cncn32)c1] | | 276 |
| 50a | 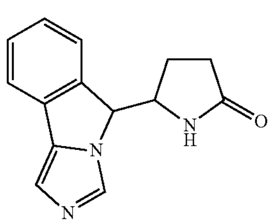 [SMILES: O=C1CCC(C2c3ccccc3-c3cncn32)N1] | ¹H NMR (300 MHz, CD₃OD) δ 8.05 (s, 1H), 7.70 (d, J = 7.6 Hz, 1H), 7.54 (d, J = 7.7 Hz, 1H), 7.50 (t, J = 7.6 Hz, 1H), 7.35 (t, J = 7.6 Hz, 1H), 7.24 (s, 1H), 5.50 (d, J = 4.0 Hz, 1H), 4.53 (dt, J = 8.2, 4.0 Hz, 1H), 2.23-1.99 (m, 2H), 1.85-1.76 (m, 1H), 1.45-1.37 (m, 1H). | 240.2 |

TABLE 1-continued
| Example # | Structure | ¹H NMR | MS (M + H)⁺ |
|---|---|---|---|
| 50b | 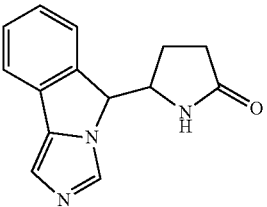 [SMILES: O=C1CCC(C2c3ccccc3-c3cncn32)N1] | The same as 50a | 240.2 |
| 50c | 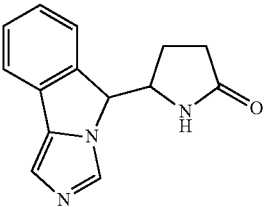 [SMILES: O=C1CCC(C2c3ccccc3-c3cncn32)N1] | ¹H NMR (300 MHz, CD₃OD) δ 7.80 (s, 1H), 7.68 (d, J = 7.6 Hz, 1H), 7.54 (d, J = 7.6 Hz, 1H), 7.47 (t, J = 7.5 Hz, 1H), 7.37 (t, J = 8.0 Hz, 1H), 7.25 (s, 1H), 5.56 (d, J = 3.0 Hz, 1H), 4.63-4.48 (m, 1H), 2.24-2.15 (m, 1H), 1.88-1.71 (m, 2H), 1.06-0.90 (m, 1H). | 240.2 |
| 50d | 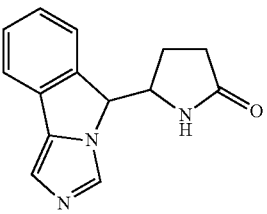 [SMILES: O=C1CCC(C2c3ccccc3-c3cncn32)N1] | The same as 50c. | 240.2 |
| 51 | 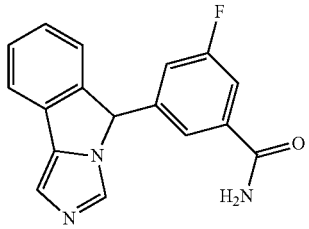 [SMILES: NC(=O)c1cc(F)cc(C2c3ccccc3-c3cncn32)c1] |  | 294 |
| 52 | 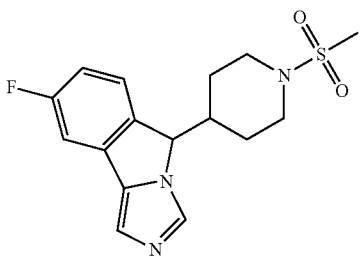 [SMILES: CS(=O)(=O)N1CCC(C2c3ccc(F)cc3-c3cncn32)CC1] | ¹H NMR (Chloroform-d, 400 MHz): δ (ppm) 7.70 (s, 1H), 7.29 (dd, J = 8.4, 4.8 Hz, 1H), 7.25-7.18 (m, 2H), 7.03-6.88 (m, 1H), 5.13 (d, J = 2.8 Hz, 1H), 3.83 (dddt, J = 23.6, 11.9, 4.5, 2.3 Hz, 2H), 2.75 (s, 3H), 2.63 (dtd, J = 18.2, 12.1, 2.7 Hz, 2H), 2.24-2.08 (m, 1H), 1.65 (dt, J = 13.0, 3.0 Hz, 1H), 11.60-1.46 (m, 2H), 1.38-1.25 (m, 1H). | 336.3 |
| 53 | 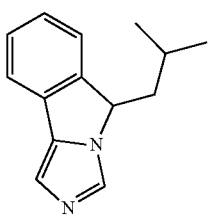 [SMILES: CC(C)CC1c2ccccc2-c2cncn21] | ¹H NMR (Chloroform-d, 400 MHz): δ (ppm) 7.70 (s, 1H), 7.55 (dt, J = 7.5, 0.9 Hz, 1H), 7.40-7.32 (m, 2H), 7.25 (td, J = 7.5, 1.1 Hz, 1H), 7.19 (s, 1H), 5.18 (dd, J = 8.6, 4.9 Hz, 1H), 1.96-1.74 (m, 1H), 1.92-1.72 (m, 2H), 1.07 (d, J = 6.5 Hz, 3H), 1.00 (d, J = 6.6 Hz, 3H). | 213.4 |

TABLE 1-continued

| Example # | Structure | ¹H NMR | MS (M + H)⁺ |
|---|---|---|---|
| 54 | 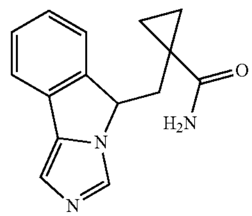 [SMILES: NC(=O)C1(CC2c3ccccc3-c3cncn32)CC1] | ¹H NMR (400 MHz, DMSO-d₆) δ 7.78 (s, 1H), 7.62-7.56 (m, 1H), 7.51 (d, J = 7.6 Hz, 1H), 7.42-7.31 (m, 2H), 7.31-7.22 (m, 1H), 7.11 (s, 1H), 7.08 (s, 1H), 5.47 (dd, J = 8.8, 6.2 Hz, 1H), 2.39 (dd, J = 14.6, 5.8 Hz, 1H), 1.90-1.80 (m, 1H), 1.21-1.14 (m, 1H), 1.08-1.00 (m, 1H), 0.61-0.51 (m, 1H). | 254.3 |
| 55a | 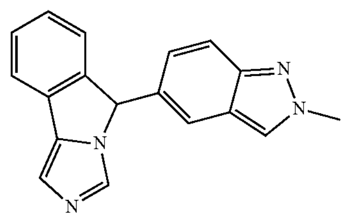 [SMILES: Cn1cc2cc(C3c4ccccc4-c4cncn43)ccc2n1] | | 287 |
| 55b | 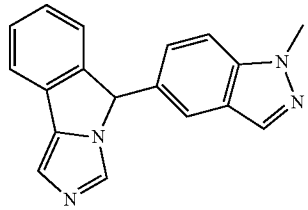 [SMILES: Cn1ncc2cc(C3c4ccccc4-c4cncn43)ccc21] | | 287 |
| 56 | 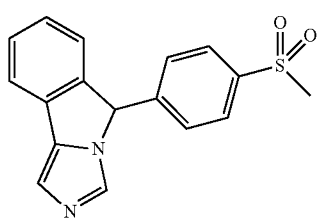 [SMILES: CS(=O)(=O)c1ccc(C2c3ccccc3-c3cncn32)cc1] | | 311 |
| 57 | 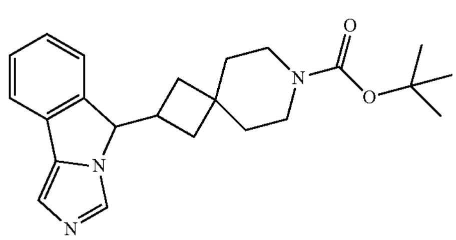 [SMILES: CC(C)(C)OC(=O)N1CCC2(CC1)CC(C1c3ccccc3-c3cncn31)C2] | | 381 |
| 58 | 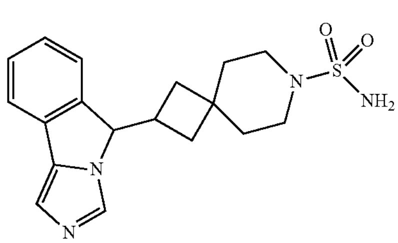 [SMILES: NS(=O)(=O)N1CCC2(CC1)CC(C1c3ccccc3-c3cncn31)C2] | | 358 |

TABLE 1-continued

| Example # | Structure | ¹H NMR | MS (M + H)⁺ |
|---|---|---|---|
| 59 | 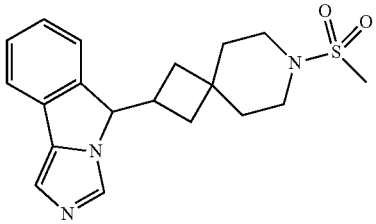 [SMILES: CS(=O)(=O)N1CCC2(CC1)CC(C1c3ccccc3-c3cncn31)C2] | | 359 |
| 60a | 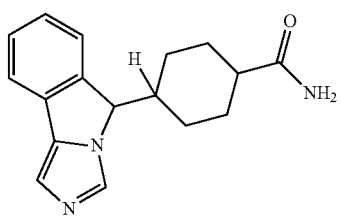 [SMILES: NC(=O)C1CCC(C2c3ccccc3-c3cncn32)CC1] | 1H NMR (500 MHz, DMSO-d6) δ 7.76 (s, 1H), 7.57 (dt, J = 7.5, 0.9 Hz, 1H), 7.44 (dq, J = 7.6, 0.9 Hz, 1H), 7.36 (tt, J = 7.5, 0.8 Hz, 1H), 7.26 (td, J = 7.5, 1.1 Hz, 1H), 7.11 (s, 1H), 7.06 (s, 1H), 6.65 (s, 1H), 5.24 (d, J = 3.2 Hz, 1H), 2.36 (s, 1H), 2.14-1.89 (m, 3H), 1.48-1.30 (m, 4H), 1.12-0.99 (m, 2H). | 282.3 |
| 60b | 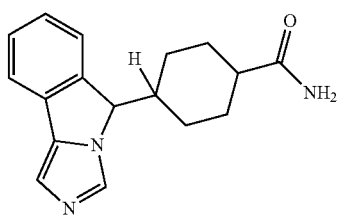 [SMILES: NC(=O)C1CCC(C2c3ccccc3-c3cncn32)CC1] | 1H NMR (500 MHz, DMSO-d6) δ 7.76 (s, 1H), 7.57 (dt, J = 7.7, 0.9 Hz, 1H), 7.44 (dq, J = 7.6, 1.0 Hz, 1H), 7.36 (tt, J = 7.5, 0.8 Hz, 1H), 7.26 (td, J = 7.6, 1.1 Hz, 1H), 7.11 (s, 1H), 7.06 (s, 1H), 6.65 (s, 1H), 5.24 (d, J = 3.2 Hz, 1H), 2.36 (d, J = 3.3 Hz, 1H), 2.02 (d, J = 7.5 Hz, 1H), 1.93 (d, J = 13.4 Hz, 1H), 1.48-1.29 (m, 4H), 1.12-0.99 (m, 2H). | 282.3 |
| 60c | 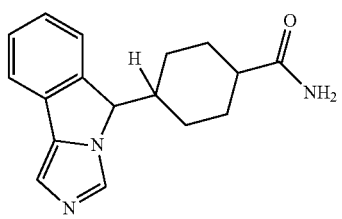 [SMILES: NC(=O)C1CCC(C2c3ccccc3-c3cncn32)CC1] | 1H NMR (500 MHz, DMSO-d6) δ 7.89 (s, 1H), 7.58 (dt, J = 7.7, 0.9 Hz, 1H), 7.50 (dq, J = 7.6, 0.9 Hz, 1H), 7.38 (tt, J = 7.6, 0.8 Hz, 1H), 7.28 (td, J = 7.6, 1.1 Hz, 1H), 7.13 (s, 1H), 7.10 (s, 1H), 6.66-6.57 (m, 1H), 5.29 (d, J = 2.8 Hz, 1H), 2.14 (ddt, J = 12.2, 9.2, 3.0 Hz, 1H), 1.92 (tt, J = 12.0, 3.6 Hz, 1H), 1.82-1.72 (m, 1H), 1.70-1.57 (m, 2H), 1.37 (qd, J = 12.9, 3.5 Hz, 1H), 1.30-1.13 (m, 3H), 0.69 (qd, J = 12.8, 2.7 Hz, 1H). | 282.3 |
| 60d | 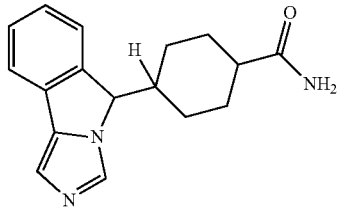 [SMILES: NC(=O)C1CCC(C2c3ccccc3-c3cncn32)CC1] | 1H NMR (500 MHz, DMSO-d6) δ 7.89 (s, 1H), 7.58 (dt, J = 7.6, 0.8 Hz, 1H), 7.50 (dq, J = 7.6, 0.9 Hz, 1H), 7.38 (tt, J = 7.5, 0.8 Hz, 1H), 7.28 (td, J = 7.5, 1.1 Hz, 1H), 7.13 (s, 1H), 7.10 (s, 1H), 6.66-6.58 (m, 1H), 5.29 (d, J = 2.8 Hz, 1H), 2.14 (ddt, J = 12.2, 9.2, 3.0 Hz, 1H), 1.92 (tt, J = 12.0, 3.6 Hz, 1H), 1.82-1.73 (m, 1H), 1.70-1.57 (m, 2H), 1.37 (qd, J = 12.9, 3.5 Hz, 1H), 1.31-1.13 (m, 3H), 0.69 (qd, J = 12.9, 2.7 Hz, 1H). | 282.3 |
| 61 | 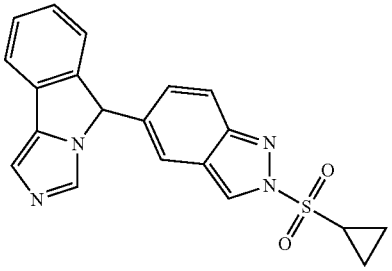 [SMILES: O=S(=O)(C1CC1)n1cc2cc(C3c4ccccc4-c4cncn43)ccc2n1] | | 377 |

TABLE 1-continued

| Example # | Structure | ¹H NMR | MS (M + H)⁺ |
|---|---|---|---|
| 62a | 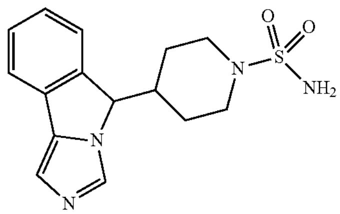 [SMILES: NS(=O)(=O)N1CCC(C2c3ccccc3-c3cncn32)CC1] | | 319 |
| 62b | 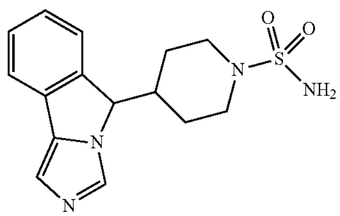 [SMILES: NS(=O)(=O)N1CCC(C2c3ccccc3-c3cncn32)CC1] | | 319 |
| 63 | 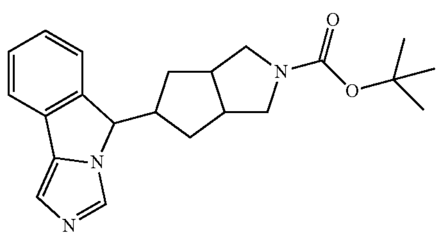 [SMILES: CC(C)(C)OC(=O)N1CC2CC(C3c4ccccc4-c4cncn43)CC2C1] | 1H NMR (400 MHz, DMSO-d6) δ 7.94 (s, 1H), 7.59 (dt, J = 7.6, 0.9 Hz, 1H), 7.55-7.47 (m, 1H), 7.42-7.34 (m, 1H), 7.26 (td, J = 7.6, 1.2 Hz, 1H), 7.14 (s, 1H), 5.39 (d, J = 5.8 Hz, 1H), 3.35-3.25 (m, 2H), 3.12 (s, 1H), 2.96 (s, 1H), 2.56 (s, 1H), 2.46 (s, 1H), 2.07 (s, 1H), 1.74 (d, J = 10.5 Hz, 1H), 1.48 (dt, J = 21.3, 10.4 Hz, 1H), 1.38 (s, 9H), 0.95 (s, 1H). | 366.3 |
| 64 | 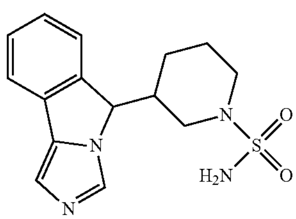 [SMILES: NS(=O)(=O)N1CCCC(C2c3ccccc3-c3cncn32)C1] | | 319 |
| 65 | 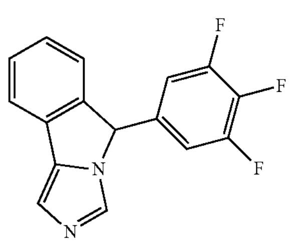 [SMILES: Fc1cc(C2c3ccccc3-c3cncn32)cc(F)c1F] | | 287 |
| 66 | 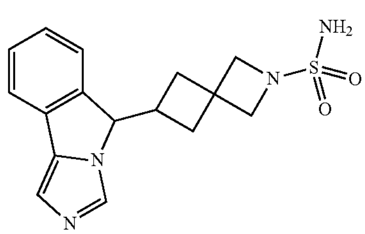 [SMILES: NS(=O)(=O)N1CC2(CC(C3c4ccccc4-c4cncn43)C2)C1] | | 331 |

TABLE 1-continued
| Example # | Structure | ¹H NMR | MS (M + H)⁺ |
|---|---|---|---|
| 67 | 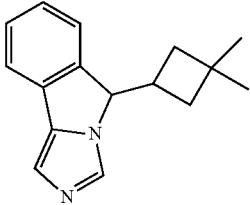 [SMILES: CC1(C)CC(C2c3ccccc3-c3cncn32)C1] | | 239 |
| 68 | 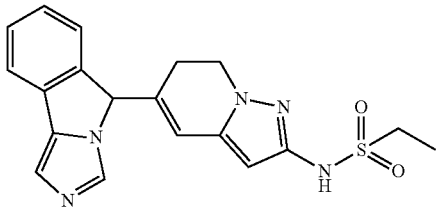 [SMILES: CCS(=O)(=O)Nc1cc2n(n1)CCC(C1c3ccccc3-c3cncn31)=C2] | | 382 |
| 69 | 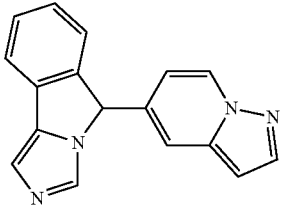 [SMILES: c1ccc2c(c1)-c1cncn1C2c1ccn2nccc2c1] | ¹H NMR (300 MHz, CD₃OD) δ 8.18 (s, 2H), 7.93 (s, 2H), 7.80-7.58 (m, 6H), 7.56-7.24 (m, 8H), 7.13 (dd, J = 8.9, 7.0 Hz, 2H), 6.80 (d, J = 2.3 Hz, 2H), 6.34 (s, 2H), 1.31 (s, 1H) | 273.3 |
| 70 | 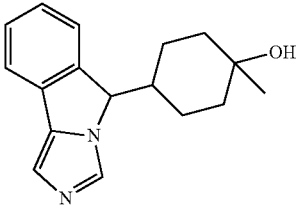 [SMILES: CC1(O)CCC(C2c3ccccc3-c3cncn32)CC1] | | 269 |
| 71 | 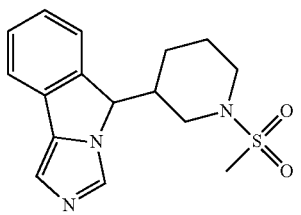 [SMILES: CS(=O)(=O)N1CCCC(C2c3ccccc3-c3cncn32)C1] | | 318 |
| 72a | 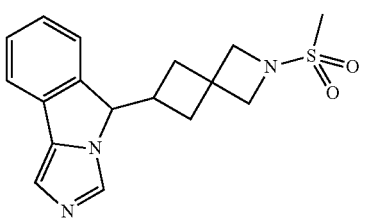 [SMILES: CS(=O)(=O)N1CC2(CC(C3c4ccccc4-c4cncn43)C2)C1] | | 330 |

TABLE 1-continued

| Example # | Structure | ¹H NMR | MS (M + H)⁺ |
|---|---|---|---|
| 72b | 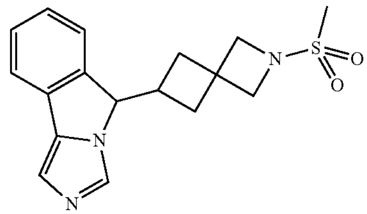 [SMILES: CS(=O)(=O)N1CC2(CC(C3c4ccccc4-c4cncn43)C2)C1] | | 330 |
| 73a | 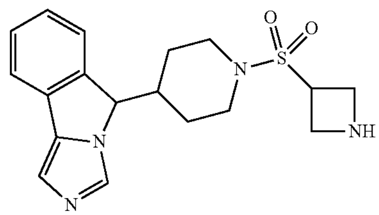 [SMILES: O=S(=O)(C1CNC1)N1CCC(C2c3ccccc3-c3cncn32)CC1] | | 359 |
| 73b | 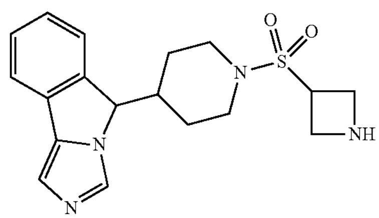 [SMILES: O=S(=O)(C1CNC1)N1CCC(C2c3ccccc3-c3cncn32)CC1] | | 359 |
| 74a | 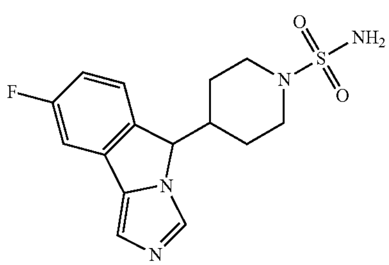 [SMILES: NS(=O)(=O)N1CCC(C2c3ccc(F)cc3-c3cncn32)CC1] | ¹H NMR (DMSO-d₆, 400 MHz): δ (ppm) 7.98 (s, 1H), 7.55 (dd, J = 8.4, 5.0 Hz, 1H), 7.50 (dd, J = 9.0, 2.5 Hz, 1H), 7.19 (s, 1H), 7.11 (ddd, J = 9.6, 8.4, 2.5 Hz, 1H), 6.73 (s, 2H), 5.37 (d, J = 2.3 Hz, 1H), 3.52 (d, J = 11.6 Hz, 1H), 3.41 (d, J = 11.8 Hz, 1H), 2.47-2.34 (m, 2H), 2.25 (td, J = 12.3, 3.1 Hz, 1H), 1.62 (d, J = 12.9 Hz, 1H), 1.44 (qd, J = 12.6, 4.3 Hz, 1H), 1.29 (d, J = 13.1 Hz, 1H), 0.92 (qd, J = 12.6, 4.3 Hz, 1H). | 337.3 |
| 74b | 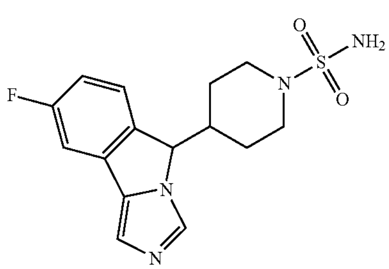 [SMILES: NS(=O)(=O)N1CCC(C2c3ccc(F)cc3-c3cncn32)CC1] | Same as 50a | 337.3 |
| 75a | 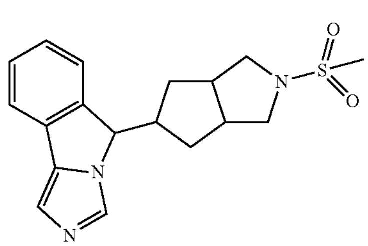 [SMILES: CS(=O)(=O)N1CC2CC(C3c4ccccc4-c4cncn43)CC2C1] | 1H NMR (400 MHz, Chloroform-d) δ 7.78 (s, 1H), 7.57-7.53 (m, 1H), 7.41-7.36 (m, 2H), 7.28-7.23 (m, 1H), 7.20 (s, 1H), 5.12 (d, J = 6.2 Hz, 1H), 3.33-3.11 (m, 5H), 2.83 (s, 3H), 2.80-2.63 (m, 2H), 2.34-2.16 (m, 3H), 1.33 (td, J = 11.3, 8.2 Hz, 1H). | 344.2 |

TABLE 1-continued

| Example # | Structure | ¹H NMR | MS (M + H)⁺ |
|---|---|---|---|
| 75b | 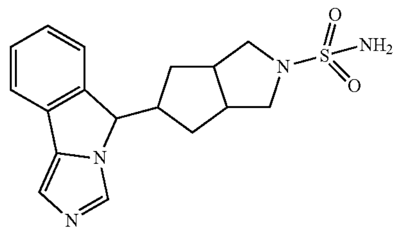 [SMILES: NS(=O)(=O)N1CC2CC(C3c4ccccc4-c4cncn43)CC2C1] | 1H NMR (400 MHz, DMSO-d6) δ 7.91 (s, 1H), 7.60 (dt, J = 7.6, 0.9 Hz, 1H), 7.51 (dt, J = 7.6, 1.0 Hz, 1H), 7.43-7.36 (m, 1H), 7.27 (td, J = 7.6, 1.2 Hz, 1H), 7.15 (s, 1H), 6.75 (s, 2H), 5.35 (d, J = 6.2 Hz, 1H), 3.01-2.88 (m, 3H), 2.83 (dd, J = 9.6, 2.4 Hz, 1H), 2.70-2.53 (m, 2H), 2.30-2.09 (m, 2H), 1.93-1.81 (m, 1H), 1.45 (td, J = 12.1, 8.8 Hz, 1H), 1.05 (td, J = 12.1, 8.9 Hz, 1H). | 345.2 |
| 76 | 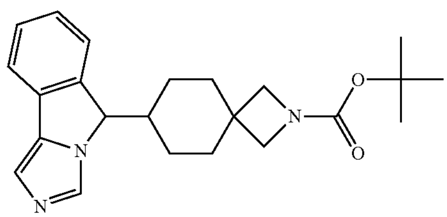 [SMILES: CC(C)(C)OC(=O)N1CC2(CCC(C3c4ccccc4-c4cncn43)CC2)C1] | ¹H NMR (400 MHz, DMSO-d₆) δ 7.92 (s, 1H), 7.59 (d, J = 7.6 Hz, 1H), 7.49 (d, J = 7.6 Hz, 1H), 7.40-7.36 (m, 1H), 7.30-7.26 (m, 1H), 7.14 (s, 1H), 5.28 (d, J = 2.1 Hz, 1H), 3.49-3.37 (m, 4H), 2.13-2.07 (m, 1H), 1.88-1.85 (m, 1H), 1.74-1.71 (m, 1H), 1.81-1.60 (m, 1H), 1.58-1.55 (m, 1H), 1.48-1.42 (m, 1H), 1.35 (s, 9H), 1.31-1.24 (m, 1H), 1.09-1.06 (m, 1H), 0.69-0.53 (m, 1H). | 380.3 |
| 77 | 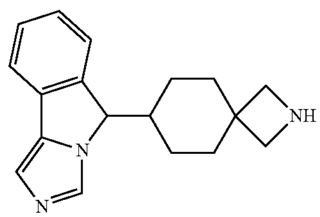 [SMILES: c1ccc2c(c1)-c1cncn1C2C1CCC2(CC1)CNC2] | ¹H NMR (400 MHz, DMSO-d₆) δ 7.88 (s, 1H), 7.58 (d, J = 7.6 Hz, 1H), 7.48 (d, J = 7.6 Hz, 1H), 7.38 (t, J = 7.7 Hz, 1H), 7.27 (td, J = 7.6, 1.2 Hz, 1H), 7.13 (s, 1H), 5.30-5.24 (m, 1H), 3.27-3.11 (m, 3H), 2.13-1.96 (m, 2H), 1.86 (d, J = 13.0 Hz, 1H), 1.53 (d, J = 12.5 Hz, 1H), 1.37 (t, J = 13.0 Hz, 1H), 1.22 (q, J = 12.7 Hz, 2H), 1.08 (d, J = 12.7 Hz, 1H), 0.67-0.57 (m, 1H). | 280.3 |
| 78a | 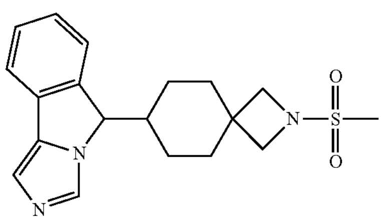 [SMILES: CS(=O)(=O)N1CC2(CCC(C3c4ccccc4-c4cncn43)CC2)C1] | ¹H NMR (300 MHz, CD₃OD) δ 7.92 (s, 1H), 7.68-7.59 (m, 2H), 7.46-7.37 (m, 1H), 7.34-7.26 (m, 1H), 7.20 (d, J = 2.4 Hz, 1H), 7.12 (s, 1H), 5.98 (d, J = 2.1 Hz, 1H), 5.44 (d, J = 1.8 Hz, 1H), 4.75 (d, J = 12 Hz, 1H), 4.39-4.00 (m, 2H), 2.50-2.39 (m, 2H), 2.18-2.06 (m, 1H), 1.81-1.60 (m, 2H). | 358.3 |
| 78b | 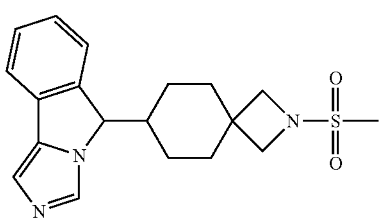 [SMILES: CS(=O)(=O)N1CC2(CCC(C3c4ccccc4-c4cncn43)CC2)C1] | The same as 76a. | 358.3 |
| 79a | 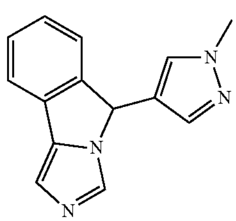 [SMILES: Cn1cc(C2c3ccccc3-c3cncn32)cn1] | ¹H NMR (300 MHz, CD₃OD) δ 7.78 (s, 1H), 7.72-7.57 (m, 2H), 7.50-7.26 (m, 4H), 7.18 (s, 1H), 6.40 (s, 1H), 3.88 (s, 3H). | 237.3 |

TABLE 1-continued
| Example # | Structure | ¹H NMR | MS (M + H)⁺ |
|---|---|---|---|
| 79b | 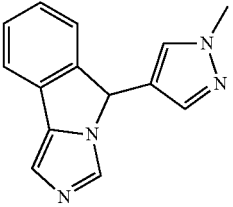 | The same as 78a. | 237.3 |
| 80a | 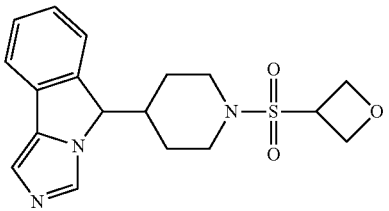 [SMILES: O=S(=O)(C1COC1)N1CCC(C2c3ccccc3-c3cncn32)CC1] | | 360 |
| 80b | 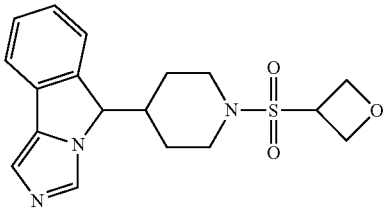 [SMILES: O=S(=O)(C1COC1)N1CCC(C2c3ccccc3-c3cncn32)CC1] | | 360 |
| 80c | 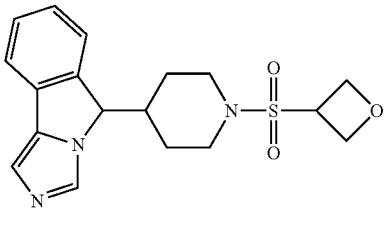 [SMILES: O=S(=O)(C1COC1)N1CCC(C2c3ccccc3-c3cncn32)CC1] | | 360 |
| 81 | 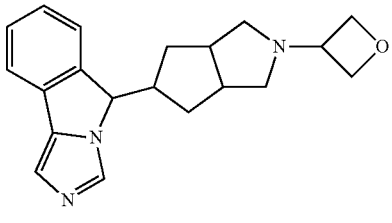 [SMILES: c1ccc2c(c1)-c1cncn1C2C1CC2CN(C3COC3)CC2C1] | | 322 |
| 82a | 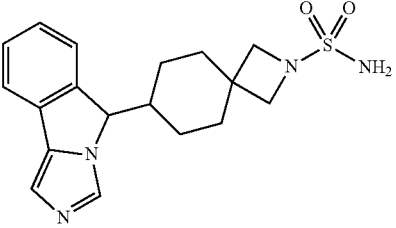 [SMILES: NS(=O)(=O)N1CC2(CCC(C3c4ccccc4-c4cncn43)CC2)C1] | ¹H NMR (300 MHz, CD₃OD) δ 7.90 (s, 1H), 7.58 (d, J = 7.5 Hz, 1H), 7.48 (d, J = 7.5 Hz, 1H), 7.40-7.25 (m, 2H), 7.13 (s, 1H), 6.77 (s, 2H), 5.23 (d, J = 3.6 Hz, 1H), 3.42-3.28 (m, 4H), 2.13-2.06 (m, 1H), 1.92-1.88 (m, 1H), 1.76-1.72 (m, 1H), 1.58-1.07 (m, 1H), 0.70-0.49 (m, 1H). | 359.2 |

TABLE 1-continued

| Example # | Structure | ¹H NMR | MS (M + H)⁺ |
|---|---|---|---|
| 82b | 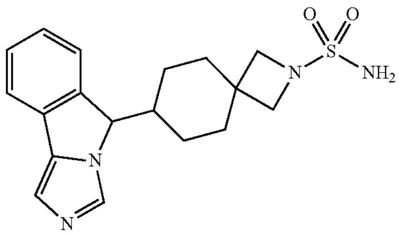 [SMILES: NS(=O)(=O)N1CC2(CCC(C3c4ccccc4-c4cncn43)CC2)C1] | The same as 82a. | 359.2 |
| 83a | 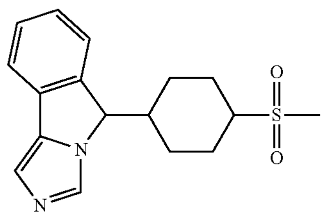 [SMILES: CS(=O)(=O)C1CCC(C2c3ccccc3-c3cncn32)CC1] | ¹H NMR (300 MHz, Methanol-d₄) δ 7.93 (s, 1H), 7.66-7.57 (m, 1H), 7.56-7.27 (m, 3H), 7.17 (s, 1H), 5.34 (d, J = 2.8 Hz, 1H), 2.99-2.92 (m, 1H), 2.86 (s, 3H), 2.35-2.09 (m, 3H), 1.88 (d, J = 12.5 Hz, 1H), 1.73-1.24 (m, 5H), 1.02-0.89 (m, 1H). | 317.2 |
| 83b | 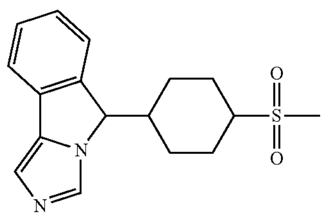 [SMILES: CS(=O)(=O)C1CCC(C2c3ccccc3-c3cncn32)CC1] | The same as 83a. | 317.2 |
| 84a | 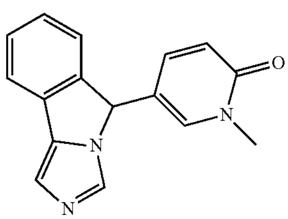 [SMILES: Cn1cc(C2c3ccccc3-c3cncn32)ccc1=O] | ¹H NMR (300 MHz, DMSO) δ 7.97 (s, 1H), 7.79 (s, 1H), 7.68 (d, J = 7.5 Hz, 1H), 7.46-7.43 (m, 1H), 7.32-7.25 (m, 2H), 7.21 (s, 1H), 6.73 (d, J = 12.0 Hz, 1H), 6.32 (d, J = 12.0 Hz, 1H), 6.24 (s, 1H), 3.47 (s, 3H). | 264.3 |
| 84b | 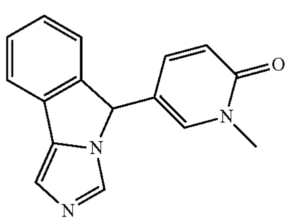 [SMILES: Cn1cc(C2c3ccccc3-c3cncn32)ccc1=O] | The same as 84a. | 264.3 |
| 85a | 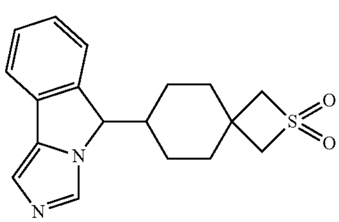 [SMILES: O=S1(=O)CC2(CCC(C3c4ccccc4-c4cncn43)CC2)C1] | ¹H NMR (300 MHz, DMSO-d₆) δ 8.12 (s, 1H), 7.62 (d, J = 7.5 Hz, 1H), 7.53 (d, J = 7.5 Hz, 1H), 7.44-7.29 (m, 2H), 7.25 (s, 1H), 5.36 (d, J = 3.6 Hz, 1H), 3.93-3.76 (m, 4H), 2.22-2.15 (m, 1H), 2.01-1.96 (m, 1H), 1.85-1.81 (m, 1H), 1.66-1.12 (m, 5H), 0.71-0.65 (m, 1H). | 329.2 |

TABLE 1-continued

| Example # | Structure | ¹H NMR | MS (M + H)⁺ |
|---|---|---|---|
| 85b | 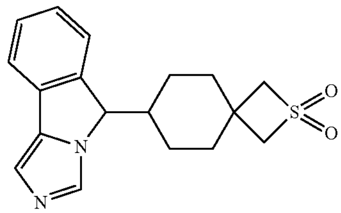 [SMILES: O=S1(=O)CC2(CCC(C3c4ccccc4-c4cncn43)CC2)C1] | The same as 85a. | 329.2 |
| 86a | 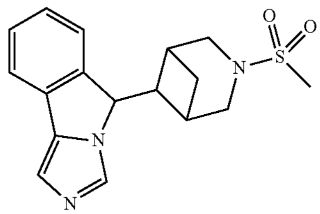 [SMILES: CS(=O)(=O)N1CC2CC(C1)C2C1c2ccccc2-c2cncn21] | | 330 |
| 86b | 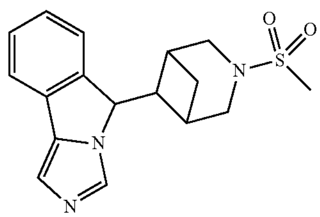 [SMILES: CS(=O)(=O)N1CC2CC(C1)C2C1c2ccccc2-c2cncn21] | | 330 |
| 86c | 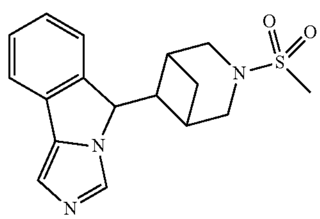 [SMILES: CS(=O)(=O)N1CC2CC(C1)C2C1c2ccccc2-c2cncn21] | | 330 |
| 86d | 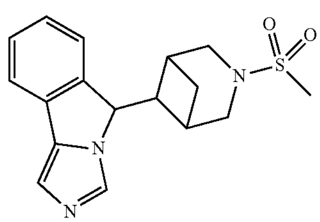 [SMILES: CS(=O)(=O)N1CC2CC(C1)C2C1c2ccccc2-c2cncn21] | | 330 |
| 87 | 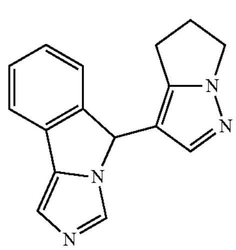 [SMILES: c1ccc2c(c1)-c1cncn1C2c1cnn2c1CCC2] | ¹H NMR (400 MHz, DMSO-d$_6$) δ 7.77 (s, 1H), 7.64 (d, J = 7.6 Hz, 1H), 7.52 (s, 1H), 7.42-7.38 (m, 1H), 7.32 (d, J = 7.6 Hz, 1H), 7.28-7.24 (m, 2H), 6.42 (s, 1H), 3.98 (t, J = 5.4 Hz, 2H), 2.43-2.31 (m, 2H), 2.29-2.22 (m, 2H). | 263.2 |

TABLE 1-continued

| Example # | Structure | ¹H NMR | MS (M + H)⁺ |
|---|---|---|---|
| 88 | 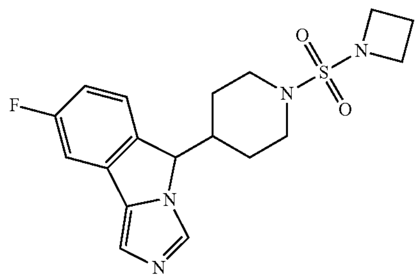 [SMILES: O=S(=O)(N1CCC1)N1CCC(C2c3ccc(F)cc3-c3cncn32)CC1] | | 377 |
| 89 | 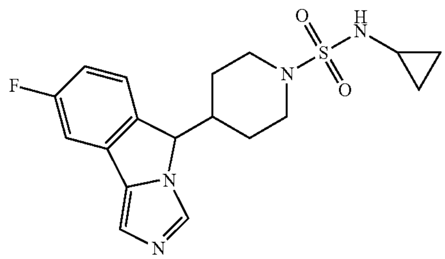 [SMILES: O=S(=O)(NC1CC1)N1CCC(C2c3ccc(F)cc3-c3cncn32)CC1] | | 377 |
| 90 | 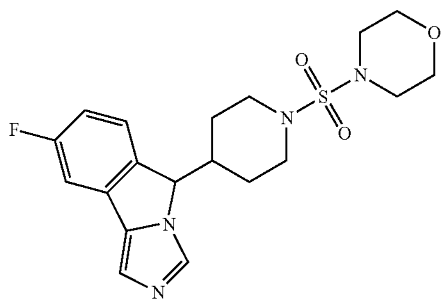 [SMILES: O=S(=O)(N1CCOCC1)N1CCC(C2c3ccc(F)cc3-c3cncn32)CC1] | | 407 |
| 91a | 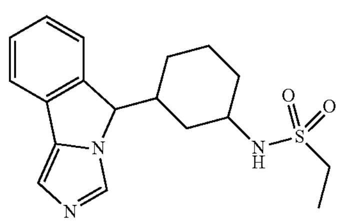 [SMILES: CCS(=O)(=O)NC1CCCC(C2c3ccccc3-c3cncn32)C1] | | 346 |
| 91b | 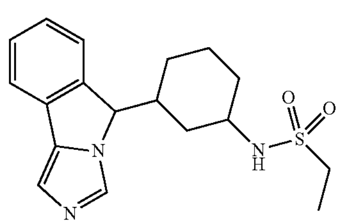 [SMILES: CCS(=O)(=O)NC1CCCC(C2c3ccccc3-c3cncn32)C1] | | 346 |
| 91c | 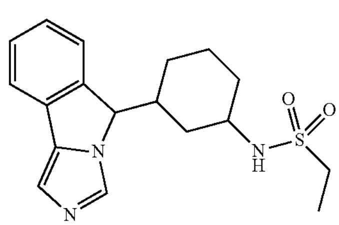 [SMILES: CCS(=O)(=O)NC1CCCC(C2c3ccccc3-c3cncn32)C1] | | 346 |

TABLE 1-continued

| Example # | Structure | ¹H NMR | MS (M + H)⁺ |
|---|---|---|---|
| 91d | 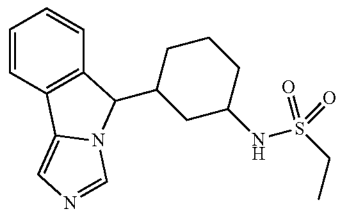 [SMILES: CCS(=O)(=O)NC1CCCC(C2c3ccccc3-c3cncn32)C1] | | 346 |
| 92a | 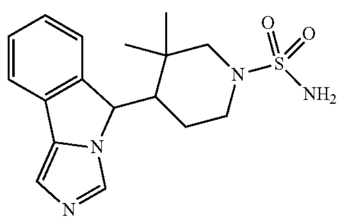 [SMILES: CC1(C)CN(S(N)(=O)=O)CCC1C1c2ccccc2-c2cncn21] | | 347 |
| 92b | 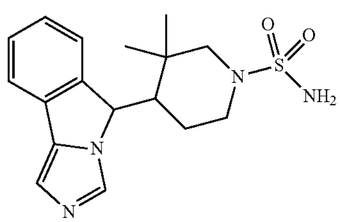 [SMILES: CC1(C)CN(S(N)(=O)=O)CCC1C1c2ccccc2-c2cncn21] | | 347 |
| 93 | 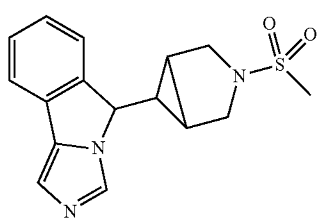 [SMILES: CS(=O)(=O)N1CC2C(C1)C2C1c2ccccc2-c2cncn21] | | 316 |
| 94 | 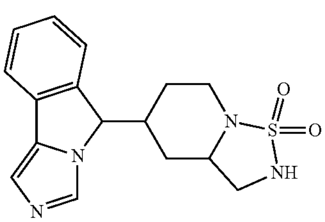 [SMILES: O=S1(=O)NCC2CC(C3c4ccccc4-c4cncn43)CCN21] | ¹H NMR (300 MHz, Methanol-d4) 7.98 (d, J = 8.4 Hz, 1H), 7.77-7.28 (m, 5H), 7.19 (d, J = 2.4 Hz, 1H), 5.43 (t, J = 3.5 Hz, 1H), 4.07-3.67 (m, 1H), 3.56-3.21 (m, 2H), 3.05-2.78 (m, 2H), 2.46-2.38 (m, 1H), 2.09-0.80 (m, 2H). | 331.1 |
| 95a | 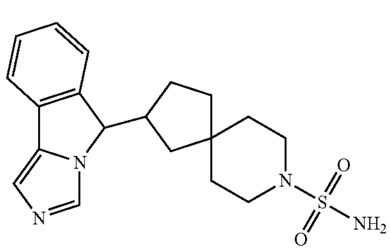 [SMILES: NS(=O)(=O)N1CCC2(CCC(C3c4ccccc4-c4cncn43)C2)CC1] | ¹H NMR (400 MHz, DMSO-d₆) δ 7.82 (s, 1H), 7.63 (d, J = 7.2 Hz, 1H), 7.54 (d, J = 7.2 Hz, 1H), 7.42-7.239 (m, 1H), 7.32-7.28 (m, 1H), 7.25 (s, 1H), 6.65 (s, 2H), 5.41 (d, J = 5.6 Hz, 1H), 2.93-2.89 (m, 4H), 2.61-2.51 (m, 1H), 1.76-1.71 (m, 1H), 1.62-1.23 (m, 9H). | 373.3 |

TABLE 1-continued
| Example # | Structure | ¹H NMR | MS (M + H)⁺ |
|---|---|---|---|
| 95b | 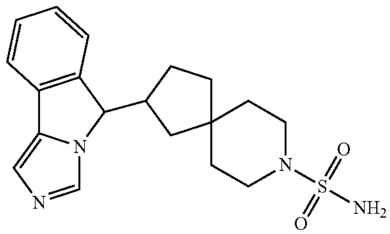 [SMILES: NS(=O)(=O)N1CCC2(CCC(C3c4ccccc4-c4cncn43)C2)CC1] | The same as 95a. | 373.3 |
| 95c | 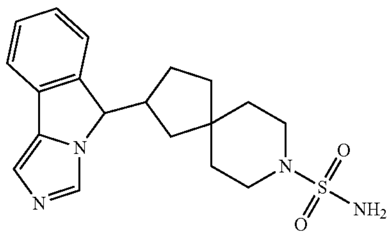 [SMILES: NS(=O)(=O)N1CCC2(CCC(C3c4ccccc4-c4cncn43)C2)CC1] | ¹H NMR (400 MHz, DMSO-d₆) δ 7.92 (s, 1H), 7.60 (d, J = 7.6 Hz, 1H), 7.52 (d, J = 7.6 Hz, 1H), 7.40-7.36 (m, 1H), 7.30-7.25 (m, 1H), 7.25 (s, 1H), 6.58 (s, 2H), 5.41 (d, J = 5.6 Hz, 1H), 2.93-2.69 (m, 5H), 1.94-1.80 (m, 2H), 1.48-1.31 (m, 8H). | 373.3 |
| 95d | 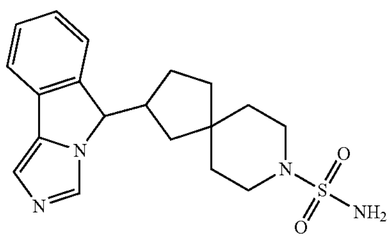 [SMILES: NS(=O)(=O)N1CCC2(CCC(C3c4ccccc4-c4cncn43)C2)CC1] | The same as 95c. | 373.3 |
| 96 | 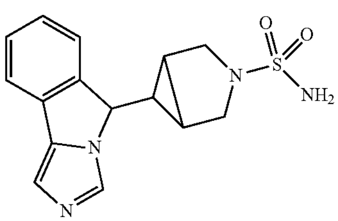 [SMILES: NS(=O)(=O)N1CC2C(C1)C2C1c2ccccc2-c2cncn21] | | 317 |
Example 01: (R)-(3-(5H-imidazo[5,1-a]isoindol-5-yl)phenyl)methanol and (S)-(3-(5H-imidazo[5,1-a]isoindol-5-yl)phenyl)methanol
-continued
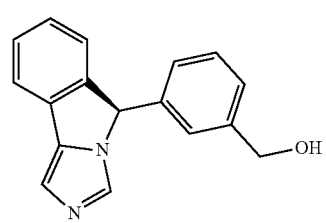
01a
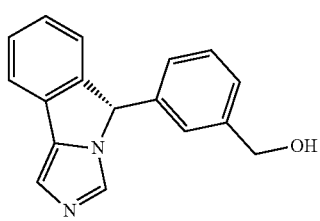
01b

Synthetic Route

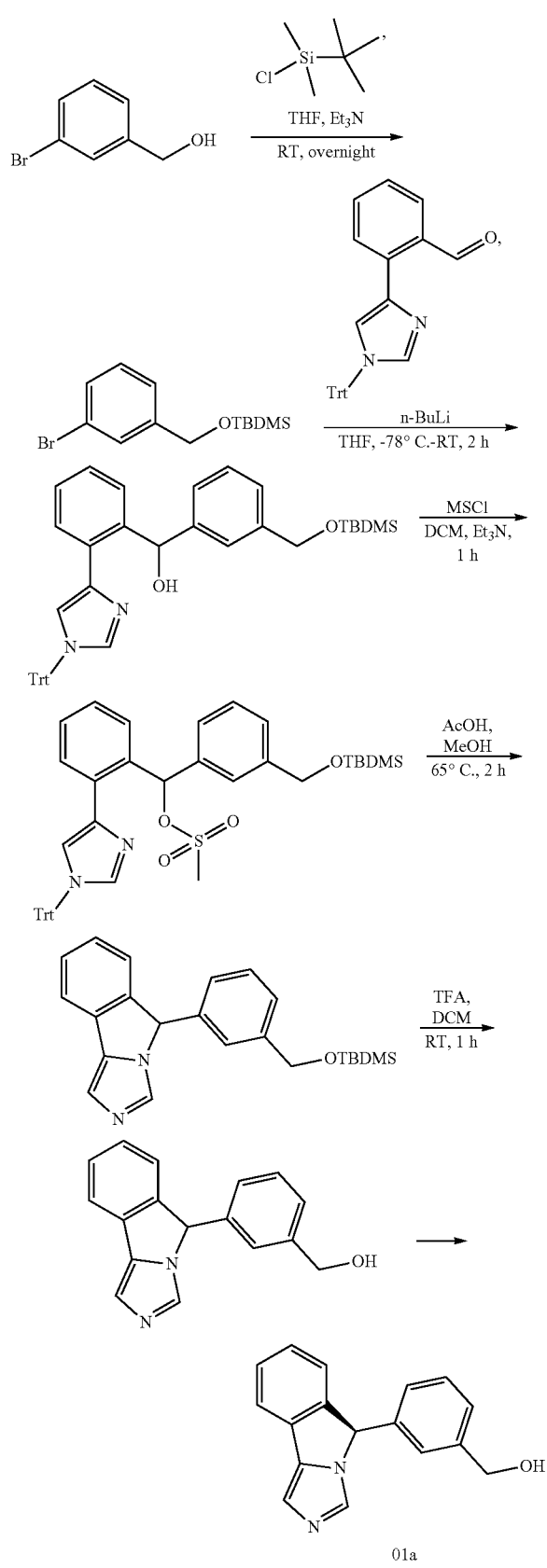

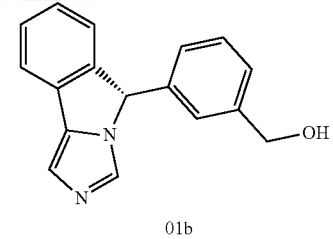

Step 1:

(3-bromobenzyloxy)(tert-butyl)dimethylsilane

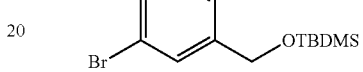

A solution of (3-bromophenyl)methanol (15 g, 80.20 mmol) and triethylamine (16.2 g, 160.10 mmol) in THF (150 mL) was added tert-butyl(chloro)dimethylsilane (15.9 g, 105.49 mmol). The resulting solution was stirred for 6 h at room temperature. The reaction was then quenched by the addition of water (300 mL). The resulting solution was extracted with EA (2×300 mL) and the organic layers were combined. The solution was concentrated under vacuum. The residue was purified by silica gel column eluting with EA/petroleum ether (1:5). This resulted in 18 g (74%) of [(3-bromophenyl)methoxy](tert-butyl)dimethylsilane as white oil. LCMS (ESI, m/z): 302.2 [M+H]$^+$.

Step 2:

(3-((tert-butyldimethylsilyloxy)methyl)phenyl)(2-(1-trityl-1H-imidazol-4-yl)phenyl)methanol

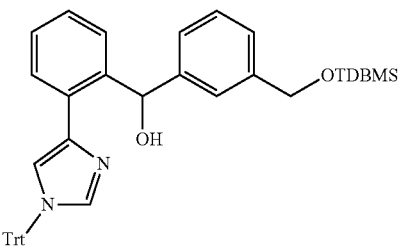

Under nitrogen, a solution of [(3-bromophenyl)methoxy](tert-butyl)dimethylsilane (7.3 g, 24.23 mmol) in THF (50 mL) was added n-BuLi (10 mL, 106.16 mmol, 2.5 M in THF) at −78° C. The resulting solution was stirred for 1 h at −78° C. Then 2-[1-(triphenylmethyl)-1H-imidazol-4-yl]benzaldehyde (2 g, 4.83 mmol) was added, the resulting solution was allowed to react, with stirring, for an additional 5 h at room temperature. The reaction was then quenched by water (100 mL). The resulting solution was extracted with EA (3×100 mL) and the organic layers combined. The solution was concentrated under vacuum. The residue was purified by silica gel column eluting with EA/petroleum ether (1:3). This resulted in 1.5 g (49%) of (3-[[(tert-butyldimethylsilyl)oxy]methyl]phenyl)([2-[1-(triphenylmethyl)-1H-imidazol-4-yl]phenyl])methanol as a yellow solid. LCMS (ESI, m/z): 638.2 [M+H]$^+$.

Step 3:

(3-((tert-butyldimethylsilyloxy)methyl)phenyl)(2-(1-trityl-1H-imidazol-4-yl)phenyl)methyl methanesulfonate

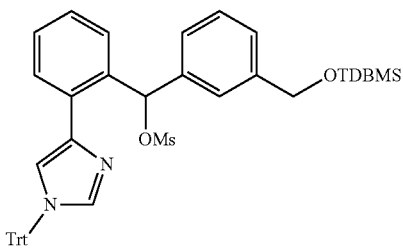

A solution of (3-[[(tert-butyldimethylsilyl)oxy]methyl]phenyl)([2-[1-(triphenylmethyl)-1H-imidazol-4-yl]phenyl])methanol (400 mg, 0.63 mmol) and triethylamine (95 mg, 0.94 mmol) in DCM (5 mL) was added MsCl (79 mg, 0.69 mmol). The resulting solution was stirred for 1 h at room temperature. The resulting mixture was concentrated under vacuum. This resulted in 380 mg (85%) of (3-[[(tert-butyldimethylsilyl)oxy]methyl]phenyl)([2-[1-(triphenylmethyl)-1H-imidazol-4-yl]phenyl])methyl methanesulfonate as yellow oil. LCMS (ESI, m/z): 715.2 [M+H]⁺.

Step 4:

5-(3-((tert-butyldimethylsilyloxy)methyl)phenyl)-5H-imidazo[5,1-a]isoindole

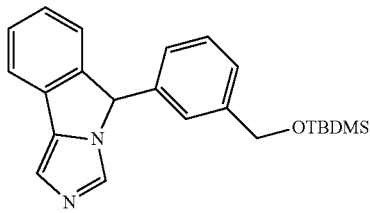 [SMILES: CC(C)(C)[Si](C)(C)OCc1cccc(C2c3ccccc3-c3cncn32)c1]

A solution of (3-[[(tert-butyldimethylsilyl)oxy]methyl]phenyl)([2-[1-(triphenylmethyl)-1H-imidazol-4-yl]phenyl])methyl methanesulfonate (380 mg, 0.53 mmol) in methanol (5 mL) and AcOH (1 mL) was stirred for 1 h at 70° C. The resulting mixture was concentrated under vacuum. The residue was purified by silica gel column eluting with DCM/methanol (10:1). This resulted in 210 mg (crude) of 5-(3-[[(tert-butyldimethylsilyl)oxy]methyl]phenyl)-5H-imidazo[4,3-a]isoindole as a yellow solid. LCMS (ESI, m/z): 377.2 [M+H]⁺.

Step 5:

(R)-(3-(5H-imidazo[5,1-a]isoindol-5-yl)phenyl)methanol
(S)-(3-(5H-imidazo[5,1-a]isoindol-5-yl)phenyl)methanol 01a

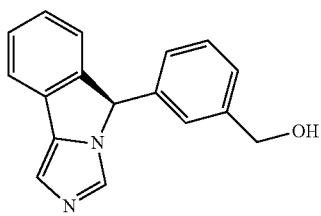

01b

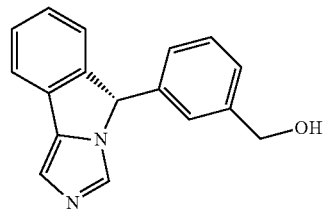

A solution of 5-(3-[[(tert-butyldimethylsilyl)oxy]methyl]phenyl)-5H-imidazo[4,3-a]isoindole (1.43 g, 3.8 mmol) in DCM (50 mL) was added TFA (3 mL). The resulting solution was stirred for 1 h at room temperature. The resulting mixture was concentrated under vacuum. The residue was purified by silica gel column eluting with DCM/methanol (10:1). The crude product was further isolated by Prep-HPLC and chiral separation.

The absolute configuration of isomer 01a was determined by X-ray crystallography. The absolute configuration of isomer 01b was determined through its enantiomer 01a.

Example 01a: (R)-(3-(5H-imidazo[5,1-a]isoindol-5-yl)phenyl)methanol (21.7 mg, 2%) as a white solid. LCMS (ESI, m/z): 263.2 [M+H]⁺. ¹H NMR (300 MHz, CD₃OD) δ 7.71 (d, J=7.5 Hz, 2H), 7.51-7.35 (m, 3H), 7.35-7.24 (m, 3H), 7.24-7.10 (m, 2H), 6.39 (s, 1H), 4.59 (s, 2H). tR=1.640 min (Lux Cellulose-4, 0.46*5 cm; 3 um, Hex (0.1% DEA): EtOH=50:50, 1.0 ml/min). 01a and 1b are enantiomers.

Example 01b: (S)-(3-(5H-imidazo[5,1-a]isoindol-5-yl)phenyl)methanol (22.3 mg, 2%) as a white solid. LCMS (ESI, m/z): 263.2 [M+H]⁺. tR=2.577 min (Lux Cellulose-4, 0.46*5 cm; 3 um, Hex (0.1% DEA):EtOH=50:50, 1.0 ml/min). 01a and 01b are enantiomers.

Example 02: 3-((5H-imidazo[5,1-a]isoindol-5-yl)methyl)-N-methylpyridin-2-amine

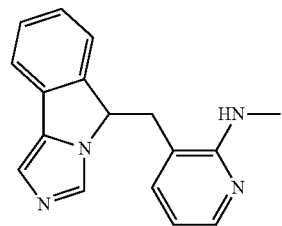 [SMILES: CNc1ncccc1CC1c2ccccc2-c2cncn21]

Synthetic Route

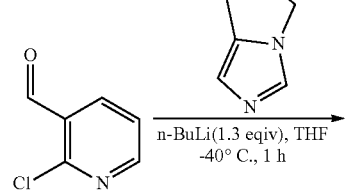

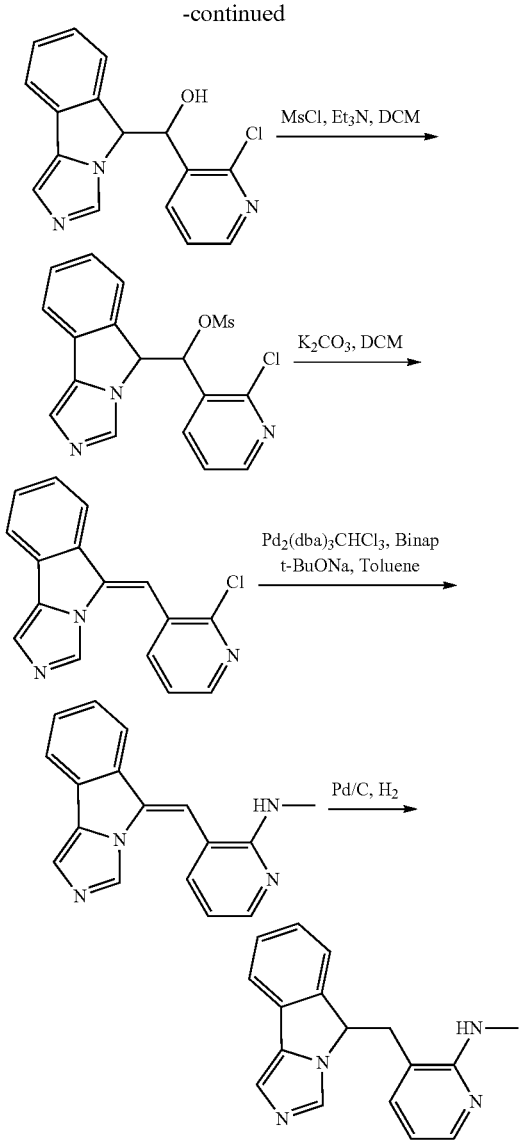

Step 1:

(2-chloropyridin-3-yl)(5H-imidazo[5,1-a]isoindol-5-yl)methanol

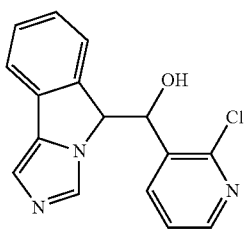

Under nitrogen, a solution of 5H-imidazo[4,3-a]isoindole (3.14 g, 20.11 mmol) in THF (50 mL) was added n-BuLi (12 mL, 468.35 mmol, 2.5 M in THF) at −40° C. The resulting solution was stirred for 4 h at −40° C. After 2-chloropyridine-3-carbaldehyde (3.38 g, 23.89 mmol) was added, the resulting solution was stirred for 1 overnight at room temperature. The reaction was then quenched by the addition of water (5 mL). The resulting mixture was concentrated under vacuum. The residue was purified by silica gel column eluting with DCM/methanol (10:1). This resulted in 3.5 g (49%) of (2-chloropyridin-3-yl)(5H-imidazo[4,3-a]isoindol-5-yl)methanol as a brown solid. LCMS (ESI, m/z): 298.2 [M+H]⁺.

Step 2:

(2-chloropyridin-3-yl)(5H-imidazo[5,1-a]isoindol-5-yl)methyl methanesulfonate

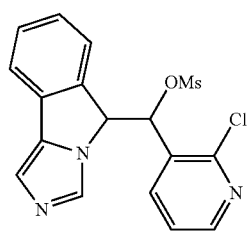 [SMILES: CS(=O)(=O)OC(c1cccnc1Cl)C1c2ccccc2-c2cncn21]

A solution of (2-chloropyridin-3-yl)(5H-imidazo[4,3-a]isoindol-5-yl)methanol (3.5 g, 11.76 mmol) in DCM (150 mL) was added MsCl (1.8 mL, 23.26 mmol) and triethylamine (3.4 mL, 24.46 mmol) at 0° C. The resulting solution was stirred for 2 h at room temperature. The reaction was quenched with water (100 mL). The resulting mixture was extracted with DCM (2×100 mL). The resulting mixture was concentrated under vacuum. This resulted in 4 g (91%) of (2-chloropyridin-3-yl)(5H-imidazo[4,3-a]isoindol-5-yl)methyl methanesulfonate as a brown solid. LCMS (ESI, m/z): 376.2 [M+H]⁺.

Step 3:

(E)-5-((2-chloropyridin-3-yl)methylene)-5H-imidazo[5,1-a]isoindole

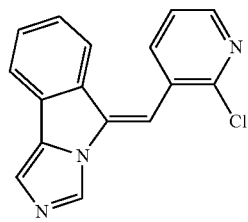 [SMILES: Clc1ncccc1/C=c1\c2ccccc2c2cncn12]

A solution of (2-chloropyridin-3-yl)(5H-imidazo[4,3-a]isoindol-5-yl)methanol (4 g, 13.44 mmol) in DCM (100 mL) and N,N-dimethylformamide (10 mL) was added potassium carbonate (14 g, 101.30 mmol). The resulting solution was stirred for 4 h at room temperature. The resulting mixture was washed water. The resulting mixture was concentrated under vacuum. The residue was purified by silica gel column eluting with DCM/methanol (10:1). This resulted in 3.5 g (93%) of (E)-5-((2-chloropyridin-3-yl)methylene)-5H-imidazo[5,1-a]isoindole as a brown solid. LCMS (ESI, m/z): 280.2 [M+H]⁺.

Step 4:

(E)-3-((5H-imidazo[5,1-a]isoindol-5-ylidene)methyl)-N-methylpyridin-2-amine

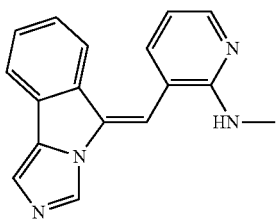 [SMILES: CNc1ncccc1/C=c1\c2ccccc2c2cncn12]

Under nitrogen, a solution of (E)-5-((2-chloropyridin-3-yl)methylene)-5H-imidazo[5,1-a]isoindole (560 mg, 2.00 mmol), methanamine (2 mL, 2.00 equiv, 2M in THF), Pd$_2$(dba)$_3$CHCl$_3$ (207 mg, 0.20 mmol), Binap (249 mg, 0.40 mmol), t-BuONa (384 mg, 3.996 mmol, 1.996 equiv) in toluene (20 mL) was stirred for 4 h at 90° C. The resulting mixture was concentrated under vacuum. The residue was purified by silica gel column eluting with DCM/methanol (10:1). This resulted in 0.3 g (55%) of (E)-3-((5H-imidazo[5,1-a]isoindol-5-ylidene)methyl)-N-methylpyridin-2-amine as a yellow solid. LCMS (ESI, m/z): 275.3 [M+H]$^+$.

Step 5:
(R)-3-((5H-imidazo[5,1-a]isoindol-5-yl)methyl)-N-methylpyridin-2-amine
(S)-3-((5H-imidazo[5,1-a]isoindol-5-yl)methyl)-N-methylpyridin-2-amine

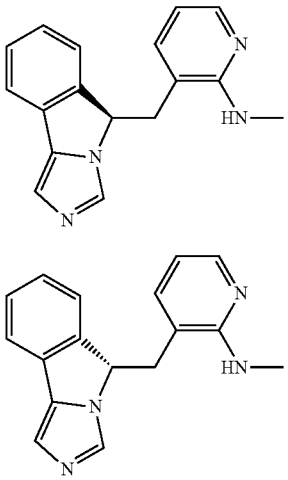

02a

02b

Under hydrogen, a slurry of (E)-3-((5H-imidazo[5,1-a]isoindol-5-ylidene)methyl)-N-methylpyridin-2-amine (300 mg, 1.09 mmol) and Palladium carbon (50 mg, 0.470 mmol) in methanol (50 mL) was stirred for 1 overnight at room temperature. The solids were filtered out. The residue was purified by silica gel column eluting with DCM/methanol (10:1). The crude product was further isolated by Prep-HPLC and chiral separation with the following conditions:

1. Column: XBridge Prep C18 OBD Column, 5 um, 19*150 mm; Mobile Phase A:Waters (10 MMOL/L NH4HCO3), Mobile Phase B: DCM:ACN=1:1; Flow rate: 30 mL/min; Gradient: 5% B to 45% B in 9 min; 254/220 nm 2. Column: Phenomenex Lux 5 u Cellulose-4, AXIA Packed, 250*21.2 mm, 5 um; Mobile Phase A:Hex—HPLC, Mobile Phase B: EtOH—HPLC; Flow rate: 20 mL/min; Gradient: 50 B to 50 B in 15 min; 254/220 nm; RT1:6.617; RT2:10.125.

The absolute configuration of all isomers 02a and 02b were assigned arbitrarily.

Example 02a: (R)-3-((5H-imidazo[5,1-a]isoindol-5-yl)methyl)-N-methylpyridin-2-amine (49.9 mg, 17%) as a white solid. LCMS (ESI, m/z): 277.2 [M+H]$^+$. $^1$H NMR (300 MHz, CDCl$_3$) δ 8.24 (dd, J=5.1, 1.8 Hz, 1H), 8.00 (s, 1H), 7.62 (d, J=7.6 Hz, 1H), 7.44 (dd, J=8.1, 7.0 Hz, 1H), 7.33-7.23 (m, 2H), 7.23-7.10 (m, 2H), 6.64 (dd, J=7.2, 5.1 Hz, 1H), 5.62 (t, J=7.3 Hz, 1H), 5.00 (s, 1H), 3.24-3.04 (m, 5H). tR=1.224 min (Lux Cellulose-4, 0.46*5 cm, 3 um, Hex (0.1% DEA):EtOH=50:50, 1.0 mL/min). 02a and 02b are enantiomers.

Example 02b: (R)-3-((5H-imidazo[5,1-a]isoindol-5-yl)methyl)-N-methylpyridin-2-amine (52 mg, 19%) as a white solid. LCMS (ESI, m/z): 277.2 [M+H]$^+$. tR=1.833 min (Lux Cellulose-4, 0.46*5 cm, 3 um, Hex (0.1% DEA):EtOH=50:50, 1.0 mL/min). 02a and 02b are enantiomers.

Example 03: (6-(5H-imidazo[5,1-a]isoindol-5-yl)pyridin-2-yl)methanol

Synthetic Route

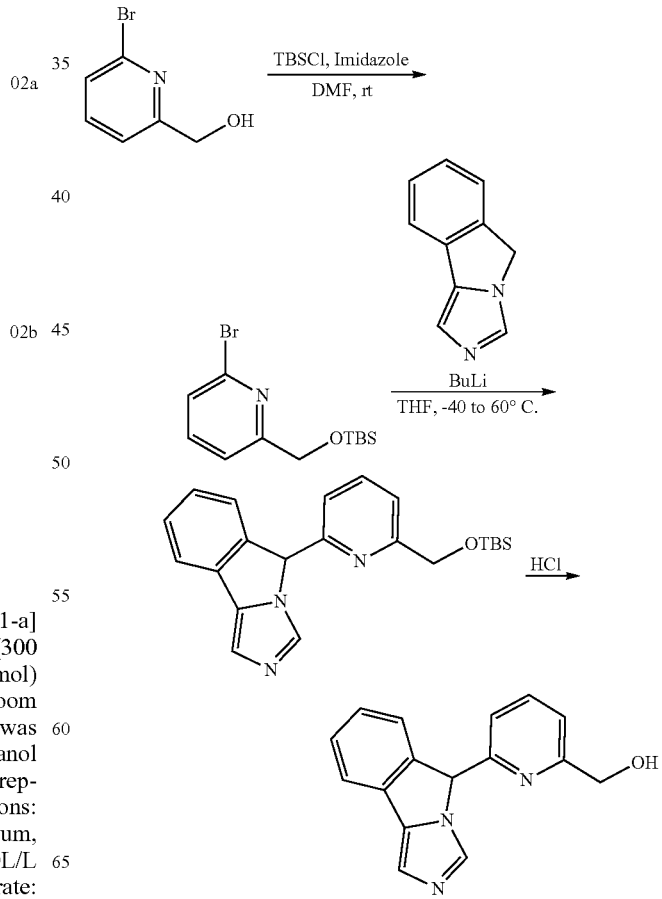

Step 1:

2-bromo-6-(((tert-butyldimethylsilyl)oxy)methyl)pyridine

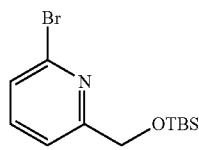 [SMILES: CC(C)(C)[Si](C)(C)OCc1cccc(Br)n1]

To a solution of (6-bromopyridin-2-yl)methanol (1.0 g, 5.32 mmol) and imidazole (398.3 mg, 5.85 mmol) in DMF (15 mL) at rt was added TBSCl (882 mg, 5.85 mmol). After stirring overnight the reaction was diluted with water (30 mL) and the product was extracted with ethyl acetate (3×40 mL). The combined organic extract was washed with water (25 mL), brine dried (Na$_2$SO$_4$) and concentrated under reduced pressure to afford crude. Chromatographic purification afforded the desired product (1.48 g, 92%). $^1$H NMR (Chloroform-d, 400 MHz): δ (ppm) 7.55 (t, J=7.7 Hz, 1H), 7.49-7.43 (m, 1H), 7.38-7.23 (m, 1H), 4.79 (s, 2H), 0.94 (s, 9H), 0.10 (s, 6H).

Step 2:

5-(6-(((tert-butyldimethylsilyl)oxy)methyl)pyridin-2-yl)-5H-imidazo[5,1-a]isoindole

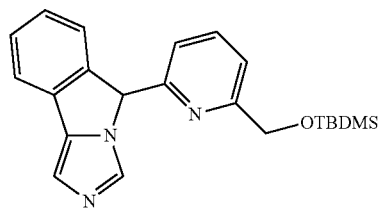 [SMILES: CC(C)(C)[Si](C)(C)OCc1cccc(C2c3ccccc3-c3cncn32)n1]

To a solution of 5H-imidazo[5,1-a]isoindole (504 mg, 3.23 mmol) in THF (10 mL) at −40° C. was added n-BuLi (1.29 mL, 3.23 mmol; 2.5 M solution in hexane). After stirring for 1 h at the same temp, 2-bromo-6-(((tert-butyldimethylsilyl)oxy)methyl)pyridine (650 mg, 2.15 mmol) was added as solution in THF (5 mL) and the mixture was stirred at rt overnight, followed by stirring at 60° C. for 4 h. After cooling to rt, the reaction was quenched by adding satd NaCl (10 mL), and the product was extracted with DCM (3×35 mL). The combined organic extract was washed with water (25 mL), brine dried (Na$_2$SO$_4$) and concentrated under reduced pressure to afford crude. The crude product was purified by CombiFlash to afford the desired product (330 mg, 40.6%). LCMS (ESI, m/z): 378.36 [M+H]$^+$. $^1$H NMR (Chloroform-d, 400 MHz): δ (ppm) 7.86 (s, 1H), 7.65 (t, J=7.9 Hz, 2H), 7.52 (d, J=8.1 Hz, 1H), 7.42 (t, J=6.9 Hz, 2H), 7.27 (t, J=7.6 Hz, 1H), 6.70 (d, J=7.6 Hz, 1H), 6.32 (s, 1H), 4.92 (s, 2H), 0.99 (s, 9H), 0.17 (s, 6H).

Step 3:

(6-(5H-imidazo[5,1-a]isoindol-5-yl)pyridin-2-yl)methanol

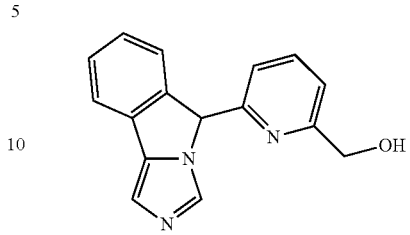

To a solution of 5-(6-(((tert-butyldimethylsilyl)oxy)methyl)pyridin-2-yl)-5H-imidazo[5,1-a]isoindole (0.320 mg, 847 mmol) in MeOH (3 mL) at 0° C. was added HCl (1 mL, 4.24 mmol, 4.0 M in dioxane). The reaction was allowed to warm to rt and stirred for 2 h. The reaction mixture was basified by adding sat NaHCO$_3$ solution, the product was extracted with 5% trifluoroethanol in DCM (3×30 mL). The combined organic extract was dried over Na$_2$SO$_4$ and the solvent was removed under reduced pressure to afford the crude residue which was purified by CombiFlash to afford the desired product as off-white solid (170 mg, 76%). LCMS (ESI, m/z): 264.14 [M+H]$^+$. $^1$H NMR (Chloroform-d, 400 MHz): δ (ppm) 8.09 (s, 1H), 7.66 (dt, J=7.9, 3.8 Hz, 2H), 7.46 (t, J=7.0 Hz, 2H), 7.39-7.24 (m, 2H), 6.83 (d, J=8.0 Hz, 1H), 6.45 (s, 1H), 4.85 (s, 2H).

Example 06: 3-(5H-imidazo[5,1-a]isoindol-5-yl)benzenesulfonamide

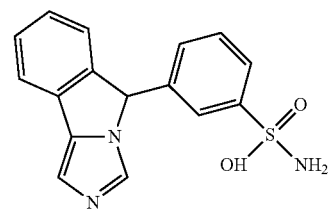

(R)-3-(5H-imidazo[5,1-a]isoindol-5-yl)benzenesulfonamide
(S)-3-(5H-imidazo[5,1-a]isoindol-5-yl)benzenesulfonamide
Synthetic Route

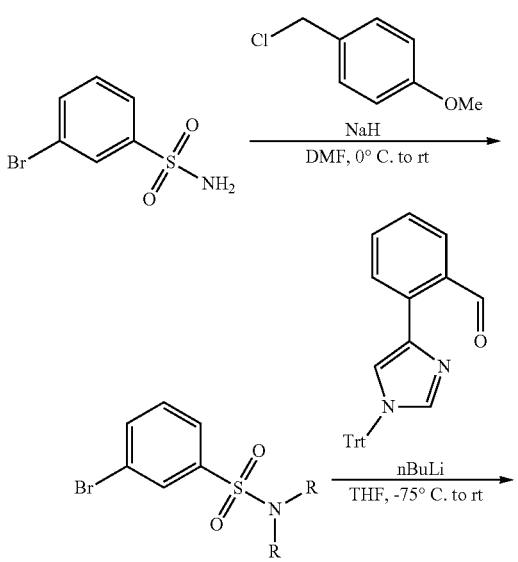

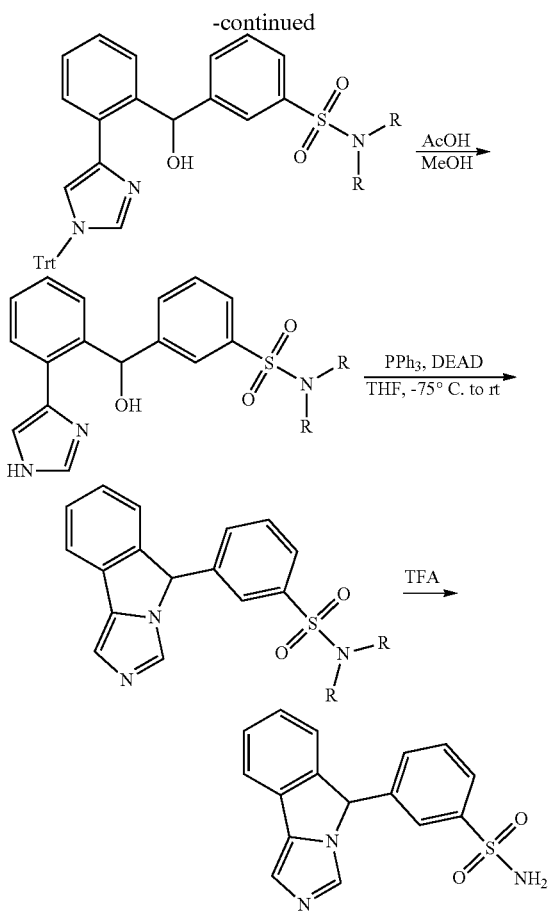

R = p-OMe-benzyl

Step 1:

3-Bromo-N,N-bis(4-methoxybenzyl)benzenesulfonamide

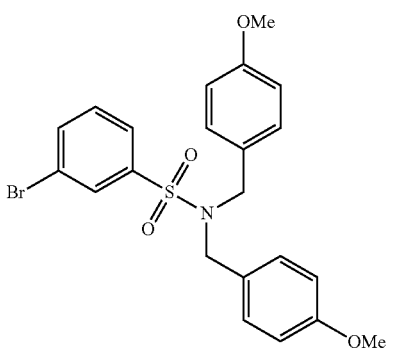 [SMILES: COc1ccc(CN(Cc2ccc(OC)cc2)S(=O)(=O)c2cccc(Br)c2)cc1]

To a suspension of NaH (533 mg, 13.34 mmol; 60 suspension in mineral oil) in DMF (30 mL) at 0° C. was added a solution of 3-bromobenzenesulfonamide (1.5 g, 6.35 mmol) in anhydrous DMF (6 mL). After stirring for 1 h at 0° C., 1-(chloromethyl)-4-methoxybenzene (2.09 g, 13.34 mmol) was added and the mixture stirred at rt overnight, the mixture was stirred at 50° C. for 1 h. After cooling to rt, the reaction was quenched by adding satd NH$_4$Cl solution (10 mL) and the mixture was diluted with water (100 mL). The product was extracted with DCM (3×50 mL), the combined organic extract was dried over Na$_2$SO$_4$ and concentrated under reduced pressure to afford the crude, chromatographic purification afforded the desired product as white solid (2.6 g, 85.9%). $^1$H NMR (DMSO-d6, 400 MHz): δ (ppm) 7.86 (t, J=7.9 Hz, 2H), 7.79 (s, 1H), 7.54 (t, J=7.9 Hz, 1H), 7.05 (d, J=8.4 Hz, 4H), 6.82 (d, J=8.4 Hz, 4H), 4.26 (s, 4H), 3.73 (s, 6H).

Step 2:

3-(Hydroxy(2-(1-trityl-1H-imidazol-4-yl)phenyl)methyl)-N,N-bis(4-methoxybenzyl)benzenesulfonamide

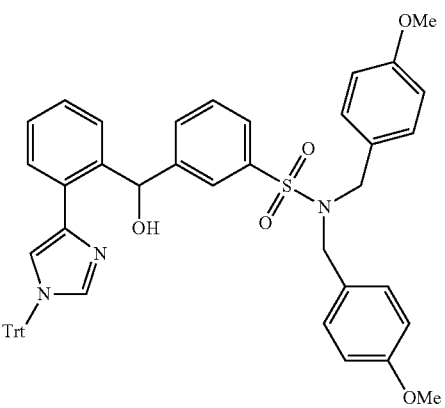

To a solution of 3-bromo-N,N-bis(4-methoxybenzyl)benzenesulfonamide (2.10 g, 3.55 mmol) in THF (25 mL) at −78° C. was added n-BuLi (1.54 mL, 3.38 mmol, 2.2 M solution in hexane) dropwise over a period of 5 minutes, the resulting yellow solution was stirred at −78° C. for 1 h. To the reaction mixture, a solution of 2-(1-trityl-1H-imidazol-4-yl)benzaldehyde (700 mg, 1.69 mmol) in THF (10 mL) was added. After stirring for 2 h at −78° C. the reaction was allowed to warm to rt and stirred for another 4 h at rt. The reaction was quenched by adding satd NH$_4$Cl solution (10 mL) and water (45 mL). The product was extracted with DCM (3×50 mL), the combined organic extract was dried over Na$_2$SO$_4$ and concentrated under reduced pressure to afford the crude, chromatographic purification afforded the desired product as white solid (618 mg, 45%). $^1$H NMR (400 MHz, Chloroform-d) δ 7.85 (s, 1H), 7.75 (d, J=7.8 Hz, 1H), 7.60 (d, J=7.7 Hz, 1H), 7.52-7.05 (m, 21H), 6.98-6.90 (m, 5H), 6.75 (d, J=8.7 Hz, 4H), 4.32-4.03 (m, 4H), 3.78 (s, 6H).

Step 3:

3-((2-(1H-Imidazol-4-yl)phenyl)(hydroxy)methyl)-N,N-bis(4-methoxybenzyl)benzenesulfonamide

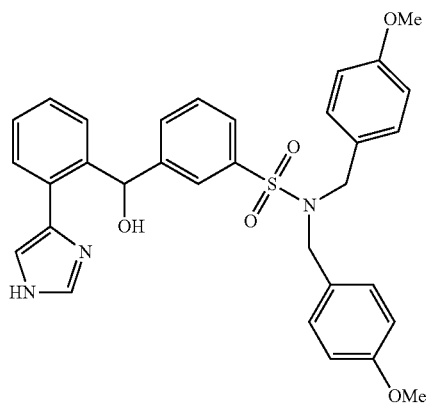 [SMILES: COc1ccc(CN(Cc2ccc(OC)cc2)S(=O)(=O)c2cccc(C(O)c3ccccc3-c3c[nH]cn3)c2)cc1]

A solution of 3-(hydroxy(2-(1-trityl-1H-imidazol-4-yl)phenyl)methyl)-N,N-bis(4-methoxybenzyl)benzenesulfonamide in a mixture of acetic acid (2 mL) and methanol (20 mL) was stirred at 90° C. overnight. After cooling to rt, the solvent was distilled-off and the crude was basified with 50% Na₂CO₃ solution (15 mL), the product was extracted with CH₂Cl₂ (3×35 mL). The combined organic extract was dried over Na₂SO₄ and concentrated under reduced pressure to afford the crude. The crude was purified by CombiFlash to afford the desired product as yellow gel (125 mg). LCMS (ESI, m/z): 570.24 [M+H]⁺.

Step 4:

3-(5H-Imidazo[5,1-a]isoindol-5-yl)-N,N-bis(4-methoxybenzyl)benzenesulfonamide

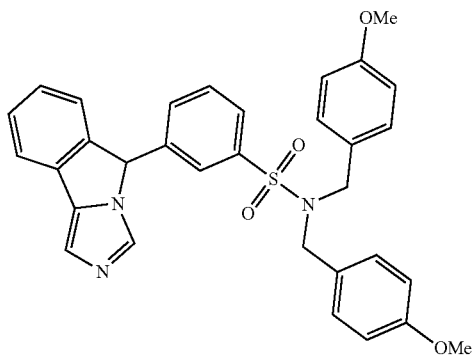 [SMILES: COc1ccc(CN(Cc2ccc(OC)cc2)S(=O)(=O)c2cccc(C3c4ccccc4-c4cncn43)c2)cc1]

To a solution of 3-((2-(1H-imidazol-4-yl)phenyl)(hydroxy)methyl)-N,I-bis(4-methoxybenzyl)benzenesulfonamide (115 mg, 0.202 mmol) in THF (3 mL) at 0° C. was added PPh₃ (68.8 mg, 0.262 mmol and DEAD (0.119 mL, 0.262 mmol). The mixture was allowed to warm to rt and stirred for 5 h at rt. The solvent was distilled-off under reduced pressure and the crude was purified by CombiFlash to afford the desired product as yellow gel (76 mg, 68%). LCMS (ESI, m/z): 552.19 [M+H]⁺.

Step 5:

3-(5H-Imidazo[5,1-a]isoindol-5-yl)benzenesulfonamide

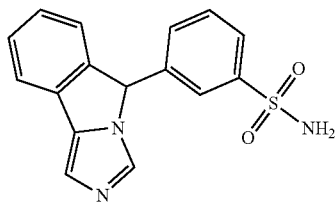

A solution of 3-(5H-imidazo[5,1-a]isoindol-5-yl)-N,N-bis(4-methoxybenzyl)benzenesulfonamide (95 mg) in TFA (3 mL) was stirred at rt for 3 h. The solvent was distilled-off under reduced pressure, the crude was basified by satd NaHCO₃ (5 mL) and water (15 mL) and the product was extracted with 5% trifluoroethanol in DCM (3×30 mL), the combined organic extract was concentrated under reduced pressure and the crude was purified by CombiFlash to afford the desired product as beige solid (35 mg, 65%). The stereoisomers were separated by chiral SFC. LCMS (ESI, m/z): 312.23 [M+H]⁺. ¹H NMR (Chloroform-d, 400 MHz): δ (ppm) 7.93-7.89 (m, 1H), 7.85 (m, 1H), 7.57 (d, J=7.7 Hz, 1H), 7.47 (s, 1H), 7.45 (t, J=7.8 Hz, 1H), 7.39 (t, J=6.9 Hz, 1H), 7.27-7.10 (m, 4H), 6.15 (s, 1H).

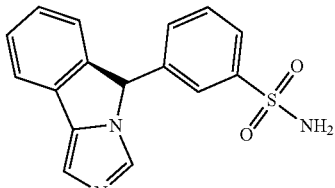

06a

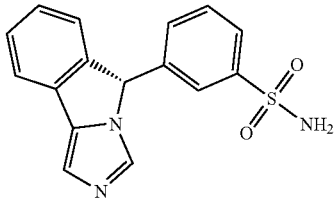 [SMILES: NS(=O)(=O)c1cccc(C2c3ccccc3-c3cncn32)c1]

06b

Example 06a: (R)-3-(5H-imidazo[5,1-a]isoindol-5-yl)benzenesulfonamide. LCMS (ESI, m/z): 312.23 [M+H]⁺. ¹H NMR (Chloroform-d, 400 MHz): δ (ppm) 7.93-7.89 (m, 1H), 7.85 (m, 1H), 7.57 (d, J=7.7 Hz, 1H), 7.47 (s, 1H), 7.45 (t, J=7.8 Hz, 1H), 7.39 (t, J=6.9 Hz, 1H), 7.27-7.10 (m, 4H), 6.15 (s, 1H).

Example 06b: (S)-3-(5H-imidazo[5,1-a]isoindol-5-yl)benzenesulfonamide. LCMS (ESI, m/z): 312.23 [M+H]⁺. ¹H NMR (Chloroform-d, 400 MHz): Same as 06a Example 09: (3-fluoro-5-(5H-imidazo[5,1-a]isoindol-5-yl)phenyl)methanol

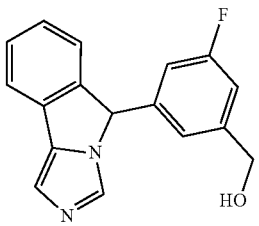 [SMILES: OCc1cc(F)cc(C2c3ccccc3-c3cncn32)c1]

Step 1:

((3-bromo-5-fluorobenzyl)oxy)(tert-butyl)dimethylsilane

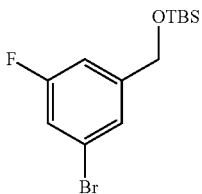 [SMILES: CC(C)(C)[Si](C)(C)OCc1cc(F)cc(Br)c1]

To a 50 mL flask containing 3-bromo-5-fluorobenzyl alcohol (500 mg, 2.67 mmol) and TBSCl (483 mg, 3.21 mmol) in DMF (15 mL) was added imidazole (237 mg, 3.48 mmol). The reaction was stirred at 25° C. for 18 hr. The reaction was poured into water (10 mL) and the aqueous layer was extracted with ethyl acetate (2×20 mL). The combined organic extracts were dried over Na₂SO₄, filtered and concentrated. The crude was purified by combi-flash to give the product. 1H NMR (400 MHz, Chloroform-d) δ 7.25 (dtt, J=1.9, 1.0, 0.5 Hz, 1H), 7.13 (dddt, J=8.1, 2.4, 1.8, 0.6 Hz, 1H), 7.01 (dddd, J=9.4, 3.3, 1.5, 0.9 Hz, 1H), 4.71 (q, J=0.8 Hz, 2H), 0.98-0.94 (m, 9H), 0.14-0.11 (m, 6H).

Step 2:

(3-(((tert-butyldimethylsilyl)oxy)methyl)-5-fluoro-phenyl)(2-(1-trityl-1H-imidazol-4-yl)phenyl)methanol

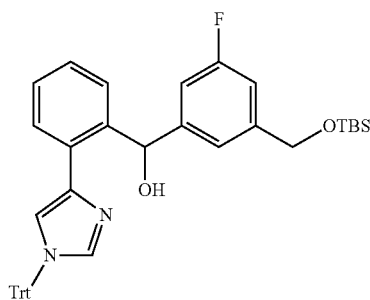

To a solution of ((3-bromo-5-fluorobenzyl)oxy)(tert-butyl)dimethylsilane (105 mg, 0.579 mmol) in anhydrous THF (4 mL) at −78° C. was added n-BuLi (0.24 mL, 0.531 mmol, 2.2 M solution cyclohexane). After stirring for 0.5 hr at −78° C., a solution of 2-(1-trityl-1H-imidazol-4-yl)benzaldehyde (200 mg, 0.483 mmol) in THF (2 mL) was added and the reaction was allowed to warm to room temperature over a period of 2 hr and continued stirring overnight (18 h). The reaction was quenched by adding satd. NH₄Cl (5 mL) and the reaction was diluted with water (30 mL), the product was extracted with DCM (3×40 mL). The combined organic extract was dried over Na₂SO₄ and concentrated under reduced pressure, the crude was purified by column chromatography to give desired product as gel (520 mg, 79%). 1H NMR (400 MHz, Chloroform-d) δ 7.38 (dd, J=5.2, 2.0 Hz, 11H), 7.35-7.29 (m, 7H), 7.09-7.03 (m, 7H), 5.86 (s, 1H), 4.63 (s, 2H), 0.90 (s, 9H).

Step 3:

5-(3-(((tert-butyldimethylsilyl)oxy)methyl)-5-fluoro-phenyl)-5H-imidazo[5,1-a]isoindole

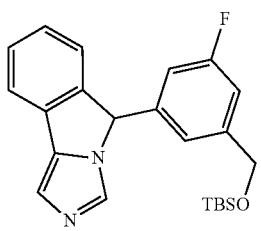 [SMILES: CC(C)(C)[Si](C)(C)OCc1cc(F)cc(C2c3ccccc3-c3cncn32)c1]

(3-(((tert-butyldimethylsilyl)oxy)methyl)-5-fluorophe-nyl)(2-(1-trityl-1H-imidazol-4-yl)phenyl)methanol was dissolved in DCM (10 mL), methanesulfonyl chloride (71 uL, 1.1 mmol) and triethylamine (0.16 mL, 1.37 mmol) was added at 25° C. After 1 hr, the reaction mixture was quenched by water (15 mL). The product was extracted with DCM (3×15 mL). The combined organic extract was dried over Na₂SO₄ and concentrated under reduced pressure, the crude was dissolved in MeOH (5 mL) and add acetic acid (1 mL), and refluxed for 1 hr. The reaction mixture was concentrated. The crude was dissolved in DCM (30 mL) and washed with satd. aq. NaHCO₃ (10 mL), dried over sodium sulfate, filtered and concentrated. The crude was used directly in the next step. LCMS (ESI, m/z): 395.2 [M+H]⁺;

Step 4:

(S)-(3-fluoro-5-(5H-imidazo[5,1-a]isoindol-5-yl)phenyl) methanol (R)-(3-fluoro-5-(5H-imidazo[5,1-a]isoindol-5-yl)phenyl) methanol

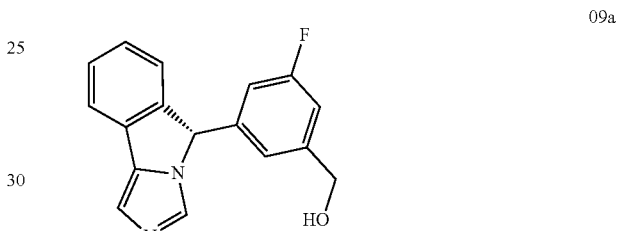

09a

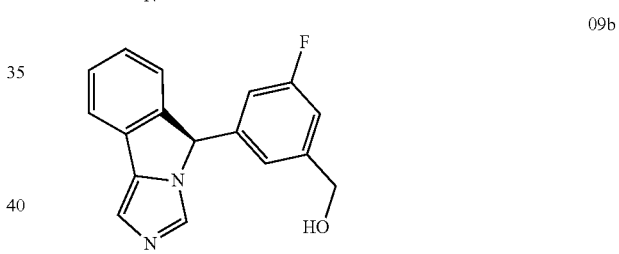

09b

The crude 5-(3-(((tert-butyldimethylsilyl)oxy)methyl)-5-fluorophenyl)-5H-imidazo[5,1-a]isoindole was dissolved in EtOH (10 mL) and 4 M HCl in dioxane (1.9 mL, 7.6 mmol) was added and stirred at room temperature for 2 hr. The reaction mixture was concentrated. The crude was dissolved in DCM (30 mL) and washed with satd. aq. NaHCO₃ (10 mL), dried over sodium sulfate, filtered and concentrated. The crude product was purified by combi-flash using MeOH/DCM as eluent to obtain the desired product as white solid (150 mg, 70%). The product was further isolated by chiral separation to afford 2 isomers as white solid. The stereochemistry of each isomer was arbitrarily assigned.

Example 09a: (S)-(3-fluoro-5-(5H-imidazo[5,1-a] isoindol-5-yl)phenyl)methanol

LCMS (ESI, m/z): 281.3 [M+H]⁺; 1H NMR (400 MHz, DMSO-d6) δ 7.79 (t, J=0.7 Hz, 1H), 7.69 (dt, J=7.6, 0.9 Hz, 1H), 7.40 (tdd, J=7.7, 1.3, 0.6 Hz, 1H), 7.31-7.21 (m, 4H), 7.11 (ddt, J=9.7, 2.6, 1.1 Hz, 1H), 6.99 (dt, J=9.5, 2.0 Hz, 1H), 6.85 (td, J=1.5, 0.7 Hz, 1H), 6.51 (s, 1H), 5.35 (t, J=5.7 Hz, 1H), 4.46 (s, 2H).

Example 09b: (R)-(3-fluoro-5-(5H-imidazo[5,1-a]isoindol-5-yl)phenyl)methanol

LCMS (ESI, m/z): 281.3 [M+H]⁺; 1H NMR is the same as Example 09a.

Example 10: 1-(3-(5H-imidazo[5,1-a]isoindol-5-yl)phenyl)ethan-1-ol

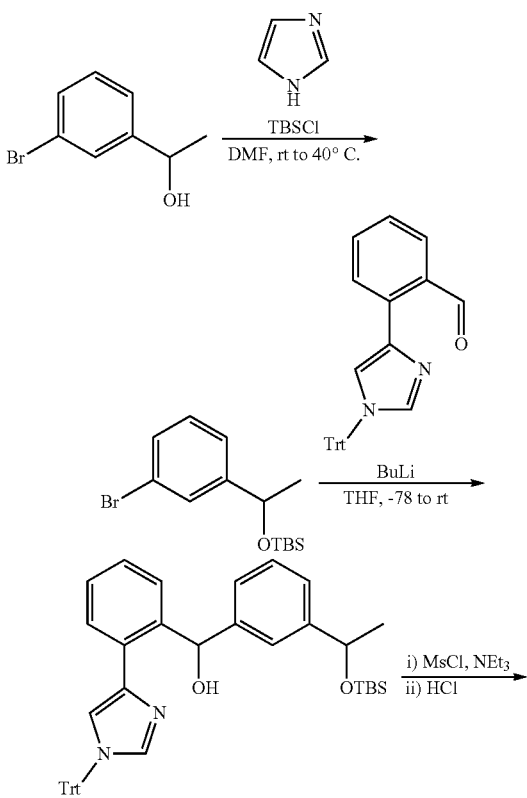

(S)-1-(3-((S)-5H-imidazo[5,1-a]isoindol-5-yl)phenyl)ethan-1-ol (R)-1-(3-((S)-5H-imidazo[5,1-a]isoindol-5-yl)phenyl)ethan-1-ol (S)-1-(3-((R)-5H-imidazo[5,1-a]isoindol-5-yl)phenyl)ethan-1-ol (R)-1-(3-((R)-5H-imidazo[5,1-a]isoindol-5-yl)phenyl)ethan-1-ol Synthetic Route

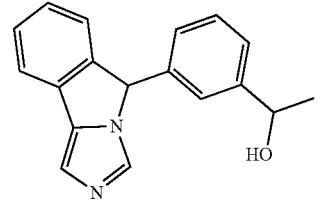

Step 1:

(1-(3-Bromophenyl)ethoxy)(tert-butyl)dimethylsilane

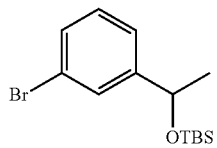

To a solution of 1-(3-bromophenyl)ethan-1-ol (2.0 g, 9.95 mmol) in DMF (15 mL) at rt was added imidazole (812 mg, 11.94 mmol) and TBSCl (1.57 g, 10.44 mmol). After stirring overnight at 40° C., the reaction was diluted with water (50 mL) and the product was extracted with EtOAc (3×50 mL). The combined organic extract was washed with water (50 mL), dried over Na₂SO₄ and concentrated under reduced pressure to afford the crude. Chromatographic purification afforded the desired product as colorless oil (2.6 g, 82.9%). ¹H NMR (Chloroform-d, 400 MHz): δ (ppm) 7.50 (s, 1H), 7.37 (d, J=7.9 Hz, 1H), 7.27 (d, J=7.7 Hz, 1H), 7.20 (t, J=7.7 Hz, 1H), 4.85 (q, J=6.3 Hz, 1H), 1.41 (d, J=6.3 Hz, 3H), 0.93 (s, 9H), 0.08 (s, 3H), 0.01 (s, 3H).

Step 2:

(3-(1-((tert-Butyldimethylsilyl)oxy)ethyl)phenyl)(2-(1-trityl-1H-imidazol-4-yl)phenyl)methanol

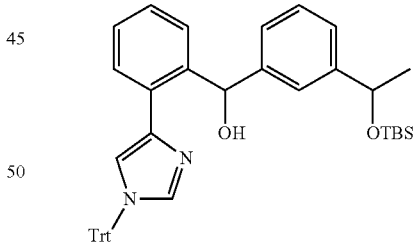

To a solution of (1-(3-bromophenyl)ethoxy)(tert-butyl)dimethylsilane (1.10 g, 3.47 mmol) in THF (15 mL) at −78° C. was added n-BuLi (1.58 mL, 1.59 mmol; 2.2 M solution in hexanes). After stirring for 1.5 h, 2-(1-trityl-1H-imidazol-4-yl)benzaldehyde (900 mg, 2.17 mmol) was added as a solution in THF (6 mL). The mixture was allowed to warm to rt and stirred overnight. The reaction was diluted with water (30 mL) and the product was extracted with EtOAc (3×50 mL). The combined organic extract was washed with water (50 mL), dried over Na₂SO₄ and concentrated under reduced pressure to afford the crude mixture. The crude was purified by CombiFlash to afford the desired product as white solid (1.28 g, 90.5%). ¹H NMR (400 MHz, Chloroform-d) δ 7.47-7.01 (m, 24H), 6.88 (d, J=10.9 Hz, 1H), 5.91

(s, 1H), 4.91-4.70 (m, 1H), 1.31 (dd, J=6.2, 3.9 Hz, 3H), 0.84 (d, J=20.4 Hz, 9H), −0.00−−0.20 (m, 6H).

Step 3:

1-(3-(5H-Imidazo[5,1-a]isoindol-5-yl)phenyl)ethan-1-ol

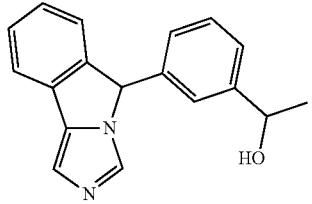 [SMILES: CC(O)c1cccc(C2c3ccccc3-c3cncn32)c1]

To a solution of (3-(1-((tert-butyldimethylsilyl)oxy)ethyl)phenyl)(2-(1-trityl-1H-imidazol-4-yl)phenyl)methanol (1.20 g, 1.84 mmol) in anhydrous DCM (12 mL) at 0° C. was added NEt$_3$ (242 mg, 2.40 mmol). After stirring for 10 min at 0° C., MsCl (253 mg, 2.21 mmol) was added and the reaction was allowed to warm to rt and stirred for 1.5 h. The reaction was quenched by adding water (15 mL) and the product was extracted with CH$_2$C$_{12}$ (3×35 mL), the combined organic extract was dried over Na$_2$SO$_4$ and concentrated under reduced pressure to afford the crude which was stirred in 4M HCl in dioxane (3 mL). After stirring for 1 h the solvent was distilled-off and the crude was diluted with DCM (20 mL), water (10 mL) and basified with satd. NaHCO$_3$ solution (20 mL). The product was extracted with DCM (3×35 mL). The combined organic extract was dried over Na$_2$SO$_4$ and concentrated under reduced pressure to afford the crude. The crude was purified by CombiFlash to afford the desired product as white solid and the stereoisomers were separated by chiral SFC. LCMS (ESI, m/z): 277.21 [M+H]$^+$.

09a
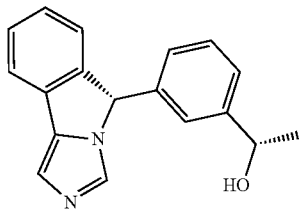

09b
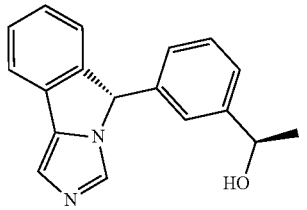

09c
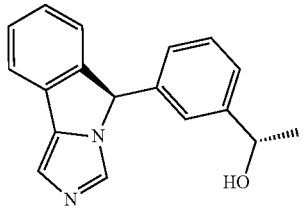

09d
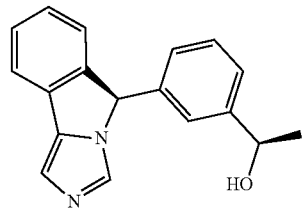

Example 10a: (S)-1-(3-((S)-5H-imidazo[5,1-a]isoindol-5-yl)phenyl)ethan-1-ol

LCMS (ESI, m/z): 277.21 [M+H]$^+$. $^1$H NMR (400 MHz, DMSO-d6) δ 7.73 (s, 1H), 7.67 (d, J=7.6 Hz, 1H), 7.43-7.36 (m, 1H), 7.35-7.27 (m, 2H), 7.26-7.20 (m, 3H), 7.17 (s, 1H), 6.99 (dt, J=6.9, 1.9 Hz, 1H), 6.47 (s, 1H), 5.15 (d, J=4.2 Hz, 1H), 4.68 (qd, J=6.5, 4.2 Hz, 1H), 1.28 (d, J=6.4 Hz, 3H).

Example 10b: LC MS (ESI, m/z): 277.21 [M+H]$^+$. $^1$H NMR (400 MHz, DMSO-d6) δ 7.73 (s, 1H), 7.67 (dd, J=7.6, 1.0 Hz, 1H), 7.43-7.36 (m, 1H), 7.35-7.28 (m, 2H), 7.23 (dt, J=3.9, 1.0 Hz, 3H), 7.17 (d, J=2.0 Hz, 1H), 6.98 (dt, J=6.5, 2.2 Hz, 1H), 6.47 (s, 1H), 5.17 (d, J=4.2 Hz, 1H), 4.68 (qd, J=6.4, 4.1 Hz, 1H), 1.28 (d, J=6.4 Hz, 3H).

Example 10c: LC MS (ESI, m/z): 277.21 [M+H]$^+$. $^1$H NMR (400 MHz, DMSO-d$_6$ same as example 10b Example 10d: LC MS (ESI, m/z): 277.21 [M+H]$^+$. $^1$H NMR (400 MHz, DMSO-d$_6$ same as example 10a Example 11: 3-(5H-imidazo[5,1-a]isoindol-5-yl)benzamide

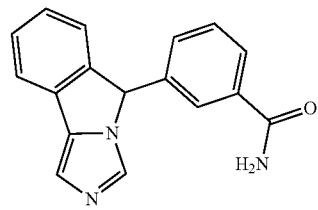 [SMILES: NC(=O)c1cccc(C2c3ccccc3-c3cncn32)c1]

Step 1:

3-(hydroxy(2-(1-trityl-1H-imidazol-4-yl)phenyl)methyl)benzonitrile

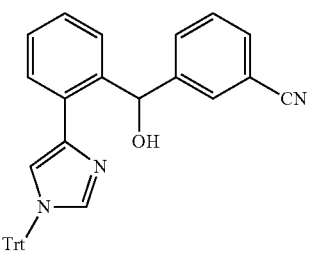

To a solution of 3-bromobenzonitrile (659 mg, 3.62 mmol) in anhydrous THF (10 mL) at −78° C. was added n-BuLi (1.45 mL, 3.63 mmol, 2.5 M solution in hexane). After stirring for 0.5 hr at −78° C., a solution of 2-(1-trityl-1H-imidazol-4-yl)benzaldehyde (1 g, 2.41 mmol) in THF (6 mL) was added and the reaction was allowed to warm to room temperature over a period of 2 hr and continued stirring overnight (18 hr). The reaction was quenched by adding satd. NH$_4$Cl (5 mL) and the reaction was diluted with water (30 mL), the product was extracted with DCM (2×30 mL). The combined organic extract was dried over Na$_2$SO$_4$ and concentrated under reduced pressure. The crude was purified to obtain 0.6 g of product (48% yield). LCMS (ESI, m/z): 518.4 [M+H]$^+$; 1H NMR (400 MHz, Chloroform-d) δ 7.70 (d, J=10.2 Hz, 1H), 7.58 (s, 3H), 7.52 (d, J=7.6 Hz, 2H), 7.47-7.16 (m, 29H), 7.12-6.93 (m, 8H), 6.93-6.83 (m, 1H), 5.87 (s, 1H).

Step 2:

3-(5H-imidazo[5,1-a]isoindol-5-yl)benzonitrile

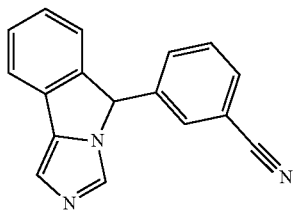 [SMILES: N#Cc1cccc(C2c3ccccc3-c3cncn32)c1]

3-(hydroxy(2-(1-trityl-1H-imidazol-4-yl)phenyl)methyl)benzonitrile (0.6 g, 1.16 mmol) was dissolved in DCM (10 mL), methanesulfonyl chloride (108 uL, 1.39 mmol) and triethyl amine (0.24 mL, 1.74 mmol) was added at room temperature. The reaction mixture was quenched by water (15 mL). The product was extracted with DCM (3×15 mL). The combined organic extract was dried over Na$_2$SO$_4$ and concentrated under reduced pressure. The crude product was purified by combi-flash using DCM/MeOH as eluent to give the product. LCMS (ESI, m/z): 258.2 [M+H]$^+$; 1H NMR (400 MHz, DMSO-d$_6$) δ 10.21 (s, 3H), 8.54 (s, 1H), 7.94-7.86 (m, 3H), 7.82 (dt, J=7.6, 0.9 Hz, 1H), 7.70-7.56 (m, 3H), 7.55-7.41 (m, 3H), 7.41-7.32 (m, 6H), 6.78 (s, 1H).

Step 3:

3-(5H-imidazo[5,1-a]isoindol-5-yl)benzamide

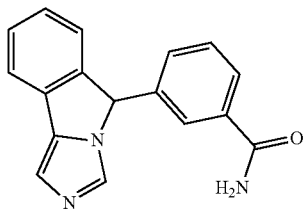 [SMILES: NC(=O)c1cccc(C2c3ccccc3-c3cncn32)c1]

To the solution of 3-(5H-imidazo[5,1-a]isoindol-5-yl)benzonitrile (220 mg, 0.86 mmol) in methanol (15 mL), sodium hydroxide (342 mg, 8.55 mmol) and 30% hydrogen peroxide (0.86 mL, 8.55 mmol) were added and stirred for 2 hr at room temperature. Solvent was removed and crude product was extracted with 5% 2,2,2-trifluoroethanol in DCM. Combined organic layers were washed with water, brine, dried over sodium sulfate and purified on combi-flash to yield product. LCMS (ESI, m/z): 276.2 [M+H]$^+$; 1H NMR (400 MHz, DMSO-d$_6$) δ 8.06 (s, 1H), 7.85 (ddd, J=7.8, 1.8, 1.1 Hz, 1H), 7.78 (t, J=0.7 Hz, 1H), 7.72-7.67 (m, 2H), 7.50-7.43 (m, 2H), 7.40 (dddd, J=7.5, 6.8, 1.7, 0.6 Hz, 1H), 7.32-7.19 (m, 5H), 6.54 (s, 1H).

Example 20: 5-(2-cyclohexylethyl)-5H-imidazo[5,1-a]isoindole

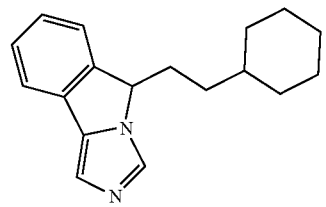 [SMILES: c1ccc2c(c1)-c1cncn1C2CCC1CCCCC1]

To a solution of 5H-imidazo[5,1-a]isoindole (858 mg, 5.49 mmol) in anhydrous THF (10 mL) at −40° C. was added n-BuLi (2.20 mL, 5.49 mmol, 2.5 M solution hexanes). After stirring for 1.0 h at −40° C., (2-bromoethyl)cyclohexane (700 mg, 3.66 mmol) was added and the reaction was allowed to warm to −30° C. and stirred overnight. The reaction was quenched by adding satd NH$_4$Cl (10 mL) and water (20 mL), the product was extracted with DCM (3×30 mL). The combined organic extract was dried over Na$_2$SO$_4$ and concentrated under reduced pressure to afford crude mixture, the crude mixture was purified by CombiFlash to yield the desired product as yellow oil (0.780 g, 80%). LCMS (ESI, m/z): 267.24 [M+H]$^+$. $^1$H NMR (Chloroform-d, 400 MHz): δ (ppm) 7.58 (s, 1H), 7.39 (d, J=7.5 Hz, 1H), 7.25-7.18 (m, 2H), 7.15-7.09 (m, 1H), 7.08 (s, 1H), 4.98 (t, J=5.7 Hz, 1H), 2.09-1.95 (m, 1H), 1.80 (ddt, J=11.3, 8.9, 6.2 Hz, 1H), 1.63-1.46 (m, 5H), 1.16-0.92 (m, 6H), 0.81-0.65 (m, 2H).

Example 23: 5-(3,3,3-trifluoropropyl)-5H-imidazo[5,1-a]isoindole

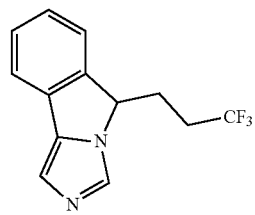 [SMILES: FC(F)(F)CCC1c2ccccc2-c2cncn21]

To a solution of 5H-imidazo[5,1-a]isoindole (500 mg, 3.2 mmol) in anhydrous THF (15 mL) at −78° C. was added n-BuLi (1.28 mL, 3.2 mmol, 2.5 M solution in hexanes). After stirring for 1 hr at −40° C., 3-bromo-1,1,1-trifluoro-propanein (0.85 g, 4.8 mmol) was added to the above solution. The reaction was warmed up to 25° C. slowly and stir for overnight. The reaction was quenched with water (1 mL) and NH$_4$Cl solution (20 mL). The separated aqueous layer was subsequently extracted with DCM (20 mL×3). Combined organic phase was dried over Na$_2$SO$_4$, filtrated and purified on Combi-Flash using MeOH/DCM (2%-3%). LCMS (ESI, m/z): 282.3 [M+H]$^+$; 1H NMR (400 MHz, Chloroform-d) δ 7.86 (s, 1H), 7.59 (dt, J=7.6, 1.0 Hz, 1H), 7.43 (tdd, J=7.6, 1.3, 0.6 Hz, 1H), 7.40-7.36 (m, 1H), 7.34 (dd, J=7.4, 1.1 Hz, 1H), 5.40 (t, J=4.8 Hz, 1H), 2.56-2.44 (m, 1H), 2.41-2.29 (m, 1H), 1.76 (dddd, J=21.2, 10.5, 6.3, 4.7 Hz, 2H).

Example 48: 1-((5H-imidazo[5,1-a]isoindol-5-yl)methyl)cyclopropane-1-carbonitrile

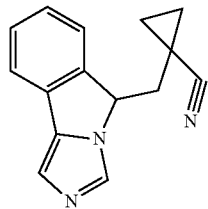 [SMILES: N#CC1(CC2c3ccccc3-c3cncn32)CC1]

Step 1:

1-((5H-imidazo[5,1-a]isoindol-5-yl)methyl)cyclopropane-1-carbonitrile

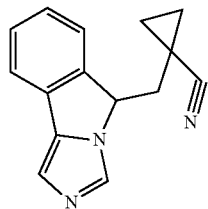 [SMILES: N#CC1(CC2c3ccccc3-c3cncn32)CC1]

To the solution of 5H-imidazo[5,1-a]isoindole (1.5 g, 9.6 mmol) in anhydrous THF (35 mL) at −50° C., n-butyllithium (3.84 mL, 9.6 mmol, 2.5M solution in hexanes) was added and reaction mixture was stirred for 30 minutes at −50° C. Solution of 1-(bromomethyl)cyclopropane-1-carbonitrile (1 g, 6.4 mmol) in anhydrous THF (1 mL) was added slowly and the reaction mixture was slowly allowed to warm to 0 C over a period of 4 hours. Reaction was then quenched by cooling the mixture to −50 C and adding saturated ammonium chloride solution (15 mL). Crude product was extracted using dichloromethane which was further purified on a Combi-Flash. LCMS (ESI, m/z): 236.2 [M+H]⁺. ¹H NMR (400 MHz, DMSO-d₆) δ 7.98 (s, 1H), 7.64-7.58 (m, 2H), 7.43-7.38 (m, 1H), 7.29 (td, J=7.6, 1.1 Hz, 1H), 7.15 (s, 1H), 5.58-5.44 (m, 1H), 2.48-2.43 (m, 1H), 2.12 (dd, J=14.9, 7.0 Hz, 1H), 1.26-1.12 (m, 2H), 0.88-0.81 (m, 2H).

Example 52: 8-fluoro-5-(1-(methylsulfonyl)piperidin-4-yl)-5H-imidazo[5,1-a]isoindole

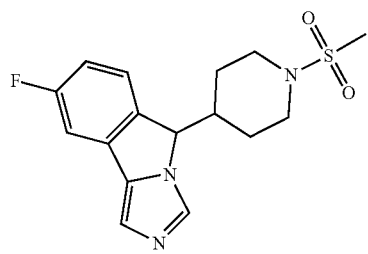 [SMILES: CS(=O)(=O)N1CCC(C2c3ccc(F)cc3-c3cncn32)CC1]

Synthetic Route

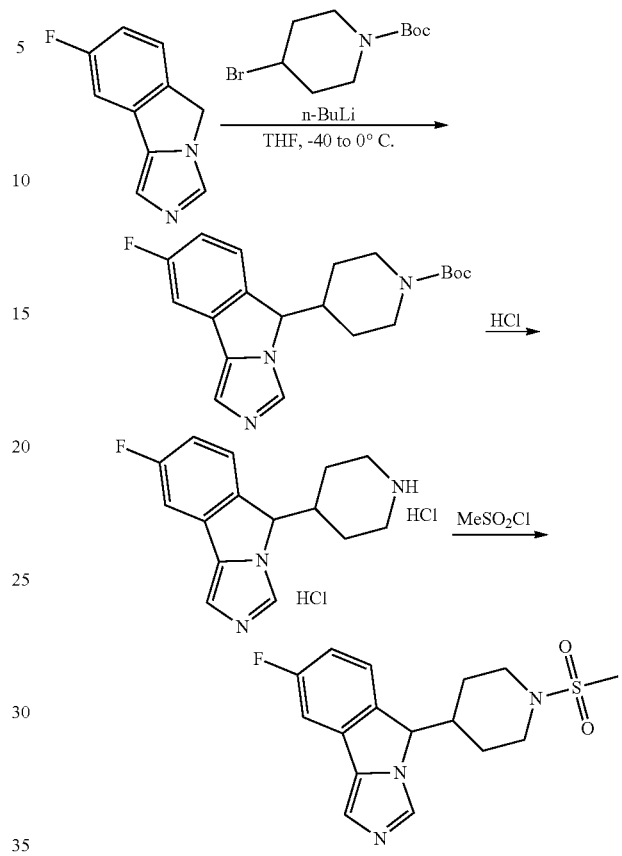

Step 1:

tert-Butyl 4-(8-fluoro-5H-imidazo[5,1-a]isoindol-5-yl)piperidine-1-carboxylate

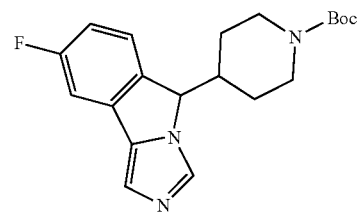 [SMILES: CC(C)(C)OC(=O)N1CCC(C2c3ccc(F)cc3-c3cncn32)CC1]

To a solution of 8-fluoro-5H-imidazo[5,1-a]isoindole (1.0 g, 6.06 mmol) in anhydrous THF (15 mL) at −40° C. was added n-BuLi (2.91 mL, 7.27 mmol, 2.5 M solution hexanes). After stirring for 1.0 h at −40° C. tert-butyl 4-bromopiperidine-1-carboxylate (1.60 g, 6.06 mmol) was added and the reaction was allowed to warm to −0° C. and stirred for 3 h. The reaction was quenched by adding satd NH₄Cl (10 mL) and water (20 mL), the product was extracted with CH₂Cl₂ (3×40 mL). The combined organic extract was dried over Na₂SO₄ and concentrated under reduced pressure to afford crude mixture, the crude mixture was purified by CombiFlash to yield the desired product as yellow gel (1.32 g, 61%). LCMS (ESI, m/z): 358.32 [M+H]⁺. ¹H NMR (Chloroform-d, 400 MHz): δ (ppm) 7.72

(s, 1H), 7.39-7.26 (m, 1H), 7.26-7.17 (m, 2H), 6.96 (t, J=8.7 Hz, 1H), 5.12 (s, 1H), 4.16 (br s, 2H), 2.65 (dt, J=28.0, 12.9 Hz, 2H), 2.10-2.22 (m, 2H), 1.58-1.28 (m, 12H).

Step 2:

8-Fluoro-5-(piperidin-4-yl)-5H-imidazo[5,1-a]isoindole dihydrochloride

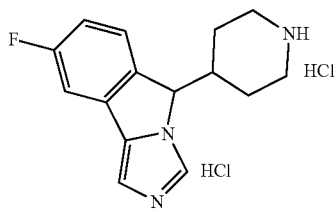 [SMILES: Fc1ccc2c(c1)-c1cncn1C2C1CCNCC1 ; Cl ; Cl]

A solution of tert-butyl 4-(8-fluoro-5H-imidazo[5,1-a]isoindol-5-yl)piperidine-1-carboxylate (1.3 g, 3.64 mmol) in HCl (9 mL, 36.37 mmol, 4 M solution in dioxane) was stirred at rt for 3 h. The solvent was removed under reduced pressure to afford the crude which was used as such for the next step. LCMS (ESI, m/z): 258.31 [M+H]$^+$.

Step 3:

8-Fluoro-5-(1-(methylsulfonyl)piperidin-4-yl)-5H-imidazo[5,1-a]isoindole

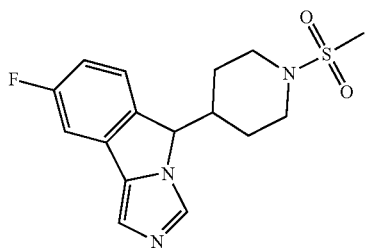 [SMILES: CS(=O)(=O)N1CCC(C2c3ccc(F)cc3-c3cncn32)CC1]

To a suspension of 8-fluoro-5-(piperidin-4-yl)-5H-imidazo[5,1-a]isoindole dihydrochloride (232 mg, 0.703 mmol) in anhydrous DCM (15 mL) at rt was added DIPEA (276 mg, 2.14 mmol). After stirring for 10 minutes, the mixture was cooled to 0° C. and methanesulfonyl chloride was added dropwise over a period of 1-2 min. The mixture was stirred for 2 h at 0° C. and the reaction was quenched by adding 50% NaHCO$_3$ (5 mL) solution. The product was extracted with 5% trifluoroethanol in DCM (3×40 mL). The solvent was removed under reduced pressure to afford the crude which was purified by CombiFlash to afford off-white solid (110 mg, 54%). LCMS (ESI, m/z): 336.31 [M+H]$^+$. $^1$H NMR (Chloroform-d, 400 MHz): δ (ppm) 7.70 (s, 1H), 7.29 (dd, J=8.4, 4.8 Hz, 1H), 7.25-7.18 (m, 2H), 7.03-6.88 (m, 1H), 5.13 (d, J=2.8 Hz, 1H), 3.83 (dddt, J=23.6, 11.9, 4.5, 2.3 Hz, 2H), 2.75 (s, 3H), 2.63 (dtd, J=18.2, 12.1, 2.7 Hz, 2H), 2.24-2.08 (m, 1H), 1.65 (dt, J=13.0, 3.0 Hz, 1H), 11.60-1.46 (m, 2H), 1.38-1.25 (m, 1H).

Example 53: 5-isobutyl-5H-imidazo[5,1-a]isoindole

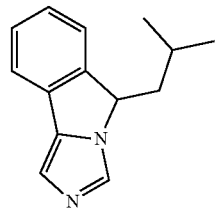 [SMILES: CC(C)CC1c2ccccc2-c2cncn21]

To a solution of 5H-imidazo[5,1-a]isoindole (0.500 g, 3.20 mmol) in anhydrous THF (15 mL) at −40° C. was added nBuLi (1.28 mL, 3.20 mmol, 2.5 M solution hexanes). After stirring for 1.0 h at −40° C., 1-iodo-2-methylpropane (589.1 mg, 3.20 mmol) was added and the reaction was allowed to warm to −30° C. and stirred for 2 h. The reaction was quenched by adding satd NH$_4$Cl (10 mL) and water (20 mL), the product was extracted with DCM (3×35 mL). The combined organic extract was dried over Na$_2$SO$_4$ and concentrated under reduced pressure to afford crude mixture, the crude mixture was purified by CombiFlash to yield the desired product as beige powder (90 mg, 13%). LCMS (ESI, m/z): 213.41 [M+H]$^+$. $^1$H NMR (Chloroform-d, 400 MHz): δ (ppm) 7.70 (s, 1H), 7.55 (dt, J=7.5, 0.9 Hz, 1H), 7.40-7.32 (m, 2H), 7.25 (td, J=7.5, 1.1 Hz, 1H), 7.19 (s, 1H), 5.18 (dd, J=8.6, 4.9 Hz, 1H), 1.96-1.74 (m, 1H), 1.92-1.72 (m, 2H), 1.07 (d, J=6.5 Hz, 3H), 1.00 (d, J=6.6 Hz, 3H).

Example 54: 1-((5H-imidazo[5,1-a]isoindol-5-yl)methyl)cyclopropane-1-carboxamide

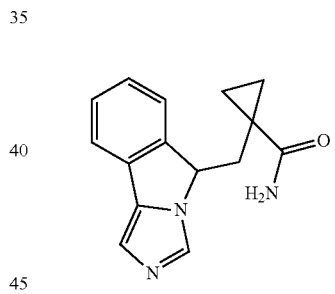

Step 1:

1-((5H-imidazo[5,1-a]isoindol-5-yl)methyl)cyclopropane-1-carboxamide

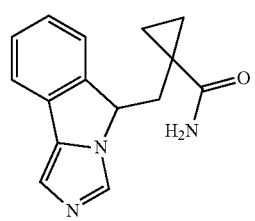 [SMILES: NC(=O)C1(CC2c3ccccc3-c3cncn32)CC1]

To the solution of 1-((5H-imidazo[5,1-a]isoindol-5-yl)methyl)cyclopropane-1-carbonitrile (180 mg, 0.76 mmol) in methanol (10 mL) was added sodium hydroxide (305 mg, 7.65 mmol) and hydrogen peroxide (1.2 mL, 15.3 mmol, 30% solution in water). Reaction mixture was stirred at room temperature overnight. Crude product was extracted using 5% TFE in DCM which was further purified on a Combi-Flash. LCMS (ESI, m/z): 254.3 [M+H]$^+$. $^1$H NMR (400 MHz, DMSO-d$_6$) δ 7.78 (s, 1H), 7.62-7.56 (m, 1H), 7.51 (d, J=7.6 Hz, 1H), 7.42-7.31 (m, 2H), 7.31-7.22 (m, 1H), 7.11 (s, 1H), 7.08 (s, 1H), 5.47 (dd, J=8.8, 6.2 Hz, 1H), 2.39 (dd, J=14.6, 5.8 Hz, 1H), 1.90-1.80 (m, 1H), 1.21-1.14 (m, 1H), 1.08-1.00 (m, 1H), 0.61-0.51 (m, 1H).

Example 60: 4-(5H-imidazo[5,1-a]isoindol-5-yl)cyclohexane-1-carboxamide

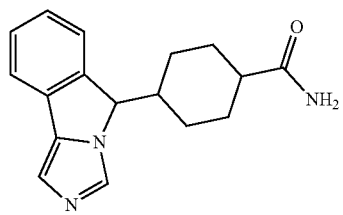 [SMILES: NC(=O)C1CCC(C2c3ccccc3-c3cncn32)CC1]

(1S,4R)-4-((S)-5H-imidazo[5,1-a]isoindol-5-yl)cyclohexane-1-carboxamide (1S,4S)-4-((R)-5H-imidazo[5,1-a]isoindol-5-yl)cyclohexane-1-carboxamide (1R,4S)-4-((S)-5H-imidazo[5,1-a]isoindol-5-yl)cyclohexane-1-carboxamide (1R,4R)-4-((R)-5H-imidazo[5,1-a]isoindol-5-yl)cyclohexane-1-carboxamide Synthetic Route

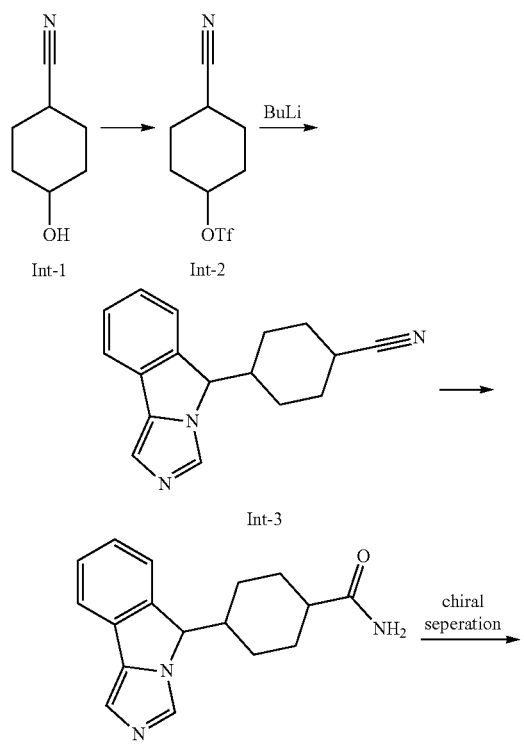
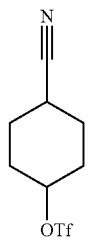

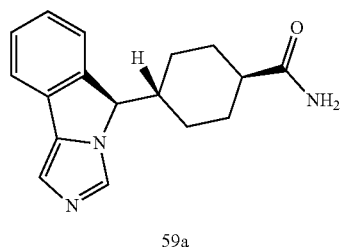
59a

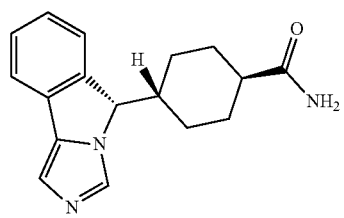
59b

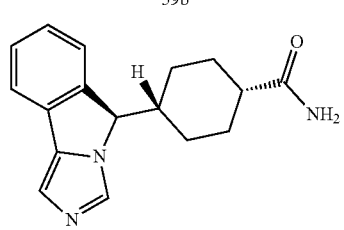
59c

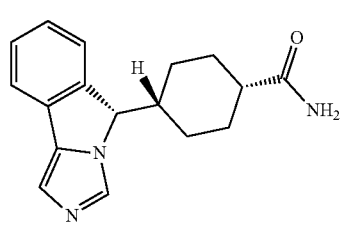
59d

Step 1:

4-cyanocyclohexyl trifluoromethanesulfonate

To a mixture of 4-hydroxycyclohexane-1-carbonitrile (1.5 g, 12 mmol) and pyridine (1.16 mL, 14.4 mmol) in DCM (30 mL) was added triflic anhydride (2.7 mL, 14.4 mmol) at about −20° C. The solution was then kept at −5 to 0° C. by an ice-salt bath. After 1 hr, the mixture was diluted with hexane (double the volume of DCM) and filtered through a pad of Celite. The solvent was evaporated to afford the crude triflates that were used directly for the coupling reaction.

Step 2:

4-(5H-imidazo[5,1-a]isoindol-5-yl)cyclohexane-1-carbonitrile

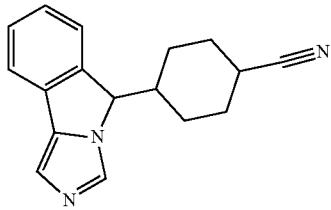 [SMILES: N#CC1CCC(C2c3ccccc3-c3cncn32)CC1]

To a solution of 5H-imidazo[5,1-a]isoindole (1.9 g, 12 mmol) in anhydrous THF (30 mL) at −78° C. was added n-BuLi (4.9 mL, 12.16 mmol, 2.5 M solution in exanes). After stirring for 1 hr at −40° C., a solution of 4-cyanocyclohexyl trifluoromethanesulfonate in 5 mL THF was added to the above solution. After 1 hr at −78° C., the reaction was warmed up to 25° C. and keep it for overnight. The reaction was quenched with water (2 mL) and NH$_4$Cl solution (50 mL) and extracted with DCM (40 mL×3). Combined organic layers were washed with water, brine, dried over sodium sulfate and purified on combi-flash to yield product (1g, 31% yield). dr=2/1. LCMS (ESI, m/z): 264.2 [M+H]$^+$ Step 3:
(1S,4R)-4-((S)-5H-imidazo[5,1-a]isoindol-5-yl)cyclohexane-1-carboxamide
(1S,4S)-4-((R)-5H-imidazo[5,1-a]isoindol-5-yl)cyclohexane-1-carboxamide
(1R,4S)-4-((S)-5H-imidazo[5,1-a]isoindol-5-yl)cyclohexane-1-carboxamide
(1R,4R)-4-((R)-5H-imidazo[5,1-a]isoindol-5-yl)cyclohexane-1-carboxamide

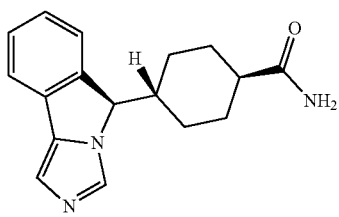
60a

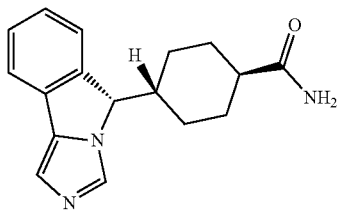
60b

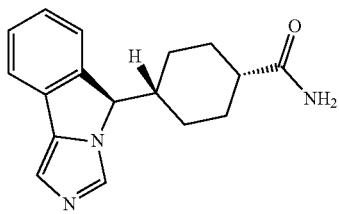
60c

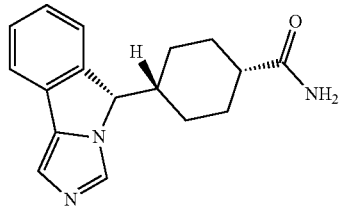
60d

To the solution of 4-(5H-imidazo[5,1-a]isoindol-5-yl)cyclohexane-1-carbonitrile (980 mg, 3.8 mmol) in methanol (25 mL), sodium hydroxide (1.52 g, 38 mmol) and 30% hydrogen peroxide (3.82 mL, 38 mmol) were added and stirred for overnight at room temperature. Solvent was removed and crude product was extracted with 5% 2,2,2-trifluoroethanol in DCM. Combined organic layers were washed with water, brine, dried over sodium sulfate. The residue was applied onto combiflash separation with dichloromethane/methanol (10:1). The product was further isolated by chiral separation to afford 4 isomers as white solid. The stereochemistry of each isomer was arbitrarily assigned.

Example 60a: (1R,4R)-4-((R)-5H-imidazo[5,1-a]isoindol-5-yl)cyclohexane-1-carboxamide LCMS (ESI, m/z): 282.3 [M+H]$^+$; 1H NMR (500 MHz, DMSO-d$_6$) δ 7.76 (s, 1H), 7.57 (dt, J=7.5, 0.9 Hz, 1H), 7.44 (dq, J=7.6, 0.9 Hz, 1H), 7.36 (tt, J=7.5, 0.8 Hz, 1H), 7.26 (td, J=7.5, 1.1 Hz, 1H), 7.11 (s, 1H), 7.06 (s, 1H), 6.65 (s, 1H), 5.24 (d, J=3.2 Hz, 1H), 2.36 (s, 1H), 2.14-1.89 (m, 3H), 1.48-1.30 (m, 4H), 1.12-0.99 (m, 2H).

Example 60b: (1S,4S)-4-((R)-5H-imidazo[5,1-a]isoindol-5-yl)cyclohexane-1-carboxamide LCMS (ESI, m/z): 282.3 [M+H]$^+$; 1H NMR (500 MHz, DMSO-d$_6$) δ 7.76 (s, 1H), 7.57 (dt, J=7.7, 0.9 Hz, 1H), 7.44 (dq, J=7.6, 1.0 Hz, 1H), 7.36 (tt, J=7.5, 0.8 Hz, 1H), 7.26 (td, J=7.6, 1.1 Hz, 1H), 7.11 (s, 1H), 7.06 (s, 1H), 6.65 (s, 1H), 5.24 (d, J=3.2 Hz, 1H), 2.36 (d, J=3.3 Hz, 1H), 2.02 (d, J=7.5 Hz, 1H), 1.93 (d, J=13.4 Hz, 1H), 1.48-1.29 (m, 4H), 1.12-0.99 (m, 2H).

Example 60c: (1S,4R)-4-((S)-5H-imidazo[5,1-a]isoindol-5-yl)cyclohexane-1-carboxamide LCMS (ESI, m/z): 282.3 [M+H]$^+$; 1H NMR (500 MHz, DMSO-d$_6$) δ 7.89 (s, 1H), 7.58 (dt, J=7.7, 0.9 Hz, 1H), 7.50 (dq, J=7.6, 0.9 Hz, 1H), 7.38 (tt, J=7.6, 0.8 Hz, 1H), 7.28 (td, J=7.6, 1.1 Hz, 1H), 7.13 (s, 1H), 7.10 (s, 1H), 6.66-6.57 (m, 1H), 5.29 (d, J=2.8 Hz, 1H), 2.14 (ddt, J=12.2, 9.2, 3.0 Hz, 1H), 1.92 (tt, J=12.0, 3.6 Hz, 1H), 1.82-1.72 (m, 1H), 1.70-1.57 (m, 2H), 1.37 (qd, J=12.9, 3.5 Hz, 1H), 1.30-1.13 (m, 3H), 0.69 (qd, J=12.8, 2.7 Hz, 1H).

Example 60d: (1R,4S)-4-((S)-5H-imidazo[5,1-a]isoindol-5-yl)cyclohexane-1-carboxamide LCMS (ESI, m/z): 282.3 [M+H]$^+$; 1H NMR (500 MHz, DMSO-d$_6$) δ 7.89 (s, 1H), 7.58 (dt, J=7.6, 0.8 Hz, 1H), 7.50 (dq, J=7.6, 0.9 Hz, 1H), 7.38 (tt, J=7.5, 0.8 Hz, 1H), 7.28 (td, J=7.5, 1.1 Hz, 1H), 7.13 (s, 1H), 7.10 (s, 1H), 6.66-6.58 (m, 1H), 5.29 (d, J=2.8 Hz, 1H), 2.14 (ddt, J=12.2, 9.2, 3.0 Hz, 1H), 1.92 (tt, J=12.0, 3.6 Hz, 1H), 1.82-1.73 (m, 1H), 1.70-1.57 (m, 2H), 1.37 (qd, J=12.9, 3.5 Hz, 1H), 1.31-1.13 (m, 3H), 0.69 (qd, J=12.9, 2.7 Hz, 1H).

Example 63: tert-butyl 5-(5H-imidazo[5,1-a]isoindol-5-yl)hexahydrocyclopenta[c]pyrrole-2 (1H)-carboxylate

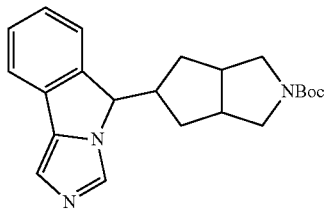 [SMILES: CC(C)(C)OC(=O)N1CC2CC(C3c4ccccc4-c4cncn43)CC2C1]

Synthetic Route

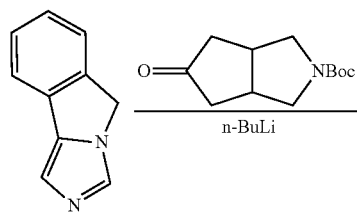

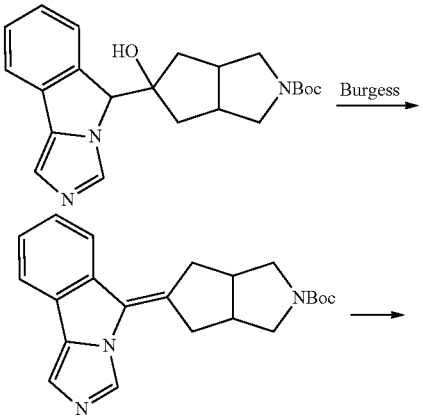

Step 1:

tert-butyl 5-hydroxy-5-(5H-imidazo[5,1-a]isoindol-5-yl)hexahydrocyclopenta[c]pyrrole-2 (1H)-carboxylate

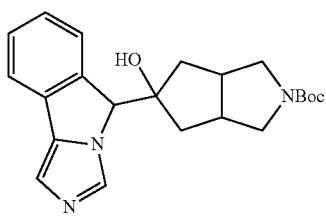 [SMILES: CC(C)(C)OC(=O)N1CC2CC(O)(C3c4ccccc4-c4cncn43)CC2C1]

To a solution of 5H-imidazo[5,1-a]isoindole (600 mg, 3.84 mmol) in anhydrous THF (15 mL) at −78° C. was added n-BuLi (1.54 mL, 3.84 mmol, 2.5 M solution in hexanes). After stirring for 1 hr at −78° C., the solution was warm up to 0° C. In the second flask containing a mixture of tert-butyl 5-oxohexahydrocyclopenta[c]pyrrole-2 (1H)-carboxylatecarbonitrile (473 mg, 3.84 mmol) in 10 mL THF was cooled to −78° C., which was treated with the above in-situ generated lithium reagent dropwise in 10 min. After 1 hr at −78° C., the reaction was quenched with water (1 mL) and NH$_4$Cl solution (20 mL). The separated aqueous layer was subsequently extracted with DCM (20 mL×3). Combined organic phase was dried over Na$_2$SO$_4$, filtrated and purified on Combi-Flash using MeOH/DCM (2%-6%). LCMS (ESI, m/z): 382.4 [M+H]$^+$; 1H NMR (400 MHz, Chloroform-d) δ 7.62-7.58 (m, 1H), 7.54 (dq, J=7.9, 0.9 Hz, 1H), 7.44 (dddd, J=8.2, 7.0, 1.1, 0.6 Hz, 1H), 7.31 (dt, J=7.6, 1.0 Hz, 1H), 7.24 (t, J=0.9 Hz, 1H), 3.54 (dd, J=11.2, 8.5 Hz, 1H), 3.48-3.40 (m, 2H), 3.32 (dd, J=11.2, 4.6 Hz, 1H), 2.71 (qt, J=8.6, 4.2 Hz, 1H), 2.53-2.35 (m, 2H), 2.02 (d, J=14.2 Hz, 1H), 1.68 (dd, J=13.9, 9.1 Hz, 1H), 1.52 (dd, J=18.0, 4.7 Hz, 1H), 1.44 (s, 9H).

Step 2:

tert-butyl 5-(5H-imidazo[5,1-a]isoindol-5-ylidene)hexahydrocyclopenta[c]pyrrole-2 (1H)-carboxylate

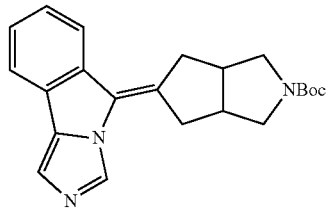 [SMILES: CC(C)(C)OC(=O)N1CC2CC(=c3c4ccccc4c4cncn34)CC2C1]

To a solution of tert-butyl 5-hydroxy-5-(5H-imidazo[5,1-a]isoindol-5-yl)hexahydrocyclopenta[c]pyrrole-2 (1H)-carboxylate (60 mg, 0.16 mmol) in anhydrous THF (3 mL) at room temperature was added Burgess reagent (75 mg, 0.31 mmol). The mixture was heated to reflux for 3 hr. Solvent was removed under vacuum and the residue was purified on Combi-Flash using MeOH/DCM (2%-6%). LCMS (ESI, m/z): 364.3 [M+H]$^+$.

Step 3:

tert-butyl 5-(5H-imidazo[5,1-a]isoindol-5-yl)hexahydrocyclopenta[c]pyrrole-2 (1H)-carboxylate

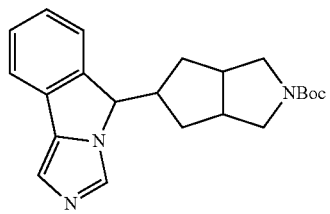 [SMILES: CC(C)(C)OC(=O)N1CC2CC(C3c4ccccc4-c4cncn43)CC2C1]

To a solution of tert-butyl 5-(5H-imidazo[5,1-a]isoindol-5-ylidene)hexahydrocyclopenta[c]pyrrole-2 (1H)-carboxylate (240 mg, 0.66 mmol) and 10% Pd/C (70 mg) in EtOAc/MeOH/AcOH (2/2/1) solution was charged with hydrogen gas three times after vacuum. The reaction mixture was then placed with a hydrogen gas balloon at room temperature. After overnight, the solid was filtrated through a pad of celite. After removing solvent under vacuum, the residue was purified on Combi-flash (5% MeOH/DCM). LCMS (ESI, m/z): 366.3 [M+H]⁺; 1H NMR (400 MHz, DMSO-d₆) δ 7.94 (s, 1H), 7.59 (dt, J=7.6, 0.9 Hz, 1H), 7.55-7.47 (m, 1H), 7.42-7.34 (m, 1H), 7.26 (td, J=7.6, 1.2 Hz, 1H), 7.14 (s, 1H), 5.39 (d, J=5.8 Hz, 1H), 3.12 (s, 1H), 2.96 (s, 1H), 2.56 (s, 1H), 2.46 (s, 1H), 2.07 (s, 1H), 1.74 (d, J=10.5 Hz, 1H), 1.48 (dt, J=21.3, 10.4 Hz, 1H), 1.38 (s, 9H), 0.95 (s, 1H).

5-(2-(methylsulfonyl)octahydrocyclopenta[c]pyrrol-5-yl)-5H-imidazo[5,1-a]isoindole Example 74: 4-(8-fluoro-5H-imidazo[5,1-a]isoindol-5-yl)piperidine-1-sulfonamide

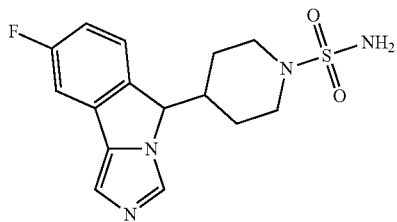

(S)-4-(8-fluoro-5H-imidazo[5,1-a]isoindol-5-yl)piperidine-1-sulfonamide
(R)-4-(8-fluoro-5H-imidazo[5,1-a]isoindol-5-yl)piperidine-1-sulfonamide To the solution of chlorosulfonyl isocyanate (80 mg, 0.565 mmol) in methylene chloride (3.0 mL) at 0° C. was added a solution of tert-butyl alcohol (42 mg, 0.565 mmol). The resulting mixture was stirred at 0° C. for 10 min then warmed to room temperature and stirred for 1 h. The mixture was then added to a stirred solution of 8-fluoro-5-(piperidin-4-yl)-5H-imidazo[5,1-a]isoindole dihydrochloride (215 mg, 0.650 mmol) and N,N-diisopropylethylamine in dichloromethane (10 mL) at 0° C. After stirring at 0° C. for 1 h, the reaction was allowed warm to rt and stirred for 2 h. The reaction mixture was quenched with saturated NaHCO₃ solution (5 mL) and water (15 mL) the product was extracted with DCM (3×30 mL). The combined organic extracts were dried over Na₂SO₄ and concentrated. The crude product was stirred with anhydrous HCl (3 mL, 4.0 M solution in dioxane) in dioxane at rt. After stirring for 2 h, the solvent was distilled-off and the crude was basified with 50% satd NaHCO₃ solution (10 mL). The product was extracted with 5% trifluoroethanol in DCM (3×30 mL). The combined organic extracts were dried over Na₂SO₄ and concentrated to afford the crude, the crude was purified by CombiFlash to afford off-white solid (100 mg, 53%). The enantiomers were separated by chiral SFC and absolute configuration was assigned arbitrarily. LCMS (ESI, m/z): 337.31 [M+H]⁺. ¹H NMR (DMSO-d₆, 400 MHz): δ (ppm) 7.98 (s, 1H), 7.55 (dd, J=8.4, 5.0 Hz, 1H), 7.50 (dd, J=9.0, 2.5 Hz, 1H), 7.19 (s, 1H), 7.11 (ddd, J=9.6, 8.4, 2.5 Hz, 1H), 6.73 (s, 2H), 5.37 (d, J=2.3 Hz, 1H), 3.52 (d, J=11.6 Hz, 1H), 3.41 (d, J=11.8 Hz, 1H), 2.47-2.34 (m, 2H), 2.25 (td, J=12.3, 3.1 Hz, 1H), 1.62 (d, J=12.9 Hz, 1H), 1.44 (qd, J=12.6, 4.3 Hz, 1H), 1.29 (d, J=13.1 Hz, 1H), 0.92 (qd, J=12.6, 4.3 Hz, 1H).

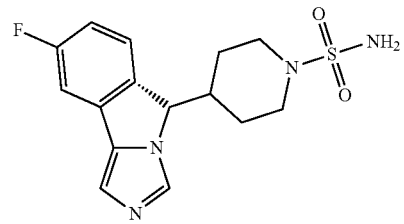 [SMILES: NS(=O)(=O)N1CCC(C2c3ccc(F)cc3-c3cncn32)CC1]

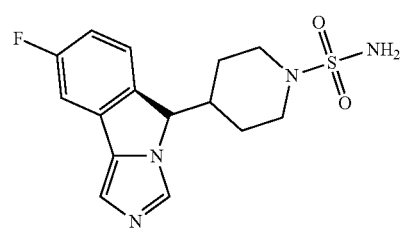

Example 74a: (S)-4-(8-fluoro-5H-imidazo[5,1-a]isoindol-5-yl)piperidine-1-sulfonamide. LCMS (ESI, m/z): 337.31 [M+H]⁺. ¹H NMR (DMSO-d₆, 400 MHz): δ (ppm) 7.98 (s, 1H), 7.55 (dd, J=8.4, 5.0 Hz, 1H), 7.50 (dd, J=9.0, 2.5 Hz, 1H), 7.19 (s, 1H), 7.11 (ddd, J=9.6, 8.4, 2.5 Hz, 1H), 6.73 (s, 2H), 5.37 (d, J=2.3 Hz, 1H), 3.52 (d, J=11.6 Hz, 1H), 3.41 (d, J=11.8 Hz, 1H), 2.47-2.34 (m, 2H), 2.25 (td, J=12.3, 3.1 Hz, 1H), 1.62 (d, J=12.9 Hz, 1H), 1.44 (qd, J=12.6, 4.3 Hz, 1H), 1.29 (d, J=13.1 Hz, 1H), 0.92 (qd, J=12.6, 4.3 Hz, 1H).

Example 74b: LC MS (ESI, m/z): 337.31 [M+H]⁺. ¹H NMR (DMSO-d₆, 400 MHz): Same as 74a Example 75a: 5-(2-(methylsulfonyl)octahydrocyclopenta[c]pyrrol-5-yl)-5H-imidazo[5,1-a]isoindole

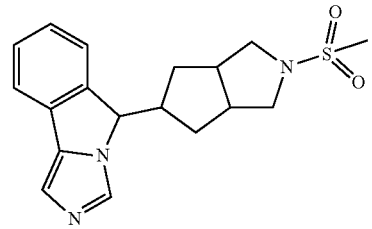 [SMILES: CS(=O)(=O)N1CC2CC(C3c4ccccc4-c4cncn43)CC2C1]

Step 1:

5-(octahydrocyclopenta[c]pyrrol-5-yl)-5H-imidazo[5,1-a]isoindole

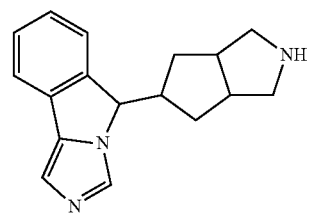 [SMILES: c1ccc2c(c1)-c1cncn1C2C1CC2CNCC2C1]

To a solution of tert-butyl 2-(5H-imidazo[5,1-a]isoindol-5-yl)-7-azaspiro[3.5]nonane-7-carboxylate (Example 62, 250 mg, 0.395 mmol) in anhydrous DCM (6 mL) was added trifluoroacetic acid (1.57 mL, 11.86 mmol) at room temperature and stirred for another 1 hr. The reaction was monitored by LC-MS. After consumption of the starting material, the solvent was evaporated and the crude product was dried by vacuum. The crude product was used directly for the next step without further purification.

Step 2:

5-(2-(methylsulfonyl)octahydrocyclopenta[c]pyrrol-5-yl)-5H-imidazo[5,1-a]isoindole

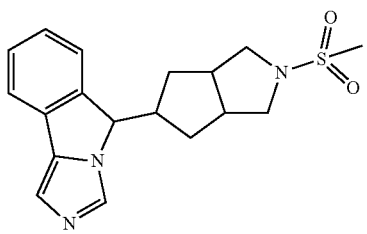 [SMILES: CS(=O)(=O)N1CC2CC(C3c4ccccc4-c4cncn43)CC2C1]

To a solution of 5-(7-azaspiro[3.5]nonan-2-yl)-5H-imidazo[5,1-a]isoindole (100 mg, 0.37 mmol) in anhydrous DCM (4 mL) was added triethylamine (0.16 mL, 1.130 mmol) at 0° C. Methanesulfonyl chloride (32 μL, 0.41 mmol) was then added into the mixture. The reaction was warmed to room temperature and stirred for another 2 hr. The reaction was quenched by adding saturated NaHCO₃ aqueous solution (10 mL). The crude product was extracted with DCM (3× mL) and the organic phase was combined, dried over anhydrous Na₂SO₄, and concentrated. The product was separated by CombiFlash and was eluted with DCM:MeOH=94:6. LCMS (ESI, m/z): 344.2 [M+H]⁺; 1H NMR (400 MHz, Chloroform-d) δ 7.78 (s, 1H), 7.57-7.53 (m, 1H), 7.41-7.36 (m, 2H), 7.28-7.23 (m, 1H), 7.20 (s, 1H), 5.12 (d, J=6.2 Hz, 1H), 3.33-3.11 (m, 5H), 2.83 (s, 3H), 2.80-2.63 (m, 2H), 2.34-2.16 (m, 3H), 1.33 (td, J=11.3, 8.2 Hz, 1H).

Example 75b: 5-(5H-imidazo[5,1-a]isoindol-5-yl)hexahydrocyclopenta[c]pyrrole-2 (1H)-sulfonamide

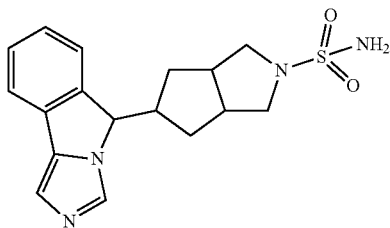 [SMILES: NS(=O)(=O)N1CC2CC(C3c4ccccc4-c4cncn43)CC2C1]

Step 1:

5-(octahydrocyclopenta[c]pyrrol-5-yl)-5H-imidazo[5,1-a]isoindole

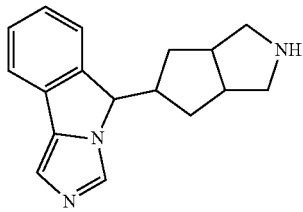 [SMILES: c1ccc2c(c1)-c1cncn1C2C1CC2CNCC2C1]

To a solution of tert-butyl 2-(5H-imidazo[5,1-a]isoindol-5-yl)-7-azaspiro[3.5]nonane-7-carboxylate (Example 62, 250 mg, 0.395 mmol) in anhydrous DCM (6 mL) was added trifluoroacetic acid (1.57 mL, 11.86 mmol) at room temperature and stirred for another 1 hr. The reaction was monitored by LC-MS. After consumption of the starting material, the solvent was evaporated and the crude product was dried by vacuum. The crude product was used directly for the next step without further purification.

Step 2:

tert-butyl ((5-(5H-imidazo[5,1-a]isoindol-5-yl)hexahydrocyclopenta[c]pyrrol-2 (1H)-yl)sulfonyl)carbamate

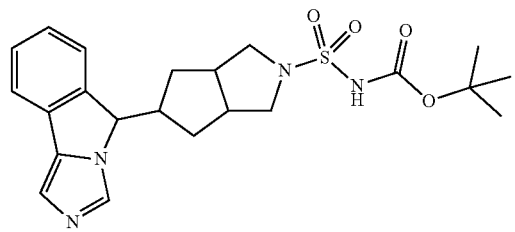 [SMILES: CC(C)(C)OC(=O)NS(=O)(=O)N1CC2CC(C3c4ccccc4-c4cncn43)CC2C1]

To the solution of chlorosulfonyl isocyanate (72 μL, 0.83 mmol) in anhydrous methylene chloride (5 mL) at 0° C. was added tert-butyl alcohol (114 μL, 1.51 mmol). The resulting mixture was stirred at 0° C. for 10 min then warmed to room temperature and stirred for another 1 h. The mixture was then added to a stirred solution of 5-(octahydrocyclopenta[c]pyrrol-5-yl)-5H-imidazo[5,1-a]isoindole (200 mg, 0.75 mmol) and triethylamine (0.32 mL, 0.31 mmol) in dichloromethane (5 mL) at 0° C. The reaction was allowed warm to room temperature and stirred for another 2 hr. The reaction mixture was quenched with saturated NaHCO₃solution (10 mL) then extracted with CH₂C₁₂ (3×10 mL). The combined extracts were dried over anhydrous Na₂SO₄ and concentrated. The crude product was directly used for the next step without further purification.

Step 3:

5-(5H-imidazo[5,1-a]isoindol-5-yl)hexahydrocyclopenta[c]pyrrole-2 (1H)-sulfonamide

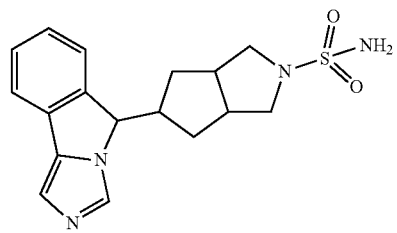 [SMILES: NS(=O)(=O)N1CC2CC(C3c4ccccc4-c4cncn43)CC2C1]

tert-butyl ((5-(5H-imidazo[5,1-a]isoindol-5-yl)hexahydrocyclopenta[c]pyrrol-2 (1H)-yl)sulfonyl)carbamate was stirred with HCl (3 mL, 4.0 M solution in dioxane) in anhydrous methanol (10 mL) at room temperature. After stirring for 2 hr, the solvent was distilled-off and the crude was basified with saturated NaHCO₃solution (10 mL). The product was extracted with DCM (3×10 mL). The organic phase was combined, dried over anhydrous Na₂SO₄, and concentrated. The product was separated by CombiFlash and was eluted with DCM:MeOH=95:5. LCMS (ESI, m/z): 345.2 [M+H]$^+$; 1H NMR (400 MHz, DMSO-d$_6$) δ 7.91 (s, 1H), 7.60 (dt, J=7.6, 0.9 Hz, 1H), 7.51 (dt, J=7.6, 1.0 Hz, 1H), 7.43-7.36 (m, 1H), 7.27 (td, J=7.6, 1.2 Hz, 1H), 7.15 (s, 1H), 6.75 (s, 2H), 5.35 (d, J=6.2 Hz, 1H), 3.01-2.88 (m, 3H), 2.83 (dd, J=9.6, 2.4 Hz, 1H), 2.70-2.53 (m, 2H), 2.30-2.09 (m, 2H), 1.93-1.81 (m, 1H), 1.45 (td, J=12.1, 8.8 Hz, 1H), 1.05 (td, J=12.1, 8.9 Hz, 1H).

IDO1 and TDO2 Cell Assay

The NFK GreenScreen™ (NTRC, Netherlands) uses a specific chemical probe that binds to N-Formylkynurenine (NFK), a product of tryptophan catabolism facilitated by IDO or TDO and causes fluorescence at 510 nm when excited at 410 nm. The assay is used to assess compound inhibition of TDO and IDO leading to decreased levels of NFK in SW48 cells (high TDO expressing cells) and to determine whether compounds are selective against A172+ IFNg cells (high IDO expressing cells) or are dual inhibitors in cells. The assay is multiplexed with Cell Titer-Glo® (Promega) to determine if compounds are cytotoxic. Briefly, SW48 or A172 cells are harvested in growth media, RPMI 1640 with 10% FBS, 2 mM L-glutamine, and 1× pen/strep. Cells are re-suspended in assay media, tryptophan-free RPMI 1640 supplemented with 2% dialyzed FBS, 2 mM L-glutamine, and 1× pen/strep. Cells are counted on a Vi-Cell (Beckman Coulter). SW48 cells are diluted to 1×10^6 cells/ml in assay media. A172 cells are diluted to 0.24×10^6 cells/ml in assay media. 25 ul of cells are dispensed with a Multi-Flo (Bio-Tek) dispenser to a 384 well greiner μclear plate (Greiner, 781091) with 14 compounds in duplicate. Compounds are dispensed into plates with an Echo® (Labcyte) starting at the highest concentration of 25 uM and are diluted approximately 3× in a 10 point titration. 5 ul of assay media containing 1.2 mM tryptophan are added to the SW48 cells for a final concentration of 200 uM tryptophan in each well. 5 ul of assay media containing 600 uM tryptophan and 600 ng/ml IFNγ are added to the A172 cells for a final concentration of 100 uM tryptophan and 100 ng/ml IFNγ in each well. The final DMSO concentration is 0.5%. Cell plates are placed at room temperature in a closed TC hood with the blower off to allow cells to settle for approximately 30 min. Plates are then moved to an incubator set at 37° C., 5% CO$_2$ for 24 hours. After the 24 hour compound incubation, 8 ul of NFK green reagent is added to each well with a Multidrop™ Combi dispenser (Thermo Scientific). Plates are sealed and incubated at 37° C., 5% CO$_2$ for 5 hours, then read on a PHERAstar® (BMG labtech). Data are analyzed by normalizing to DMSO and high inhibitor controls. After the plates have been read for NFK green, 25 ul of Cell Titer-Glo® (Promega) are added to each well, incubated for 15 minutes at room temperature, and read on the Envision (Perkin Elmer). Cell Titer-Glo data are analyzed by normalizing to the DMSO controls. Four-parameter curve fitting is used and EC50 data are reported.

TABLE 2

| Ex. # | IDO cell Fluor EC50 [μM] | TDO2 cell Fluor EC50 [μM] |
|---|---|---|
| 01a | 25.0 | 11.0 |
| 01b | 8.5 | 0.31 |
| 02a | 11.0 | 5.1 |
| 02b | 25.0 | 25.0 |
| 03 | 25.0 | 13.0 |
| 04 | 12.0 | 2.3 |
| 05a | 25.0 | 1.1 |
| 05b | 25.0 | 1.7 |
| 05c | 25.0 | 24.0 |
| 06 | 7.8 | 0.88 |
| 07a | 25.0 | 7.2 |
| 07b | 6.5 | 0.79 |
| 08 |  | 1.5 |
| 09a | 21.0 | 0.69 |
| 09b | 3.3 | 0.096 |
| 10a | 5.0 | 0.32 |
| 10b | 25.0 | 5.7 |
| 10c | 22.0 | 0.59 |
| 10d | 25.0 | 5.0 |
| 11 |  | 0.65 |
| 12 | 11.0 | 1.8 |
| 13 | 20.0 | 12.0 |
| 14 | 15.0 | 0.81 |
| 15 | 25.0 | 5.0 |
| 16 | 0.93 | 0.15 |
| 17 | 16.0 | 2.0 |
| 18 | 19.0 | 9.6 |
| 19a | 10.0 | 17.0 |
| 19b | 0.416 | 0.033 |
| 20 | 25.0 | 16.0 |
| 21 | 9.7 | 0.36 |
| 22 | 1.1 | 2.3 |
| 23 | 9.0 | 0.65 |
| 24a | 7.9 | 17.0 |
| 24b | 0.54 | 0.32 |
| 25 | 25.0 | 14.0 |
| 26 | 9.7 | 3.2 |
| 27 | 6.5 | 0.29 |
| 28 | 9.8 | 0.28 |
| 29 | 2.2 | 0.38 |
| 30 | 5.0 | 0.34 |
| 31a | 4.9 | 0.31 |
| 31b | 24.0 | 8.7 |
| 32 | 25.0 | 9.5 |
| 33 | 3.9 | 0.54 |
| 34 | 2.4 | 0.99 |
| 35 | 6.1 | 1.4 |
| 36 | 25.0 | 13.0 |
| 37 | 25.0 | 4.1 |
| 38 | 13.0 | 16.0 |
| 39 | 11.0 | 0.59 |
| 40 | 3.8 | 0.29 |
| 41 | 25.0 | 2.5 |
| 42 | 25.0 | 1.8 |
| 43a | 5.9 | 0.4 |
| 43b | 7.8 | 5.9 |
| 44a | 9.1 | 1.0 |
| 44b | 1.7 | 0.085 |
| 45 | 1.9 | 0.14 |
| 46 | 2.0 | 0.027 |
| 47a |  | 22.0 |
| 47b | 0.4 | 0.053 |
| 47c |  | 2.0 |
| 47d |  | 25.0 |
| 48 |  | 6.2 |
| 49 | 7.1 | 0.59 |
| 50a | 25.0 | 25.0 |
| 50b | 25.0 | 25.0 |
| 50c | 25.0 | 25.0 |
| 50d | 19.0 | 0.26 |
| 51 | 3.1 | 0.12 |
| 52 | 5.7 | 0.3 |
| 53 | 4.4 | 0.87 |
| 54 | 25.0 | 5.4 |
| 55a | 8.5 | 0.55 |
| 55b | 8.1 | 0.78 |
| 56 | 4.6 | 0.64 |
| 57 | 0.91 | 1.5 |
| 58 | 1.2 | 0.42 |
| 59 | 1.5 | 0.24 |
| 60a | 25.0 | 25.0 |
| 60b | 1.5 | 0.27 |
| 60c | 6.4 | 25.0 |
| 60d | 17.0 | 10.0 |

TABLE 2-continued

| Ex. # | IDO cell Fluor EC50 [µM] | TDO2 cell Fluor EC50 [µM] |
|---|---|---|
| 61 | 2.7 | 0.37 |
| 62a | 0.66 | 0.034 |
| 62b | 25.0 | 16.0 |
| 63 | 3.2 | 2.9 |
| 64 | 4.4 | 0.41 |
| 65 | 1.9 | 0.21 |
| 66 | 20.0 | 1.1 |
| 67 | 0.9 | 0.21 |
| 68 | 25.0 | 1.4 |
| 69 | 18.0 | 11.0 |
| 70 | 0.86 | 0.18 |
| 71 | 14.0 | 0.56 |
| 72a | 3.0 | 0.73 |
| 72b | 25.0 | 17.0 |
| 73a | 25.0 | 8.3 |
| 73b | 6.1 | 0.76 |
| 74a | 25.0 | 25.0 |
| 74b | 4.8 | 0.064 |
| 75a | 7.6 | 2.1 |
| 75b | 7.2 | 1.5 |
| 76 | 0.14 | 1.8 |
| 77 | 25.0 | 25.0 |
| 78a | 18.0 | 10.0 |
| 78b | 1.4 | 2.5 |
| 79a | 25.0 | 10.0 |
| 79b | 8.5 | 0.53 |
| 80a | 1.0 | 0.26 |
| 80b | 25.0 | 25.0 |
| 80c | 0.49 | 0.089 |
| 81 | 12.0 | 4.9 |
| 82a | 25.0 | 25.0 |
| 82b | 4.4 | 1.5 |
| 83a | 25.0 | 22.0 |
| 83b | 2.3 | 0.77 |
| 84a | 25.0 | 7.1 |
| 84b | 12.0 | 0.36 |
| 85a | | |
| 85b | 25.0 | 25.0 |
| 86a | 25.0 | 25.0 |
| 86b | 25.0 | 7.6 |
| 86c | 2.4 | 0.24 |
| 86d | 25.0 | 25.0 |
| 87 | 25.0 | 2.7 |
| 88 | 5.3 | 0.9 |
| 89 | 5.9 | 0.22 |
| 90 | 4.9 | 0.6 |
| 91a | 25.0 | 25.0 |
| 91b | 2.0 | 0.11 |
| 91c | 25.0 | 23.0 |
| 91d | 16.0 | 0.5 |
| 92a | 9.8 | 0.14 |
| 92b | 2.7 | 10.0 |
| 93 | 8.6 | 0.77 |
| 94 | 7.1 | 0.42 |
| 95a | 2.7 | 0.097 |
| 95b | 25.0 | 5.2 |
| 95c | 19.0 | 13.0 |
| 95d | 2.6 | 0.14 |
| 96 | 9 | 0.39 |

We claim:

1. A compound of formula (I):

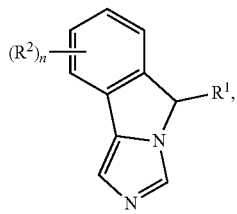

or a stereoisomer thereof, or a pharmaceutically acceptable salt thereof, wherein $R^1$ is aryl or heteroaryl, wherein the aryl and the heteroaryl are optionally fused to aryl, heteroaryl, $C_{3-7}$ cycloalkyl or 3-7 membered heterocyclyl;

wherein $R^1$ is substituted by one, two, three, or four $R^a$ groups, wherein each $R^a$ is independently oxo, halogen, cyano, nitro, $C_{1-6}$ alkyl, —$C_{1-6}$ haloalkyl, $C_{1-6}$alkyl-cyano, $C_{3-7}$ cycloalkyl, 3-7 membered heterocyclyl, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

n is 0, 1, 2, 3 or 4;

each $R^2$ is independently halogen, cyano, $C_{1-6}$alkyl, $C_3$cycloalkyl, —OR, —$NR_2$ or —SR; and each R is hydrogen, $C_{1-6}$ alkyl, $C_{1-6}$ haloalkyl, aryl substituted with cyano, 3-7 membered heterocyclyl or $C_{3-6}$ cycloalkyl;

provided that (a) $R^1$ is not substituted with —$NR_2$ or —OH on the carbon atom bonded to the 5H-imidazo[5,1-a]isoindolyl, or on a carbon atom adjacent to the carbon atom bonded to the 5H-imidazo[5,1-a]isoindolyl.

2. The compound of claim 1 wherein $R^1$ is substituted by one, two, three, or four $R^a$ groups, wherein each $R^a$ is independently oxo, halogen, cyano, nitro, $C_{1-6}$ alkyl, —$C_{1-6}$alkyl-OR, —$C_{1-6}$ haloalkyl, $C_{1-6}$ alkyl-cyano, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

3. A compound of Formula (II),

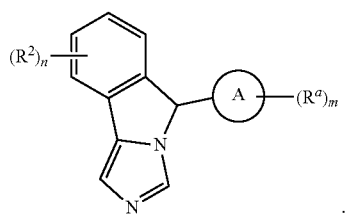

or a stereoisomer thereof, or a pharmaceutically acceptable salt thereof, wherein n is 0, 1, 2, 3 or 4;

each $R^2$ is independently halogen, cyano, $C_{1-6}$ alkyl, $C_3$cycloalkyl, —$C_{1-6}$ haloalkyl, —OR, —$NR_2$ or —SR;

ring A is aryl or heteroaryl;

m is 0, 1, 2, 3 or 4;

each $R^a$ is independently oxo, halogen, cyano, $C_{1-6}$ alkyl, —$C_{1-6}$ alkyl-OR, —$C_{1-6}$ haloalkyl, $C_{1-6}$ alkyl-cyano, —OR, —$NR_2$, —SR, —C(O)OR, —C(O)N(R)$_2$, —C(O)R, —C(O)-aryl, —S(O)R, —S(O)OR, —S(O)N(R)$_2$, —S(O)$_2$R, —N(R)S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$; and each R is hydrogen, $C_{1-6}$ alkyl, $C_{1-6}$ haloalkyl, aryl substituted with cyano, 3-7 membered heterocyclyl or $C_{3-6}$ cycloalkyl.

4. The compound of claim 3 wherein, each $R^a$ is independently, halogen, cyano, $C_{1-6}$ alkyl, —$C_{1-6}$ alkyl-OR—C(O)OR, —C(O)N(R)$_2$, —S(O)$_2$R, — or —S(O)$_2$N(R)$_2$, wherein each R is hydrogen, $C_{1-6}$ alkyl, $C_{1-6}$ haloalkyl, aryl substituted with cyano, 3-7 membered heterocyclyl or $C_{3-6}$ cycloalkyl.

5. The compound of claim 3, wherein

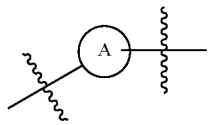

is aryl.

6. The compound of claim 3, wherein

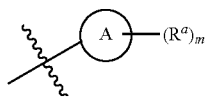

is

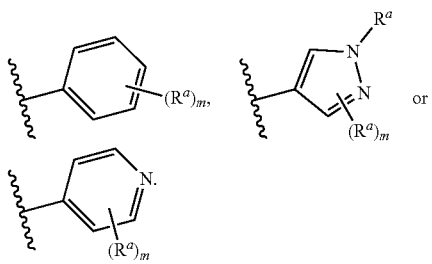

7. The compound of claim 3, wherein

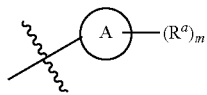

is

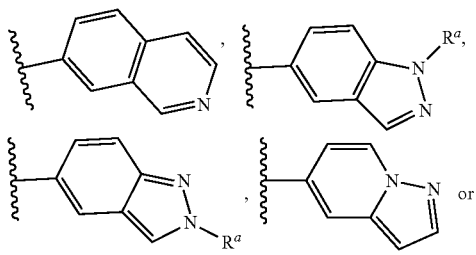

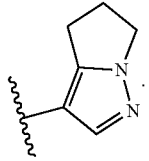

8. A compound that is
(3-(5H-imidazo[5,1-a]isoindol-5-yl)phenyl)methanol;
5-(3-(2,2-difluoroethyl)phenyl)-5H-imidazo[5,1-a]isoindole;
3-(5H-imidazo[5,1-a]isoindol-5-yl)benzenesulfonamide;
(3-fluoro-5-(5H-imidazo[5,1-a]isoindol-5-yl)phenyl)methanol;
1-(3-(5H-imidazo[5,1-a]isoindol-5-yl)phenyl)ethan-1-ol;
3-(5H-imidazo[5,1-a]isoindol-5-yl)benzamide;
5-(m-tolyl)-5H-imidazo[5,1-a]isoindole;
5-(isoquinolin-7-yl)-5H-imidazo[5,1-a]isoindole;
5-(3-fluorophenyl)-5H-imidazo[5,1-a]isoindole;
5-phenyl-5H-imidazo[5,1-a]isoindole;
5-(3-chloro-5-fluorophenyl)-5H-imidazo[5,1-a]isoindole;
5-(2-fluoro-4-methylphenyl)-5H-imidazo[5,1-a]isoindole;
5-(3-fluoro-5-methylphenyl)-5H-imidazo[5,1-a]isoindole;
5-(3,5-difluorophenyl)-5H-imidazo[5,1-a]isoindole;
3-fluoro-5-(5H-imidazo[5,1-a]isoindol-5-yl)benzonitrile;
3-fluoro-5-(5H-imidazo[5,1-a]isoindol-5-yl)benzamide;
5-(1-methyl-1H-indazol-5-yl)-5H-imidazo[5,1-a]isoindole;
5-(4-(methylsulfonyl)phenyl)-5H-imidazo[5,1-a]isoindole;
5-(2-(cyclopropylsulfonyl)-2H-indazol-5-yl)-5H-imidazo[5,1-a]isoindole;
5-(3,4,5-trifluorophenyl)-5H-imidazo[5,1-a]isoindole;
5-(1-methyl-1H-pyrazol-4-yl)-5H-imidazo[5,1-a]isoindole;
or a pharmaceutically acceptable salt thereof, or an enantiomer or diastereoisomer thereof, or a racemic mixture thereof.

9. A pharmaceutical composition comprising a compound according to claim 1 and a pharmaceutically acceptable diluent, excipient, or carrier.

10. A method for treating tryptophan 2,3-dioxygenase (TDO2) mediated immunosuppression associated with a disease in a subject in need thereof, comprising administering an effective tryptophan 2,3-dioxygenase inhibiting amount of a compound according to claim 1.

11. The method of claim 10, wherein the disease is cancer.

12. A pharmaceutical composition comprising a compound according to claim 8 and a pharmaceutically acceptable diluent, excipient, or carrier.

13. A method for treating tryptophan 2,3-dioxygenase (TDO2) mediated immunosuppression associated with a disease in a subject in need thereof, comprising administering an effective tryptophan 2,3-dioxygenase inhibiting amount of a compound according to claim 8.

14. The method of claim 13, wherein the disease is cancer.

* * * * *